(12) United States Patent
Beeson, IV et al.

(10) Patent No.: US 9,617,524 B2
(45) Date of Patent: Apr. 11, 2017

(54) CYTOKININ SYNTHASE ENZYMES, CONSTRUCTS, AND RELATED METHODS

(71) Applicant: Dow AgroSciences LLC, Indianapolis, IN (US)

(72) Inventors: William T. Beeson, IV, Indianapolis, IN (US); Patrick John Westfall, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 7 days.

(21) Appl. No.: 14/718,585

(22) Filed: May 21, 2015

(65) Prior Publication Data
US 2016/0076010 A1 Mar. 17, 2016

Related U.S. Application Data

(60) Provisional application No. 62/001,849, filed on May 22, 2014.

(51) Int. Cl.
| | |
|---|---|
| C12N 15/82 | (2006.01) |
| C12P 19/32 | (2006.01) |
| C12N 9/10 | (2006.01) |
| A01N 43/90 | (2006.01) |
| C12P 17/18 | (2006.01) |
| C12N 9/88 | (2006.01) |

(52) U.S. Cl.
CPC ........... *C12N 9/1085* (2013.01); *A01N 43/90* (2013.01); *C12N 9/88* (2013.01); *C12P 17/182* (2013.01); *C12P 19/32* (2013.01)

(58) Field of Classification Search
None
See application file for complete search history.

(56) References Cited

U.S. PATENT DOCUMENTS

| | | |
|---|---|---|
| 6,992,237 B1 | 1/2006 | Habben et al. |
| 7,531,723 B2 | 5/2009 | Habben et al. |
| 8,962,920 B2 | 2/2015 | Sakakibara et al. |

OTHER PUBLICATIONS

Adila, et al., Comparison of methods for isolating high qualify DNA & RNA from oleaginous fungus Cunninghamella bainieri strain 2a1, (2007) Mal. J. Microbiol. 3(1): 7-13.
Altschul et al., Gapped BLAST and PSI-BLAST: a new generation of protein database search programs, (1997) Nucleic Acids Research, 25(17): 3389-3402.
Anjard, et al., Cytokinins induce sporulation in Dictyostelium, (2008) Development 135: 819-827.
Barry et al., Identification of a cloned cytokinin biosynthetic gene, (1984) Proc. Natl. Acad. Sci. USA 81: 4776-4780.
Blackwell et al., Cloned Agrobacterium Tumefaciens IPT1 Gene Product, DMAPP:AMP Isopentenyl Transferease (1993) Phytochemistry, 34(6): 1477-1481.
Chu, et al., Crystal structure and substrate specificy of plant adenylate isopentenyltransferease from Humulus lupulus: distinctive binding affinity for purine andpyrimidine nucleotides, (2010) Nucleic Acids Research, 38(5): 1738-1748.
Creason et al., Analysis of Genome Sequences from Plant Pathogenic I Reveals Genetic Novelties in Virulence Loci, (2014) PLOS ONE 9(7): 1-17.
Dewitte et al., Dynamics of Cytokinins in Apical Shoot Meristems of a Day-Neutral Tobacco during Floral Transitiona and Flower Formation, (1999) Plant Physiology,119: 111-121.
Dzurová et al., Support Information for the three-dimendional structure of "Lonely Guy" from Claviceps purpurea provides insights into the phosphoribohydrolase function of Rossmann fold-containing lysine decarboxylase-like proteins, (2015) pp. 1-9 (retrieved from http://onlinelibrary.wiley.com/store/10.1002/prot.24835/asset/supinfo/prot24835-sup-0001-suppinfo.pdf?v=1&s=6d8edb7e43a12170d86d705ae09edc10502ed4cd).
Dzurová et al., The three-dimendional structure of "Lonely Guy" from Claviceps purpurea provides insights into the phosphoribohydrolase function of Rossmann fold-containing lysine decarboxylase-like proteins, (2015) Proteins 0:000-000, pp. 1-8.
Eaton, et al., Disruption of Signaline in Fungal-Grass Symbiosis Leads to Pathogenesis, (2010) Plant Physiology 153: 1780-1794.
Faiss et al., Conditional transgenic expression of the ipt gene incicates a function for cytokinins in paracrine signaling in whole tobacco plants, (1997) The Plant Journal 12(2): 401-415.
Held et al., Lotus japonicus Cytokinin Receptors Work Partially Redundantly to Mediate Nodule Formation, (2014) The Plant Cell 26: 678-694.
Hinsch et al., De novo biosynthesis of cytokinins in the biotrophic fungus Claviceps purpurea, (2015) Environmentla Microbiogy, doi:10.1111/1462-2920.12838, pp. 1-17.
International Search Report and Written Opinion, International Application No. PCT/US15/31942, mailed Nov. 19, 2015.
Kurakawa, et al., Direct Control of shoot meristem activity ty a cytokinin-activating enzyme, (2007) Nature, 445: 652-655.
Kuroha, et al., Functional Analyses of LONELY GUY Cytokinin-Activating Enzymens reveal the Importance of the Direct Activation Pathway in Arabidopsis, (2009) The Plant Cell 21: 3152-3169.
Merewitz et al., Elevated cytokinin content in ipt transgenic creeping bentgrass promotes drought tolerance through regulating metabolite accumulation, (2012) J. Experimental Botany 63(3): 1315-1328.
Motyka et al., Changes in Cytokinin Content and Cytokinin Oxidase Activity in Response to Derepression of ipt Gene Transcriptin in Transgenic Tobacco Calli and Plants, (1996) Plant Physiol. 112: 1035-1043.
Sakakibara, Cytokinins: Activity, Biosynthesis and Translocation, (2006) The Annu. Rev. of Plant Biol. 57: 431-49.
Sakakibara, et al., Agrobacterium tumefaciens increases cytokinin production in plastids by modifying the biosynthetic pathway in the host plant, (2005) Proc. Natl. Acad. Sci. USA 102(28): 9972-9977.

(Continued)

*Primary Examiner* — Brent Page
(74) *Attorney, Agent, or Firm* — Marcos P. Rivas

(57) ABSTRACT

The present disclosure relates to a new class of cytokinin biosynthetic enzymes, cytokinin synthases, which have two domains: an isopentenyl transfer (IPT)-like domain and a cytokinin nucleotide phosphoribohydrolase (PRH)-like domain. The invention provides compositions and methods for the recombinant production of cytokinin synthase, host cells and transformants that include the cytokinin synthases, as well as compositions and formulations that include the disclosed cytokinin synthase.

27 Claims, 30 Drawing Sheets

(56) References Cited

OTHER PUBLICATIONS

Schardl, et al., Plant-Symbiotic Fungi as Chemical Engineers: Multi-Geneome Analysis of the Clavicipitaceae Reveals Dynamics of Alkaloid Loci, (2013) PLOS Genetics, 9 (2): 1-26.
Schwartz et al., Accurate gene synthesis with tag-directed retrieval of sequence-verfied DNA molecules, (2012) NIH Public Access, Author Manuscript for Nat. Methods 9(9): 913-915 (doi:10.1038/nmeth.2137).
Shardl et al., Plant-Symbiotic Fungi as Chemical Engineers: Multi-Geneome Analysis of Clavicipitaceae Revewal Dynamics of Alkaloid Loci, (2013) PLOS Genetics 9((2): 1-26.
Shürmann et al., De Novo Biosynthesis of Cytokinins by Claviceps Purpurea—Identification of the First Fungal Biosynthesis Gene, (2014) Rhoades Hellas XVI Meeting Jul. 6-10, Abstract No. P233.
Stoll et al., Hormonal changes induced by partial rootzone drying of irrigated grapevine, (2000) Journal of Experimental Botany, 51(350, WE Special Issue): 1627-1634.
Sugawara, et al., Structural insight into the reaction mechanism and evolution of cytokinin biosynthesis, (2008) Proc. Natl. Acad. Sci. USA105(7): 2734-2739.
Takei et al., Identification of Genes Encoding Adenylate Isopentenyltransferase, a Cytokinin Biosynthesis Enzyme in Arabidopsis thaliana, (2001) Journal of Biological Chem 276: 26405-26410.
Tian et al., Advancing high-throughput gene synthesis technology, (2009) Molecular BioSystems 5: 714-722.
United States Environmental Protection Agency Reregistration Eligibility Decision (RED), Cytokinin List D Case 4107 (Dec. 1995) 1-208.

EfCKS.1 cDNA sequence

```
ATGATGCCAACACGAAAGCTCTCCATTGCCATTTTTGGCCCTACCGCTTCTGGAAAGACCAAGCTAGGTGTGACCA
TTGCCAAAGCATATCTAGGCGAGGTCATTTCTATAGACAGCCTGCAGTGCTATAAGCCGGGAGGTATTGCCACGGC
GAAACCTTGTCCGGAGGAGACTCAGGGGGTTCCCCATCATTTGATAGACTACTTGGACGCCGAAGAGGAGCCACAA
GACTTTGTCTCGAGAGCCATCGCCACAATAGACGACATCACCACTCGTAACGGACTTCCAGTTCTCGTCGGTGGGT
CAACATCCCTCATCATTCCTCTGTTGCAGCAAGTTTTCAGCAGAGAGTACGAGGTTCTCATCATTACCCTGGTGCC
CCATCAGTCAAGCTATGGGCGACTCATCGAATCCAGGGGTGGGGAGATGTTGAAGAGGGGCCTGCTGGACGAGCTC
GCCGAGCTGAAGCGCCTCGAGAAAGTACTGCTCGACGGCAAAAGCGATTTCAATAAAGGTGTCTGGAAGACCATAG
GCTATCAGGAGTTTCTCCCTTATCTTCGAGCCGTCGGGAAGGTGAATGGCGTGTCCAATACCTACGAGGATCTATA
CGAGGAGGGACGAGCATCAATGAACGCCAGCACTCTTCGTTACGGCCAGTACCAGCTCGAATGGATACGACACACC
CTGACGCCCTTCATAGACCGGCACAAGGCGGCCACCATCAGCCTCTGTGTCACCGACCAGGCTGCCTGGGCATCTG
ACATAGAGAGACCTGCGATGACAATGGCTGGCGAGTTCTACCATGGCTCTCAGGTGAGGAGACTTCCGTCAAGGAA
TTCTTCGAATAGACGCGTTGTTTGTCTCTTTGGTGGATCGTCTTCTGGCCGCGACGAAAGTCACATCGAGGCAGCC
AAATCTCTCGCCGTCGCCCTGCACCGCCACGAAATCGCACTCGTGTACGGTGGAGGAACTACTGGGATCATGGAG
CAGTCGCGAGCACCCTCGTCGCGCTGTCTGGGCCAGGGGCTGTCCACGGAATCGTCCCCGCCGCTCTTGCTAGATA
CGAAGACGAGCTCGGCGACGGTCGTATCAGCGCAGAATACTCGTCACAGTTTGGCAGGAGAACGATTGTGACAGAC
ATGCACACACGAAAGCGCCTCATGACGCAGGCGGTCCTCGAAGGAGCTCCGGGAAGTGGATTCGTTGCCTTGAGTG
GTGGGTACGGCACCATGGAGGAACTGCTCGAGGTCACGACATGGTACCAACTGGGAATTCATGATCGCCGCGTGAG
CGTCTTCAATGTGAATGGATTCTATGACGGACTGCTCAGCTGGATTGGCCAAGTCGCGCGAGACGGCTTTGTTAGA
CCAAGAGACGCCAACATACTTGGTGTCGCCAACACAGCCGATGAAGTGATTGCTTGTCTTGCGAACCAGCGGCTGG
ATGCGGAGAAGCCCAGTTTGGAGTGGCTCTGA (SEQ ID NO:1)
```

FIGURE 8

>EfCKS.1. *E coli* optimized coding sequence

ATGATGCCGACCCGTAAACTGAGCATTGCAATTTTTGGTCCGACCGCAAGCGGTAAAACCAAACTGGGTG
TTACCATTGCAAAAGCATATCTGGGTGAAGTGATTAGCATTGATAGCCTGCAGTGTTATAAACCGGGTGG
TATTGCAACCGCAAAACCGTGTCCGGAAGAAACCCAGGGTGTTCCGCATCATCTGATTGATTATCTGGAT
GCAGAAGAAGAACCGCAGGATTTTGTTAGCCGTGCAATTGCCACCATTGATGATATTACCACCCGTAATG
GTCTGCCGGTTCTGGTTGGTGGTAGCACCAGCCTGATTATTCCGCTGCTGCAACAGGTTTTTAGCCGTGA
ATATGAAGTGCTCATTATTACCCTGGTGCCGCATCAGAGCAGCTATGGTCGTCTGATTGAAAGCCGTGGT
GGTGAAATGCTGAAACGTGGTCTGCTGGATGAACTGGCAGAACTGAAACGTCTGGAAAAAGTTCTGCTGG
ACGGTAAAAGCGATTTTAACAAAGGTGTGTGGAAAACCATCGGCTATCAAGAATTTCTGCCGTATCTGCG
TGCAGTTGGTAAAGTTAATGGTGTGAGCAATACCTATGAGGATCTGTATGAAGAGGGTCGTGCAAGCATG
AATGCAAGCACCCTGCGTTATGGTCAGTATCAGCTGGAATGGATTCGTCATACCCTGACCCCGTTTATTG
ATCGTCATAAAGCCGCAACCATTAGCCTGTGTGTTACCGATCAGGCCGCATGGGCAAGCGATATTGAACG
TCCGGCAATGACCATGGCAGGCGAATTTTATCATGGTAGCCAGGTTCGTCGTCTGCCGAGCCGTAATAGC
AGTAATCGTCGTGTTGTTTGTCTGTTTGGTGGTTCAAGCAGTGGTCGTGATGAAAGCCATATTGAAGCCG
CAAAAAGCCTGGCAGTTGCACTGCATCGTCATGAAATTGCACTGGTTTATGGTGGTGGTACAACCGGTAT
TATGGGTGCAGTTGCCAGCACCCTGGTTGCACTGAGCGGTCCGGGTGCCGTTCATGGTATTGTTCCGGCA
GCACTGGCACGTTATGAAGATGAGCTGGGTGATGGTCGTATTAGCGCAGAATATAGCAGTCAGTTTGGTC
GTCGTACCATTGTTCGTGATATGCATACCCGCAAACGTCTGATGACCCAGGCAGTTCTGGAAGGTGCACC
GGGTAGCGGTTTTGTTGCACTGTCAGGTGGTTATGGCACCATGGAAGAACTGCTGGAAGTTACCACCTGG
TATCAACTGGGTATTCATGATCGTCGCGTTAGCGTTTTTAATGTGAACGGTTTTATGATGGCCTGCTGA
GCTGGATTGGTCAGGTTGCACGTGATGGTTTTGTTCGTCCGCGTGATGCAAATATTCTGGGTGTTGCAAA
TACCGCAGATGAAGTTATTGCATGTCTGGCAAATCAGCGTCTGGATGCCGAAAAACCGAGCCTGGAATGG
CTGTAA (SEQ ID NO:2)

>EfCKS.1. amino acid sequence

MMPTRKLSIAIFGPTASGKTKLGVTIAKAYLGEVISIDSLQCYKPGGIATAKPCPEETQGVPHHLIDYLD
AEEEPQDFVSRAIATIDDITTRNGLPVLVGGSTSLIIPLLQQVFSREYEVLIITLVPHQSSYGRLIESRG
GEMLKRGLLDELAELKRLEKVLLDGKSDFNKGVWKTIGYQEFLPYLRAVGKVNGVSNTYEDLYEEGRASM
NASTLRYGQYQLEWIRHTLTPFIDRHKAATISLCVTDQAAWASDIERPAMTMAGEFYHGSQVRRLPSRNS
SNRRVVCLFGGSSSGRDESHIEAAKSLAVALHRHEIALVYGGGTTGIMGAVASTLVALSGPGAVHGIVPA
ALARYEDELGDGRISAEYSSQFGRRTIVRDMHTRKRLMTQAVLEGAPGSGFVALSGGYGTMEELLEVTTW
YQLGIHDRRVSVFNVNGFYDGLLSWIGQVARDGFVRPRDANILGVANTADEVIACLANQRLDAEKPSLEW
L (SEQ ID NO:3)

FIGURE 9

>EfCKS.1. *E. coli* optimized coding sequence with N-His-tag

ATGGGTAGCAGCCATCATCATCACCATCATATGATGCCGACCCGTAAACTGAGCATTGCAATTTTTGGTC
CGACCGCAAGCGGTAAAACCAAACTGGGTGTTACCATTGCAAAAGCATATCTGGGTGAAGTGATTAGCAT
TGATAGCCTGCAGTGTTATAAACCGGGTGGTATTGCAACCGCAAAACCGTGTCCGGAAGAAACCCAGGGT
GTTCCGCATCATCTGATTGATTATCTGGATGCAGAAGAAGAACCGCAGGATTTTGTTAGCCGTGCAATTG
CCACCATTGATGATATTACCACCCGTAATGGTCTGCCGGTTCTGGTTGGTGGTAGCACCAGCCTGATTAT
TCCGCTGCTGCAACAGGTTTTTAGCCGTGAATATGAAGTGCTGATTATTACCCTGGTGCCGCATCAGAGC
AGCTATGGTCGTCTGATTGAAAGCCGTGGTGGTGAAATGCTGAAACGTGGTCTGCTGGATGAACTGGCAG
AACTGAAACGTCTGGAAAAAGTTCTGCTGGACGGTAAAAGCGATTTTAACAAAGGTGTGTGGAAAACCAT
CGGCTATCAAGAATTTCTGCCGTATCTGCGTGCAGTTGGTAAAGTTAATGGTGTGAGCAATACCTATGAG
GATCTGTATGAAGAGGGTCGTGCAAGCATGAATGCAAGCACCCTGCGTTATGGTCAGTATCAGCTGGAAT
GGATTCGTCATACCCTGACCCCGTTTATTGATCGTCATAAAGCCGCAACCATTAGCCTGTGTGTTACCGA
TCAGGCCGCATGGGCAAGCGATATTGAACGTCCGGCAATGACCATGGCAGGCGAATTTATCATGGTAGC
CAGGTTCGTCGTCTGCCGAGCCGTAATAGCAGTAATCGTCGTGTTGTTTGTCTGTTTGGTGGTTCAAGCA
GTGGTCGTGATGAAAGCCATATTGAAGCCGCAAAAAGCCTGGCAGTTGCACTGCATCGTCATGAAATTGC
ACTGGTTTATGGTGGTGGTACAACCGGTATTATGGGTGCAGTTGCCAGCACCCTGGTTGCACTGAGCGGT
CCGGGTGCCGTTCATGGTATTGTTCCGGCAGCACTGGCACGTTATGAAGATGAGCTGGGTGATGGTCGTA
TTAGCGCAGAATATAGCAGTCAGTTTGGTCGTCGTACCATTGTTCGTGATATGCATACCCGCAAACGTCT
GATGACCCAGGCAGTTCTGGAAGGTGCACCGGGTAGCGGTTTTGTTGCACTGTCAGGTGGTTATGGCACC
ATGGAAGAACTGCTGGAAGTTACCACCTGGTATCAACTGGGTATTCATGATCGTCGCGTTAGCGTTTTTA
ATGTGAACGGTTTTTATGATGGCCTGCTGAGCTGGATTGGTCAGGTTGCACGTGATGGTTTTGTTCGTCC
GCGTGATGCAAATATTCTGGGTGTTGCAAATACCGCAGATGAAGTTATTGCATGTCTGGCAAATCAGCGT
CTGGATGCCGAAAAACCGAGCCTGGAATGGCTGTAA    (SEQ ID NO:4)

>EfCKS.1 N-His-tagged amino acid sequence

MGSSHHHHHHMMPTRKLSIAIFGPTASGKTKLGVTIAKAYLGEVISIDSLQCYKPGGIATAKPCPEETQG
VPHHLIDYLDAEEEPQDFVSRAIATIDDITTRNGLPVLVGGSTSLIIPLLQQVFSREYEVLIITLVPHQS
SYGRLIESRGGEMLKRGLLDELAELKRLEKVLLDGKSDFNKGVWKTIGYQEFLPYLRAVGKVNGVSNTYE
DLYEEGRASMNASTLRYGQYQLEWIRHTLTPFIDRHKAATISLCVTDQAAWASDIERPAMTMAGEFYHGS
QVRRLPSRNSSNRRVVCLFGGSSSGRDESHIEAAKSLAVALHRHEIALVYGGGTTGIMGAVASTLVALSG
PGAVHGIVPAALARYEDELGDGRISAEYSSQFGRRTIVRDMHTRKRLMTQAVLEGAPGSGFVALSGGYGT
MEELLEVTTWYQLGIHDRRVSVFNVNGFYDGLLSWIGQVARDGFVRPRDANILGVANTADEVIACLANQR
LDAEKPSLEWL    (SEQ ID NO:5)

FIGURE 10

>EfCKS.1 (1-255) E. coli optimized coding sequence with N-His-tag

ATGGGTAGCAGCCATCATCATCACCATCATATGATGCCGACCCGTAAACTGAGCATTGCAATTTTTGGTC
CGACCGCAAGCGGTAAAACCAAACTGGGTGTTACCATTGCAAAAGCATATCTGGGTGAAGTGATTAGCAT
TGATAGCCTGCAGTGTTATAAACCGGGTGGTATTGCAACCGCAAAACCGTGTCCGGAAGAAACCCAGGGT
GTTCCGCATCATCTGATTGATTATCTGGATGCAGAAGAAGAACCGCAGGATTTTGTTAGCCGTGCAATTG
CCACCATTGATGATATTACCACCCGTAATGGTCTGCCGGTTCTGGTTGGTGGTAGCACCAGCCTGATTAT
TCCGCTGCTGCAACAGGTTTTTAGCCGTGAATATGAAGTGCTGATTATTACCCTGGTGCCGCATCAGAGC
AGCTATGGTCGTCTGATTGAAAGCCGTGGTGGTGAAATGCTGAAACGTGGTCTGCTGGATGAACTGGCAG
AACTGAAACGTCTGGAAAAAGTTCTGCTGGACGGTAAAAGCGATTTTAACAAAGGTGTGTGGAAAACCAT
CGGCTATCAAGAATTTCTGCCGTATCTGCGTGCAGTTGGTAAAGTTAATGGTGTGAGCAATACCTATGAG
GATCTGTATGAAGAGGGTCGTGCAAGCATGAATGCAAGCACCCTGCGTTATGGTCAGTATCAGCTGGAAT
GGATTCGTCATACCCTGACCCCGTTTATTGATCGTCATAAAGCCGCAACCATTAGCCTGTGTGTTACCGA
TCAGGCCGCATGGGCAAGCGATATTTAA (SEQ ID NO:6)

>EfCKS.1.(1-255)N-His-tagged amino acid sequence

MGSSHHHHHHMMPTRKLSIAIFGPTASGKTKLGVTIAKAYLGEVISIDSLQCYKPGGIATAKPCPEETQG
VPHHLIDYLDAEEEPQDFVSRAIATIDDITTRNGLPVLVGGSTSLIIPLLQQVFSREYEVLIITLVPHQS
SYGRLIESRGGEMLKRGLLDELAELKRLEKVLLDGKSDFNKGVWKTIGYQEFLPYLRAVGKVNGVSNTYE
DLYEEGRASMNASTLRYGQYQLEWIRHTLTPFIDRHKAATISLCVTDQAAWASDI (SEQ ID NO:7)

FIGURE 11

>AtCKS.1 cDNA sequence

```
ATGTTGAACCGGAAACCCGCCGTCGCCATCCTCGGCCCCACGGCCTCGGGCAAGACGCAGCTCGGCGTGG
CCATCGCCAAGGCCTTCCTCGGCGAGGTCATCTCCGTCGACAGCCTGCAGTGCTACAAACCCGGGGGCAT
CGTCACGGCGCGGCCGCGCCCGGACGAGACGGCCGGCGTGCCGCACCACCTGGTGGGCTACCTCGAGGCC
GACGAGGAGCCCCACGACTACGTCGCGCAGGCGGCCTCCATCATGGACGACATGACGGCCCGCGACGGGC
TCCCCGTCCTCGTCGGCGGCTCCACCTCCCTCACCCTCCCGCTCCTGCAGGAGGTCTTTGCCCGCGACTA
CGACGTGCTGGCCGTCACGCTGGTGCCCCACCGCTCGACCTACCAGCGGCTCGTCGAGGCACGCGCCGAC
CAGATGCTCGAGAGGGGCCTCCTGGGCGAGCTGGCCGAGCTGAAGCGCCTCGAGAAGACGCTGCTGCATG
GCAAGCGCGACTTTGGCAAGGGCGTCTGGAAGGCCATCGGGTACCAGGAGCTCTACCCCTATCTTCAGGC
CGCCGCCGCCGGCGGCCTGGCGCCCATGAACGGCGCGGGCTCCGGCGCCGCCGCCGACTGCGAGCGTCTG
CGCGACCAGGGATGGGCCGAGATGAGCGCCAACACGCTGCAGTACGGCCAGTACCAGCTCGAATGGATGC
GCCACACCCTGACGCCCTTCTGCACCGGCACAAGGCCGTCGCCATCAGCCTCTGCGTCACGGACAAGGC
CTCGTGGGAGGCCGAAGTCCTCGGCCGGCCATGACCATGACGGGGGAGTTCTGCCACGGGTCTCGCCTG
ACGAGGCTTCCGCCGAGGGGGGCCCTGGTGAGGCGGGTTGTCTGTCTCTTTGGCGGATCCTCCTCGGGCC
ACACGCCCGCCCACGTCGAGGCCGCCAAGTCCCTCGCCGTCGCCCTCCACCTCCACGACGTGACGCTCGT
CTACGGCGGCGGCACAACCGGCATCATGGGCGCCGTCGCGAGCACCCTCGTCGCGCTCTCGGGCCCCAGC
GCCGTCCATGGCATCGTCCCCGCCGCGCTCGCCCGGTACGAGGACGAGCGCCGCGGCGGCACCGGCACCG
GGCGCATCAACCAAGACTACGCCTGGCGCTTCGGCCGCCGCACCGTCGTCCGCGACATGCACACGCGGAA
GCGCCTCATGACGCAGATGGTGCTCGACGGCGCCCCGGCAGCGGCTTCGTCGCCCTCAGCGGCGGCTAC
GGCACCATGGAGGAGCTCCTCGAGGCCACGACCTGGCACCAGCTCGGCATCCACCACCGGCCCGTCACCG
TCTTCAACGTCGACGGCTTCTACGACGGGCTGCTCGACTGGGTCCGCCACGTCGTCCGCGGCGGCTTCGT
CGGCCCCAAGCACGCCGACATCATCGGCGTCGCCCACTCCGCCGACGAGGTCATTTCTTCCCTGGCGCGT
CCGGGCCTGCAGGACGGGCCGCTGCCGGACAAGAAGCAACAGCGGCTGGAGTGGCTGTAG
(SEQ ID NO:8)
```

>AtCKS.1 amino acid sequence

```
MLNRKPAVAILGPTASGKTQLGVAIAKAFLGEVISVDSLQCYKPGGIVTARPRPDETAGVPHHLVGYLEA
DEEPHDYVAQAASIMDDMTARDGLPVLVGGSTSLTLPLLQEVFARDYDVLAVTLVPHRSTYQRLVEARAD
QMLERGLLGELAELKRLEKTLLHGKRDFGKGVWKAIGYQELYPYLQAAAAGGLAPMNGAGSGAAADCERL
RDQGWAEMSANTLQYGQYQLEWMRHTLTPFLHRHKAVAISLCVTDKASWEAEVLGPAMTMTGEFCHGSRL
TRLPPRGALVRRVVCLFGGSSSGHTPAHVEAAKSLAVALHLHDVTLVYGGGTTGIMGAVASTLVALSGPS
AVHGIVPAALARYEDERRGGTGTGRINQDYAWRFGRRTVVRDMHTRKRLMTQMVLDGAPGSGFVALSGGY
GTMEELLEATTWHQLGIHHRPVTVFNVDGFYDGLLDWVRHVVRGGFVGPKHADIIGVAHSADEVISSLAR
PGLQDGPLPDKKQQRLEWL  (SEQ ID NO:9)
```

FIGURE 12

>AtCKS.1 E. coli optimized coding sequence with N-His-tag

ATGGGTAGCAGCCATCATCATCACCATCATATGCTGAATCGTAAACCGGCAGTTGCAATTCTGGGTCCGA
CCGCAAGCGGTAAAACACAGCTGGGTGTTGCAATTGCCAAAGCATTTCTGGGTGAAGTTATTAGCGTTGA
TAGCCTGCAGTGTTATAAACCGGGTGGTATTGTTACCGCACGTCCGCGTCCGGATGAAACCGCAGGCGTT
CCGCATCATCTGGTTGGTTATCTGGAAGCAGATGAAGAACCGCATGATTATGTTGCACAGGCAGCAAGCA
TTATGGATGATATGACCGCACGTGATGGTCTGCCGGTTCTGGTGGGTGGTAGCACCAGCCTGACCCTGCC
GCTGCTGCAAGAAGTTTTTGCACGCGATTATGATGTTCTGGCAGTTACCCTGGTGCCGCATCGTAGCACC
TATCAGCGTCTGGTTGAAGCACGTGCAGATCAGATGCTGGAACGTGGTCTGCTGGGTGAACTGGCAGAAC
TGAAACGTCTGGAAAAAACCCTGCTGCATGGTAAACGTGATTTTGGTAAAGGTGTTTGGAAAGCCATTGG
CTATCAAGAACTGTATCCGTATCTGCAGGCAGCAGCAGCCGGTGGTCTGGCACCGATGAATGGTGCAGGT
AGCGGTGCAGCCGCAGATTGTGAACGTCTGCGTGATCAGGGTTGGGCAGAAATGAGCGCAAATACCCTGC
AGTATGGTCAGTATCAGCTGGAATGGATGCGTCATACCCTGACCCCGTTTCTGCATCGTCATAAAGCAGT
TGCCATTAGCCTGTGTGTTACCGATAAAGCAAGCTGGGAAGCAGAAGTGCTGGGTCCGGCAATGACCATG
ACCGGTGAATTTTGTCATGGTAGCCGTCTGACCCGTCTGCCTCCGCGTGGTGCACTGGTTCGTCGTGTTG
TTTGTCTGTTTGGTGGTAGCTCAAGCGGTCATACACCGGCACATGTTGAAGCAGCAAAAAGCCTGGCCGT
TGCACTGCATCTGCATGATGTGACCCTGGTTTATGGTGGTGGTACAACCGGTATTATGGGTGCCGTTGCA
AGCACCCTGGTTGCACTGAGCGGTCCGAGCGCAGTTCATGGCATTGTTCCGGCAGCACTGGCACGTTATG
AAGATAACGTCGTGGTGGCACCGGCACCGGTCGTATTAATCAGGATTATGCATGGCGTTTTGGTCGTCG
TACCGTTGTTCGTGATATGCATACCCGTAAACGTCTGATGACCCAGATGGTTCTGGATGGTGCACCGGGT
AGCGGTTTTGTTGCACTGTCAGGTGGTTATGGCACCATGGAAGAACTGCTGGAAGCAACCACCTGGCATC
AGCTGGGTATTCATCATCGTCCGGTTACCGTTTTTAATGTGGATGGTTTTTATGATGGCCTGCTGGATTG
GGTTCGTCATGTGGTTCGTGGTGGTTTTGTGGGTCCGAAACATGCAGATATTATTGGTGTTGCACATAGT
GCCGATGAAGTGATTAGCAGTCTGGCACGTCCGGGTCTGCAGGATGGTCCGCTGCCGGATAAAAAACAGC
AGCGCCTGGAATGGCTGTAA (SEQ ID NO:10)

>AtCKS.1 N-His-tagged amino acid sequence

MGSSHHHHHHMLNRKPAVAILGPTASGKTQLGVAIAKAFLGEVISVDSLQCYKPGGIVTARPRPDETAGV
PHHLVGYLEADEEPHDYVAQAASIMDDMTARDGLPVLVGGSTSLTLPLLQEVFARDYDVLAVTLVPHRST
YQRLVEARADQMLERGLLGELAELKRLEKTLLHGKRDFGKGVWKAIGYQELYPYLQAAAAGGLAPMNGAG
SGAAADCERLRDQGWAEMSANTLQYGQYQLEWMRHTLTPFLHRHKAVAISLCVTDKASWEAEVLGPAMTM
TGEFCHGSRLTRLPPRGALVRRVVCLFGGSSSGHIPAHVEAAKSLAVALHLHDVTLVYGGGTTGIMGAVA
STLVALSGPSAVHGIVPAALARYEDERRGGTGTGRINQDYAWRFGRRTVVRDMHTRKRLMTQMVLDGAPG
SGFVALSGGYGTMEELLEATTWHQLGIHHRPVTVFNVDGFYDGLLDWVRHVVRGGFVGPKHADIIGVAHS
ADEVISSLARPGLQDGPLPDKKQQRLEWL (SEQ ID NO:11)

FIGURE 13

> BoCKS cDNA sequence

ATGTTGGCAAACCGAAAACTCTTCGTTGCCATTCTTGGTCCCACCGCTTCCGGAAAGACCAAGCTGGGAG
TAGCCATTGCCAAGGCATTCCAGGGCGAGGTAGTCTCCGTAGACAGTTTACAGTGTTACAAGCCAGGAAC
AATCATCACTGCAAAACCTCTCCCAGAAGAGATTGAGGGAATCCCCCATCACCTAATAGACTACCTAGAA
GCCGAGGAGGAGCCACACGACTATACCGACAGAGCTATTGCGGCAATAGACAACATTACCGCCCGCAACA
GGCTGCCAATCCTCGTGGGCGGGTCAACATCTCTCACTATGCCTCTCCTGCGGGAAGTGTTTCATGCGCA
GTACAAAGTCCTGGCCATTAGTCTGGTGCCGCATCATACGGTCTACCAACAATTAATCGAGGACAGAGGC
GAGGATATGCTCCGCAGGGGCCTATTAAACGAGCTCGTCGAGCTGCAACGCCTTGAAAAAGTCCTCCTTA
ATGGCAAATGCGACTTCAAGAAAGGAATCTGGAAAGCAATCGGGTACCAAGAATTCTACCCGTATCTCCA
GGCAGTGGGGAAGTTAAACGGGGCATCCAAGACCAATCCTGGGGATTTATACAAAAAGGGCCGAGCCCTG
CTGTTTGCCAATACACTACAATATGGACTGGGCCAGCTCGAGTGGATGCGACACACCCTGGCCCCTTTC
TGCACCAACACAAGGCAGTTACCATGAGCCTTAGTGTTACGGAGAAGGCCTCCTGGATACCAGACGTGCA
AGGGCCTGCTATGTCTATGATCAGCGAGTTCTATCATGATTCTCAGGTGACTAAGAGTCTCTTCCGAAAG
AGGTCTTTGAAGAAGCGTGTCGTCTGCCTTTTTGGCGGGTCGTCTGCTGGCAACGATCCAACTCACATCG
AGGCAGCCAAATCTCTAGCTGCCGCCCTGCATCACCACGACATCTCGCTTGTGTACGGTGGAGGAACGAC
TGGGATCATGGGTCAAGTCGCGAGTTCCCTTGTCGAGCTGTCCGGGCCAAACGCTGTCAAGGGATTCATT
CCTGCTGCTCTCGCCGGGCACGAAGAGGAGCTCGGGGACGACGGTACTGTGATGGGCGGGGAGTACTTGT
CTCGGTTTGGAAGGAGAACCATTGTGAAAGATATGCACACACGAAAGCGCTTCATGATCCAGAATGTACT
TCAAGGAGCGCCCGGGAGTGGATTCGTCGCGCTGAGCGGCGGCTACGGCACTTTAGAGGAACTGCTCGAG
ATCACGACATGGTCTCAGCTGGGCATACACGATTGCGTGGTTGTCGTTTTTAGCGTTGACGGCTTCTACG
ATGGTCTGCTCGACTGGATTGAGCAGGTAGCTCGACGTGGCTTCATCAGCACGACACATGCCAACATAGT
CCGCGTCGCTAAGACGGCAGACAAGGTGATTGCATGTCTTTCGGATTGTCGGATTCAACCGAGGAGACAC
GTGTTAGAGTGGCTCTAG (SEQ ID NO:12)

> BoCKS amino acid sequence

MLANRKLFVAILGPTASGKTKLGVAIAKAFQGEVVSVDSLQCYKPGTIITAKPLPEEIEGIPHHLIDYLE
AEEEPHDYTDRAIAAIDNITARNRLPILVGGSTSLTMPLLREVFHAQYKVLAISLVPHHTVYQQLIEDRG
EDMLRRGLLNELVELQRLEKVLLNGKCDFKKGIWKAIGYQEFYPYLQAVGKLNGASKTNPGDLYKKGRAL
LFANTLQYGLGQLEWMRHTLAPFLHQHKAVTMSLSVTEKASWIPDVQGPAMSMISEFYHDSQVTKSLFRK
RSLKKRVVCLFGGSSAGNDPTHIEAAKSLAAALHHHDISLVYGGGTTGIMGQVASSLVELSGPNAVKGFI
PAALAGHEEELGDDGTVMGGEYLSRFGRRTIVKDMHTRKRFMIQNVLQGAPGSGFVALSGGYGTLEELLE
ITTWSQLGIHDCVVVVFSVDGFYDGLLDWIEQVARRGFISTTHANIVRVAKTADKVIACLSDCRIQPRRH
VLEWL (SEQ ID NO:13)

FIGURE 14

>BoCKS.1. *E. coli* optimized coding sequence with N-His-tag

ATGGGTAGCAGCCATCATCATCACCATCATATGCTGGCAAATCGTAAACTGTTTGTTGCAATTCTGGGTC
CGACCGCAAGCGGTAAAACCAAACTGGGTGTTGCCATTGCAAAAGCATTTCAGGGTGAAGTTGTTAGCGT
TGATAGCCTGCAGTGTTATAAACCGGGTACAATTATTACCGCAAAACCGCTGCCGGAAGAAATTGAAGGT
ATTCCGCATCATCTGATCGATTATCTGGAAGCCGAAGAAGAACCGCACGATTATACCGATCGTGCAATCG
CAGCAATTGATAACATTACCGCACGTAATCGTCTGCCGATTCTGGTTGGTGGTAGCACCAGCCTGACCAT
GCCGCTGCTGCGTGAAGTTTTTCATGCACAGTATAAAGTTCTGGCCATTAGCCTGGTGCCGCATCATACC
GTTTATCAGCAGCTGATTGAAGATCGTGGTGAAGATATGCTGCGTCGTGGTCTGCTGAATGAACTGGTTG
AACTGCAGCGTCTGGAAAAAGTTCTGCTGAACGGTAAATGCGATTTCAAAAAAGGTATCTGGAAAGCCAT
CGGCTACCAAGAATTTTATCCGTATCTGCAGGCAGTTGGCAAACTGAATGGTGCAAGCAAAACCAATCCG
GGTGATCTGTACAAAAAAGGCCGTGCACTGCTGTTTGCAAATACCCTGCAGTATGGTCTGGGTCAGCTGG
AATGGATGCGTCATACCCTGGCACCGTTTCTGCATCAGCATAAAGCAGTTACCATGAGCCTGAGCGTTAC
CGAAAAAGCAAGCTGGATTCCGGATGTTCAGGGTCCGGCAATGAGCATGATTAGCGAATTTTACCATGAT
AGCCAGGTTACCAAAAGCCTGTTTCGTAAACGTAGCCTGAAAAAACGTGTTGTTTGTCTGTTTGGTGGTT
CAAGCGCAGGTAATGATCCGACCCATATTGAAGCAGCAAAAAGCCTGGCAGCAGCACTGCATCATCATGA
TATTAGTCTGGTTTATGGTGGTGGTACAACCGGTATTATGGGTCAGGTTGCAAGCAGCCTGGTGGAACTG
AGCGGTCCGAATGCAGTTAAAGGTTTTATTCCTGCAGCACTGGCAGGTCATGAAGAGGAACTGGGAGATG
ATGGTACAGTTATGGGTGGTGAATATCTGAGCCGTTTTGGTCGTCGTACCATTGTTAAAGATATGCATAC
CCGTAAACGCTTTATGATTCAGAATGTTCTGCAGGGTGCACCGGGTTCAGGTTTTGTTGCCCTGAGCGGT
GGTTATGGCACCCTGGAAGAACTGCTGGAAATTACCACCTGGTCACAGCTGGGTATTCATGATTGCGTTG
TTGTTGTTTTTAGCGTGGATGGTTTTTATGATGGCCTGCTGGATTGGATTGAACAGGTTGCACGTCGTGG
TTTTATTAGTACCACCCATGCAAATATTGTTCGTGTTGCAAAAACCGCAGATAAAGTTATTGCATGTCTG
AGCGATTGTCGTATTCAGCCTCGTCGTCATGTTCTGGAATGGCTGTAA (SEQ ID NO:14)

>BoCKS.1. N-His-tagged amino acid sequence

MGSSHHHHHHMLANRKLFVAILGPTASGKTKLGVAIAKAFQGEVVSVDSLQCYKPGTIITAKPLPEEIEG
IPHHLIDYLEAEEEPHDYTDRAIAAIDNITARNRLPILVGGSTSLTMPLLREVFHAQYKVLAISLVPHHT
VYQQLIEDRGEDMLRRGLLNELVELQRLEKVLLNGKCDFKKGIWKAIGYQEFYPYLQAVGKLNGASKTNP
GDLYKKGRALLFANTLQYGLGQLEWMRHTLAPFLHQHKAVTMSLSVTEKASWIPDVQGPAMSMISEFYHD
SQVTKSLFRKRSLKKRVVCLFGGSSAGNDPTHIEAAKSLAAALHHHDISLVYGGGTTGIMGQVASSLVEL
SGPNAVKGFIPAALAGHEEELGDGTVMGGEYLSRFGRRTIVKDMHTRKRFMIQNVLQGAPGSGFVALSG
GYGTLEELLEITTWSQLGIHDCVVVVFSVDGFYDGLLDWIEQVARRGFISTTHANIVRVAKTADKVIACL
SDCRIQPRRHVLEWL (SEQ ID NO:15)

FIGURE 15

>IrCKS.1 cDNA sequence

ATGAAATCTGTTCGCAAGCTTGCGATTGGTATTTTCGGTCCTACCGCTTCGGGGAAGACTAAGCTGGGCA
TAGCCATCGCCAGGGCGTTTCTTGGCGAAGTTGTCTCGGTCGACAGCCTGCAATGTTACAAGCCAGGGAC
CATCACTACAGCCAAACCTGAGCCTGAAGAGACCCAAGAAGTGCCCCACCATTTGATTGATTTCCTTGAA
GCTGACGAGGAGCCTGATGATTTTGTGGCGTTGGCTCTCGCCAAAATGGAAGAGATCACTCGTCGCAAAA
GGCTCCCCATCCTTGTCGGAGGATCAACATCCCTTACTATTCCCCTCTTACTTGAAGCCTTCAACAGCAA
GTACCAAATGCTTGCAATTACATTGATGCCACATCAGTCAACTTACCAGTCACTCATTCAATCCAGGGGT
GAAGAGATGCTGGAAAGGGGGCTCTTGGATGAGCTCGCCGGACTTCAAGCTCTTGAGCAGGTCTTGCTCA
ATGGCGAATCAAACTTCCGCAAAGGAATTTGGAAGGCAATCGGATACCAGGAGTTCCATTCATACCTTCA
AGCTGACCAGTCCGTTGGAGGGCGTGAGCATTTGTTCCAAAATGGACTGGCCTTGACGGCCGCCAACACT
TTACAATACGGCTTTTACCAGCTTGAATGGATACGACACACCCTCACTCCATTCTTACACCAAGAGAAAG
CCACTTGTATCAGCCTTTCCGTCACTGACAAAGCATCCTGGCCAATGGAAGTGGAGGGGCTGGCCATTTC
CATGGCTAGCGATTCTTGTACGGTTCTCAAGTGATTGGATTTCCACCCAAGGAATCATCCGAGTCTCGT
GTGGTCTGTCTCTTTGGTGGATCGTCTTCTGGCAACAATCCCGTGCACATCGAGGCAGCCAAGTCGCTCG
CTGTCGTCCTACACCAGCACGATATAAAGCTAGTCTACGGCGGCGGAACCACTGGAATCATGGGAACCAT
CGCAAGCACTCTTGTGGAACTGTCTGGACCTAGCGCTGTTCACGGCATCGTACCTGCTGCCCTTGCCAGG
TACGAAGAAAAGATGACAAACGAGCACATCGAACAATCCTACTCCTCAAGTTCGGTATGCGGACTATTG
TGAGGGATATGCACACTCGCAAGCGACTCATGATCCAAAGCGTCCTTGATGGGACTCCGGGGAGCGGTTT
CGTCGCTTTGAGTGGCGGCTATGGTACAATGGAGGAGCTGCTTGAGATAACTACGTGGTACCAGTTGGGC
ATCCACAAATGCAGTGTCTGTGTTTTCAGTGTGAATGGATTCTTTGATGGTCTGGTCACTTGGATCGGTC
AAGTTGCACAGGACGGGTTCATAGGCCCAATGGACTCCGACATAATTCAAGTCGCAAGATCAGCGGATGA
AGTTGTTGAGTGTCTTGCTGATCTCCACCGGTACTCAAGGAATGGAGAACTACAGTGGCTTTAG
(SEQ ID NO:16)

>IrCKS.1 amino acid sequence

MKSVRKLAIGIFGPTASGKTKLGIAIARAFLGEVVSVDSLQCYKPGTITTAKPEPEETQEVPHHLIDFLE
ADEEPDDFVALALAKMEEITRRKRLPILVGGSTSLTIPLLLEAFNSKYQMLAITLMPHQSTYQSLIQSRG
EEMLERGLLDELAGLQALEQVLLNGESNFRKGIWKAIGYQEFHSYLQADQSVGGREHLFQNGLALTAANT
LQYGFYQLEWIRHTLTPFLHQEKATCISLSVTDKASWPMEVEGLAISMASDFLYGSQVIGFPPKESSESR
VVCLFGGSSSGNNPVHIEAAKSLAVVLHQHDIKLVYGGGTTGIMGTIASTLVELSGPSAVHGIVPAALAR
YEEKMTNEHIEQSYSSKFGMRTIVRDMHTRKRLMIQSVLDGTPGSGFVALSGGYGTMEELLEITTWYQLG
IHKCSVCVFSVNGFFDGLVTWIGQVAQDGFIGPMDSDIIQVARSADEVVECLADLHRYSRNGELEWL
(SEQ ID NO:17)

FIGURE 16

>IrCKS.1 *E. coli* optimized coding sequence with N-His-tag

ATGGGTAGCAGCCATCATCATCACCATCATATGAAAAGCGTTCGTAAACTGGCCATTGGTATTTTTGGTC
CGACCGCAAGCGGTAAAACCAAACTGGGTATTGCAATTGCCCGTGCATTTCTGGGTGAAGTTGTTAGCGT
TGATAGCCTGCAGTGTTATAAACCGGGTACAATTACCACCGCAAAACCGGAACCGGAAGAAACCCAAGAA
GTTCCGCATCATCTGATTGATTTTCTGGAAGCAGATGAAGAACCGGATGATTTTGTTGCACTGGCACTGG
CAAAAATGGAAGAAATTACCCGTCGTAAACGTCTGCCGATTCTGGTTGGTGGTAGCACCAGCCTGACCAT
TCCGCTGCTGGAAGCATTTAATAGCAAATATCAGATGCTGGCCATTACCCTGATGCCTCATCAGAGC
ACCTATCAGAGCCTGATTCAGAGCCGTGGTGAAGAAATGCTGGAACGTGGTCTGCTGGATGAACTGGCAG
GTCTGCAGGCACTGGAACAGGTTCTGCTGAATGGTGAAAGCAATTTTCGTAAAGGTATCTGGAAAGCCAT
CGGCTATCAAGAATTTCATAGCTATCTGCAGGCCGATCAGAGCGTTGGTGGTCGTGAACACCTGTTTCAG
AATGGTCTGGCACTGACCGCAGCAAATACCCTGCAGTATGGTTTTTATCAGCTGGAATGGATTCGTCATA
CCCTGACCCCGTTTCTGCATCAAGAAAAAGCAACCTGTATTAGCCTGAGCGTTACCGATAAAGCAAGCTG
GCCGATGGAAGTTGAAGGTCTGGCAATTAGCATGGCAAGCGATTTTCTGTATGGTAGCCAGGTTATTGGT
TTTCCGCCTAAAGAAAGCAGCGAAAGCCGTGTTGTTTGTCTGTTTGGTGGTTCAAGCAGCGGTAATAATC
CGGTTCATATTGAAGCAGCAAAAAGCCTGGCAGTTGTGCTGCATCAGCATGATATTAAACTGGTTTATGG
TGGTGGTACGACCGGTATTATGGGCACCATTGCAAGCACCCTGGTTGAACTGAGCGGTCCGAGCGCAGTT
CATGGTATTGTTCCGGCAGCCCTGGCACGTTATGAAGAAAAAATGACGAACGAACATATCGAGCAGAGCT
ATAGCAGCAAATTTGGTATGCGTACCATTGTGCGTGATATGCATACCCGTAAACGCCTGATGATTCAGTC
AGTTCTGGATGGTACACCGGGTAGCGGTTTTGTTGCCCTGAGCGGTGGTTATGGCACCATGGAAGAACTG
CTGGAAATTACCACCTGGTATCAGCTGGGTATTCATAAATGTAGCGTTTGCGTTTTTAGCGTGAACGGTT
TTTTTGATGGTCTGGTTACCTGGATTGGTCAGGTTGCACAGGATGGTTTTATCGGTCCGATGGATAGCGA
TATTATTCAGGTTGCCCGTAGTGCCGATGAAGTGGTTGAATGCCTGGCCGATCTGCATCGTTATAGCCGT
AATGGTGAACTGGAATGGCTGTAA (SEQ ID NO:18)

>IrCKS.1 N-His-tagged amino acid sequence

MGSSHHHHHHMKSVRKLAIGIFGPTASGKTKLGIAIARAFLGEVVSVDSLQCYKPGTITTAKPEPEETQE
VPHHLIDFLEADEEPDDFVALALAKMEEITRRKRLPILVGGSTSLTIPLLEAFNSKYQMLAITLMPHQS
TYQSLIQSRGEEMLERGLLDELAGLQALEQVLLNGESNFRKGIWKAIGYQEFHSYLQADQSVGGREHLFQ
NGLALTAANTLQYGFYQLEWIRHTLTPFLHQEKATCISLSVTDKASWPMEVEGLAISMASDFLYGSQVIG
FPPKESSESRVVCLFGGSSSGNNPVHIEAAKSLAVVLHQHDIKLVYGGGTTGIMGTIASTLVELSGPSAV
HGIVPAALARYEEKMTNEHIEQSYSSKFGMRTIVRDMHTRKRLMIQSVLDGTPGSGFVALSGGYGTMEEL
LEITTWYQLGIHKCSVCVFSVNGFFDGLVTWIGQVAQDGFIGPMDSDIIQVARSADEVVECLADLHRYSR
NGELEWL (SEQ ID NO:19)

FIGURE 17

>AhCKS.1 cDNA

ATGCTAGCAAGCCGAAATCTCTGCGTTGCCATTCTTGGCCCCACCGCTTCTGGGAAGACCAAGCTTGGTG
TGGCCCGTTGCCAAAGCCTTCCTAGGCGAGGTCATCTCTGTAGACAGCTTACAATGTTACAAGCCGGGAAC
GATCATCACAGCAAAACCAGTTCCAGAAGAGACTGAAGGAATCCCCCATCACCTAATAGACTACCTAGAA
GCCGAGGAGGAACCACACGACTATGTCGAAAGAGCCACCGCCACAATAGATAACATTACCACTCGCAACA
AGCTCCCAATCCTCGTGGGAGGGTCAACATCCCTCACCATGCCTCTCTTGCAGGAAGTTTTCAATGCACA
ATACGAGGTTCTCGTTATAACTCTAGTACCGCATCATTCGGTCTACCAACAACTCACCGACTCTAGGGGT
GAGGAAATGCTACGCAATGGCCTATTAAACGAGCTCATCGAGCTGCAACGCCTTGAAAAAGTTCTCCTTA
ATGGCCAAAGCGACTTCACGAGAGGTATCTGGAAAGCGATCGGGTACCAAGAATTCTACCCGTATCTTCA
AGCTGTGGGGAAGTTGAATGAGGCATCGAAGAACAACCCTGGACATTTATATAAAAAGGGCAGAGCATTG
ATGTTCGCCAACACTTTACAATATGGTCAGAGCCAGCTCGAGTGGATGCGGCACACCCTGGCCCCCTTCC
TACACCAACACAAGGCTGCTACTATTAGCCTCAATGTCACCGACAAGGCGTCCTGGATATCAGACGTGCA
AAGACCTGCTCTGACTATGGTCAGCGAGTTCTATCACAGTTCTCAGGTGACGAAGAGCCTTTCACTAAGG
CGGTCTTCGAAGAAGCGTGTTGTTTGCCTCTTTGGCGGATCGTCTTGCGGCAATGACCCAACTCACATTG
AGGCAGCCAAATCTCTAGCTGTGGCCCTACACCACCACGATATCTCACTTGTGTACGGTGGAGGAACCAC
TGGGATCATGGGCCAAGTCGCGAGCTCCCTCGTTGCGCTGTCCGGGCCAAACGCTGTCCAAGGAATCATC
CCTGCTGCTCTTGCCAGGTACGAAGAGGAACTCGGAGATGACGGTCCCATCATCGATGGGGAGTACATGT
CTCGGTTTGGAAAGAGAACGATAGTAAGAGATATGCGCACGCGAAAGCGCCTCATGATCCAGAATGTTCT
CCAAGGGGCGCCCGGGAGTGGATTTGTCGTAATGAGTGGCGGCTATGGGACGTTAGAGGAATTACTCGAG
ATGACGACATGGTCACAACTGGGACTACATGATTGCGTCATTACCGTGTTTAGTGTCGATGGCTTCTACG
ACGGTCTGCTCGATTGGATCGACCAAGTGGTACGACGCGGCTTCATCAGTACTAAACACGCCAACATAGT
CCGGGTCGCAAAGTCGGCAGACAAAGTGATCGCATGTCTCGCGGATGGGCGGCTTCATCCGCGGAGACAT
GTGCTGGAGTGGCTCTAG (SEQ ID NO:20)

>AhCKS.1 amino acid sequence

MLASRNLCVAILGPTASGKTKLGVAVAKAFLGEVISVDSLQCYKPGTIITAKPVPEETEGIPHHLIDYLE
AEEEPHDYVERATATIDNITTRNKLPILVGGSTSLTMPLLQEVFNAQYEVLVITLVPHHSVYQQLTDSRG
EEMLRNGLLNELIELQRLEKVLLNGQSDFTRGIWKAIGYQEFYPYLQAVGKLNEASKNNPGHLYKKGRAL
MFANTLQYGQSQLEWMRHTLAPFLHQHKAATISLNVIDKASWISDVQRPALTMVSEFYHSSQVTKSLSLR
RSSKKRVVCLFGGSSCGNDPTHIEAAKSLAVALHHHDISLVYGGGTTGIMGQVASSLVALSGPNAVQGII
PAALARYEEELGDDGPIIDGEYMSRFGKRTIVRDMRTRKRLMIQNVLQGAPGSGFVVMSGGYGTLEELLE
MTTWSQLGLHDCVITVFSVDGFYDGLLDWIDQVVRRGFISTKHANIVRVAKSADKVIACLADGRLHPRRH
VLEWL (SEQ ID NO:21)

FIGURE 18

>AhCKS.1 E. coli optimized, N-His-tagged

ATGGGTAGCAGCCATCATCATCACCATCATATGCTGGCAAGCCGTAATCTGTGTGTTGCAATTCTGGGTC
CGACCGCAAGCGGTAAAACCAAACTGGGTGTTGCAGTTGCAAAAGCATTTCTGGGTGAAGTTATTAGCGT
TGATAGCCTGCAGTGTTATAAACCGGGTACAATTATTACCGCAAAACCGGTTCCGGAAGAAACCGAAGGT
ATTCCGCATCATCTGATTGATTATCTGGAAGCCGAAGAGGAACCGCATGATTATGTTGAACGTGCAACCG
CAACCATTGATAACATTACCACCCGTAATAAACTGCCGATTCTGGTTGGTGGTAGCACCAGCCTGACCAT
GCCGCTGCTGCAAGAAGTTTTTAACGCACAGTATGAAGTTCTGGTTATTACCCTGGTGCCGCATCATAGC
GTTTATCAGCAGCTGACCGATAGCCGTGGTGAAGAAATGCTGCGTAATGGTCTGCTGAATGAACTGATTG
AACTGCAGCGTCTGGAAAAAGTTCTGCTGAACGGTCAGAGCGATTTTACCCGTGGTATTTGGAAAGCAAT
TGGCTACCAAGAATTCTATCCGTATCTGCAGGCAGTTGGTAAACTGAATGAAGCCAGCAAAAACAATCCG
GGTCATCTGTACAAAAAAGGTCGTGCACTGATGTTTGCAAATACCCTGCAGTATGGTCAGAGCCAGCTGG
AATGGATGCGTCATACCCTGGCACCGTTTCTGCATCAGCATAAAGCAGCAACCATTAGCCTGAATGTTAC
CGATAAAGCAAGCTGGATTAGTGATGTTCAGCGTCCGGCACTGACCATGGTTAGCGAATTTTATCATAGC
AGCCAGGTTACCAAAAGCCTGAGCCTGCGTCGTAGCAGCAAAAAACGTGTTGTTTGTCTGTTTGGTGGTT
CAAGCTGTGGTAATGATCCGACCCATATTGAAGCAGCGAAAAGCCTGGCAGTTGCACTGCATCATCATGA
TATTAGCCTGGTTTATGGTGGTGGTACAACCGGTATTATGGGTCAGGTTGCAAGCAGCCTGGTTGCACTG
AGCGGTCCGAATGCAGTTCAGGGTATTATTCCGGCAGCACTGGCACGTTATGAAGAGGAACTGGGTGATG
ATGGTCCGATTATTGATGGTGAATATATGAGCCGTTTTGGCAAACGTACCATTGTTCGTGATATGCGTAC
CCGTAAACGTCTGATGATTCAGAATGTTCTGCAGGGTGCACCGGGTAGCGGTTTTGTTGTTATGAGCGGT
GGTTATGGCACCCTGGAAGAACTGCTGGAAATGACCACCTGGTCACAGCTGGGTCTGCATGATTGTGTTA
TTACCGTTTTTAGCGTGGATGGCTTTTATGATGGCCTGCTGGATTGGATTGATCAGGTTGTTCGTCGTGG
TTTTATTAGCACCAAACATGCCAATATTGTGCGTGTTGCAAAAAGCGCAGATAAAGTTATTGCATGTCTG
GCAGATGGTCGTCTGCATCCGCGTCGTCATGTTCTGGAATGGCTGTAA (SEQ ID NO:22)

>AhCKS.1 N-his-tagged amino acid sequence

MGSSHHHHHHMLASRNLCVAILGPTASGKTKLGVAVAKAFLGEVISVDSLQCYKPGTIITAKPVPEETEG
IPHHLIDYLEAEEEPHDYVERATATIDNITTRNKLPILVGGSTSLTMPLLQEVFNAQYEVLVITLVPHHS
VYQQLTDSRGEEMLRNGLLNELIELQRLEKVLLNGQSDFTRGIWKAIGYQEFYPYLQAVGKLNEASKNNP
GHLYKKGRALMFANTLQYGQSQLEWMRHTLAPFLHQHKAATISLNVTDKASWISDVQRPALTMVSEFYHS
SQVTKSLSLRRSSKKRVVCLFGGSSCGNDPTHIEAAKSLAVALHHHDISLVYGGGTTGIMGQVASSLVAL
SGPNAVQGIIPAALARYEEELGDDGPIIDGEYMSRFGKRTIVRDMRTRKRLMIQNVLQGAPGSGFVVMSG
GYGTLEELLEMTTWSQLGLHDCVITVFSVDGFYDGLLDWIDQVVRRGFISTKHANIVRVAKSADKVIACL
ADGRLHPRRHVLEWL (SEQ ID NO:23)

FIGURE 19

>FfCKS.1 CDS

ATGCAATCCAATCAAAAGCTCTGCATCGCTATCTTTGGCCCTACCGCCTCGGGGAAGACCAAACTGGGGG
TCGCCATTGCAAAAGCCTTTCCGAGCGAGGTTATCTCCGTCGACAGTCTACAGTGCTACAAAGCGGGAAG
CATTATCACAGCTAAGCCTACTGCTCATGAGATAGCTGATGTTCCTCATCATCTGATTGACTACCTCGAG
GCTGATGAGGAGCCCAATGACTTTGTGGCCCAAGCTGCTGACAAGATGGAAGATATCACAAATCGAGGAA
AACTCCCCATTCTTGTCGGCGGTTCGACTTCTCGCGATACCTTTGCTGCACGAGGCACTGAAGCGGCA
GTATCGGTTCGTGGCTGCAACTCTGATCCCGCGTCAGTCAACATACTGGCAGTCCATCCAAGTCAGAGCC
AGCGAGATGCTCGAGAGGGGTCTTCTGGCCGAACTAGAGGAGTTGAGAGACCTGCAGCAGAGTCTCCTCG
ATGACAACGCATGCTTCCATAAGGGAGTATGGAAGGCCATTGGGTATCAACAGTTCTATCCCTATCTCGA
GGCAGAGTCGTCATGCAACGCCCGTCAGTCGTCATTCCAGAGGGGTCTCGCACTGATGAATGCAAACACT
CTGCAGTACGGCTTCCATCAACTCGAGTGGATTCGTTCTATCCTCAACCCTTTTCTGCACCAAGCCGGCG
TCGTATGCATGAGCCTCCCTGTCACTGACAATGCTTCGTGGATGTCAGATGTCCAGATACCTGCTATCTC
AATGCTCAACGACCTGTGCTACAGTTTGCGAACGATCAAAGTCTCCACCAATGGAACACTAAACTCTAGC
CCCAAGTTTCGAGTCGTTGGTCTATTTGGCGGATCTTCTCCGGGGAATGATCCGGGTCACATCGATGCGG
CTAAAAGGCTTGCGTTTGCTCTACACCAACATAGCTACAAACTCGTCTACGGCGGCGGAACAACTGGGAT
CATGGGCGCCATTGCCAGCACTCTGGTGCAACTCTCTGGACCAAGTGCCGTCCAGGGCATCATTCCCGTT
GCACTCGCCAAGTACGAAGAAAGACTCACTAAGAAAAGGGCCGACCCTTCAAAGTTCGGGAACAGGACTG
TCGTCAAAGACATGCATACACGCAAGAGACTCATGATCGAGGCAGTCATTGGTGGCGCTCCAGGGAGCGG
CTTTGTAGCTCTCAGTGGGGGATACGGTACCTTGGAGGAACTCCTCGAGACAACGACTTGGTACCAGCTT
GGTATTCATCAATGTGGAATCTGTGTGTTTGACGTATGCGGATTTTACAAGGGTTTAATGGACTGGGTTT
GTCAGGCTGCACAGGCAGGGTTTGTTGGCACAGAGGATGCTACTATTCTGCGGGTTGCAACGACGGCTGA
GGATGTCATCGGCTGCCTAGGCAGTAATGATCATCGTTATTCGCGGATGGGTGAGCTGGAATGGGATTAG
(SEQ ID NO:24)

>FfCKS.1 amino acid sequence

MQSNQKLCIAIFGPTASGKTKLGVAIAKAFPSEVISVDSLQCYKAGSIITAKPTAHEIADVPHHLIDYLE
ADEEPNDFVAQAADKMEDITNRGKLPILVGGSTSLAIPLLHEALKRQYRFVAATLIPRQSTYWQSIQVRA
SEMLERGLLAELEELRDLQQSLLDDNACFHKGVWKAIGYQEFYPYLEAESSCNARQSSFQRGLALMNANT
LQYGFHQLEWIRSILNPFLHQAGVVCMSLPVTDNASWMSDVQIPAISMLNDLCYSLRTIKVSTNGTLNSS
PKFRVVGLFGGSSPGNDPGHIDAAKRLAFALHQHSYKLVYGGGTTGIMGAIASTLVQLSGPSAVQGIIPV
ALAKYEERLTKKRADPSKFGNRTVVKDMHTRKRLMIEAVIGGAPGSGFVALSGGYGTLEELLETTTWYQL
GIHQCGICVFDVCGFYKGLMDWVCQAAQAGFVGTEDATILRVATTAEDVIGCLGSNDHRYSRMGELEWD
(SEQ ID NO:25)

FIGURE 20

\>FfCKS.1 *E. coli* optimized, N-His-tagged

ATGGGTAGCAGCCATCATCATCACCATCATATGCAGAGCAATCAGAAACTGTGCATTGCAATTTTTGGTC
CGACCGCAAGCGGTAAAACCAAACTGGGTGTTGCAATTGCCAAAGCATTTCCGAGCGAAGTTATTAGCGT
TGATAGCCTGCAGTGTTATAAAGCCGGTAGCATTATTACCGCAAAACCGACCGCACATGAAATTGCAGAT
GTTCCGCATCATCTGATCGATTATCTGGAAGCAGATGAAGAACCGAATGATTTGTTGCACAGGCAGCAG
ATAAAATGGAAGATATTACCAATCGTGGCAAACTGCCGATTCTGGTTGGTGGTAGCACCAGCCTGGCAAT
TCCGCTGCTGCATGAAGCACTGAAACGTCAGTATCGTTTTGTTGCCGCAACCCTGATTCCGCGTCAGAGC
ACCTATTGGCAGAGCATTCAGGTTCGTGCAAGCGAAATGCTGGAACGTGGTCTGCTGGCAGAACTGGAAG
AACTGCGTGATCTGCAGCAGAGCCTGCTGGATGATAATGCATGTTTTCATAAAGGTGTGTGGAAAGCCAT
TGGCTACCAAGAATTTTATCCGTACCTGGAAGCCGAAAGCAGCTGTAATGCACGTCAGAGTAGCTTTCAG
CGTGGTCTGGCACTGATGAATGCAAATACCCTGCAGTATGGTTTTCATCAGCTGGAATGGATTCGTAGCA
TTCTGAATCCGTTTCTGCATCAGGCAGGCGTTGTTTGTATGAGCCTGCCGGTTACCGATAATGCAAGCTG
GATGAGTGATGTTCAGATTCCGGCAATTAGCATGCTGAATGATCTGTGTTATAGCCTGCGTACCATTAAA
GTTAGCACCAATGGCACCCTGAATAGCAGCCCTAAATTTCGTGTTGTTGGTCTGTTTGGTGGTTCAAGTC
CGGGTAATGATCCGGGTCATATTGATGCAGCAAAACGTCTGGCATTTGCACTGCATCAGCATAGCTATAA
ACTGGTTTATGGTGGTGGTACAACCGGTATTATGGGTGCAATTGCGAGCACCCTGGTTCAGCTGAGCGGT
CCGAGCGCAGTTCAGGGTATTATTCCGGTTGCACTGGCAAAATATGAAGAACGTCTGACCAAAAAACGTG
CAGATCCGAGCAAATTTGGTAATCGTACCGTTGTGAAAGATATGCATACCCGTAAACGTCTGATGATTGA
AGCAGTTATTGGTGGCGCACCGGGTAGCGGTTTTGTGGCACTGAGCGGTGGTTATGGTACGCTGGAAGAA
CTGCTGGAAACCACCACCTGGTATCAACTGGGTATCCATCAGTGTGGTATTTGCGTTTTTGATGTGTGCG
GTTTCTATAAAGGCCTGATGGATTGGGTTTGTCAGGCAGCCCAGGCAGGTTTTGTTGGTACAGAAGATGC
AACCATTCTGCGTGTTGCCACCACCGCAGAAGATGTTATTGGTTGTCTGGGTAGCAATGATCATCGTTAT
AGCCGTATGGGTGAACTGGAATGGATTAA (SEQ ID NO:26)

\>FfCKS.1

MGSSHHHHHHMQSNQKLCIAIFGPTASGKTKLGVAIAKAFPSEVISVDSLQCYKAGSIITAKPTAHEIAD
VPHHLIDYLEADEEPNDFVAQAADKMEDITNRGKLPILVGGSTSLAIPLLHEALKRQYRFVAATLIPRQS
TYWQSIQVRASEMLERGLLAELEELRDLQQSLLDDNACFHKGVWKAIGYQEFYPYLEAESSCNARQSSFQ
RGLALMNANTLQYGFHQLEWIRSILNPFLHQAGVVCMSLPVTDNASWMSDVQIPAISMLNDLCYSLRTIK
VSTNGTLNSSPKFRVVGLFGGSSPGNDPGHIDAAKRLAFALHQHSYKLVYGGGTTGIMGAIASTLVQLSG
PSAVQGIIPVALAKYEERLTKKRADPSKFGNRTVVKDMHTRKRLMIEAVIGGAPGSGFVALSGGYGTLEE
LLETTTWYQLGIHQCGICVFDVCGFYKGLMDWVCQAAQAGFVGTEDATILRVATTAEDVIGCLGSNDHRY
SRMGELEWD (SEQ ID NO:27)

FIGURE 21

>Atu.IPT Ec.his codon optimized for E.coli

ATGGGCAGCAGCCATCATCATCATCATCACAGCAGCGGCCTGGTGCCGCGCGGCAGCCATATGGATCTGC
ATCTGATTTTTGGTCCGACCTGTACCGGTAAAACCACCACCGCAATTGCACTGGCACAGCAGACAGGTCT
GCCGGTTCTGAGCCTGGATCGTGTTCAGTGTTGTCCGCAGCTGAGCACCGGTAGCGGTCGTCCGACCGTT
GAAGAACTGAAAGGCACCACCCGTCTGTATCTGGATGATCGTCCGCTGGTTGAAGGTATTATTGCAGCAA
AACAGGCACATCATCGTCTGATTGAAGAAGTGTATAATCACGAAGCAAATGGTGGTCTGATTCTGGAAGG
TGGTAGCACCAGCCTGCTGAATTGTATGGCACGTAATAGTTATTGGAGCGCAGATTTTCGCTGGCATATT
ATTCGTCATAAACTGCCGGATCAAGAAACCTTTATGAAAGCAGCAAAAGCCCGTGTTAAACAAATGCTGC
ATCCGGCAGCAGGTCATAGCATTATTCAAGAACTGGTTTATCTGTGGAATGAACCGCGTCTGCGTCCGAT
TCTGAAAGAAATTGATGGTTATCGTTATGCCATGCTGTTTGCAAGCCAGAACCAGATTACCGCAGATATG
CTGCTGCAGCTGGATGCAAATATGGAAGGTAAACTGATTAATGGCATTGCCCAAGAGTATTTTATCCATG
CACGTCAGCAAGAACAGAAATTTCCGCAGGTTAATGCAGCAGCCTTTGATGGTTTTGAAGGTCATCCGTT
TGGCATGTATTAA (SEQ ID NO:28)

>Atu.IPT Ec.his amino acid sequence

MGSSHHHHHHSSGLVPRGSHMDLHLIFGPTCTGKTTTAIALAQQTGLPVLSLDRVQCCPQLSTGSGRPTV
EELKGTTRLYLDDRPLVEGIIAAKQAHHRLIEEVYNHEANGGLILEGGSTSLLNCMARNSYWSADFRWHI
IRHKLPDQETFMKAAKARVKQMLHPAAGHSIIQELVYLWNEPRLRPILKEIDGYRYAMLFASQNQITADM
LLQLDANMEGKLINGIAQEYFIHARQQEQKFPQVNAAAFDGFEGHPFGMY (SEQ ID NO:29)

FIGURE 22

```
>jgi|Botdo1_1|289339 [Botryosphaeria dothidea]
MIPIIAIVGPTGVGKTKLSITIAKALGAAEIVSVDSLQVYREAPIMTAQASTEEMEGVRHHLMCYLNAAEEPRD
FVPLALKAIESIRCRGNIPILCGGSTSLMQPLLIHPYLAKSKRYILGLACPMSVLGPLLDARISQMVHDGLLDE
VCKLLRLEAEHHPQKPCGVWKAIGYTELKPWASARSVDAVFVLDQGLEDMRQHTRHYAETQMLWMLLELFPSL
EKLPIKTEMLVLRSRSEFESQVVAPALELCSSFGLSDEFIEATRSLALEIHLRGWSLVYGGGTRGLMGVLAESL
VKLSGPSSVHGITPRPFLQTSTGICTPDESRFGRTTVVSTMHERKALMAKEADAFLALPGGYGTMEELFEMITW
NQLGIHTRPVVLLNTNGFFDGLICWIEKAMCQGFISAEARNIVDVAETADEVIEKIEIYQSPIVAELEWL
(SEQ ID NO:34)

>gi|399168795 [Claviceps purpurea 20.1]
MSTRKLAIAIVGPTASGKTKLGVAIAKAYLGEVISVDSLQCYKPGGIITARPLPEETDDVPHHLIDYLEADEEP
EDYVSQAVRIMEDISARDGLPILVGGSTSLTMPLLQAAFAREYEVLALTLVPQRSAYQRLVETRGEEMLQRGLL
EELEELHHLEKRLLHGVSDLSRGVWKAIGYREYLPYLQAVRSVNGKADGCSSQEEYLREEGRLSMNASTLHYGQ
DQLEWMRHTLVPFLHRHRAATVSLCVTNKAAWEAEVQGPALTMAGEFCHGASRARHALGFFPKKKRVVCVFGGS
SGGHDSSHIDAAKALAVTLHRHDMCLVYGGGTTGIMGAVASTLVALSGPSAVHGVVPAALARYESGGAGDGRVN
GEYASRFGRRTVVRDMHTRKRLMTQMVREGAPGSGFVALSGGYGTLEELLEAATWHQLGIHRCGVSVFSVDGFY
DGLLDWIRRVAGHGFVGNKDADIIRVARTAEEVVACLDEGSRGGDHGLEWV (SEQ ID NO:35)

>gi|591501391 [Fusarium oxysporum f. sp. vasinfectum 25433]
MTRTHKPAVAIFGPTASGKTKLGVAVSKAFLGEVISVDSLQCYKPGSIITAKPEHDEIQDIPHHLIDYLQADEE
PDDFISLAINKMEDIISRNKIPVLVGGSTSLTTPLLQQALKHHYIILGIMLVPHPSSYQQLIETRGDAMVKQGL
LAELRELKALEKTLLQGERDFNRGVWKAIGYPEFSPYLDYDGASDIKREVLYHQGVTMMRASTLQYGFNQLEWL
RHTLTPFLHQQKVATISLNVTDKQSWAAEVEGPALSMANQFFHGTHSVTPVPGKVSKPRVVCLFGGSSSGNDPS
HVKAAKDLSLELHRNNITLIYGGGTTGVMGAAASTLVELSGPSSVHGIVPAALAKFEENETGQSHMSKFGSRTV
VRDMHTRKRLMIEAVLNGGPGSGFVALSGGYGTMEELLEVATWYQIGIHNCNVCVLNVDGFYDGLLDWVSKVSE
KGFIGAKDHTIIQVASSAEGLVRCLEGKTQHSEQRRIEWI (SEQ ID NO:36)

>gi|590069068 [Fusarium oxysporum f. sp. raphani 54005]
MTRTHKPAVAIFGPTASGKTKLGVAVSKAFLGEVISVDSLQCYKPGSIITAKPEHDEIQDIPHHLIDYLQADEE
PDDFISLAINKMEDIISRNKIPVLVGGSTSLTTPLLQQALKHHYIILGIMLVPHPSSYQQLIETRGDAMVKQGL
LAELRELKALEKTLLQGERDFNRGVWKAIGYPEFSPYLDYDGASDIKREVLYHQGVTMMRASTLQYGFNQLEWL
RHTLTPFLHQRKVATISLNVTDKQSWAAEVEGPALSMADQFFHGTHSVTPVPGKVSSPRVVCLFGGSSSGNDPS
HVKAAKDLSLELHRNNITLIYGGGTTGVMGAAASTLVELSGPSSVHGIVPAALAKFEENETGQSHRSKFGSRTV
VRDMHTRKRLMIEAVLNGGPGSGFVALSGGYGTMEELLEVATWYQIGIHNCNVCVLNVDGFYDGLLDWVSKVSE
KGFIRAKDRTIIQVASSAEGLVRCLEGKTQHSEQRRIEWI (SEQ ID NO:37)
```

FIGURE 24

```
>gi|342882308 [Fusarium oxysporum Fo5176]
MTRIHKPAVAIFGPTASGKTKLGVAVSKAFLGEVISVDSLQCYKPGSIITAKPEHDEIQDIPHHLIDYLQADEE
PDDFISLAINKMEDIISRNKIPVLVGGSTSLTTPLLQQALKHHYIILGIMLVPHPSSYQQLIETRGDAMVKQGL
LAELRELKALEKTLLQGERDFNRGVWKAIGYPEFSPYLDYDGASDIKREVLYHQGVTMMRASTLQYGFNQLEWL
RHTLTPFLHQRKVATISLNVTDKQSWAAEVEGPALSMASQFFHGTHSVTPVPGKVSNPRVVCLFGGSSSGNDPS
HVKAAKDLSLELHRNNITLIYGGGTMGVMGAAASTLVELSGPSSVHGIVPAALAKFEENETGQSHMSKFGSRTV
VRDMHTRKRLMIEAVLNGGPGSGFVALSGGYGTMEELLEVATWYQIGIHNCNVCVLNVDGFYDGLLDWVSKVSE
KGFIGATDRTIIQVASSAEGLVRCLEGKTQHSEQRRIEWI (SEQ ID NO:38)

>gi|587753796 [Fusarium oxysporum f. sp. pisi HDV247]
MTRTHKPAVAIFGPTASGKTKLGVAVSKAFLGEVISVDSLQCYKPGSIITAKPEHDEIQDIPHHLIEYLQADEE
PDDFISLAINKMEDIISRNKIPVLVGGSTSLTTPLLQQALKHHYIILGIMLVPHPSSYQQLIETRGDAMVKQGL
LAELRELKALEKTLLQGERDFNRGVWKAIGYPEFSPYLDYDGASDIKREVLYHQGVTMMRASTLQYGFNQLEWL
RHTLTPFLHQRKVATISLNVTDKQSWAAEVEGPALSMADQFFHGTHSVTPVPGKVSSPRVVCLFGGSSSGNDPS
HVKAAKDLSLELHRNNITLIYGGGTTGVMGAAASTLVELSGPSSVHGIVPAALAKFEENETGQSHRSKFGSRTV
VRDMHTRKRLMIEAVLNGGPGSGFVALSGGYGTMEELLEVATWYQIGIHNCNVCVLNVDGFYDGLLDWVSKVSE
KGFIRAKDRTIIQVASSAEGLVRCLEGKTQHSEQRRIEWI (SEQ ID NO:39)

>gi|587670126 [Fusarium oxysporum FOSC 3-a]
MTRTHKPAVAILGPTASGKTKLGVAVSKAFLGEVISVDSLQCYKPGSIITAKPEHDEIQDIPHHLIDYLQADEE
PDDFIPLAINKMEDIISRNRIPVLVGGSTSLTIPLLQQALKHHYIILGIMLVPQPSNYQQLIETRGDAMVKQGL
LAELRELRALEKTLLQGGRDFNRGVWKAIGYPEFSPYLDYDGVSDIKRDVLYHQGVTMMRASTLQYGFNQLEWL
RHTLTPFLHQQKVATISLNVTDKQFWAAEVEGPALSMANQFFHGTHSVTPVPGKISNPRVVCLFGGSSSGNDPS
HVKAAKDLSLELHRKNITLIYGGGMTGVMGAAASTLVELSGPSSVHGIVPAALAKFEENVTGQSHMSKFGSRTV
VRDMHTRKRLMIEAVLNGGPGSGFVALSGGYGTMEELLEVTTWYQLGIHNCNVCVLNVDGFYDGLLDWVSKVSE
KGFIGAKDRTIIQVASSAEGLVRCLEGKTQQSEQRRIEWI(SEQ ID NO:40)

>gi|590047683 [Fusarium oxysporum f. sp. melonis 26406]
MTRTHKPAVAIFGPTASGKTKLGVAVSKAFLGEVISVDSLQCYKPGSIITAKPEHDEIQNIPHHLIDYLQADEE
PDDFISLAINKMEDIISRNRIPVLVGGSTSLTIPLLQQALKHHYIILGIMLVPQPSNYQQLIETRGDAMVKQGL
LAELSELKALEKTLLQGERDFNRGVWKAIGYPEFSPYLDYDGVSDIKREVLYHQGVTMMRASTLQYGFNQLEWL
RHTLTPFLHQQKVATISLNVTDKQFWAAEVEGPALSMANQFFHGTHSVIPVPGKASNPRVVCLFGGSSSGNDPS
HVKAAKDLSLELHRNNITLIYGGGMTGVMGAAASALVALSGPSSVHGIVPAALAKFEENVTGQSHMSKFGSRTV
VRDMHTRKRLMIEAVLNGGPGSGFVALSGGYGTMEELLEVTTWYQLGIHNCNVCVLNVDGFYDGLLDWVSKVSE
KGFIGAKDRTIIQVASSAEGLVRCLEGKTQHSEQRRIEWI(SEQ ID NO:41)
```

FIGURE 25

>gi|591490727 [Fusarium oxysporum f. sp. vasinfectum 25433]
MQANQKLCIAIFGPTASGKTKLGVAIAKAFPSEVISVDSLQCYKAGSILTAKPTVQEIDDVPHHMVDYLEADEE
PHDFVAMAADKMEEVTNRGKLPILVGGSTSLAIPFLHEALKRQYRFIAATLIPRQSTYWQFIQVRANEMLERGL
LGELEELRDLQQSLLDDNACFHKGVWKAIGYQEFYPYLEADMSCSARQSSFQRGLALMNANTLQYGFHQLEWIR
SVLNPFLQQAGVVCMSLPVTNKASWTLDVEIPAISMLNELCYSFRTIRLSNNGTLNSNSKSRVVCLFGGSSSGN
DPKHIQAAKNLAFALHSNNYKLVYGGGTTGIMGAIASTLVQLSGPSAVQGIIPVALAKYEEKLTKKNADPSKFG
SRTVVKDMHTRKRLMIDAVIGGAPGSGFVALSGGYGTLEELLETTTWYQLGIHQCGICVFDVCGFYKGLLDWVD
QAAQAGFVGTEDVDILRIATTAEEVIGYLGSQNGRYSRKGELEWD(SEQ ID NO:42)

>gi|591441911 [Fusarium oxysporum f. sp. conglutinans race 2 54008]
MQANEKLCIAIFGPTASGKTKLGVAIAKAFPSEVISVDSLQCYKAGSILTAKPTVQEIDDVPHHMVDYLEADEE
PHDFVAMAADKMEEVTNRGKLPILVGGSTSLAIPLLHEALKRQYRFIAATLIPRQSTYWQFIQVRANEMLERGL
LGELEELRDLQQSLLDDNACFHKGVWKAIGYQEFYPYLEADMSCSARQSSFQRGLALMNANTLQYGFHQLEWIR
SVLNPFLQQAGVVCMSLPVTNKASWTLDVEIPAISMLNELCYSFRTIRLSNNGTLNSNSKSRVVCLFGGSSSGN
DPKHIQAAKNLAFALHSNNYKLVYGGGTTGIMGAIASTLVQLSGPSAVQGIIPVALAKYEEKLTKKNADPSKFG
SRTVVKDMHTRKRLMIDAVIGGAPGSGFVALSGGYGTLEELLETTTWYQLGIHQCGICVFDVCGFYKGLLDWVD
QAAQAGFVGTEDVDILRIATTAEEVIGYLGSQNGRYSRMGELEWD (SEQ ID NO:43)

>gi|590053069 [Fusarium oxysporum f. sp. raphani 54005]
MQANQKLCIAIFGPTASGKTKLGVAIAKAFPSEVISVDSLQCYKAGSILTAKPTVQEIDDVPHHMVDYLEADEE
PHDFVAMAADKMEEVTNRGKLPILVGGSTSLAIPFLHEALKRQYRFIAATLIPRQSTYWQFIQVRANEMLERGL
LGELEELRDLQQSLLDDNACFHKGVWKAIGYQEFYPYLEADMSCSARQSSFQRGLALMNANTLQYGFHQLEWIR
SVLNPFLQQAGVVCMSLPVTNKASWTLDVEIPAISMLNELCYSFRTIRLSNNGTLNSNSKSRVVCLFGGSSSGN
DPKHIQAAKNLAFALHSNNYKLVYGGGTTGIMGAIASTLVQLSGPSAVQGIIPVALAKYEEKLTKKNADPSKFG
SRTVVKDMHTRKRLMIDAVIGGAPGSGFVALSGGYGTLEELLETTTWYQLGIHQCGICVFDVCGFYKGLLDWVD
QAAQAGFVGTEDVDILRIATTAEEVIGYLGSQNGRYSRMGELEWD (SEQ ID NO:44)

>gi|591467821 [Fusarium oxysporum f. sp. cubense tropical race 4 54006]
MQANQKLCIAIFGPTASGKTKLGVAIAKAFPSEVISVDSLQCYKAGSILTAKPTVQEIDDVPHHMVDYLEADEE
PHDFVDMAADKMEEVTNRGKLPILVGGSTSLAIPLLHEALKRQYRFIAATLIPRQSAYWQFIQVRASEMLERGL
LVELEELRDLQQSLLDDNACFHKGVWKAIGYQEFYPYLEADMSCSARQSSFQRGLALMNANTLQYGFHQLEWIR
SILNPFLQQAGVVCMSLPVTNKASWTLDVEIPAISMLNELCYSFRTIRLSNNGTLNSNSKSRVVSLFGGSSSGN
DPKHIQAAKNLAFALHSNNYKLVYGGGITGIMGAIASTLVQLSGPSAVQGIIPVALAKYEEKLTKKNADPSKFG
SRTVVKDMHTRKRLMIDAVIGGAPGSGFVALSGGYGTLEELLETTTWCQLGIHQCGICVFDVCGFYKGLLDWVD
QAAQAGFVGTEDVDILRIATTAEEVIGYLGSQNGRYSRMGELEWD(SEQ ID NO:45)

FIGURE 26

>gi|587748549 [Fusarium oxysporum f. sp. pisi HDV247]
MQANQKLCIAIFGPTASGKTKLGVAIAKAFPSEVISVDSLQCYKAGSILTAKPTVQEIDDVPHHMVDYLEADEE
PHDFVAMAADKMEEVTNRGKLPILVGGSISLAIPLLHEALKREYRFIAATLIPRQSTYWQFIQVRASEMLERGL
LGELEELRDLQQSLLDDNACFHKGVWKAIGYQEFYPYLEADMSCSARQSSFQRGLALMNANTLQYGFHQLEWIR
SVLNPFLQQAGVVCMSLPVTNKASWTLDVEIPAISMLNELCYSFRTIRLSNNGTLNSNSKSRVVCLFGGSSSGN
DPKHIQAAKNLAFALHSNNYKLVYGGGTTGIMGAIASTLVQLSGPSAVQGIIPVALAKYEEKLTKKNADPSKFG
SRTVLKDMHTRKRLMIDAVIGGAPGSGFVALSGGYGTLEELLETTTWYQLGIHQCGICVFDVCGFYKGLLDWVD
QAAQAGFVGTEDVDILRIATTAEEVIGYLGSQNGRYSRMGELEWD (SEQ ID NO:46)

>gi|517314372 [Fusarium fujikuroi IMI 58289]
MESNNRFMIGVFGPTGAGKTKLGVSIAKSVHGQVISVDSLQCYSPGSIITAKPSPEETDGIDHHMIGYLEADEE
PTNFVAEAIETLEKLCDHGIIPVVVGGSTSLTLPLLQDALNRGWRMAAITLLPHQSTYLSNIASRLDDMVDAGL
LEELSGLKLLEDKYLNEKPNFRKGVWKAIGYQELYPYLEAQRGGGQYDQLLKTGLASMKENTFQYGMMQLEWIR
QELCPFLHAEKIANVSLTVVDKTSWISDVEKPAIRMASDFCHASASINLRSINGARPRVLCIFGGSSSGNEPAH
IEAAKSLGRVCHENSIKLVYGGGTTGVMGAIASTLVELSGPDAVHGIIPEALLKYEAKELGRHPKDPTCARYGK
RTVVQDMHTRKRLMIQEVIDGGEGSGFVALSGGYGTLEELFEVTTWHQLGIHDRGVCLLNTGGFFDGLVDWLAN
VVQKGFIGLEDAAILNIASTADGAVKCLDHKPGFSRKGVLDWV (SEQ ID NO:47)

>gi|685861465 [Fusarium pseudograminearum CS3096]
MESTNRFMIGVFGPTGVGKTKLGVSIAKSVHGQVISVDSLQCYSPGGIVTAKPTPEEMDGIEHHMIGYLEAEEE
PTNFVAEAVERLEKLCDHGAIPVVVGGSTSLTLPLLRGALNRGWRMAAITLLPHQSTYLGNIESRVDDMLEAGL
LEELSGLKSLEDRNLNGKPNFHKGIWKTIGYQELYPYLEAQRSDGHCDELLKSGLASMKENTFQYGNTQLEWIR
QALSPFLHAEKIANMSLTVVDKTSWTRGVEKPAIRMASDFCYASTSISFHPINEPKPRVICIFGGSSSGNDPAH
MEAAKSLGRVCHENSIKLVYGGGTTGVMGAIASTLVELSGPNAVHGIIPEALLKYEAKESGRHAQDSAFARYGR
RTVVKDMHTRKRLMIQEVIDGGDGSGFVGLSGGYGTLEELFEVITWHQLGIHDRGVCLLNMDGFFDGLVNWLGN
VVKKGFIGLQDAAILSIASTAEGVVKCLDQKPGFSRKGELEWV (SEQ ID NO:48)

>gi|584135303 [Fusarium verticillioides 7600]
MESTNRFMIGVFGPTGTCKTKLGVSIAKSIYGQVVSVDSLQCYSPGSIVTAKPTTEETDGVDHHMIGYLEANEE
PTSFVAEAIERLEELRDHEAIPVVVGGSTSLTLPLLRDALNRGWRMAAITLLPHQSTYLSNIKSRLDDMVEAGL
LEELSGLKVLEDKHLNGKPDFHKGIWKAIGYQELYPYLAARKMDVHCDQLLKSGLASMKANTFQYGITQLEWIR
QVLCPFLHAEKIANMSLTVVDKTSWILDVGKPAIRMASDFCHASTSISFHSINGSNPRVLCIFGGSSSGNDPAH
IEAAKSLGRICHENNIKIVYGGGTTGVMGAIASTLVDLSGPDAVHGIIPEALLKYEAKESGRHPKDPAYARYGK
QTVVKDMHTRKRLMIQEVITGGEGSGFVGLSGGYGTLEELFEVVTWHQLGIHDRGVCLLNTGGFFDGLVNWLGN
VVQEGFIGLEDASVLSIASTAEGVVRCLVQTPEFSRKGELEWV (SEQ ID NO:49)

FIGURE 27

>EgCKS.1 [Epichloe gansuensis]
MPTRKLSVAIFGPTASGKTKIGVTIAKAYLGEVISIDSLQCYKPGGIATAKPCPEETQGVPHHLIDYLDAEEEP
KDFVSRAIAKVDDINTRNGLPILVGGSTSLIIPLLQEVFSREYEVLVITLVPHQSSYLRLIESRGREMLKKGLL
NELTELQRLEKVLLNGKSGFNKGVWKVIGYQEFLPYLRAVGKLNGVSNNYDHLYEEGRASMNASTLHYGQYQLE
WMRHTLIPFIHRHKAITVSLCVTDQASWVSDVERPAMTMTGEFYHGSQVRRLPSRNSSKKRVICLFGGSSSGNN
RIHIEAAKSLAVALHNHEIALVYGGGTTGIMGAVASTLVALSGPETVHGIVPAALAKYEDELGDGRINAEYLSQ
FGRRTIVRDMHTRKRLMTQAVFEGAPGSGFVALSGGYGTMEELLEVTTWYQLGIHDCRVSVFNVDGFYDGLLNW
MGQVAREGFVSPKDANILGVANTANEVIACLANQQQHEEKPNLEWL (SEQ ID NO:50)

>AteCKS.1 [Atkinsonella texensis]
MLASRKLVAILGPTASGKTKLGVAIAKAFLGEVVSVDSLQCYKPGTIITAKPLPEETEGIPHHLIDYLEAEKEP
HDYIERAIVAIDDITARNRLPILVGGSTSLTMPLLREVFHAQYEVLAINLVPHPSLYQQLIESRGEEMLRRGLL
NELVELQRLEKVLLNGECDFTRGIWKAIGYQEFYFYLQTVQKLNAASKTNPGHLYKKGRALLFANTLRYGQGQL
EWMRHTLAPFLYQHKAATISLSVTDKASWISDVQEPALTLISEFYNDTQVTKSLLRRRSSKKRFVCLFGGSSAG
NDPTHIEAAKSLAVALHHNDISLVYGGGTTGIMGQVASSLVALSGPNAVQGFIPAALARHEEELGNDGPIINGE
YLSRFGRRTIVRDVHTRKRLMIQNVLQGTPGSGFVALSGGYGTLEELLEITTWSQLGIHDCVVAVFSVDGFYDG
LLDWIDQVVRSGFISTKNANIVRVANSADKVIACLADGRIQPRRHVLEWL (SEQ ID NO:51)

>CfCKS.1 [Claviceps fusiformis]
MSTRKLAIAILGPTASGKTKLGVAFGKAYLGEVISVDSLQCYKQGGIITARPYPEEMKVVPHHLIDYLEADEEP
HDFVSRALTIMDDISARHALPILVGGSTSLTIPLLQQVFKKDYEVLVTLVPHRTRYQRLVESRGEEMLRRGLL
SELAELHGLEKILLQGKGEFGKVWKAIGYQEFFPYLQAVGSVNGASNTKTDRDLLDKGRAAMDANTVQYGQYQ
LEWIRHTLTPFLHQHKTTIISLSVTDKASWESDVQGPAMSMASEFCHGSRMTKHLSRGDSCSRKRVICLFGGSS
SGNDVVHVEAAKSLAIALHQHDISLVYGGGTTGIMGAVASTLVALSGPSAVHGIVPAALATYEDQLGDGRIDSE
YALRFGKRIVVRDMHTRKRLMTQMVLGGAPGSGFVALSGGYGTMEELLESTTWSQLGIHNCRVSVFNVDGFYDG
LLDWIRHVARSGFIGGKDADIIRVARTADEVVACLAHQHPLQAKRGCQGLEWL (SEQ ID NO:52)

>EbCKS.1 [Epichloë baconii]
MMPTRKLSIAIFGPTASGKTKLGVTIAKAYLGEVISIDSLQCYKPGGIATAKPCPKETQGVPHHLIDYLDAGEE
PQDFVSRAIATIDDITTRNGLPVLVGGSTSLIIPLLQQVFSREHEVLIITLVPHQSGYGRLIESRGEEMLKRGL
LDELAELKRLEKVLLDGKSDFNKGVWKTIGYREFLPYLQAVGKVNGVSNTYEDLYEEGRVSMNASTLRYGQYQL
EWIRHTLAPFIDRHKAATLSLCVTDQASWASDIERPAMTMAGEFYHGSQLRRLPSRNSSNKRVVCLFGGSSSGR
DESHIEAAKSLAVALHRHEIALVYGGGTTGIMGAVASTLVALSGPGAVHGIVPAALARYEDELGDGRINAEYSS
QFGRRTIVRDMHTRKRLMMQTVLEGAPGSGFVALSGGYGTMEELLEITTWYQLGIHDRRVSVFNVGFYDGLLS
WIGQVARDGFIRPRDANILGVANTADQVIACLANQRLDAEKPSLEWL (SEQ ID NO:53)

FIGURE 28

>CpaCKS.1 [Claviceps paspali]
MSTSKIAIAILGPTASGKTKLGVAMARAYLGEVISVDSLQCYKPGSIVTARPTAEEMCDVPHHLVGYLEADEEP
SDFVSRAVASMDDISSRDRLPILVGGSTSLTILPLLQAALNRGYRMLAVMLAPHPSTYQRLVESRADEMLQMGLL
RELAELRRLEETMVGAGAGCGRGVWKTIGYREFLPYLRAVGWTNGNSNGSAGTDEDLREKGRRSMNASTLQYGQ
YQLEWARHTLMPFLQRHTVATISLCVTDKESWESDVEGPAMTMAGEFCYGSRTMRLPSRGPGPKKRVVCLFGGS
SSGNEAKHIDAAKSLGVALHRHGISLVYGGGTTGIMGAVARMLVALSGPDAVHGIVPAALARYEDMLSGGRLDD
DERVARFGRRTVVRDMHTRKRLMTRAVVEGAPGSGFVAMSGGYGTMEELLESTTWFQLGIHSCRISVLSVDGFY
DGLVDWIREAGVGSGFVGHKDADIIRVARTADEVIANLSEQPAFPRLGLEWL (SEQ ID NO:54)

CYTOKININ SYNTHASE ENZYMES, CONSTRUCTS, AND RELATED METHODS

CROSS-REFERENCE TO RELATED APPLICATIONS

The present application claims priority to U.S. Provisional Application No. 62/001,849, filed May 22, 2014, which is incorporated herein by reference in its entirety.

REFERENCE TO SEQUENCE LISTING SUBMITTED ELECTRONICALLY

The substitute sequence listing filed electronically via EFS-Web on Nov. 30, 2015 as the ASCII formatted file named "75913_ST25v3.txt" was created Nov. 30, 2015, has a size of 189 kilobytes, is part of the specification, and is herein incorporated by reference in its entirety.

FIELD OF THE INVENTION

The invention relates generally to the fields of molecular biology and biochemistry. More specifically the invention relates to a class of cytokinin synthase enzymes that produce cytokinin. The invention provides recombinant polynucleotides that encode these enzymes and methods for the production of cytokinins in vitro, in host cells, and in plants. The invention further provides plants and compositions that include recombinant polynucleotides of the invention, the cytokinin synthases of the invention, and/or cytokinins produced by the cytokinin synthases of the invention.

BACKGROUND

Cytokinins are small molecules produced by plants that regulate growth and development processes under normal growing conditions as well as under stress conditions. It is well established that cytokinins stimulate growth and differentiation of cultured plant cells. Cytokinin signaling has been shown to correlate with production of tissues during bud outgrowth and root nodule formation. Faiss et al., *Plant J.*, 12(2): 401-15 (1997); Ferguson et al., *Plant Physiol.*, 149(4): 1929-1944 (2009), Tirichine et al., *Science*, 315 (5808):104-107 (2007) and Held et al., *Plant Cell*, 26(2): 678-694 (2014). Cytokinin inactivation during abiotic stress, e.g., due to drought, cold, or excess salt leads to decreased plant productivity, reduced seed size, increased tip kernel abortion and decreased seed set. (Jones and Setter, in CSSA Special Publication No. 29, pp. 25-42. American Society of Agronomy, Madison, Wis. (1999)). Transgenic expression of cytokinin biosynthesis enzymes has been reported to increase plant productivity, including under abiotic stress. Rivero et al., *Proc. Natl. Acad. Sciences USA*, 104(49) 19631-36 (2007); Merewitz et al., *J. Exp. Bot.*, 63(3): 1315-1328 (2012). Additionally, formulations of cytokinin derived from algae and other formulations of cytokinin (benzyl adenine) have been registered and approved for uses that include application to field crops, vegetable crops, small fruits, vines, tree fruit, young trees, ornamentals, and golf courses to increase fruit size, yield, blossoms, branching, healthy appearance, and other desirable growth effects. U.S. Environmental Protection Agency Registration Eligibility Decision (RD), EPA-738-R-95-025, December 1995 and N-6 benzyladenine Registration Review Case 2040 (PC Code 116901) March 2011. In plant leaves, foliar applications of exogenous cytokinin (benzyl adenine) have been used to reverse the effects of drying roots, which can be sustained by repeated applications and leads to development of lateral shoots. Stoll et al. *J. Exp. Bot.*, 51(350): 1627-1634 (2000).

The biosynthesis of cytokinins in plants is complex and involves a primary and secondary pathway. Motkya et al., *Plant Physiol.* 112: 1035-1043 (1996). In the primary pathway, cytokinins are synthesized de novo in a multiple step reaction that begins with the activity of adenosine phosphate-isopentenyltransferases (IPTs), which preferably catalyzes the condensation of adenosine diphosphate (ADP) or adenosine triphosphate (ATP) with prenyl donors to form iP riboside 5'-diphosphate (iPRDP) or iP riboside 5'-triphosphate (iPRTP), respectively. These precursors are either hydrolyzed by cytokinin nucleotide phosphoribohydrolases to form the cytokinin $N_6$-($\Delta_2$-isopentenyl)adenine (iP) or, alternatively, they are converted to corresponding trans-zeatin nucleotides (tZN), which are then hydrolyzed to form the cytokinin trans-zeatin (tZ). In the secondary pathway, cytokinins are generated by degradation of transfer RNA (tRNA). The first step of the pathway involves tRNA-isopentenyltransferase (tRNA-IPT) enzyme that post-transcriptionally modifies tRNA to make prenylated tRNA. This precursor is further modified and condensed with adenine to generate cis-zeatin riboside (cZR) which is hydrolyzed to generate primarily cis-zeatin. Generally, the cytokinin pool produced by the primary pathway is understood to be biologically more active.

The infectious crown gall forming bacterium *Agrobacterium tumefaciens* has two genes which encode IPTs that preferentially catalyzes the condensation of adenosine monophosphate (AMP) with hydroxymethylbutenyl diphosphate (HMBDP) or dimethylallyl diphosphate (DMAPP) to form trans-zeatin ribosyl monophosphate (tZRMP) which is subsequently hydrolyzed by cytokinin nucleotide phosphoribohydrolases to form trans-zeatin (tZ). Thus, the mechanism of cytokinin biosynthesis in *Agrobacterium* involves at least two enzymes and produces predominantly tZ cytokinin.

There is a desire for new compositions and methods that can be used to produce or regulate the production of cytokinin in vitro or in vivo. For example, there is a desire for compositions and methods that use a single polypeptide to produce cytokinin directly from precursor. These can be less dependent on the presence of additional upstream or downstream effectors for the production of cytokinins. Such compositions and methods can be used to produce cytokinin formulations for applications to plants. Additionally such can be used to modulate cytokinin production in plants and thereby regulate plant growth and development.

BRIEF SUMMARY

The disclosed invention is based, in part, on the discovery of a class of genes in certain plant-associated fungi that encode a cytokinin biosynthetic enzyme ("cytokinin synthase") having two domains: an isopentenyl transfer (IPT)-like domain and a cytokinin nucleotide phosphoribohydrolase (PRH)-like domain. Multiple members of this class of cytokinin synthases are identified and characterized herein including, for example, *Epichloe festucae* (EfCKS), *Balansia obtecta* (BoCKS), *Ilyonectria radicola* (IrCKS), *Aciculosporium take* (AtCKS), *Atkinsonella hypoxylon* (AhCKS), *Fusarium fujikuroi* (FfCKS), and others disclosed herein. The cytokinin synthase of the invention can be used to catalyze the conversion of cytokinin precursors (e.g., adenosine monophosphate (AMP) or a prenyl donor such as dimethylallyl diphosphate (DMAPP)) directly to a cytokinin (isopentenyl adenine).

Thus the invention provides a method that includes contacting a cytokinin precursor (e.g., AMP or DMAPP) with a two-domain cytokinin synthase of the invention, wherein the cytokinin synthase converts the precursor to cytokinin such as isopentenyl adenine. The invention improves upon prior isopentenyl transferase (IPT) enzymes that, because they only catalyze an initial step, may require one or more additional enzymes (a transhydroxylase (CYP735) or phosphoribohydrolase (CKA)), to effectively complete the conversion of AMP or DMAPP to a cytokinin such as transzeatin (tz) or isopentenyl adenine (iP). See FIG. 2.

The disclosure provides cytokinin synthases that vary in amino acid sequence while retaining enzymatic function. Thus, the invention discloses a cytokinin synthase having at least 57%, at least 60%, at least 65%, at least 70%, at least 80%, at least 90%, or at least 95% amino acid sequence identity to a disclosed cytokinin synthase. The invention further provides a recombinant polynucleotide that comprises (a) a coding sequence for any of the two-domain cytokinin synthase disclosed herein and (b) a heterologous nucleotide sequence such as, e.g., a heterologous promoter sequence, vector sequence, or a host-genome targeting sequence. In certain embodiments, the two-domain cytokinin synthase coding sequence is optimized for expression in a host cell, e.g., a bacteria, yeast, or plant host cell. In some embodiments, the cytokinin synthase coding sequence is covalently linked to a heterologous amino acid sequence, such as a protein fusion tag.

The disclosed invention identifies and provides functionally important domains, motifs, and individual residues. For example, the disclosure provides methods for identifying and/or making isopentenyl transfer (IPT)-like domain and cytokinin nucleotide phosphoribohydrolase (PRH)-like domains. Thus, the invention provides a two-domain cytokinin synthase that includes these motifs. Referring to the sequence alignment of FIG. 6, a first motif was identified at consensus positions 13-20: GPTX$aa_1$X$aa_2$GKT (SEQ ID NO:30), wherein X$aa_1$ is G or A and X$aa_2$ is V, S, or A; a second motif was identified at consensus positions 96-104: PX$aa_3$X$aa_4$X$aa_5$GGSX$aa_6$S (SEQ ID NO:31), wherein X$aa_3$ is I or V, X$aa_4$ is L or V, X$aa_5$ is V or C, and X$aa_6$ is T or I; a third motif was identified at consensus positions 333-338: XaaXaaYGGG X$aa_7$X$aa_8$YGGG (SEQ ID NO:32), wherein X$aa_7$ is L or I, and X$aa_8$ is V or I; and a fourth motif was identified at consensus/alignment positions 426-438 X$aa_9$GGYGT X$aa_{10}$EEL (SEQ ID NO:33), where X$aa_9$ is S or P and X$aa_{10}$ is L or M. The foregoing motifs, as exemplified in fungal cytokinin synthases, are set forth more fully in Example 8 herein.

The motifs identified in the IPT-like domains of the fungal two-domain cytokinin synthases were also compared to non-fungal isopentenyl transferases to identify residues that could be varied within cytokinin synthases of the invention. Thus, in a different aspect, the invention provides two-domain cytokinin synthases wherein one or more of the disclosed motifs within the IPT-like domain (SEQ ID NO:30, SEQ ID NO:31, or SEQ ID NO:32) is varied to include the corresponding motifs identified in non-fungal IPT domains as more fully described in Example 9.

Additionally, the invention discloses for the first time individual amino acid residues which are functionally important for cytokinin synthase activity as revealed by the results of alanine scanning mutagenesis. Individual residues are indicated in FIG. 6 and their effect on activity is shown in FIG. 7, and discussed in more detail herein.

In further embodiments, the recombinant polynucleotide encoding the two-domain cytokinin synthase is transformed into a host cell. In some embodiments, the host cell is a transgenic plant cell and the encoded cytokinin synthase modulates cytokinin activity in the plant cell. In certain embodiments, the plant cell is regenerated to create transgenic plant tissue or a transgenic plant that includes the recombinant polynucleotide of the invention. In particular embodiments, the recombinant polynucleotide expresses the encoded cytokinin synthase and thereby modulates cytokinin levels in the transgenic plant. In additional embodiments, the host cell is an expression host cell (e.g., a bacteria or yeast) that can be used to produce the encoded cytokinin synthase. The cytokinin synthase can be isolated or purified from the host cell material. Thus, the invention also provides an isolated or purified cytokinin synthase polypeptide that has an IPT-like domain and a PRH-like domain. In certain embodiments, the invention provides an isolated or purified cytokinin synthase fused to a heterologous amino acid sequence such as a protein fusion tag.

The invention provides methods of using the recombinant polynucleotides of the invention to produce cytokinins in host cells, plants, and in vitro. In one aspect, the invention provides a method of using the recombinant polynucleotide to express a two domain cytokinin synthase that is capable of converting cytokinin precursor (e.g., adenosine monophosphate (AMP) or dimethylallyl diphosphate (DMAPP)) directly to cytokinin in a host cell, a plant, or in vitro. By contrast, prior art polynucleotides encoding a prior art isopentenyl transferase (IPT) also required expression of one or more additional enzymes to complete the conversion of AMP or DMAPP to a cytokinin such as tZ or iP. See FIG. 2.

In yet another aspect, the cytokinin synthase of the invention can be used to produce cytokinins in a host cell or in vitro, which can be isolated or purified for use as an active ingredient. The cytokinins produced according to the invention can be mixed with inert ingredients to create formulations which are useful for application to field crops, vegetable crops, small fruits, vines, tree fruit, young trees, ornamentals, and grasses in industrial applications.

The compositions and methods of the invention are disclosed in more detail herein.

BRIEF DESCRIPTION OF THE FIGURES

FIG. 8 provides cDNA sequence of polynucleotide (SEQ ID NO:1) encoding cytokinin synthase polypeptide EfCKS.1.

FIG. 9 provides an *E. coli* codon optimized coding sequence polynucleotide (SEQ ID NO:2) and the encoded cytokinin synthase polypeptide EfCKS.1 (SEQ ID NO:3).

FIG. 10 provides an *E. coli* codon optimized coding sequence polynucleotide (SEQ ID NO:4) and the encoded cytokinin synthase polypeptide EfCKS.1 (SEQ ID NO:5) which includes an N-terminal fused protein (polyhistidine) tag.

FIG. 11 provides an *E. coli* codon optimized coding sequence polynucleotide (SEQ ID NO:6) and the encoded IPT-like domain of EfCKS.1 (SEQ ID NO:7), which is truncated at the amino acid corresponding to position 255 of full-length EfCKS.1 and which includes an N-terminal fused polyhistidine tag.

FIG. 12 provides the sequence of polynucleotide (SEQ ID NO:8) encoding cytokinin synthase polypeptide AtCKS.1 (SEQ ID NO:9).

FIG. 13 provides an *E. coli* codon optimized coding sequence polynucleotide (SEQ ID NO:10) and the encoded cytokinin synthase polypeptide AtCKS.1 (SEQ ID NO:11) which includes an N-terminal fused protein (polyhistidine) tag.

FIG. 14 provides the sequence of polynucleotide (SEQ ID NO:12) encoding cytokinin synthase polypeptide BoCKS.1 (SEQ ID NO:13).

FIG. 15 provides an *E. coli* codon optimized coding sequence polynucleotide (SEQ ID NO:14) and the encoded cytokinin synthase polypeptide BoCKS.1 (SEQ ID NO:15) which includes an N-terminal fused protein (polyhistidine) tag.

FIG. 16 provides the sequence of polynucleotide (SEQ ID NO:16) encoding cytokinin synthase polypeptide IrCKS.1 (SEQ ID NO:17).

FIG. 17 provides an *E. coli* codon optimized coding sequence polynucleotide (SEQ ID NO:18) and the encoded cytokinin synthase polypeptide IrCKS.1 (SEQ ID NO:19) which includes an N-terminal fused protein (polyhistidine) tag.

FIG. 18 provides the sequence of polynucleotide (SEQ ID NO:20) encoding cytokinin synthase polypeptide AhCKS.1 (SEQ ID NO:21).

FIG. 19 provides an *E. coli* codon optimized coding sequence polynucleotide (SEQ ID NO:24) and the encoded cytokinin synthase polypeptide AhCKS.1 (SEQ ID NO:23) which includes an N-terminal fused protein (polyhistidine) tag.

FIG. 20 provides the sequence of polynucleotide (SEQ ID NO:24) encoding cytokinin synthase polypeptide FfCKS.1 (SEQ ID NO:25).

FIG. 21 provides an *E. coli* codon optimized coding sequence polynucleotide (SEQ ID NO:26) and the encoded cytokinin synthase polypeptide FfCKS.1 (SEQ ID NO:27) which includes an N-terminal fused protein (polyhistidine) tag.

FIG. 22 provides an *E. coli* codon optimized coding sequence polynucleotide (SEQ ID NO:16) and the encoded IPT with N-terminal fused polyhistidine tag (SEQ ID NO:17) of AtuCKS.1.

FIG. 24 provides the following cytokinin synthases of the invention: SEQ ID NO:34, SEQ ID NO:35, SEQ ID NO:36, and SEQ ID NO:37.

FIG. 25 provides the following cytokinin synthases of the invention: SEQ ID NO:38, SEQ ID NO:39, SEQ ID NO:40, and SEQ ID NO:41.

FIG. 26 provides the following cytokinin synthases of the invention: SEQ ID NO:42, SEQ ID NO:43, SEQ ID NO:44, and SEQ ID NO:45, FIG. 27 provides the following cytokinin synthases of the invention: SEQ ID NO:46, SEQ ID NO:47, SEQ ID NO:48, and SEQ ID NO:49.

FIG. 28 provides the following cytokinin synthases of the invention: SEQ ID NO:50, SEQ ID NO:51, SEQ ID NO:52, and SEQ ID NO:53, FIG. 29 provides the following cytokinin synthases of the invention: SEQ ID NO:54

TERMS

Figure 1:
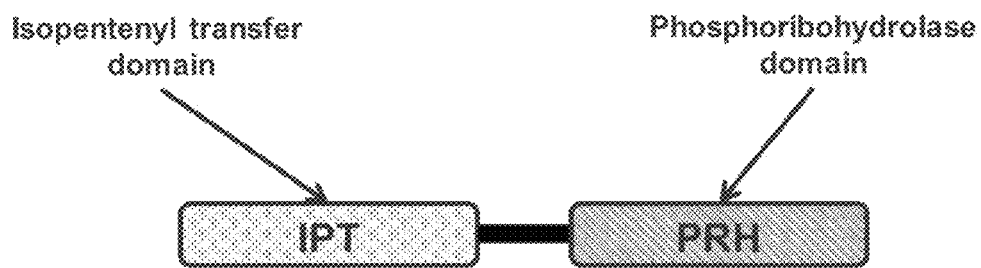
FIG. 1 is a schematic diagram of the domain architecture of a cytokinin synthase of the invention, including IPT-like domain and PRH-like domain.
Figure 2:
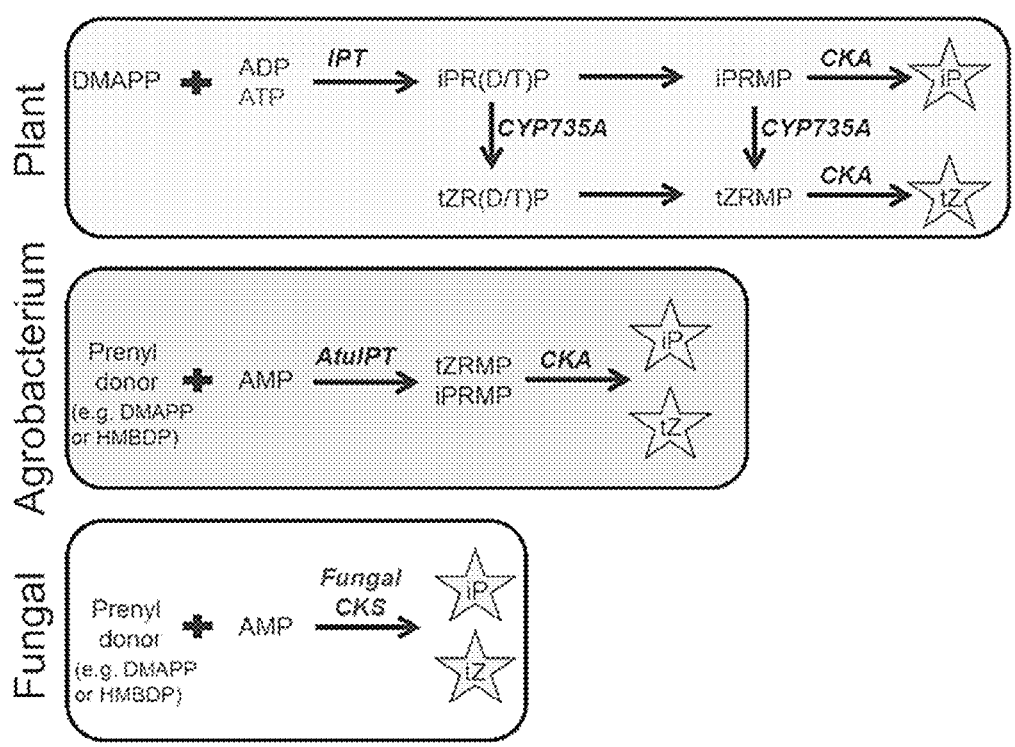
FIG. 2 provides models of cytokinin biosynthesis in plants and *Agrobacterium* and a model of fungal cytokinin biosynthesis based on the cytokinin synthases disclosed herein.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values. The term "about 100%" means less than 100%.

As used herein, the term "plant" includes a whole plant and any descendant, cell, tissue, or plant part. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

A plant cell is the structural and physiological unit of the plant. Plant cells, as used herein, includes protoplasts and protoplasts with a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant part" in embodiments herein.

The term "dicot" or "dicotyledonous" refers to plants having two cotyledons. Examples include crop plants such as soybean, sunflower, cotton, canola, rape, and mustard.

The term "monocot" or "monocotyledonous" refers to plants having a single cotyledon. Examples include crop plants such as maize, rice, wheat, oat, and barley.

The term "heterologous" is used herein to describe a nucleotide sequence that is not found in ant naturally occurring polynucleotide that encodes a cytokinin kinase.

The term "recombinant" means with regard to a polynucleotide or a host cell that the polynucleotide or host cell has been altered by recombinant methods. For example, the term recombinant polynucleotide refers to a polynucleotide that includes a first nucleic acid sequence (e.g. a sequence encoding cytokinin synthase of the invention) that has been covalently linked to a heterologous molecule (e.g., a heterologous nucleic acid) by ligation, cloning, amplification recombination, or chemical modification. The term recombinant also refers to a polynucleotide that has been artificially synthesized in a laboratory or industrial setting.

The term "recombinant" with regard to a polypeptide means that the polypeptide has been produced by recombinant methods, e.g., by expressing a recombinant polynucleotide that encodes the recombinant polypeptide. The term recombinant also refers to a polypeptide that has been artificially synthesized in a laboratory or industrial setting.

The term "transgenic" refers to a cell or organism comprising a transgene, for example a "transgenic plant" refers to a plant comprising a transgene, i.e., a nucleic acid molecule artificially incorporated into the organism's genome as a result of human intervention.

The term "transgenic event" in reference to a plant refers to a recombinant plant produced by transformation and regeneration of a single plant cell with heterologous DNA, for example, an expression cassette that includes a transgene of interest. The term event refers to the original transformant and/or progeny of the transformant that includes the heterologous DNA. The term event also refers to progeny produced by a sexual outcross between the transformant and another plant. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. In embodiments of the subject disclosure the particular event comprises a gene expression cassette polynucleotide inserted within a genomic locus.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein, the term "codon-optimized" or "codon optimization" refers to a process of modifying an existing coding sequence (or designing a coding sequence) to improve transcription of a coding sequence and/or to improve translation of a transcript RNA molecule transcribed from the coding sequence, for example, in a host cell. Codon optimization includes, but is not limited to, processes that include selecting codons for the coding sequence to suit the codon preference of an expression host organism. Polynucleotide can be prepared or altered synthetically to take advantage of the known codon preferences of the host where the polynucleotide is intended to be expressed. For example, although polynucleotides may be expressed in some embodiments in both monocotyledonous and dicotyledonous plant species, a polynucleotide sequence may be modified (e.g., optimized) to account for the specific codon preferences and GC content preferences of monocots or dicots. See, e.g., Murray et al. (1989) *Nucl. Acids Res.* 17:477-98 (Maize codon usage for 28 genes from maize plants).

The term "isolated" as used herein means that a polynucleotide or a polypeptide has been removed from its natural environment. An "isolated polynucleotide" or "isolated polypeptide" also encompasses a polynucleotide or polypeptide, respectively, which has been synthesized or amplified under laboratory or industrial conditions.

The term "purified," as used herein relates to the isolation of a molecule or compound in a form that is substantially free of contaminants normally associated with the molecule or compound in a native or natural environment. The term describes a molecule or compound that has been increased in purity as a result of being separated from other components of the original composition.

The terms "polypeptide," "peptide," and "protein" are used interchangeably to refer to a polymer of amino acid residues. The term also applies to amino acid polymers in which one or more amino acids are chemical analogues or modified derivatives of a corresponding naturally-occurring amino acids.

The term "heterologous sequence" as used herein is any nucleic acid sequence that is (i) covalently bound to and flanking another nucleic acid sequence, and (i) not found in nature flanking the other nucleic acid. Thus, when a nucleic acid of interest is removed from its native location and inserted into a new location that alters the sequences flanking the nucleic acid of interest, the flanking sequences in the new location are "heterologous sequence." For example, an exogenous DNA sequence may comprise a sequence from another species, vector, and/or gene cassette.

A "fusion" molecule is a molecule in which two or more subunit molecules are linked, for example, covalently. The subunit molecules can be the same chemical type of molecule, or can be different chemical types of molecules.

For the purposes of the present disclosure, a "gene," includes a DNA region encoding a gene product, as well as all DNA regions which regulate the production of the gene product, whether or not such regulatory sequences are adjacent to coding and/or transcribed sequences. Accordingly, a gene may include, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, interfering RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

As used herein, the term isopentenyl transfer (IPT)-like domain refers to a sequence of amino acids identified by the National Center for Biotechnology (NCBI) CCD conserved domain database as a domain in the ATP-binding cassette transporter nucleotide-binding (ABC_ATPase) domain superfamily (e.g., accession: c121455) that is characteristic of an isopentenylpyrophosphate domain. Such domains include, for example, MiaA and miaA tRNA dimethyltransferase tRNA delta(2)-isopentenylpyrophosphate transferases (accessions: COG0324 and PRK00091, respectively), tRNA dimethylallyltransferases (accessions: TIGR00174, PLN02840, or PLN02748); adenylate isopentenyltransferase (accession: PLN02165); and IPP transferase, EC:2.5.1.8; tRNA delta(2)-isopentenylpyrophosphate transferase, (accession: pfam01715). For information regarding the CCD conserved domain database see Marchler-Bauer A et al. (2015), *Nucl. Acids Res.,* 43:D222-226 and Marchler-Bauer A et al. (2011), *Nucl. Acids Res.,* 39:D225-229, which are incorporated herein by reference in their entirety.

As used herein, the term phosphoribohydrolase (PRH)-like domain refers to a sequence of amino acids identified by NCBI's CCD conserved domain database as a domain in the bacterial Toll-like receptors (TIR) domain superfamily (e.g., accession c122440) that is characteristic of TIGR00730 family protein and potential lysine decarboxylases. Such domains include, for example, LOG_family_protein_YJL055W (accession TIGR00730); lysine decarboxylase (accession pfam03641); and predicted Rossman fold nucleotide-binding protein (accession COG1611). For information regarding the CCD conserved domain database see Marchler-Bauer A et al. (2015), *Nucl. Acids Res.,* 43:D222-226 and Marchler-Bauer A et al. (2011), *Nucl. Acids Res.,* 39:D225-229, which are incorporated herein by reference in their entirety. To the extent they have been annotated in genomic databases, the PRH-like domain of the cytokinin synthases disclosed herein were mistakenly annotated as being lysine decarboxylases. This annotation was also mistakenly applied to other proteins containing the same domain as verified by Kurakawa et al. (2007), Nature 445(8): 652-655.

The term "sequence identity" or "identity," as used herein in the context of two nucleic acid sequences or two polypeptide sequences, refers to the residues in the two sequences that are the same when aligned for maximum correspondence over a specified comparison window.

As used herein, references to "percentage of sequence identity" or "percent (%) sequence identity" refers to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. Methods for aligning sequences for comparison are well-known in the art. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucl. Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50. A detailed consideration of sequence alignment methods and homology calculations can be found in, e.g., Altschul et al. (1990) *J. Mol. Biol.* 215:403-10. The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (BLASTN) program may be employed using the default parameters. Nucleic acid sequences with progressively greater similarity to the reference sequences will show increasing percentage identity when assessed by this method. For comparison of amino acid sequences, the BLAST™ (BLASTP or blastp suite) program may be used with the default parameters, which employs the BLOSUM62 matrix as a default to create an alignment of amino acid sequences and determine whether aligned amino acids are "positives" (identical or conservative substitutions) at each position in the alignment. See Altschul et al. (1997), *Nucl. Acids Res.* 25(17):3389-3402.

As used herein, the terms "specifically hybridizable" and "specifically complementary" are terms that indicate a sufficient degree of complementarity, such that stable and specific binding occurs between the nucleic acid molecule and a target nucleic acid molecule under non-stringent conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na+ and/or Mg++ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) Molecular Cloning: A Laboratory Manual, 3rd ed., vol. 1-3, Cold Spring Harbor Laboratory Press, Cold Spring Harbor, N.Y., 2001, chapters 9, 10 and 11; and Hames and Higgins (eds.) Nucleic Acid Hybridization, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, N.Y., 1993; and Ausubel et al., Eds., *Current Protocols in Molecular Biology*, Chapter 2, Greene Publishing and Wiley-Interscience, NY, 1995.

As used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize. The following are representative, non-limiting hybridization conditions.

High Stringency condition (detects sequences that share at least 90% sequence identity): Hybridization in 5×SSC and 0.1% SDS buffer at 65° C. for 16 hours; wash twice in 2×SSC and 0.1% SDS buffer at room temperature for 15 minutes each; and wash twice in 0.5×SSC and 0.1% SDS buffer at 65° C. for 20 minutes each.

Moderate Stringency condition (detects sequences that share at least 80% sequence identity): Hybridization in 5×-6×SSC and 0.1% SDS buffer at 65-70° C. for 16-20 hours; wash twice in 2×SSC and 0.1% SDS buffer at room temperature for 5-20 minutes each; and wash twice in 1×SSC and 0.1% SDS buffer at 55-70° C. for 30 minutes each.

Non-stringent control condition (sequences that share at least 50% sequence identity will hybridize): Hybridization in 6×SSC and 0.1% SDS buffer at room temperature to 55° C. for 16-20 hours; wash at least twice in 2×-3×SSC and 0.1% SDS buffer at room temperature to 55° C. for 20-30 minutes each.

As used herein, the term "substantially homologous" or "substantial homology," with regard to a contiguous nucleic acid sequence, refers to contiguous nucleotide sequences that hybridize under stringent conditions to the reference nucleic acid sequence. For example, nucleic acid sequences that are substantially homologous to a reference nucleic acid sequence are those nucleic acid sequences that hybridize under moderate stringent conditions to the reference nucleic acid sequence. Substantially homologous sequences have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; about 99.9%, and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired.

As used herein, two nucleic acid sequence molecules are said to be "complementary" or exhibit "complementarity" when every nucleotide of a sequence read in the 5' to 3' direction is complementary to every nucleotide of the other sequence when read in the 3' to 5' direction. A nucleotide sequence that is complementary to a reference nucleotide sequence will exhibit a sequence identical to the reverse complement sequence of the reference nucleotide sequence. These terms and descriptions are well defined in the art, and are easily understood by those of ordinary skill in the art.

When determining the percentage of sequence identity between amino acid sequences, it is well-known by those of skill in the art that the identity of the amino acid in a given position provided by an alignment may differ without affecting desired properties of the polypeptides comprising the aligned sequences. In these instances, the percent sequence identity may be adjusted to account for similarity between conservatively substituted amino acids. These adjustments are well-known and commonly used by those of skill in the art. See, e.g., Myers and Miller (1988) *Computer Applications in Biosciences* 4:11-7. Statistical methods are known in the art and can be used in analysis of the identified 5,286 optimal genomic loci.

As used herein, the term "operably linked" refers to a linkage between two moieties that establishes a functional relationship between the two moieties. For example two amino acid sequences can be operably linked, or two nucleotide sequence can be operably linked, to form a contiguous sequence wherein the first sequence imparts functionality to the second. For instance, a promoter is operably linked to a coding sequence if the promoter affects the transcription or expression of the coding sequence. When recombinantly produced, operably linked nucleotide sequences are generally contiguous and, where necessary to join two protein-coding regions, in the same reading frame. However, nucleotide sequences need not be contiguous to be operably linked.

The term, "operably linked," when used in reference to a regulatory sequence and a coding sequence, means that the regulatory sequence affects the expression of the linked coding sequence. "Regulatory sequences," "regulatory elements," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule. In a further example, a right and left T-DNA border when operably linked to a T-DNA sequence will allow the transfer of the T-DNA from a plasmid to another location.

When used in reference to two or more amino acid sequences, the term "operably linked" means that the first amino acid sequence is in a functional relationship with at least one of the additional amino acid sequences.

As used herein, the term "transformation" or "transforming" refers to the transfer and integration of a nucleic acid or fragment thereof into a host organism, resulting in genetically stable inheritance. Host organisms containing a transforming nucleic acid are referred to as "transgenic," "recombinant," or "transformed" organisms. Known methods of transformation include, for example: *Agrobacterium*-mediated transformation (e.g., using a *Agrobacterium tumefaciens, Agrobacterium rhizogenes*, or another *Agrobacterium* bacterial strain to transform the plant material); calcium phosphate transformation; polybrene transformation; electroporation; ultrasonic methods (e.g., sonoporation); liposome transformation; microinjection; transformation with naked DNA; transformation with plasmid vectors; transformation with viral vectors; biolistic transformation (e.g., microparticle bombardment); silicon carbide WHISKERS™-mediated transformation; aerosol beaming; and PEG-mediated transformation.

The terms "plasmid" and "vector," as used herein are interchangeable and refer to a recombinant element that can autonomously replicate or integrate into a chromosome in a host cell and which carries one or more gene(s) that are heterologous to the host cell. Plasmids and vectors typically are circular double-stranded DNA molecules. However, plasmids and vectors may be linear or circular nucleic acids, of a single- or double-stranded DNA or RNA, and may be derived from any source, in which a number of nucleotide sequences have been joined or recombined into a unique construction that is capable of introducing a promoter fragment and a coding polynucleotide sequence along with any appropriate 3' untranslated sequence into a cell. In examples, plasmids and vectors may comprise autonomously replicating sequences, genome integrating sequences, and/or phage or nucleotide sequences.

The term "gene expression cassette" refers to a nucleic acid construct comprising a heterologous nucleic acid which encodes a polypeptide under the control of a promoter, and terminated by a 3'-UTR.

The term "selectable marker" refers to a gene or polynucleotide whose expression allows identification of cells that have been transformed with a DNA construct or vector containing the gene or polynucleotide. Non-limiting examples of selectable markers include herbicide tolerance, antibiotic resistance, and visual reporter markers.

The term "synthesis" or "synthesize," refers to formation of a particular chemical compound from its constituent parts using an enzymatic synthesis or chemical processes.

The term "derivative," as used herein, refers to a modification of a sequence set forth in the present disclosure. Illustrative of such modifications would be the substitution, insertion, and/or deletion of one or more bases relating to a nucleic acid sequence of a coding sequence or an operon within a plasmid/vector disclosed herein that preserve, slightly alter, or increase the function of a coding sequence disclosed herein in bacterial species. Such derivatives can be readily determined by one skilled in the art, for example, using computer modeling techniques for predicting and optimizing sequence structure. The term "derivative" thus also includes nucleic acid sequences having substantial sequence identity with the disclosed coding sequences herein such that they are able to have the disclosed functionalities for use in producing embodiments of the present disclosure.

DETAILED DESCRIPTION

The disclosed invention provides a new class of polypeptides each referred to herein as a cytokinin synthase. The disclosed invention also provides polynucleotides that encode the cytokinin synthase. The cytokinin synthase of the invention has two domains: an isopentenyl transfer (IPT)-like domain and a phosphoribohydrolase (PRH)-like domain. In particular embodiments, the IPT-like domain and the PRH-like domain can be covalently linked together, as shown in FIG. 1.

Unlike conventional adenosine phosphate isopentenyltransferases (IPTs) in plants and *Agrobacterium*, the disclosed cytokinin synthase is covalently linked to a PRH-like domain. Furthermore, the IPT-like domain of the disclosed cytokinin synthase does not closely resemble the amino acid sequences of known IPTs in plants or Agrobacteria, nor does it closely resemble known tRNA-IPT enzymes. For example, the *Epichloe festucae* cytokinin synthase (EfCKS) disclosed herein comprises an IPT-like domain with less than 30% sequence identity to yeast tRNA-IPT and even lower sequence identity to plant (*Arabidopsis*) adenylate isopentenyltransferase (plant IPT1) and less than 10% sequence identity to the canonical *Agrobacterium* IPT. Surprisingly, the disclosed cytokinin synthase exhibits activity in multiple assays for de novo biosynthesis of cytokinin (iP) from adenosine 5'monophosphate (AMP).

The surprising nature of the activity disclosed herein is underscored by the fact that there is very little characterization of enzymes containing PRH domains. Moreover, genes that encode PRH-like domains are found in many organisms that do not make cytokinins. Therefore, the disclosed cyto-kinin synthase activity was not predictable before the invention disclosed herein linked cytokinin synthases to cytokinin production.

Isolated Polynucleotides and Codon-Optimized Polynucleotides

In one aspect, the invention provides an isolated polynucleotide that includes a sequence encoding the two-domain cytokinin synthase disclosed herein. As used herein the term isolated means that the polynucleotide has been removed from its natural environment or that the polynucleotide has been non-naturally synthesized or amplified, e.g., in a laboratory or industrial setting. Thus, in one embodiment the invention provides an isolated polynucleotide that encodes the cytokinin synthase of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS). The invention also provides an isolated polynucleotide that encodes the cytokinin synthase of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54. In certain embodiments, the isolated polynucleotide is a purified polynucleotide, e.g., one that is substantially free of other molecules normally associated with such a polynucleotide or a similar one in its native or natural environment. Accordingly, for example, the isolated polynucleotide encoding the cytokinin synthase of SEQ ID NO:3, SEQ ID NO:9, SEQ ID NO:13, SEQ ID NO:17, SEQ ID NO:21, or SEQ ID NO:25 can be purified so that the isolated polynucleotide is more than 50%, more than 60%, more than 70%, more than 80, more than 90%, more than 95%, more than 96%, more than 97%, more than 98%, or more than 99% free of non-polynucleotide, cellular material by dry weight. Also, for example, the isolated polynucleotide encoding the cytokinin synthase of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54 can be purified so that the isolated polynucleotide is more than 50%, more than 60%, more than 70%, more than 80, more than 90%, more than 95%, more than 96%, more than 97%, more than 98%, or more than 99% free of non-polynucleotide, cellular material by dry weight. Methods of achieving and confirming the purity of polynucleotides are known in the art. See e.g., Tan et al., *J. Biomedicine and Biotech.*, Article ID 574398 (2009); Sambrook et al., *Molecular Cloning: A Laboratory Manual*, Third Edition, Cold Spring Harbor Laboratory Press, Cold Spring Harbor, N.Y. (2001); and Adila et al. *Mal. J. Microbiol.*, 3(1): 7-13 (2007).

In particular embodiments, the isolated polynucleotide encoding the foregoing cytokinin synthase is SEQ ID NO:1 (EfCKS), SEQ ID NO:8 (AtCKS), SEQ ID NO:12 (BoCKS), SEQ ID NO:16 (IrCKS), SEQ ID NO:20 (AhCKS), or SEQ ID NO:24 (FfCKS), respectively; and in certain examples of these embodiments, the isolated polynucleotide is purified so that the isolated polynucleotide is more than 50%, more than 60%, more than 70%, more than 80, more than 90%, more than 95%, more than 96%, more than 97%, more than 98%, or more than 99% free of non-polynucleotide, cellular material by dry weight.

In other embodiments, the invention provides an isolated polynucleotide encoding a cytokinin synthase that is homologous to each of the foregoing cytokinin synthases, wherein the encoded homolog has cytokinin synthase activity. The isolated polynucleotide includes a polynucleotide encoding a cytokinin synthase that is substantially homologous to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), SEQ ID NO:25 (FfCKS), SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54. As shown by the amino acid sequence identity analysis in Example 4, the invention provides polynucleotides and encoded cytokinin synthases that have at least 57% or 58% amino acid sequence identity to one of SEQ ID NO:3 (EfCKS), SEQ ID NO:9 (AtCKS), SEQ ID NO:13 (BoCKS), SEQ ID NO:21 (AhCKS), or SEQ ID NO:25 (FfCKS) and have cytokinin synthase activity. The invention also provides polynucleotides and encoded cytokinin synthases that have at least 60%, at least 62%, at least 63%, at least 64% at least 65%, at least 66%, at least 67%, at least 70%, or at least 75% amino acid sequence identity to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS) and have cytokinin synthase activity. In another embodiment, the invention provides polynucleotides and encoded cytokinin synthases that have from about 80% to about 100% amino acid sequence identity to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS). In certain examples, the isolated polynucleotide encodes a cytokinin synthase that has about 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more amino acid sequence identity to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS). In additional examples, the invention provides an isolated polynucleotide that encodes a cytokinin synthase that has about 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more amino acid sequence identity to one of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54. Optionally, the isolated polynucleotide encoding a cytokinin synthase is purified so that the isolated polynucleotide is more than 50%, more than 60%, more than 70%, more than 80, more than 90%, more than 95%, more than 96%, more than 97%, more than 98%, or more than 99% free of non-polynucleotide, cellular material by dry weight. Amino acids that may be varied and those that should be largely conserved in homologous cytokinin synthases are discussed in more detail below. The cytokinin synthase activity homologous cytokinin synthases can be determined by any method, e.g., the methods disclosed herein or known in the art.

In still another embodiment, the invention provides additional isolated polynucleotide that encodes a cytokinin synthase, wherein the polynucleotide is substantially homologous to one of SEQ ID NO:1 (EfCKS), SEQ ID NO:8 (AtCKS), SEQ ID NO:12 (BoCKS), SEQ ID NO:16 (IrCKS), SEQ ID NO:20 (AhCKS), or SEQ ID NO:24 (FfCKS). The substantially homologous isolated polynucleotide can have, for example, from about 80% to about 100% nucleotide sequence identity to one of SEQ ID NO:1 (EfCKS), SEQ ID NO:8 (AtCKS), SEQ ID NO:12 (BoCKS), SEQ ID NO:16 (IrCKS), SEQ ID NO:20 (AhCKS), or SEQ ID NO:24 (FfCKS). For example, the polynucleotide can have about 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more nucleotide sequence identity to one of SEQ ID NO:1 (EfCKS), SEQ ID NO:8 (AtCKS), SEQ ID NO:12 (BoCKS), SEQ ID NO:16 (IrCKS), SEQ ID NO:20 (AhCKS), or SEQ ID NO:24 (FfCKS). Optionally, this isolated polynucleotide encoding a cytokinin synthase is purified so that the isolated polynucleotide is more than 50%, more than 60%, more than 70%, more than 80, more than 90%, more than 95%, more than 96%, more than 97%, more than 98%, or more than 99% free of non-polynucleotide, cellular material by dry weight.

In another aspect, the invention also provides an isolated polynucleotide encoding any of the cytokinin synthases disclosed herein, wherein the coding sequence is codon-optimized for expression in a host cell. Specific host cells and methods for codon-optimizing the coding sequence are known in the art and described herein. Thus in one embodiment of this aspect, the invention provides an isolated polynucleotide that includes a coding sequence that (i) encodes the cytokinin synthase of one of SEQ ID NO:3, SEQ ID NO:9, SEQ ID NO:13, SEQ ID NO:17, SEQ ID NO:21, or SEQ ID NO:25 and (ii) is codon-optimized for expression in a host cell such as, for example, bacteria, yeast, plant, dicot plant, monocot plant, maize, soybean, canola, cotton, wheat, *Arabidopsis thaliana*, rice, sunflower, grass, creeping bentgrass, tall fescue, tobacco, or poplar hybrid cell. In another embodiment, the invention provides an isolated polynucleotide that includes a coding sequence that (i) encodes the cytokinin synthase of one of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54 and (ii) is codon-optimized for expression in a host cell such as, for example, bacteria, yeast, plant, dicot plant, monocot plant, maize, soybean, canola, cotton, wheat, *Arabidopsis thaliana*, rice, sunflower, grass, creeping bentgrass, tall fescue, tobacco, or poplar hybrid cell.

In a further embodiment, the invention provides an isolated polynucleotide that includes a coding sequence that (i) encodes a cytokinin synthase having at least about 57%, at least about 58%, at least 60%, at least 62%, at least 63%, at least 64% at least 65%, at least 66%, at least 67%, at least 70%, or at least 75% amino acid sequence identity to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS) and (ii) is codon-optimized for expression in a host cell such as, for example, bacteria, yeast, plant, dicot plant, monocot plant, maize, soybean, canola, cotton, wheat, Arabidopsis thaliana, rice, sunflower, grass, creeping bentgrass, tall fescue, tobacco, or poplar hybrid cell. In certain embodiments, the invention provides an isolated polynucleotide that includes a coding sequence that (i) encodes a cytokinin synthase having from about 80% to about 100% amino acid sequence identity to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS) and (ii) is codon-optimized for expression in a host cell such as, for example, bacteria, yeast, plant, dicot plant, monocot plant, maize, soybean, canola, cotton, wheat, Arabidopsis thaliana, rice, sunflower, grass, creeping bentgrass, tall fescue, tobacco, or poplar hybrid cell. For example, the codon-optimized isolated polynucleotide can encode a cytokinin synthase having about 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more amino acid sequence identity to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS). In another example, the invention provides an isolated polynucleotide that includes a coding sequence that (i) encodes a cytokinin synthase having about 80% or more; 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more amino acid sequence identity to one of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54 and (ii) is codon-optimized for expression in a host cell such as, for example, bacteria, yeast, plant, dicot plant, monocot plant, maize, soybean, canola, cotton, wheat, Arabidopsis thaliana, rice, sunflower, grass, creeping bentgrass, tall fescue, tobacco, or poplar hybrid cell. Amino acids that may be varied and those that should be largely conserved in homologous cytokinin synthases are discussed in more detail below. Optionally, the isolated codon-optimized polynucleotide encoding a cytokinin synthase is purified so that the isolated polynucleotide is more than 50%, more than 60%, more than 70%, more than 80, more than 90%, more than 95%, more than 96%, more than 97%, more than 98%, or more than 99% free of non-polynucleotide, cellular material by dry weight.

The codon-optimized polynucleotides of the invention can be codon optimized for expression in bacteria, yeast, plant, dicot plant, monocot plant, maize (Zea mays), soybean (Glycine max), canola (Brassica napus or Brassica rapa), cotton (Gossypium hirsutum or Gossypium barbadense, wheat (e.g., Triticum aestivum or Triticum durum), or Arabidopsis thaliana, rice (e.g., Oryza sativa). In other embodiments the codon-optimized polynucleotides of the invention can be codon optimized for expression in sunflower (Helianthus annuus), grass, creeping bentgrass (e.g., Agrostis stolonifera), tall fescue (Festuca arundinacea), tobacco (Nicotiana tabacum), and poplar (e.g., members of genus Populus) hybrid or Liriodendron tulipifera. Methods of optimizing codon based on the codon usage frequency and patterns observed in particular species are well known and can be done, for example, using publicly available codon usage databases and software packages. See, e.g., Nakamura et al., Nucl. Acids Res., 28(1): 292 (2000); Bode et al., Nucl. Acids Res., 37 (Web Server issue):W214-221 (2009); Liu et al., Mol. Biol. Rep., 37(2)6777-684 (2010); Y. Batard et al., Arch. Biochem. Biophys., 379: 161-169 (2000); Gustafsson et al., Trends in Biotech, 22(7): 346-3536 (2004).

Any of the isolated polynucleotides of the invention can be synthesized de novo using methods for artificial gene synthesis that do not require pre-existing nucleic acid template. In some embodiments, such methods involve solid-phase DNA synthesis of gene fragments that are subsequently assembled, e.g., by annealing, ligation, and/or polymerase reactions to generate a completely synthetic isolated polynucleotides of the invention. See, e.g., Schwartz et al., Nat. Methods, 9(9): 913-915 (2012) and Tian et al., Mol. BioSyst., 5:714-722 (2009). In other embodiments, the isolated polynucleotides of the invention can be generated by more conventional recombinant techniques such as cloning, amplification by polymerase chain reaction (PCR), and/or mutagenesis (if needed). For example, cDNA encoding a cytokinin synthase may be generated from a plant associated fungus such as Epichloe festucae, Epichloe gansuensis, Balansia obtecta, Ilyonectria radicola, Aciculosporium take, Atkinsonella hypoxylon, or Fusarium fujikuroi to make a non-natural polynucleotide encoding a two-domain cytokinin synthase of the invention such as EfCKS, BoCKS, IrCKS, AtCKS, AhCKS, or FfCKS, respectively. Such cDNA may be modified by PCR, mutagenesis, site directed mutagenesis to make a variant, e.g., a codon-optimized, isolated polynucleotide of the invention.

Recombinant Polynucleotides, Host Cells and Related Methods

In a further aspect, the invention provides a recombinant polynucleotide that includes any of the cytokinin synthase-encoding polynucleotides disclosed herein covalently linked to a heterologous polynucleotide sequence. The heterologous sequence can be any sequence not found in nature covalently linked to the cytokinin synthase coding sequence. Examples of such a heterologous sequence include a heterologous promoter sequence, vector sequence, a gene cassette sequence, a promoter sequence, a termination sequence, or a sequence encoding a protein fusion tag.

Figure 6:
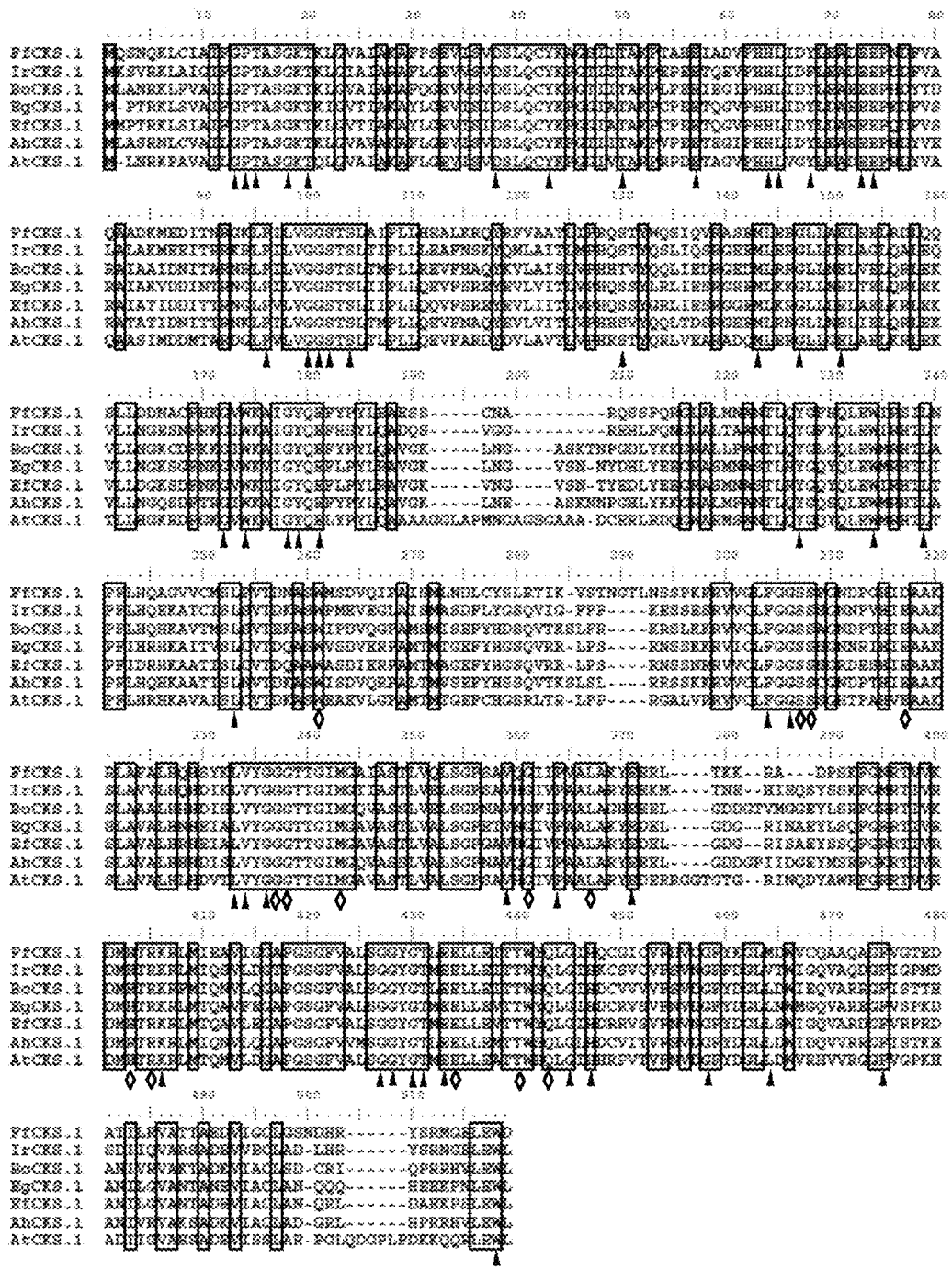
FIG. 6 is a sequence alignment of cytokinin synthases of the invention that shows conserved residues (boxed areas) and the effect of mutations on indicated conserved residues: severe effect on activity indicated by wedge (▲) or small effect on activity indicated by open diamond (◇).
Figure 30:
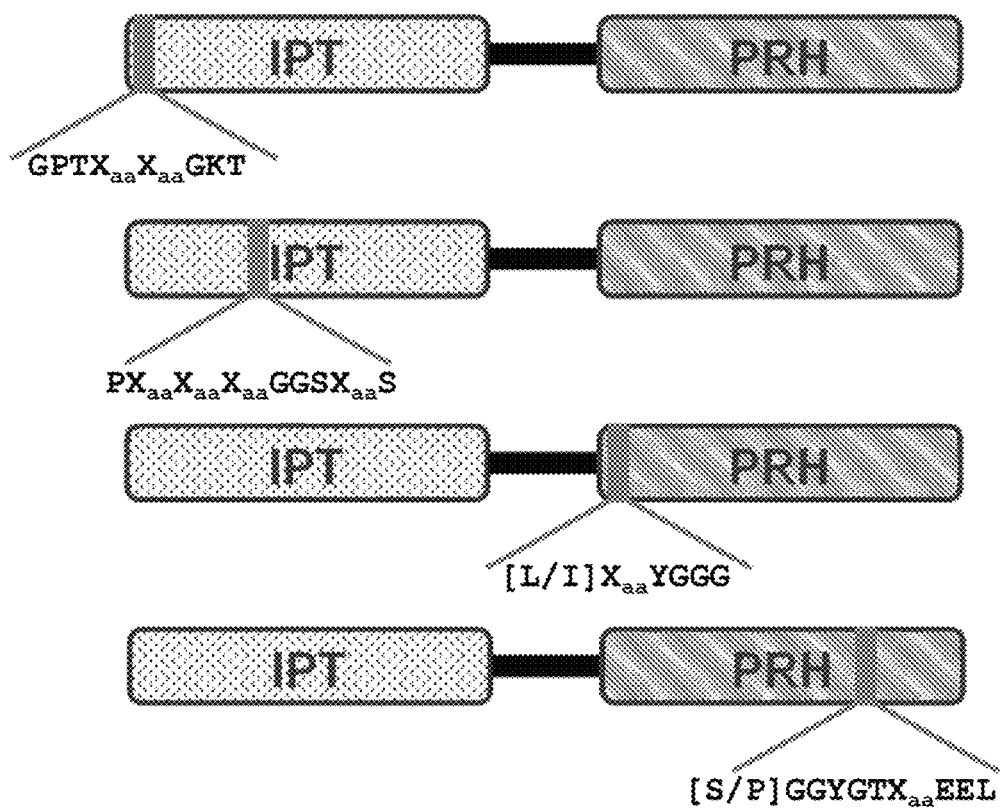
FIG. 30 is a set of schematic diagrams showing four functional motifs and their locations within the domain architecture of cytokinin synthases disclosed herein.

Thus, in one embodiment, the invention provides a recombinant polynucleotide that includes a heterologous sequence covalently linked to one of the following sequences encoding a polypeptide with cytokinin synthase activity, wherein the linked coding sequence:

(i) encodes the cytokinin synthase SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS);

(ii) encodes a cytokinin synthase that is substantially homologous to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS);

(iii) encodes a cytokinin synthase that has about 57% or more, about 58% or more, about 60% or more, about 62% or more, about 63% or more, about 64% or more, about 65% or more, about 66% or more, about 67% or more, about 70% or more, about 75% or more, about 80% or more, about 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more amino acid sequence identity to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS);

(iv) includes SEQ ID NO:1 (EfCKS), SEQ ID NO:8 (AtCKS), SEQ ID NO:12 (BoCKS), SEQ ID NO:16 (IrCKS), SEQ ID NO:20 (AhCKS), or SEQ ID NO:24 (FfCKS);

(v) includes a sequence that is substantially homologous to one of SEQ ID NO:1 (EfCKS), SEQ ID NO:8 (AtCKS), SEQ ID NO:12 (BoCKS), SEQ ID NO:16 (IrCKS), SEQ ID NO:20 (AhCKS), or SEQ ID NO:24 (FfCKS);

(vi) includes a sequence that has about 57% or more, about 58% or more, about 60% or more, about 62% or more, about 63% or more, about 64% or more, about 65% or more, about 66% or more, about 67% or more, about 70% or more, about 75% or more, about 80% or more, 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more nucleotide sequence identity to one of SEQ ID NO:1 (EfCKS), SEQ ID NO:8 (AtCKS), SEQ ID NO:12 (BoCKS), SEQ ID NO:16 (IrCKS), SEQ ID NO:20 (AhCKS), or SEQ ID NO:24 (FfCKS);

(vii) includes codon-optimized sequence encoding the cytokinin synthase of one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS), (viii) includes codon-optimized sequence encoding a cytokinin synthase having has about 57% or more, about 58% or more, about 60% or more, about 62% or more, about 63% or more, about 64% or more, about 65% or more, about 66% or more, about 67% or more, about 70% or more, about 75% or more, about 80% or more, 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more amino acid sequence identity to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS);

(ix) includes codon-optimized sequence encoding cytokinin synthase variant having about 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more amino acid sequence identity to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS), (x) encodes the cytokinin synthase of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54;

(xi) encodes a cytokinin synthase that is substantially homologous to one of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54;

(xii) encodes a cytokinin synthase that has about 57% or more, about 58% or more, about 60% or more, about 62% or more, about 63% or more, about 64% or more, about 65% or more, about 66% or more, about 67% or more, about 70% or more, about 75% or more, about 80% or more, about 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more amino acid sequence identity to one of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54, (xiii) includes a codon optimized sequence that encodes the cytokinin synthase of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54, (xiv) includes a codon optimized sequence that encodes a cytokinin synthase that has about 57% or more, about 58% or more, about 60% or more, about 62% or more, about 63% or more, about 64% or more, about 65% or more, about 66% or more, about 67% or more, about 70% or more, about 75% or more, about 80% or more, about 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more amino acid sequence identity to one of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54 or (xv) the two-domain cytokinin synthase coding sequences of any one of foregoing (i)-(xiv), wherein the coding sequence, when aligned with the consensus sequence (of SEQ ID NO:3, SEQ ID NO:9, SEQ ID NO:13, SEQ ID NO:17, SEQ ID NO:21, and SEQ ID NO:25) in FIG. 6, also includes (i) a first motif: GPTXaa$_1$Xaa$_2$GKT (SEQ ID NO:30), wherein Xaa$_1$ is G or A and Xaa$_2$ is V, S, A, or T, at consensus sequence amino acid positions 13-20; (ii) a second motif: PXaa$_3$Xaa$_4$Xaa$_5$GGSXaa$_6$S (SEQ ID NO:31), wherein Xaa$_3$ is I or V, Xaa$_4$ is L or V, Xaa$_5$ is V or C, and Xaa$_6$ is T or I, at consensus sequence amino acid positions 96-104; (iii) a third motif: Xaa$_7$Xaa$_8$YGGG (SEQ ID NO:32), wherein Xaa$_7$ is L or I, and Xaa$_8$ is V or I, at consensus sequence amino acid positions 333-338, and (iv) a fourth motif: Xaa$_9$GGYGT Xaa$_{10}$EEL (SEQ ID NO:33), where Xaa$_9$ is S or P and Xaa$_{10}$ is L or M, at consensus sequence amino acid positions 426-438. The term "when aligned with the consensus sequence" in FIG. 6, means that the cytokinin synthase coding sequence of (xv) is aligned with SEQ ID NO:3, SEQ ID NO:9, SEQ ID NO:13, SEQ ID NO:17, SEQ ID NO:21, and SEQ ID NO:25, as described in Example 6 herein. The schematic in FIG. 30 shows the relative positions of the four motifs within a two-domain cytokinin synthase coding sequence of (xv).

In certain embodiments of the invention, the recombinant polynucleotide includes any of the foregoing two-domain cytokinin synthase coding sequences (i)-(xv) covalently linked to a vector sequence, expression cassette, heterologous promoter (e.g., a plant promoter, bacterial promoter, a heterologous fungal promoter, or a yeast promoter), or heterologous terminator sequence (e.g., for use in plants, bacteria, or yeast). The recombinant polynucleotide can be used for recombinant expression of the encoded cytokinin synthase in a host cell such as a bacteria, yeast or plant. Thus, the recombinant polynucleotide can include the coding sequence of (vii), (viii), (ix), (xiii), (xiv), or (xv) which is codon-optimized for expression in bacteria and which is covalently linked to bacterial vector, expression cassette, and/or promoter. The recombinant polynucleotide can include the coding sequence (vii), (viii), (ix), (xiii), (xiv), or (xv) which is coding optimized for expression in yeast and which is covalently linked to yeast vector, expression cassette, and/or promoter. The recombinant polynucleotide can include the coding sequence (vii), (viii), (ix), (xiii), (xiv), or (xv) which is coding optimized for expression in a plant and which is covalently linked to plant vector, expression cassette, and/or promoter. In particular examples, recombinant polynucleotide includes the coding sequence (vii), (viii), (ix), (xiii), (xiv), or (xv) which is optimized for expression in a dicot plant or a monocot plant and which is covalently linked to a vector, expression cassette, and/or promoter for a dicot plant or monocot plant, respectively. In other particular examples, recombinant polynucleotide includes the coding sequence (vii), (viii), or (ix), (xiii), (xiv), or (xv) which is optimized for expression in a maize, soybean, canola, cotton, wheat, or *Arabidopsis thaliana* and which is covalently linked to a vector, expression cassette, and/or promoter for maize, soybean, canola, cotton, wheat, or *Arabidopsis thaliana*, respectively. In still other particular examples, recombinant polynucleotide includes the coding sequence of (vii), (viii), (ix), (xiii), (xiv), or (xv) which is optimized for expression in rice, sunflower, grass, creeping bentgrass, tall fescue, tobacco, or poplar hybrid and which is covalently linked to a vector, expression cassette, and/or promoter for rice, sunflower, grass, creeping bentgrass, tall fescue, tobacco, or poplar hybrid, respectively. Vectors, expression cassettes, and promoters are discussed in more detail below.

In additional examples, the recombinant polynucleotide can include the coding sequence of (vii), (viii), (ix), (xiii), (xiv), or (xv) which is coding optimized for expression in a plant and which is covalently linked to plant vector or expression cassette. The recombinant polynucleotide can include the coding sequence of (vii), (viii), (ix), (xiii), (xiv), or (xv) which is coding optimized for expression in yeast or bacteria host cell and which is covalently linked to yeast promoter or bacterial promoter, respectively.

In other embodiments of the invention, the recombinant polynucleotide includes any of the foregoing two-domain cytokinin synthase coding sequences (i)-(ix) covalently linked to a sequence encoding a protein fusion tag. The encoded protein fusion tag can be a poly-histidine, poly-arginine, haloalkane dehalogenase, streptavidin-binding, glutathione s-transferase (GST), maltose-binding protein (MBP), thioredoxin, small ubiquitin-like modifier (SUMO), N-utilization substance A (NusA), protein disulfide isomerase I (DsbA), Mistic, Ketosteroid isomerase (KSI), or TrpE, c-myc, hemaglutinin antigen (HA), FLAG, 1D4, calmodulin-binding peptide, chitin-binding domain, cellulose-binding domain, S-tag, or Softag3 protein fusion tag. These can be used in methods of producing, isolating, or purifying any cytokinin synthase of the invention.

Host Cells, Plants, and Methods of Making Recombinant Cytokinin Synthase of the Invention In another aspect the invention also provides a host cell that includes any embodiment or example of the isolated or recombinant polynucleotide disclosed herein that encodes a cytokinin synthase. In another aspect the invention provides a method of making such a host cell that includes, transforming or transfecting the isolated or recombinant polynucleotide of the invention into a host cell. Accordingly, the invention provides a bacteria, yeast or plant host cell which harbors the recombinant polynucleotide disclosed above that includes one (or more) of the foregoing two-domain cytokinin synthase coding sequences (i)-(ix). In certain embodiments, the two domain recombinant polynucleotide includes the codon-optimized two-domain cytokinin synthase coding sequences (vii), (viii), or (ix) in the appropriate host cell for which the polynucleotide is codon-optimized. For example, the invention provides a bacteria cell that includes the codon-optimized two-domain cytokinin synthase coding sequence (vii), (viii), or (ix), which is optimized for bacteria. In another example, the invention provides a yeast cell that includes the codon-optimized two-domain cytokinin synthase coding sequence (vii), (viii), or (ix), which is optimized for yeast. Methods for the transformation or transfection of bacterial and yeast host cells are known in the art. See, e.g., Sambrook et al., *Molecular Cloning: A Laboratory Manual*, Third Edition, Cold Spring Harbor Laboratory Press, Cold Spring Harbor, N.Y. (2001) and Ausubel et al., *Current Protocols in Molecular Biology*, published by Greene Publishing Assoc. and Wiley-Interscience (1987).

In still other examples, the invention provides: a transgenic dicot plant cell that includes the codon-optimized two-domain cytokinin synthase coding sequence (vii), (viii), (ix), (xiii), (xiv), or (xv) which is optimized for dicots; a transgenic monocot plant cell that includes the codon-optimized two-domain cytokinin synthase coding sequence (vii), (viii), (ix), (xiii), (xiv), or (xv) which is codon-optimized for monocots; a transgenic maize plant cell that includes the codon-optimized two-domain cytokinin synthase coding sequence (vii), (viii), or (ix), which is codon-optimized for maize; a transgenic soybean plant cell that includes the codon-optimized two-domain cytokinin synthase coding sequence (vii), (viii), (ix), (xiii), (xiv), or (xv) which is codon-optimized for soybean; a transgenic canola plant cell that includes the codon-optimized two-domain cytokinin synthase coding sequence (vii), (viii), (ix), (xiii), (xiv), or (xv) which is codon-optimized for canola; a transgenic cotton plant cell that includes the codon-optimized two-domain cytokinin synthase coding sequence (viii) or (ix) which is optimized for cotton; a transgenic wheat plant cell that includes the codon-optimized two-domain cytokinin synthase coding sequence (vii), (viii), (ix), (xiii), (xiv), or (xv) which is optimized for wheat; and a transgenic *Arabidopsis thaliana* plant cell that includes the codon-optimized two-domain cytokinin synthase coding sequence (vii), (viii), (ix), (xiii), (xiv), or (xv) which is optimized for *Arabidopsis thaliana*. In yet other examples the invention provides: a transgenic rice plant cell that includes the codon-optimized two-domain cytokinin synthase coding sequence (vii), (viii), (ix), which is codon-optimized for rice; a transgenic sunflower plant cell that includes the codon-optimized two-domain cytokinin synthase coding sequence (vii), (viii), (ix), (xiii), (xiv), or (xv) which is codon-optimized for sunflower; a transgenic creeping bentgrass plant cell that includes the codon-optimized two-domain cytokinin synthase coding sequence (vii), (viii), (ix), (xiii), (xiv), or (xv) which is codon-optimized for creeping bentgrass; a transgenic tall fescue plant cell that includes the codon-optimized two-domain cytokinin synthase coding sequence (vii), (viii), (ix), (xiii), (xiv), or (xv) which is codon-optimized for tall fescue; a transgenic tobacco plant cell that includes the codon-optimized two-domain cytokinin synthase coding sequence (vii), (viii), (ix), (xiii), (xiv), or (xv) which is codon-optimized for tobacco; and a transgenic poplar cell that includes the codon-optimized two-domain cytokinin synthase coding sequence (vii), (viii), (ix), (xiii), (xiv), or (xv) which is codon-optimized for poplar.

In another aspect, the invention provides a transgenic plant that is regenerated from any of the foregoing plant host cells. In this regard the recombinant polynucleotide can include the codon-optimized coding sequence of (vii), (viii), (ix), (xiii), (xiv), or (xv) described above, which is covalently linked to a vector or expression cassette for the plant transformant. For example, the invention provides a transgenic dicot plant that includes codon-optimized coding sequence (vii), (viii), (ix), (xiii), (xiv), or (xv) which is optimized for dicots and which is for example in an appropriate vector or expression cassette; a transgenic monocot plant that includes codon-optimized coding sequence (vii), (viii), (ix), (xiii), (xiv), or (xv) which is codon-optimized for monocots; a transgenic maize plant that includes codon-optimized coding sequence (vii), (viii), (ix), (xiii), (xiv), or (xv) which is codon-optimized for maize; a transgenic soybean plant that includes codon-optimized coding sequence (vii), (viii), (ix), (xiii), (xiv), or (xv) which is codon-optimized for soybean; a transgenic canola plant that includes codon-optimized coding sequence (vii), (viii), (ix), (xiii), (xiv), or (xv) which is codon-optimized for canola; a transgenic cotton plant that includes codon-optimized coding sequence (vii), (viii), (ix), (xiii), (xiv), or (xv) which is optimized for cotton; a transgenic wheat plant that includes codon-optimized coding sequence (viii) (ix), (xiii), (xiv), or (xv) which is optimized for wheat; a transgenic *Arabidopsis thaliana* plant that includes the codon-optimized two-domain cytokinin synthase coding sequence (vii), (viii), (ix), (xiii), (xiv), or (xv) which is optimized for *Arabidopsis thaliana*, and a transgenic rice plant that includes codon-optimized coding sequence (vii), (viii), (ix), (xiii), (xiv), or (xv) which is codon-optimized for rice. In yet other examples the invention provides: a transgenic sunflower plant that includes the codon-optimized coding sequence (vii), (viii), (ix), (xiii), (xiv), or (xv) which is codon-optimized for sunflower; a transgenic creeping bentgrass plant that includes codon-optimized two-domain cytokinin synthase coding sequence (vii), (viii), (ix), (xiii), (xiv), or (xv) which is codon-optimized for creeping bentgrass; a transgenic tall fescue plant that includes the codon-optimized two-domain cytokinin synthase coding sequence (vii), (viii), (ix), (xiii), (xiv), or (xv) which is codon-optimized for tall fescue; a transgenic tobacco plant that includes the codon-optimized two-domain cytokinin synthase coding sequence (vii), (viii), (ix), (xiii), (xiv), or (xv) which is codon-optimized for tobacco; and a transgenic poplar that includes the codon-optimized two-domain cytokinin synthase coding sequence (vii), (viii), (ix), (xiii), (xiv), or (xv) which is codon-optimized for poplar.

Methods of transforming plants to make transgenic plants are known in the art and discussed in more detail below.

The invention also provides methods of making a recombinant cytokinin synthase disclosed herein. In one aspect the method includes expressing cytokinin synthase in any of the foregoing host cells which includes any of the two-domain cytokinin synthase coding sequences (i)-(xv). In certain embodiments, the host cell has includes a recombinant polynucleotide in which the cytokinin synthase coding sequence of any one of (i)-(xv) disclosed above is covalently linked to a sequence encoding a protein fusion tag to facilitate detecting, isolating, and or purifying the cytokinin synthase encoded by anyone of (i)-(xv). In particular embodiments, the host cell includes a recombinant polynucleotide that includes the codon-optimized two-domain cytokinin synthase coding sequences (vii), (viii), (ix), (xiii), (xiv), or (xv) in the appropriate host cell for which the polynucleotide is codon-optimized. For example, the method of making a recombinant cytokinin synthase of the invention can include expressing cytokinin synthase in a bacteria cell that includes the codon-optimized two-domain cytokinin synthase coding sequence (vii), (viii), (ix), (xiii), (xiv), or (xv) which is optimized for bacteria and which, optionally, is covalently linked to a protein fusion tag. In another example, the method can include expressing cytokinin synthase in a yeast cell that includes the codon-optimized two-domain cytokinin synthase coding sequence (vii), (viii), (ix), (xiii), (xiv), or (xv) which is optimized for yeast and which, optionally, is covalently linked to a protein fusion tag.

In further embodiments the method can include isolating the expressed cytokinin synthase from the host cell and, optionally, purifying the encoded cytokinin synthase so that it is more than 50%, more than 60%, more than 70%, more than 80, more than 90%, more than 95%, more than 96%, more than 97%, more than 98%, or more than 99% free of host cellular material, e.g., by dry weight.

Isolated or Recombinant Cytokinin Synthase of the Invention

In another aspect, the invention provides an isolated or recombinant cytokinin synthase having two domains: an isopentenyl transfer (IPT)-like domain and a cytokinin nucleotide phosphoribohydrolase (PRH)-like domain. In one embodiment, the invention provides the isolated or recombinant cytokinin synthase of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS). In another embodiment, the invention provides the isolated or recombinant cytokinin synthase of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54. In certain embodiments, the isolated cytokinin synthase is purified and is substantially free of other molecules normally associated with such a polynucleotide or a similar one in its native or natural environment. Accordingly, for example, the isolated or recombinant cytokinin synthase of SEQ ID NO:3, SEQ ID NO:9, SEQ ID NO:13, SEQ ID NO:17, SEQ ID NO:21, SEQ ID NO:25, SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54 can be purified so that the cytokinin synthase is more than 50%, more than 60%, more than 70%, more than 80, more than 90%, more than 95%, more than 96%, more than 97%, more than 98%, or more than 99% free of cellular and other (non-cytokinin synthase) material by dry weight. The extent that purified cytokinin synthase is free of other material can be readily determined by art-known methods, including for example, analysis by SDS-PAGE and with protein staining. See e.g., Sambrook et al., *Molecular Cloning: A Laboratory Manual*, Third Edition, Cold Spring Harbor Laboratory Press, Cold Spring Harbor, N.Y. (2001).

In another embodiment, the invention provides an isolated or recombinant cytokinin synthase that is homologous to each of the foregoing cytokinin synthases and has cytokinin synthase activity. The isolated or recombinant cytokinin synthase can be substantially homologous to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), SEQ ID NO:25 (FfCKS), SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54. For example, the isolated or recombinant can have about 57% or more, about 58% or more, about 60% or more, about 62% or more, about 63% or more, about 64% or more, about 65% or more, about 66% or more, about 67% or more, about 70% or more, about 75% or more, or from about 80% to about 100% amino acid sequence identity to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS). In certain examples, the isolated or recombinant cytokinin synthase has about 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more amino acid sequence identity to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS). In further examples, the isolated or recombinant cytokinin synthase has about 80 or more; 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more amino acid sequence identity to one of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54. Optionally, the isolated or recombinant cytokinin synthase variant is purified so that the isolated polynucleotide is more than 50%, more than 60%, more than 70%, more than 80, more than 90%, more than 95%, more than 96%, more than 97%, more than 98%, or more than 99% free of cellular or other material by dry weight.

Amino acids may be varied by substitutions, deletions, or additions to the particular cytokinin synthase of the invention using the guidance provided by the sequence alignment shown at FIG. 6. The cytokinin synthase derivatives thus generated can be readily tested to confirm cytokinin synthase activity using any known method, e.g., the methods disclosed herein or methods known in the art. See, e.g., Barry et al., *Proc. Nat'l. Acad. Sci. USA*, 81: 4776-4780 (1984) and Kakimoto, *Plant Cell Physiol.*, 42 (7): 677-685 (2001). In this regard, the sequence of SEQ ID NO:25 (FfCKS) is only about 60% identical to the sequence of either SEQ ID NO:9 (AtCKS) or SEQ ID NO:21 (AhCKS), yet all three exhibit cytokinin synthase activity shown in FIG. 6. The sequences of SEQ ID NO:17 (IrCKS) is less than 70% identical to SEQ ID NO:3 (EfCKS) or SEQ ID NO:13 (BoCKS), yet all three of these also exhibit the cytokinin synthase activity shown in FIG. 6. Therefore, a person of ordinary skill in the art would understand that functional cytokinin synthase derivatives of the foregoing sequences can readily be made by multiple substitutions, deletions, or additions. In particular embodiments, functional cytokinin synthase derivatives can include multiple substitutions, deletions, or additions when most or all of the conserved amino acid residues identified in FIG. 6 are not varied.

Conserved amino acid residues within the cytokinin synthases in FIG. 6 are indicated by boxes. In particular embodiments of the invention, a cytokinin synthase derivative is made based on one of the sequences in FIG. 6, without varying any of the indicated conserved amino acids residues (except for the starting methionine at first position of the depicted sequences which can be readily varied, for example, when adding a protein fusion tag). In other embodiments, a small number (e.g., 1, 2, 3, 4, 5, or 6) of such conserved residues may be varied by conservative substitutions.

Additionally, cytokinin synthases can be varied at conserved amino acid positions identified as having a small effect of cytokinin synthase activity. FIG. 6 shows conserved amino acids that, when altered, have a small effect on activity by open diamond (indicated by open diamond ◇). Polynucleotides encoding cytokinin synthases that include mutations having a small effect on cytokinin synthase activity can be used when, for example, lower than wild type activity is desirable. Accordingly, the invention provides cytokinin synthases having activities that range from wild type activity to activities reduced by a small amount (e.g., mutants identified in FIG. 6 and Table 9 below as having a small effect). FIG. 6 also shows mutations to amino acids identified as having a severe effect on activity (indicated by wedge (▲) in FIG. 6. See Example 5 and Tables 8 and 9 below for more details on the effects of mutating various conserved amino acids in the cytokinin synthases specifically disclosed herein.

Additionally, considering the significant variation in sections of non-conserved amino acid residues (residues that are not boxed) among the cytokinin synthase sequences in FIG. 6 and the cytokinin synthase activity assay results disclosed in the Examples herein, it is readily apparent that each of the sequences of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), SEQ ID NO:25 (FfCKS) SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, and SEQ ID NO:54 can be varied to include up to 5, up to 10, up to 15, up to 20, up to 25, up to 30, up to 35, or up to 40 amino acid additions, deletions, or substitutions while still retaining cytokinin synthase activity. In this regard, a high probability of retaining activity will also occur if the variations are conservative substitutions. Amino acids may be placed in the following classes: non-polar, uncharged polar, basic, and acidic. Conservative substitutions whereby an amino acid of one class is replaced with another amino acid of the same type are least likely to materially alter the biological activity of the variant. Table 1 provides a listing of examples of amino acids belonging to each class.

TABLE 1

| Class of Amino Acid | Examples of Amino Acids |
| --- | --- |
| Nonpolar Side Chains | Ala, Val, Leu, Ile, Pro, Met, Phe, Trp |
| Uncharged Polar Side Chains | Gly, Ser, Thr, Cys, Tyr, Asn, Gln |
| Acidic Side Chains | Asp, Glu |
| Basic Side Chains | Lys, Arg, His |
| Beta-branched Side Chains | Thr, Val, Ile |
| Aromatic Side Chains | Tyr, Phe, Trp, His |

In some instances, non-conservative substitutions can also be made. The critical factor is that these substitutions must not significantly detract from the cytokinin synthase activity of the variant. Cytokinin synthase variants can also be designed that differ at the sequence level but that retain the same or similar overall essential three-dimensional structure, surface charge distribution, and the like. See, e.g., U.S. Pat. No. 7,058,515; Larson et al., *Protein Sci.*, 11: 2804-2813 (2002); Stemmer, *Nature*, 370: 389-391 (1994); Stemmer, *Bio/Technology*, 13: 549-553 (1995) and Crameri et al. *Nat. Med.*, 2: 100-103. (1996), Crameri et al., *Nat. Biotech.* 14: 315-319 (1996), Crameri et al., *Nat. Biotech.*, 15: 436-438 (1997), and U.S. Pat. No. 8,513,492. For example, conservative substitutions of alanine for methionine or leucine (shown at positions 343 or 367, respectively, of the consensus alignment in FIG. 6) did not substantially affect the activity of the cytokinin synthase mutant.

In particular examples of the foregoing, the isolated or recombinant cytokinin synthases is covalently linked to a protein fusion tag. Thus, the invention provides an isolated cytokinin synthase that includes a protein fusion tag linked to (a) the cytokinin synthase of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS);

(b) a cytokinin synthase that is substantially homologous to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS);

(c) a cytokinin synthase that has about 57% or more, about 58% or more, about 60% or more, about 62% or more, about 63% or more, about 64% or more, about 65% or more, about 66% or more, about 67% or more, about 70% or more, about 75% or more amino acid sequence identity to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS);

(d) a cytokinin synthase that has about 80% to about 100% amino acid sequence identity to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS);

(e) a cytokinin synthase that has about 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more amino acid sequence identity to one of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS), (f) a cytokinin synthase that includes the sequence of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), and SEQ ID NO:25 (FfCKS) with up to 5, up to 10, up to 15, up to 20, up to 25, up to 30, up to 35, or up to 40 amino acid additions, deletions, or substitutions, (g) the cytokinin synthase of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54, (h) a cytokinin synthase that has about 80% or more; about 81% or more; about 82% or more; about 83% or more; about 84% or more; about 85% or more; about 86% or more; about 87% or more; about 88% or more; about 89% or more; about 90% or more; about 91% or more; about 92% or more; about 93% or more; about 94% or more; about 95% or more; about 96% or more; about 97% or more; about 98% or more; about 98.5% or more; about 99% or more; about 99.5% or more; or about 99.9% or more amino acid sequence identity to one of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54, (i) a cytokinin synthase that includes the sequence of SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54 with up to 5, up to 10, up to 15, up to 20, up to 25, up to 30, up to 35, or up to 40 amino acid additions, deletions, or substitutions, or (j) the cytokinin synthase of any one of foregoing (a), (b), (c), (d), (e), (f), (g), (h), or (i), wherein the sequence, in alignment with coding sequences in FIG. 6, includes the motifs corresponding to FIG. 6 alignment consensus positions 13-20 (SEQ ID NO:30), at consensus positions 96-104 (SEQ ID NO:31), at consensus positions 333-338 (SEQ ID NO:32), and at consensus/alignment positions 426-438 (SEQ ID NO:33)

In particular examples, the cytokinin synthase of (a), (b), (c), (d), (e), (f), (g), (h), (i) or (j) is linked to a protein fusion tag that is a poly-histidine, poly-arginine, haloalkane dehalogenase, streptavidin-binding, glutathione s-transferase (GST), maltose-binding protein (MBP), thioredoxin, small ubiquitin-like modifier (SUMO), N-utilization substance A (NusA), protein disulfide isomerase I (DsbA), Mistic, Keto-steroid isomerase (KSI), or TrpE, c-myc, hemaglutinin antigen (HA), FLAG, 1D4, calmodulin-binding peptide, chitin-binding domain, cellulose-binding domain, S-tag, or Softag3 protein fusion tag.

Formulations of Cytokinins and Methods of Use

The isolated or recombinant cytokinins of the invention, e.g., the cytokinin synthase of (a), (b), (c), (d), (e), (f), (g), (h), (i) or (j) above, can be mixed with inert ingredients to create formulations which are useful for application to food crops, feed crops, vegetable crops, greenhouse food crops, greenhouse, non-food crops, outdoor residential plants forestry planting, and/or indoor residential plants.

Thus, the invention provides cytokinin synthase formulations that include a cytokinin (produced by a cytokinin synthase of the invention described herein) in mixture with one or more suitable inert ingredients suitable for application to one or more of the following plant classes:

Food crops: anise, asparagus, banana, broccoli, brussels sprouts, cabbage, carrot (including tops), catjang (jerusalem/marble pea), cauliflower, celery, cucumber, eggplant, fennel, garbanzos (including chick peas), garlic, leek, lettuce, melons, cantaloupe, honeydew, muskmelons, watermelons, okra, onion, parsley, peach, pepper, pepper (chili type), plantain, pumpkin, radish, shallot, spinach, squash (all or unspecified), strawberry, sweet potato, wheat, yam Food+Feed crops: apple; beans; beans, dried-type; beans, mung; beans, succulent (lima); beans, succulent (snap); beets; citrus fruits; corn; corn, field; corn (pop; or sweet); cotton; cowpea/blackeyed pea; grapes; leafy vegetables; orange; peanuts; peas, field; peas, pigeon; peas, southern; potato, white/irish; rice; sorghum; sorghum; soybeans sugar beet; tomato; triticale; wheat Feed crops: alfalfa, capes, lupine Greenhouse Food crops: asparagus; banana; beans; broccoli; broccoli, Chinese; Brussels sprouts; cabbage; carrot (including tops); cauliflower; celery; corn, pop; corn, sweet; cucumber; cucurbit vegetables; eggplant; lettuce; melons; nectarine; onion; parsley; parsley, turnip-rooted; peach; pepper; pepper (chili type); plantain; potato, white/irish; pumpkin; radish; shallot; spinach; squash (all or unspecified); squash (winter); squash (zucchini); strawberry; sweet potato; tomato Non-Food Crop: commercial/industrial lawns, fruits (unspecified), golf course turf, jujube, ornamental lawns and turf, ornamental sod farm (turf), recreation area lawns, small fruits Outdoor Residential and Greenhouse non-food: ornamental and/or shade trees, ornamental herbaceous plants, ornamental lawns and turf, ornamental nonflowering plants, ornamental woody shrubs and vines, Forestry: forest plantings (reforestation programs), pine (forest/shelter belt)

Outdoor Residential: ornamental lawns and turf

Indoor Residential: ornamental trees, ornamental herbaceous plants, ornamental nonflowering plants The invention also provides a method of applying a cytokinin as a plant regulator. The method includes applying a formulation that includes the cytokinin (produced by a cytokinin synthase of the invention described herein) in a mixture with one or more suitable inert ingredients to a plant belonging to one of the foregoing plant classes, i.e., a food crop, a food+feed crop, a feed crop, a greenhouse house food crop, a non-food crop, an outdoor residential or greenhouse non-food plant, forestry plant, an outdoor residential plant, or an indoor residential plant. In some applications the cytokinin formulation is applied at an appropriate pre-harvest interval, depending on the crop or plant class.

The cytokinin formulation provided by the invention for application to the plant classes described herein includes the cytokinin (produced by a cytokinin synthase of the invention described herein) mixed with one or more inert ingredients selected from a solvent or adjuvant. The resulting mixture can form a liquid formulation, water-soluble concentrate, emulsifiable concentrate, flowable suspension, an aqueous suspension, sprayable formulation, dry formulation, granule, pellet, wettable powder, soluble powder, water dispersible granule, or dry flowable formulation that includes the cytokinin produced by a cytokinin synthase of the invention described herein.

The invention also provides a method of manufacturing cytokinin for use in one or more of the foregoing cytokinin formulations. Generally, the method includes synthesizing or expressing a cytokinin synthase disclosed herein. The cytokinin synthase can be synthesized in vitro or expressed in a host cell. For example, host cells expressing cytokinin synthase can be cultured in fermentation containers. In some embodiments, the synthesized or expressed cytokinin synthase can be purified or isolated. In other embodiments, the synthesized or expressed cytokinin is used directly, without substantial purification or isolation or without any purification or isolation. The cytokinin synthase is provided with starting material substrate (e.g., adenosine monophosphate (AMP) or dimethylallyl diphosphate (DMAPP)), which the cytokinin synthase can then convert to a cytokinin (isopentenyl adenine). The cytokinin can be isolated or purified and then mixed with inert ingredients to make a cytokinin formulation.

Codon Optimization.

The invention provides polynucleotides encoding a cytokinin synthase, wherein the coding sequence has been modified for expression in a host cell (e.g., a plant cell).

The genetic code is redundant with 64 possible codons, but most organism preferentially use a subset of these codons. The codons that used most often in a species are called "optimal codons," and those used less often are classified as "rare" or "low-usage codons." Zhang et al. (1991) Gene 105:61-72. Codons may be substituted to reflect the preferred codon usage of a particular host in a process sometimes referred to as "codon optimization." Optimized coding sequences containing codons preferred by a particular host may be prepared, for example, to increase the rate of translation, or to produce recombinant RNA transcripts having desirable properties (e.g., a longer half-life, as compared with transcripts produced from a non-optimized sequence).

In some embodiments, the invention provides codon-optimized nucleic acid that designed or derived from a desired polypeptide or gene product (for example, a particular cytokinin synthase polypeptide) to be expressed from the nucleic acid. In particular embodiments, the desired polypeptide to be expressed may be designed or derived from a reference amino acid sequence of interest; for example, a reference protein (e.g., SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), SEQ ID NO:25 (FfCKS), SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54) or reference protein domain (e.g., IPT-like domain or PRH-like domain).

In some embodiments, only the cytokinin synthase encoding region of a nucleic acid molecule is codon-optimized to design a synthetic cytokinin synthase gene of the invention. In particular embodiments, the nucleotide sequence of a synthetic nucleic acid molecule is optimized, such that the primary structure of an encoded polypeptide (e.g., a cytokinin synthase protein) is unchanged. The structure of an encoded polypeptide is determined, to the greatest extent, by the amino acid sequence of the polypeptide. Thus, a desired structure for an encoded polypeptide places limitations on its nucleotide coding sequence that are determined by the degeneracy of the genetic code and standard codon usage.

A synthetic nucleic acid sequence of the invention may be designed and produced for a variety of reasons known to those of skill in the art; e.g., to increase expression, to adapt the nucleic acid sequence to be expressed in a new host cell or organism, and to introduce functional and/or non-functional mutations into an encoded polypeptide. Typically in embodiments where a reference amino acid sequence is a naturally-occurring gene product (e.g., native cytokinin synthase), or portion of a naturally-occurring gene product (e.g., an isolated IPT-like or PRH-like domain), a naturally-occurring nucleic acid sequence encoding the reference amino acid sequence may be obtained, for example, by searching genome databases or cloning from a source genome. In many cases, homologues or orthologs of such nucleic acid sequences may also be found in the genomes of other organisms.

A variety of methods are available to those skilled in the art for optimizing the coding sequence of a nucleic acid molecule according to predetermined parameters. For example, the skilled artisan may optimize a coding sequence by inspection, e.g., to better conform to the codon usage bias of an expression host organism. More commonly, a computer-implemented software program may be used to optimize a coding sequence. Such software programs may comprise one or more algorithms that optimize factors selected from the group comprising: factors that may affect the expression of an encoded polypeptide of interest, factors that may affect the rate of translation initiation of a transcript, and factors that may affect the rate of translational elongation of the encoded polypeptide or its precursor. Particular examples of such software programs include, without limitation, OptGene™ (Ocimum Biosolutions), Accelrys GCG™ (Accelrys Software, Inc.), OPTIMIZER™ (available for public use on the world-wide web at genomes.urv.es/OPTIMIZER), and OptimumGene™ (GenScript). In some embodiments, polynucleotides encoding cytokinin synthase have been optimized for expression in both a monocot and dicot host cell, using a hemicodon table (US Patent Publication No. 2003/0182685 A1).

Codon optimization also includes, for example, the process sometimes referred to as "codon harmonization," wherein codons of a codon sequence that are recognized as low-usage codons in the source organism are altered to codons that are recognized as low-usage in the new expression host. This process may help expressed polypeptides to fold normally by introducing natural and appropriate pauses during translation/extension. Birkholtz et al. (2008) Malaria J. 7:197-217.

Factors that may affect the expression of a polypeptide of interest that is encoded by a nucleic acid sequence may be influenced by the particular codons chosen to encode the amino acids of the polypeptide. Factors affecting the rate of production of mRNA from the template nucleic acid sequence may include: the RNA polymerase type used for transcription; the RNA polymerase level present in the expression system; and the transcription promoter sequence used. The mRNA levels may also be affected by the mRNA degradation rate, which in turn may be influenced by mRNA destabilizing motifs; RNAse recognition sequences; mRNA secondary structure; and polyA addition signals. The mRNA levels may also be affected by mRNA structures at the translational initiation site, at the ribosome binding site, at the start codon, and/or around the initial 10-50 codons of the coding sequence (or elsewhere within, or following, the open reading frame); transcriptional termination motifs present before or within the open reading frame; and signals within the transcribed sequence such as those that direct, alter, or modify mRNA splicing and/or nuclear export. A particular example of a factor affecting the rate of mRNA production from a template sequence is nucleotide repeat-induced polymerase slippage. Nucleotide repeat-induced polymerase slippage involves nucleotide sequence repeats that have been shown to cause slippage or stuttering of DNA polymerase which can result in frameshift mutations. Such nucleotide repeats can also cause slippage of RNA polymerase. For example, in an organism with a high G+C content bias, there can be a higher degree of G or C nucleotide repeats. Therefore, one method of reducing the possibility of inducing RNA polymerase slippage includes altering extended repeats of G or C nucleotides.

Factors that may affect the rate of translational initiation for a particular transcript include: the sequence of the ribosome binding site; sequences upstream of the ribosome binding site; sequences around the start codon (e.g., Kozak consensus sequences); the presence, relative location, and sequence of internal ribosome entry sites; the sequence and distance between the ribosome entry site (or the ribosome binding site or the 5' end of the mRNA) and the start codon; the mRNA structures at the translational initiation site; the mRNA structures at the ribosome binding site; the mRNA structures at the start codon; the mRNA structures around the initial 10-50 codons of the coding sequence; the sequence of the initial 10-20 codons; the GC bias of the initial 10-20 codons; the codon used at the codon adjacent to the start codon; the sequence of the start codon (AUG, UUG, or GUG); the ribosome concentration; the growth conditions before induction of expression; the growth conditions during expression; the temperature prior to induction of expression; and the temperature during expression.

Specific examples of factors that may affect the rate of translational initiation for a particular transcript include alternate translational initiation and interfering mRNA secondary structures. Alternate translational initiation may occur in a synthetic polynucleotide sequence that inadvertently contains one or more motifs capable of functioning as a ribosome binding site (RBS). These sites can result in initiating translation of a truncated protein from a gene-internal site. One method of reducing the possibility of producing a truncated protein, which can be difficult to remove during purification, includes modifying putative internal RBS sequences from an optimized polynucleotide sequence. Interfering secondary structures may sequester the RBS sequence or initiation codon, and have been correlated to a reduction in protein expression. Stem-loop structures can also be involved in transcriptional pausing and attenuation. An optimized polynucleotide sequence may thus contain minimal secondary structures in the RBS and gene coding regions of the nucleotide sequence to allow for improved transcription and translation.

Factors that may affect the rate of translational elongation include the level of charged tRNAs (Elf et al. (2003) Science 300:1718-22), which depends upon tRNA concentrations, tRNA charging rates, and amino acid availability. For example, a translational pause induced by a rare (or non-preferred) codon according to the host organism's codon usage bias may reduce the rate of heterologous protein expression. A rare codon-induced translational pause includes the presence of codons in the polynucleotide of interest that are rarely used in the host organism and may have a negative effect on protein translation due to their scarcity in the available tRNA pool. These factors also include the rate of ribosomal tRNA selection (decoding rate), which depends upon: the strength of the codon-anticodon interaction; the preceding codon (P-site codon); the wobble base of the preceding codon; and the wobble base of the codon being read. Factors that may affect ribosomal fidelity include those that influence ribosomal frameshifts, such as homopolymer stretches, G/C islands, A/T islands, and homopolymer stretches near pause sites. Furthermore, some polypeptides may be hindered in the ribosomal exit channel, which depends in part upon the sequence of the initial 10-20 amino acids of the polypeptide. In view of the foregoing, one method of improving optimal translation in a host organism includes performing codon optimization which can result in rare host codons being modified in a synthetic nucleic acid sequence.

Another class of nucleic acid sequence element that may affect (albeit indirectly) heterologous protein expression includes restriction sites. Thus, optimization of a nucleic acid sequence may include modification of restriction sites that could, for example, interfere with subsequent sub-cloning of transcription units into host expression vectors.

In some embodiments of the invention, a nucleic acid encoding a cytokinin synthase may be codon-optimized by first deducing (e.g., by in silico translation) the amino acid sequence encoded by a reference cytokinin synthase nucleic acid (e.g., SEQ ID NO:1 (EfCKS), SEQ ID NO:8 (AtCKS), SEQ ID NO:12 (BoCKS), SEQ ID NO:16 (IrCKS), SEQ ID NO:20 (AhCKS), or SEQ ID NO:24 (FfCKS) or the coding sequence for SEQ ID NO:34, SEQ ID NO:35, SEQ ID NO:36, SEQ ID NO:37, SEQ ID NO:38, SEQ ID NO:39, SEQ ID NO:40, SEQ ID NO:41 SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54). In further embodiments, the amino acid sequence of a cytokinin synthase may be used directly to obtain a codon-optimized nucleic acid sequence. For example, the amino acid sequence of a cytokinin synthase (whether deduced from a nucleic acid sequence or provided directly) may be used to deduce a codon-optimized nucleic acid sequence encoding the cytokinin synthase (e.g., in silico reverse-translation), for example, by using a computer-implemented software program that is capable of optimizing a coding sequence according to predetermined parameters. In specific examples, a codon-optimized nucleic acid may be deduced using the standard genetic code and an appropriate codon usage bias table for an expression host organism. It may be desirable in some embodiments to deduce multiple codon-optimized nucleic acid sequences encoding a cytokinin synthase protein.

All or a portion of a nucleic acid sequence may be optimized. In some examples, a desired modulation of expression may be achieved by optimizing essentially an entire reference cytokinin synthase encoding nucleic acid. In other examples, a desired modulation may be achieved by optimizing part, but not all, of a reference cytokinin synthase encoding nucleic acid.

Synthetic cytokinin synthase encoding, codon-optimized polynucleotides of the invention may be designed for use in a variety of applications, for example, to produce a recombinant polypeptide; to develop a new expression system; to compare expression properties to those of other nucleic acid sequences; and for diagnostic applications, as well as for introducing or increasing drought stress tolerance in a host organism. Additional guidance regarding the production of synthetic genes can be found in, for example, PCT International Patent Publication No. WO 97/13402, and U.S. Pat. Nos. 6,166,302 and 5,380,831.

Heterologous Sequences for Use in Recombinant Polynucleotides of the Invention

Plant Promoters.

A number of promoters that direct expression of a gene in a plant can be operably linked to a cytokinin synthase sequence disclosed herein, e.g., to create a gene expression cassette. Such promoters can be selected from constitutive, chemically-regulated, inducible, tissue-specific, and seed-preferred promoters. The promoter used to direct expression of a nucleic acid depends on the particular application. For example, a strong constitutive promoter suited to the host cell is typically used for expression and purification of expressed proteins.

Examples of plant promoters that can be used as heterologous sequence in the recombinant polynucleotides of the invention include promoter sequences derived from ZmSEE1 (Li et al. *Plant Cell Reports,* 22: 816-821 (2004) and Robson et al., *Plant Biotechnol. J.* 2: 101-112 (2004)) SAG12 (Gan et al., *Science,* 270: 1986-1988 (1995); Sýkorová et al., *J. Experimental Botany,* 59: 377-387 (2008); Zhang et al., *Journal of Integrative Plant Biology,* 52: 653-669 (2010); Zhang et al., *J. American Society for Horticultural Science,* 135: 108-115 (2010)), SAUR (Li et al., *Developmental biology,* 153: 386-395 (1992)), maize hsp70 (Medford et al., *The Plant Cell Online,* 1: 403-413 (1989)); ZmUBI1 (Hu et al., *Plant Cell Reports,* 23: 705-709 (2005)), chalcone synthase (chs) promoter (PCHS) from *Antirrhinum majus* (Wang et al., *Functional Plant Biology,*

24: 661-672 (1997)), proteinase inhibitor II (PI-IIK) (Smigocki et al., *Plant Molecular Biology,* 23: 325-335 (1993)); and SARK (Rivero et al., *Proc. Nat'l. Acad. Sci.,* 104: 19631-19636 (2007)).

Additional non-limiting examples of plant promoters that can be used in the recombinant polynucleotide of the invention include promoter sequences derived from *A. thaliana* ubiquitin-10 (ubi-10) (Callis, et al., *J. Biol. Chem.,* 265: 12486-12493 (1990); *A. tumefaciens* mannopine synthase (Δmas) (Petolino et al., U.S. Pat. No. 6,730,824); and/or Cassava Vein Mosaic Virus (CsVMV) (Verdaguer et al., *Plant Molecular Biology,* 31:1129-1139 (1996). Other constitutive promoters include, for example, the core Cauliflower Mosaic Virus 35S promoter (Odell et al. *Nature* 313:810-812 (1985)); Rice Actin promoter (McElroy et al., *Plant Cell* 2:163-171 (1990)); Maize Ubiquitin promoter (U.S. Pat. No. 5,510,474; Christensen et al., *Plant Mol. Biol.* 12:619-632 (1989) and Christensen et al., *Plant Mol. Biol.* 18:675-689 (1992)); pEMU promoter (Last et al., *Theor. Appl. Genet.,* 81:581-588 (1991)); ALS promoter (U.S. Pat. No. 5,659,026); Maize Histone promoter (Chabouté et al. *Plant Molecular Biology,* 8:179-191 (1987)); and the like.

Other useful plant promoters include tissue specific and inducible promoters. An inducible promoter is one that is capable of directly or indirectly activating transcription of one or more DNA sequences or genes in response to an inducer. The inducer can be a chemical agent such as a protein, metabolite, growth regulator, herbicide or phenolic compound or the inducer can be a physiological stress imposed by heat, cold, salt, or toxic elements. Other inducers act indirectly through the action of a pathogen or disease agent such as a virus. A plant cell containing an inducible regulatory element may be exposed to an inducer by externally applying the inducer to the cell or plant such as by spraying, watering, heating or similar methods.

Any inducible promoter can be used in the embodiments of the instant disclosure. See Ward et al., *Plant Mol. Biol.* 22: 361-366 (1993). Exemplary inducible promoters include ecdysone receptor promoters (U.S. Pat. No. 6,504,082); promoters from the ACE1 system which respond to copper (Mett et al., *Proc. Natl. Acad. Sci. USA* 90: 4567-4571 (1993)); In2-1 and In2-2 gene from maize which respond to benzenesulfonamide herbicide safeners (U.S. Pat. No. 5,364,780; Hershey et al., *Mol. Gen. Genetics* 227: 229-237 (1991) and Gatz et al., *Mol. Gen. Genetics* 243: 32-38 (1994)); Tet repressor from Tn10 (Gatz et al., *Mol. Gen. Genet.* 227: 229-237 (1991); or promoters from a steroid hormone gene, the transcriptional activity of which is induced by a glucocorticosteroid hormone, Schena et al., *Proc. Natl. Acad. Sci. USA* 88: 10421 (1991) and McNellis et al., (1998) *Plant J.* 14(2):247-257; the maize GST promoter, which is activated by hydrophobic electrophilic compounds that are used as pre-emergent herbicides (see U.S. Pat. No. 5,965,387 and International Patent Application, Publication No. WO 93/001294); and the tobacco PR-1a promoter, which is activated by salicylic acid (see Ono S, Kusama M, Ogura R, Hiratsuka K., "Evaluation of the Use of the Tobacco PR-1a Promoter to Monitor Defense Gene Expression by the Luciferase Bioluminescence Reporter System," *Biosci Biotechnol Biochem.* 2011 Sep. 23; 75(9): 1796-800). Other chemical-regulated promoters of interest include tetracycline-inducible and tetracycline-repressible promoters (see, for example, Gatz et al., (1991) *Mol. Gen. Genet.* 227:229-237, and U.S. Pat. Nos. 5,814,618 and 5,789,156).

Other regulatable promoters of interest include a cold responsive regulatory element or a heat shock regulatory element, the transcription of which can be effected in response to exposure to cold or heat, respectively (Takahashi et al., *Plant Physiol.* 99:383-390, 1992)); the promoter of the alcohol dehydrogenase gene (Gerlach et al., *Proc. Natl. Acad. Sci. USA* 79:2981-2985 (1982); Walker et al., *Proc. Natl. Acad. Sci. USA* 84(19):6624-6628 (1987)), inducible by anaerobic conditions; and the light-inducible promoter derived from the pea rbcS gene or pea psaDb gene (Yamamoto et al., *Plant J.* 12(2):255-265 (1997)); a light-inducible regulatory element (Feinbaum et al., *Mol. Gen. Genet.* 226:449 (1991); Lam and Chua, *Science* 248:471 (1990); Matsuoka et al. *Proc. Natl. Acad. Sci. USA* 90(20):9586-9590 (1993); Orozco et al. (1993) *Plant Mol. Bio.* 23(6): 1129-1138), a plant hormone inducible regulatory element (Yamaguchi-Shinozaki et al., *Plant Mol. Biol.* 15:905 (1990); Kares et al., *Plant Mol. Biol.* 15:225 (1990)), and the like. An inducible regulatory element also can be the promoter of the maize In2-1 or In2-2 gene, which responds to benzenesulfonamide herbicide safeners (Hershey et al., *Mol. Gen. Gene.* 227:229-237 (1991); Gatz et al., *Mol. Gen. Genet.* 243:32-38 (1994)), and the Tet repressor of transposon Tn10 (Gatz et al., *Mol. Gen. Genet.* 227:229-237 (1991)). Stress inducible promoters include salt/water stress-inducible promoters such as PSCS (Zang et al., (1997) *Plant Sciences* 129:81-89); cold-inducible promoters, such as, cor15a (Hajela et al., *Plant Physiol.* 93:1246-1252 (1990)), cor15b (Wilhelm et al., *Plant Mol. Biol.* 23:1073-1077 (1993)), wsc1 (Ouellet et al., (1998) *FEBS Lett.* 423-324-328), ci7 (Kirch et al., *Plant Mol Biol.* 33:897-909 (1997)), ci21A (Schneider et al., *Plant Physiol.* 113:335-45 (1997)); drought-inducible promoters, such as Trg-31 (Chaudhary et al., *Plant Mol. Biol.,* 30:1247-57 (1996)), rd29 (Kasuga et al., Nature Biotechnology 18:287-291 (1999)); osmotic inducible promoters, such as Rab17 (Vilardell et al., *Plant Mol. Biol.* 17:985-93 (1991)) and osmotin (Raghothama et al., *Plant Mol. Biol.* 23:1117-28 (1993)); and heat inducible promoters, such as heat shock proteins (Barros et al., *Plant Mol.* 19:665-75 (1992); Marrs et al., *Dev. Genet.* 14:27-41 (1993)), smHSP (Waters et al., *J Experimental Botany* 47:325-338 (1996), and the heat-shock inducible element from the parsley ubiquitin promoter (WO 03/102198). Other stress-inducible promoters include rip2 (U.S. Pat. No. 5,332, 808 and U.S. Publication No. 2003/0217393) and rd29a (Yamaguchi-Shinozaki et al., *Mol. Gen. Genetics* 236:331-340 (1993)). Certain promoters are inducible by wounding, including the *Agrobacterium* pMAS promoter (Guevara-Garcia et al., *Plant J.* 4(3):495-505 (1993)) and the *Agrobacterium* ORF13 promoter (Hansen et al., *Mol. Gen. Genet.* 254(3):337-343 (1997)).

Tissue-preferred promoters can be utilized to target enhanced transcription and/or expression within a particular plant tissue. When referring to preferential expression, what is meant is expression at a higher level in the particular plant tissue than in other plant tissue. Examples of these types of promoters include seed preferred expression such as that provided by the phaseolin promoter (Bustos et al., *The Plant Cell* Vol. 1, 839-853 (1989)), and the maize globulin-1 gene (Belanger, et al. *Genetics* 129:863-972 (1991)). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, ZmGS2, ZmSTP13, ZmGSTU6, etc. Seed-preferred promoters also include those promoters that direct gene expression predominantly to specific tissues within the seed such as, for example, the endosperm-preferred promoter of γ-zein, the cryptic promoter from tobacco (Fobert et al., *Plant J.* 4: 567-577 (1994)), the P-gene promoter from maize (Chopra et al., *Plant Cell* 7:1149-1158 (1996), Erratum in *Plant Cell.* 1:109 (1997), the globulin-1 promoter from maize (Belenger and Kriz, *Genetics* 129: 863-972 (1991)), and promoters that direct expression to the seed coat or hull of maize kernels, for example the pericarp-specific glutamine synthetase promoter (Muhitch et al., *Plant Science* 163:865-872 (2002)).

In addition to the promoter, the gene expression cassette (which can be in, e.g., a vector) typically contains a transcription unit or expression cassette that contains all the additional elements required for the expression of the nucleic acid in host cells, either prokaryotic or eukaryotic. A typical expression cassette thus contains a promoter operably linked to a nucleic acid sequence encoding a gene product (e.g., a protein). The gene expression cassette may also include additional elements which are operably linked according to methods known art: signals required for efficient polyadenylation of the transcript, transcriptional termination, ribosome binding sites, or translation termination. Additionally, the expression cassette may include enhancers and/or heterologous splicing signals.

Components of Gene Expression Cassette.

Other components of the gene expression cassette are provided as embodiments. Examples include selectable markers, targeting or regulatory sequences, transit peptide sequences such as the optimized transit peptide sequence (see U.S. Pat. No. 5,510,471) stabilizing sequences such as RB7 MAR (see Thompson and Myatt, *Plant Mol. Biol.*, 34: 687-692 (1997) and International Patent Publication No. WO9727207) or leader sequences, introns etc. General descriptions and examples of plant expression vectors and reporter genes can be found in Gruber, et al., "Vectors for Plant Transformation" in *Methods in Plant Molecular Biology and Biotechnology*, Glick et al., eds; CRC Press pp. 89-119 (1993). The selection of an appropriate expression vector will depend upon the host and the method of introducing the expression vector into the host. The gene expression cassette will also include at the 3' terminus of the heterologous nucleotide sequence of interest, a transcriptional and translational termination region functional in plants. The termination region can be native with the promoter nucleotide sequence of embodiments of the present disclosure, can be native with the DNA sequence of interest, or can be derived from another source. Convenient termination regions are available from the Ti-plasmid of *A. tumefaciens*, such as the octopine synthase and nopaline synthase (nos) termination regions (Depicker et al., *Mol. and Appl. Genet.* 1:561-573 (1982) and Shaw et al. *Nucl. Acids Research* vol. 12, No. 20 pp 7831-7846(nos) (1984)); see also Guerineau et al. *Mol. Gen. Genet.* 262:141-144 (1991); Proudfoot, *Cell* 64:671-674 (1991); Sanfacon et al. *Genes Dev.* 5:141-149 (1991); Mogen et al. *Plant Cell* 2:1261-1272 (1990); Munroe et al. *Gene* 91:151-158 (1990); Ballas et al., *Nucl. Acids Res.* 17:7891-7903 (1989); Joshi et al. *Nucl. Acids Res.* 15:9627-9639 (1987).

The gene expression cassettes can additionally contain 5' leader sequences. Such leader sequences can act to enhance translation. Translation leaders are known in the art and include by way of example, picornavirus leaders, EMCV leader (Encephalomyocarditis 5' noncoding region), Elroy-Stein et al., *Proc. Nat. Acad. Sci. USA* 86:6126-6130 (1989); potyvirus leaders, for example, TEV leader (Tobacco Etch Virus) Carrington and Freed, *J. Virology*, 64:1590-1597 (1990), MDMV leader (Maize Dwarf Mosaic Virus), Allison et al., *Virology* 154:9-20 (1986); human immunoglobulin heavy-chain binding protein (BiP), Macejak et al., *Nature* 353:90-94 (1991); untranslated leader from the coat protein mRNA of alfalfa mosaic virus (AMV RNA 4), Jobling et al., *Nature* 325:622-625 (1987); Tobacco mosaic virus leader (TMV), Gallie et al., (1989) *Molecular Biology of RNA*, pages 237-256; and maize chlorotic mottle virus leader (MCMV) Lommel et al., *Virology* 81:382-385 (1991). See also Della-Cioppa et al., *Plant Physiology* 84:965-968 (1987).

The gene expression cassette construct can also contain sequences that enhance translation and/or mRNA stability such as introns. An example of one such intron is the first intron of gene II of the histone H3.III variant of *Arabidopsis thaliana*. Chaubet et al., *J Mol. Biology,* 225:569-574 (1992).

In those instances where it is desirable for the expression cassette to express a gene product that is directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase and *Helianthus annuus* (U.S. Pat. No. 5,510,417), *Zea mays* Brittle-1 chloroplast transit peptide (Nelson et al., *Plant Physiol.* 117(4):1235-1252 (1998); Sullivan et al., *Plant Cell* 3(12):1337-48 (1991); Sullivan et al., *Planta* 196(3):477-84 (1995); Sullivan et al., *J. Biol. Chem.* 267(26):18999-9004 (1992)) and the like. In addition, chimeric chloroplast transit peptides are known in the art, such as the Optimized Transit Peptide (U.S. Pat. No. 5,510,471). Additional chloroplast transit peptides have been described previously in U.S. Pat. No. 5,717,084 and U.S. Pat. No. 5,728,925. One skilled in the art will readily appreciate the many options available in expressing a product to a particular organelle. For example, the barley alpha amylase sequence is often used to direct expression to the endoplasmic reticulum (Rogers, *J. Biol. Chem.* 260:3731-3738 (1985)).

It will be appreciated by one skilled in the art that use of recombinant DNA technologies can improve control of expression of transformed nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, stable integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno or Kozak sequences), modification of nucleic acid molecules to correspond to the codon usage of the host cell, and deletion of sequences that destabilize transcripts.

Reporter or marker genes for selection of transformed cells or tissues or plant parts or plants can be included in the transformation vectors. Examples of selectable markers include those that confer resistance to anti-metabolites such as herbicides or antibiotics, for example, dihydrofolate reductase, which confers resistance to methotrexate (Reiss, Plant Physiol. (Life Sci. Adv.) 13:143-149 (1994); see also Herrera Estrella et al., *Nature* 303:209-213, (1983); Meijer et al., *Plant Mol. Biol.* 16:807-820, (1991)); neomycin phosphotransferase, which confers resistance to the aminoglycosides neomycin, kanamycin and paromycin (Herrera-Estrella, *EMBO J.* 2:987-995 (1983) and Fraley et al., *Proc. Natl. Acad. Sci USA* 80:4803 (1983)) and hygromycin phosphotransferase, which confers resistance to hygromycin (Marsh, Gene 32:481-485, (1984); see also Waldron et al., *Plant Mol. Biol.* 5:103-108, (1985); Zhijian et al., *Plant Science* 108:219-227, (1995)); trpB, which allows cells to utilize indole in place of tryptophan; hisD, which allows cells to utilize histinol in place of histidine (Hartman, *Proc. Natl. Acad. Sci. USA* 85:8047, (1988)); mannose-6-phosphate isomerase which allows cells to utilize mannose (International Patent Application No. WO 94/20627); ornithine decarboxylase, which confers resistance to the ornithine decarboxylase inhibitor, 2-(difluoromethyl)-DL-ornithine (DFMO; McConlogue, 1987, In: *Current Communications in Molecular Biology*, Cold Spring Harbor Laboratory ed.); and deaminase from *Aspergillus terreus*, which confers resistance to Blasticidin S (Tamura, *Biosci. Biotechnol. Biochem.* 59:2336-2338, (1995)).

Additional selectable markers include, for example, a mutant acetolactate synthase, which confers imidazolinone or sulfonylurea resistance (Lee et al., *EMBO J.* 7:1241-1248, (1988)), a mutant psbA, which confers resistance to atrazine (Smeda et al., *Plant Physiol.* 103:911-917, (1993)), or a mutant protoporphyrinogen oxidase (see U.S. Pat. No. 5,767,373), or other markers conferring resistance to an herbicide such as glufosinate. Examples of suitable selectable marker genes include, but are not limited to, genes encoding resistance to chloramphenicol (Herrera Estrella et al., *EMBO J.* 2:987-992, (1983)); streptomycin (Jones et al., *Mol. Gen. Genet.* 210:86-91, (1987)); spectinomycin (Bretagne-Sagnard et al., *Transgenic Res.* 5:131-137, (1996)); bleomycin (Hille et al., *Plant Mol. Biol.* 7:171-176, (1990)); sulfonamide (Guerineau et al., *Plant Mol. Biol.* 15:127-136, (1990)); bromoxynil (Stalker et al., *Science* 242:419-423, (1988)); glyphosate (Shaw et al., *Science* 233:478-481, (1986)); phosphinothricin (DeBlock et al., *EMBO J.* 6:2513-2518, (1987)), and the like.

One option for use of a selective gene is a glufosinate-resistance encoding DNA and in one embodiment can be the phosphinothricin acetyl transferase (pat), maize optimized pat gene or bar gene under the control of the Cassava Vein Mosaic Virus promoter. These genes confer resistance to bialaphos. See, (see, Wohlleben et al., (1988) *Gene* 70: 25-37); Gordon-Kamm et al., *Plant Cell* 2:603; 1990; Uchimiya et al., *BioTechnology* 11:835, 1993; White et al., *Nucl. Acids Res.* 18:1062, 1990; Spencer et al., *Theor. Appl. Genet.* 79:625-631, 1990; and Anzai et al., *Mol. Gen. Gen.* 219:492, 1989). A version of the pat gene is the maize optimized pat gene, described in U.S. Pat. No. 6,096,947.

In addition, markers that facilitate identification of a plant cell containing the polynucleotide encoding the marker may be employed. Scorable or screenable markers are useful, where presence of the sequence produces a measurable product and can produce the product without destruction of the plant cell. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al., *EMBO J* 6(13): 3901-3907 (1987)); and alkaline phosphatase. In a preferred embodiment, the marker used is beta-carotene or provitamin A (Ye et al., *Science* 287:303-305-(2000)). The gene has been used to enhance the nutrition of rice, but in this instance it is employed instead as a screenable marker, and the presence of the gene linked to a gene of interest is detected by the golden color provided. Unlike the situation where the gene is used for its nutritional contribution to the plant, a smaller amount of the protein suffices for marking purposes. Other screenable markers include the anthocyanin/flavonoid genes in general (See discussion at Taylor and Briggs, *The Plant Cell* 2:115-127 (1990)) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., *Plant Cell* (1996) 8: 1171-1179; Scheffler et al., *Mol. Gen. Genet.* 242:40-48 (1994)) and maize C2 (Wienand et al., *Mol. Gen. Genet.* 203:202-207 (1986)); the B gene (Chandler et al., *Plant Cell* 1:1175-1183 (1989)), the p1 gene (Grotewold et al., *Proc. Natl. Acad. Sci USA* 88:4587-4591 (1991); Grotewold et al., *Cell* 76:543-553 (1994); Sidorenko et al., *Plant Mol. Biol.* (1999)39:11-19); the bronze locus genes (Ralston et al., Genetics (1988) 119:185-197; Nash et al., Plant Cell (1990) 2(11): 1039-1049), among others.

Further examples of suitable markers include the cyan fluorescent protein (CYP) gene (Bolte et al., *J. Cell Science* 117: 943-54 (2004) and Kato et al., *Plant Physiol* 129: 913-42 (2002)), the yellow fluorescent protein gene (PHI-YFP™ from Evrogen; see Bolte et al., *J. Cell Science* 117: 943-54 (2004)); a lux gene, which encodes a luciferase, the presence of which may be detected using, for example, X-ray film, scintillation counting, fluorescent spectrophotometry, low-light video cameras, photon counting cameras or multi-well luminometry (Teeri et al. *EMBO J.* 8:343 (1989)); a green fluorescent protein (GFP) gene (Sheen et al., Plant J. 8(5):777-84 (1995)); and DsRed2 where plant cells transformed with the marker gene are red in color, and thus visually selectable (Dietrich et al., *Biotechniques* 2(2): 286-293 (2002)). Additional examples include a β-lactamase gene (Sutcliffe, Proc. Nat'l. Acad. Sci. U.S.A. (1978) 75:3737), which encodes an enzyme for which various chromogenic substrates are known (e.g., PADAC, a chromogenic cephalosporin); a xylE gene (Zukowsky et al., *Proc. Nat'l. Acad. Sci. USA* 80:1101 (1983)), which encodes a catechol dioxygenase that can convert chromogenic catechols; an α-amylase gene (Ikuta et al., *Biotech.* 8:241 (1990)); and a tyrosinase gene (Katz et al., *J. Gen. Microbiol.* 129:2703 (1983)), which encodes an enzyme capable of oxidizing tyrosine to DOPA and dopaquinone, which in turn condenses to form the easily detectable compound melanin. Clearly, many such markers are available and known to one skilled in the art.

In certain embodiments, the nucleotide sequence of the transgene encoding a gene product in an expression cassette can be optionally combined with another nucleotide sequence of interest in the cassette and/or the plant. For example, in certain embodiments the transgene can be combined or "stacked" with another nucleotide sequence of interest that provides additional resistance or tolerance to glyphosate or another herbicide, and/or provides resistance to select insects or diseases and/or nutritional enhancements, and/or improved agronomic characteristics, and/or proteins or other products useful in feed, food, industrial, pharmaceutical or other uses. The "stacking" of two or more nucleic acid sequences of interest within a plant genome can be accomplished, for example, via conventional plant breeding using two or more events, transformation of a plant with a construct which contains the sequences of interest, re-transformation of a transgenic plant, or addition of new traits through integration via homologous recombination.

Such nucleotide sequences of interest include, but are not limited to, those examples of genes or coding sequences that confer (1) resistance to pests or disease, (2) resistance to herbicides, and (3) value added traits provided below:

1. Genes or Coding Sequences (e.g. iRNA) that Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium flavum* (Jones et al., 1994 Science 266:789), tomato Pto gene, which encodes a protein kinase, for resistance to *Pseudomonas syringae* pv. tomato (Martin et al., Science 262:1432 (1993)), and *Arabidopsis* RSSP2 gene for resistance to *Pseudomonas syringae* (Mindrinos et al., Cell 78:1089 (1994)).

(B) A *Bacillus thuringiensis* protein, a derivative thereof or a synthetic polypeptide modeled thereon, such as, a nucleotide sequence of a Bt δ-endotoxin gene (Geiser et al., 1986 Gene 48:109), and a vegetative insecticidal (VIP) gene (see, e.g., Estruch et al., Proc. Natl. Acad. Sci. USA 93:5389-94 (1996)). Moreover, DNA molecules encoding δ-endotoxin genes can be purchased from American Type Culture Collection (Rockville, Md.), under ATCC accession numbers 40098, 67136, 31995 and 31998.

(C) A lectin, such as, nucleotide sequences of several *Clivia miniata* mannose-binding lectin genes (Van Damme et al., Plant Molec. Biol. 24:825 (1994)).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor.

Examples of such genes include a rice cysteine proteinase inhibitor (Abe et al., J. Biol. Chem. 262:16793 (1987), a tobacco proteinase inhibitor I (Huub et al., Plant Molec. Biol. 21:985 (1993)), and an α-amylase inhibitor (Sumitani et al., Biosci. Biotech. Biochem. 57:1243 (1993)).

(F) An insect-specific hormone or pheromone such as an ecdysteroid and juvenile hormone a variant thereof, a mimetic based thereon, or an antagonist or agonist thereof, such as baculovirus expression of cloned juvenile hormone esterase, an inactivator of juvenile hormone (Hammock et al., Nature 344:458 (1990).

(G) An insect-specific peptide or neuropeptide which, upon expression, disrupts the physiology of the affected pest. Examples of such genes include an insect diuretic hormone receptor (Regan, J. Biol. Chem. 269(1):9-12 (1994)), an allatostatin identified in *Diploptera punctata* (Pratt, Biochem Biophys Res Commun. 163(3):1243-7 (1989)), and insect-specific, paralytic neurotoxins (U.S. Pat. No. 5,266,361).

(H) An insect-specific venom produced in nature by a snake, a wasp, etc., such as a scorpion insectotoxic peptide (Pang, Gene 116:165 (1992)).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., Insect Molec. Biol. 23:691 (1993)), and parsley ubi4-2 polyubiquitin gene (Kawalleck et al., Plant Molec. Biol. 21:673 (1993)).

(K) A molecule that stimulates signal transduction. Examples of such molecules include nucleotide sequences for mung bean calmodulin cDNA clones (Botella et al., Plant Molec. Biol. 24:757 (1994)) and a nucleotide sequence of a maize calmodulin cDNA clone (Griess et al., Plant Physiol. 104:1467 (1994)).

(L) A hydrophobic moment peptide. See U.S. Pat. Nos. 5,659,026 and 5,607,914; the latter teaches synthetic antimicrobial peptides that confer disease resistance.

(M) A membrane permease, a channel former or a channel blocker, such as a cecropin-β lytic peptide analog (Jaynes et al., Plant Sci. 89:43 (1993)) which renders transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. Ann. Rev. Phytopathol. 28:451 (1990).

(O) An insect-specific antibody or an immunotoxin derived therefrom. Thus, an antibody targeted to a critical metabolic function in the insect gut would inactivate an affected enzyme, killing the insect. For example, Taylor et al., Abstract #497, Seventh Int'l. Symposium on Molecular Plant-Microbe Interactions shows enzymatic inactivation in transgenic tobacco via production of single-chain antibody fragments (1994).

(P) A virus-specific antibody. See, for example, Tavladoraki et al., Nature 266:469 (1993), which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., Bio/Technology 10:1436 (1992)). The cloning and characterization of a gene which encodes a bean endopolygalacturonase-inhibiting protein is described by (Toubart et al., Plant J. 2:367 (1992)).

(R) A developmental-arrestive protein produced in nature by a plant, such as the barley ribosome-inactivating gene that provides an increased resistance to fungal disease (Longemann et al., Bio/Technology 10:3305 (1992)).

(S) RNA interference, in which a DNA polynucleotide encoding an RNA molecule is used to inhibit expression of a target gene. An RNA molecule in one example is partially or fully double stranded, which triggers a silencing response, resulting in cleavage of dsRNA into small interfering RNAs, which are then incorporated into a targeting complex that destroys homologous mRNAs. See, e.g., Fire et al., U.S. Pat. No. 6,506,559; Graham et al., U.S. Pat. No. 6,573,099.

2. Genes or Coding Sequences that Confer Resistance to a Herbicide (A) Genes encoding resistance or tolerance to a herbicide that inhibits the growing point or meristem, such as an imidazalinone, sulfonanilide or sulfonylurea herbicide. Exemplary genes in this category code for a mutant ALS enzyme (Lee et al., *EMBO J.* 7:1241 (1988)), which is also known as AHAS enzyme (Miki et al., *Theor. Appl. Genet.* 80:449 (1990)).

(B) One or more additional genes encoding resistance or tolerance to glyphosate imparted by mutant EPSP synthase and aroA genes, or through metabolic inactivation by genes such as GAT (glyphosate acetyltransferase) or GOX (glyphosate oxidase) and other phosphono compounds such as glufosinate (pat and bar genes; DSM-2), and aryloxyphenoxypropionic acids and cyclohexanediones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061. European Patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricin acetyltransferase gene is provided in European Patent application No. 0 242 246. De Greef et al., *Bio/Technology* 7:61 (1989) describes the production of transgenic plants that express chimeric bar genes coding for phosphinothricin acetyl transferase activity. Exemplary of genes conferring resistance to aryloxyphenoxypropionic acids and cyclohexanediones, such as sethoxydim and haloxyfop, are the Acc1-S1, Acc1-S2 and Acc1-S3 genes described by Marshall et al., *Theor. Appl. Genet.* 83:435 (1992).

(C) Genes encoding resistance or tolerance to a herbicide that inhibits photosynthesis, such as a triazine (psbA and gs+ genes) and a benzonitrile (nitrilase gene). Przibilla et al., *Plant Cell* 3:169 (1991) describe the use of plasmids encoding mutant psbA genes to transform *Chlamydomonas*. Nucleotide sequences for nitrilase genes in U.S. Pat. No. 4,810,648, and DNA molecules containing these genes are available under ATCC accession numbers 53435, 67441 and 67442. Cloning and expression of DNA coding for a glutathione S-transferase is described by Hayes et al., *Biochem. J.* 285:173 (1992).

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (European Patent No. 418175, European Patent No. 470856, European Patent No. 487352, European Patent No. 527036, European Patent No. 560482, European Patent No. 682659, U.S. Pat. No. 5,424,276), in particular isoxaflutole, which is a selective herbicide for maize, diketonitriles (European Patent No. 496630, and European Patent No. 496631), in particular 2-cyano-3-cyclopropyl-1-(2-SO2CH3-4-CF3 phenyl) propane-1,3-dione and 2-cyano-3-cyclopropyl-1-(2-SO2CH3-4-2,3Cl2phenyl) propane-1,3-dione, triketones (European Patent No. 625505, European Patent No. 625508, U.S. Pat. No. 5,506,195), in particular sulcotrione, and pyrazolinates. A gene that produces an overabundance of HPPD in plants can provide tolerance or resistance to such herbicides, including, for example, genes described in U.S. Pat. Nos. 6,268,549 and 6,245,968 and U.S. Patent Publication No. 20030066102.

(E) Genes encoding resistance or tolerance to phenoxy auxin herbicides, such as 2,4-dichlorophenoxyacetic acid (2,4-D) and which may also confer resistance or tolerance to aryloxyphenoxypropionate (AOPP) herbicides. Examples of such genes include the α-ketoglutarate-dependent dioxygenase enzyme (aad-1) gene, described in U.S. Pat. No. 7,838,733.

(F) Genes encoding resistance or tolerance to phenoxy auxin herbicides, such as 2,4-dichlorophenoxyacetic acid (2,4-D) and which may also confer resistance or tolerance to pyridyloxy auxin herbicides, such as fluroxypyr or triclopyr. Examples of such genes include the α-ketoglutarate-dependent dioxygenase enzyme gene (aad-12), described in WO 2007/053482 A2.

(G) Genes encoding resistance or tolerance to dicamba (see, e.g., U.S. Patent Publication No. 20030135879).

(H) Genes providing resistance or tolerance to herbicides that inhibit protoporphyrinogen oxidase (PPO) (see U.S. Pat. No. 5,767,373).

(I) Genes providing resistance or tolerance to triazine herbicides (such as atrazine) and urea derivatives (such as diuron) herbicides which bind to core proteins of photosystem II reaction centers (PS II) (See Brussian et al., *EMBO J.* 8(4): 1237-1245 (1989).

3. Genes that Confer or Contribute to a Value-Added Trait (A) Modified fatty acid metabolism, for example, by transforming maize or *Brassica* with an antisense gene or stearoyl-ACP desaturase to increase stearic acid content of the plant (Knultzon et al., *Proc. Nat. Acad. Sci. USA* 89:2624 (1992).

(B) Decreased phytate content.

(1) Introduction of a phytase-encoding gene, such as the *Aspergillus niger* phytase gene (Van Hartingsveldt et al., *Gene* 127:87 (1993)), enhances breakdown of phytate, adding more free phosphate to the transformed plant.

(2) A gene could be introduced that reduces phytate content. In maize, this, for example, could be accomplished by cloning and then reintroducing DNA associated with the single allele which is responsible for maize mutants characterized by low levels of phytic acid (Raboy et al., *Maydica* 35:383 (1990)).

(C) Modified carbohydrate composition effected, for example, by transforming plants with a gene coding for an enzyme that alters the branching pattern of starch. Examples of such enzymes include, *Streptococcus mucus* fructosyltransferase gene (Shiroza et al., *J. Bacteriol.* 170:810 (1988)), *Bacillus subtilis* levansucrase gene (Steinmetz et al., *Mol. Gen. Genel.* 200:220 (1985)), *Bacillus licheniformis* α-amylase (Pen et al., *Bio/Technology* 10:292 (1992)), tomato invertase genes (Elliot et al., (1993)), barley amylase gene (Sogaard et al., *J. Biol. Chem.* 268:22480 (1993)), and maize endosperm starch branching enzyme II (Fisher et al., *Plant Physiol.* 102:10450 (1993)).

Transgenic Plant Cells and Plants

The recombinant polynucleotide of the invention can be introduced (transformed) into a plant cell. A wide variety of plants and plant cell systems may be engineered to include the cytokinin synthase gene expression constructs of the present disclosure using one or more of the various transformation methods disclosed above. In embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., *petunia*, rose, *chrysanthemum*), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions can be used to generate transgenic plants and transgenic plants cells, including, but not limited to, species from the genera *Asparagus*, *Avena*, *Brassica*, *Citrus*, *Citrullus*, *Capsicum*, *Cucurbita*, *Daucus*, *Erigeron*, *Glycine*, *Gossypium*, *Hordeum*, *Lactuca*, *Lolium*, *Lycopersicon*, *Malus*, *Manihot*, *Nicotiana*, *Orychophragmus*, *Oryza*, *Persea*, *Phaseolus*, *Pisum*, *Pyrus*, *Prunus*, *Raphanus*, *Secale*, *Solanum*, *Sorghum*, *Triticum*, *Vitis*, *Vigna*, and *Zea mays*, transformed with a recombinant polynucleotide of the invention that includes the two-domain cytokinin synthase coding sequences (i), (ii), (iii), (iv), (v), (vi), (vii), (viii), (ix), (x), (xi), (xii), (xiii), (xiv), or (xv) described above. In particular the invention provides one of the foregoing transgenic plants or plant cells comprising a transgenic construct that includes the coding sequence of recombinant polynucleotide (vii), (viii), (ix), (xiii), (xiv), or (xv) which is optimized for expression in the plant or plant cell.

Plant transformation methods that can be used with the recombinant polynucleotide of the invention include, but are not limited to, site-specific microparticle bombardment, *Agrobacterium* transformation method, calcium phosphate transformation method, polybrene transformation method, electroporation transformation method, ultrasonic transformation method, liposome transformation method, microinjection transformation method, naked DNA transformation method, plasmid vector transformation method, viral vector transformation method, silicon carbide mediated transformation method, aerosol beaming transformation method, or PEG transformation method. Generally any plant transformation method can be used to insert DNA or any other polynucleotide sequence into the genome of a host cell. Thus, any method that provides for efficient transformation/transfection may be employed.

Numerous methods for plant transformation have been developed, including biological and physical transformation protocols for dicotyledonous plants as well as monocotyledonous plants (e.g., Goto-Fumiyuki et al., *Nature Biotech*, 17:282-286 (1999); Miki et al., *Methods in Plant Molecular Biology and Biotechnology*, Glick, B. R. and Thompson, J. E. Eds., CRC Press, Inc., Boca Raton, pp. 67-88 (1993)). In addition, vectors comprising gene expression cassettes and in vitro culture methods for plant cell or tissue transformation and regeneration of plants are available, for example, in Gruber et al., *Methods in Plant Molecular Biology and Biotechnology*, Glick, B. R. and Thompson, J. E. Eds., CRC Press, Inc., Boca Raton, pp. 8 (1993)). A large number of techniques are available for inserting DNA comprising a gene expression cassette into a plant host cell. Those techniques include transformation with disarmed T-DNA using *Agrobacterium tumefaciens* or *Agrobacterium rhizogenes* as the transformation agent, calcium phosphate transfection, polybrene transformation, protoplast fusion, electroporation, ultrasonic methods (e.g., sonoporation), liposome transformation, microinjection, naked DNA, plasmid vectors, viral vectors, biolistics (microparticle bombardment), silicon carbide WHISKERS™ mediated transformation, aerosol beaming, or Poly Ethylene Glycol mediated transformation as well as other possible methods 9-119 (1993).

For example, a gene expression cassette encoding a cytokinin synthase according to the invention may be introduced directly into the genomic DNA of the plant cell using techniques such as electroporation and microinjection of plant cell protoplasts. Such plant transformation methods include, for example, protoplast transformation through calcium chloride precipitation, poly ethylene glycol (PEG) or electroporation-mediated uptake of DNA (see Paszkowski et al. *EMBO J* 3:2717-2722 (1984), Potrykus et al. *Molec. Gen. Genet.* 199:169-177 (1985); Fromm et al. *Proc. Nat. Acad. Sci. USA* 82:5824-5828 (1985); and Shimamoto *Nature* 338:274-276 (1989)) and electroporation of plant tissues (D'Halluin et al. *Plant Cell* 4:1495-1505 (1992)).

Expression vectors encoding a cytokinin synthase can be introduced directly to plant tissue using biolistic methods, such as DNA particle bombardment (see, e.g., Klein et al. *Nature* 327:70-73 (1987)). Biolistic methods include microprojectile-mediated transformation wherein DNA is carried on the surface of microprojectiles. In this method, the expression vector is introduced into plant tissues with a biolistic device that accelerates the microprojectiles to speeds sufficient to penetrate plant cell walls and membranes. Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992).

Additional methods for plant cell transformation include microinjection via silicon carbide WHISKERS™ mediated DNA uptake (Kaeppler et al. *Plant Cell Reporter* 9:415-418 (1990)). Alternatively, the DNA construct can be introduced into the plant cell via nanoparticle transformation (see, e.g., U.S. patent application Ser. No. 12/245,685, which is incorporated herein by reference in its entirety).

A widely utilized method for introducing a vector comprising a gene expression cassette into plants is based on the natural transformation system of *Agrobacterium*. Horsch et al., *Science* 227:1229 (1985). *A. tumefaciens* and *A. rhizogenes* are plant pathogenic soil bacteria known to be useful to genetically transform plant cells. The Ti and Ri plasmids of *A. tumefaciens* and *A. rhizogenes*, respectively, carry genes responsible for genetic transformation of the plant. Kado, C. I., *Crit. Rev. Plant. Sci.* 10:1 (1991). Descriptions of *Agrobacterium* vector systems and methods for *Agrobacterium*-mediated gene transfer are also available, for example, Gruber et al., supra, Miki et al., supra, Moloney et al., *Plant Cell Reports* 8:238 (1989), and U.S. Pat. Nos. 4,940,838 and 5,464,763.

When *Agrobacterium* is used for plant transformation, DNA encoding a cytokinin synthase can be cloned into a special plasmid referred to as an intermediate vector or into a binary vector. Intermediate vectors cannot replicate in *Agrobacterium* in the absence of a helper plasmid (conjugation). The Japan Tobacco Superbinary system is an example of such a system (see review by Komari et al., (2006) In: *Methods in Molecular Biology No. 343: Agrobacterium Protocols* ($2^{nd}$ Edition, Vol. 1) (K. Wang, ed.) Humana Press Inc., Totowa, N.J., pp. 15-41; and Komori et al., *Plant Physiol.* 145:1155-1160 (2007)).

Binary vectors can replicate in both *E. coli* and in *Agrobacterium*. They comprise a selection marker gene and a linker or polylinker which are framed by the right and left T-DNA border regions. Binary vectors can be transformed directly into *Agrobacterium* (Holsters, 1978). The *Agrobacterium* can be used as a host cell comprising a plasmid, e.g., the Ti or RI plasmid carrying a vir region which, typically, is necessary for the transfer of the T-DNA into the plant cell.

The virulence of an *Agrobacterium tumefaciens* host can be used to direct the insertion of a T-strand containing DNA encoding a cytokinin synthase disclosed herein into the haploid tissue or cell that is infected by *Agrobacterium* binary T DNA vector technology (Bevan, *Nucl. Acids Res.* 12:8711-8721 (1984)) or the co-cultivation procedure (Horsch et al. *Science* 227:1229-1231 (1985)). Generally, the *Agrobacterium* transformation system is used to engineer dicotyledonous plants (Bevan et al. *Ann. Rev. Genet* 16:357-384 (1982); Rogers et al. *Methods Enzymol.* 118: 627-641 (1986)). The *Agrobacterium* transformation system may also be used to transform, as well as transfer, DNA to monocotyledonous plants and plant cells. See U.S. Pat. No. 5,591,616; Hernalsteen et al. *EMBO J*3:3039-3041 (1984); Hooykass-Van Slogteren et al. *Nature* 311:763-764 (1984); Grimsley et al. *Nature* 325:1677-179 (1987); Boulton et al. *Plant Mol. Biol.* 12:31-40 (1989); and Gould et al. *Plant Physiol.* 95:426-434 (1991).

Following introduction of the genetic construct comprising a gene expression cassette by plant transformation, plant cells can be grown and upon emergence of differentiating tissue such as shoots and roots, mature plants can be generated. In some embodiments, a plurality of plants can be generated. Methods for regenerating plants are known to those of ordinary skill in the art and can be found, for example, in *Plant Cell and Tissue Culture,* 1994, Vasil and Thorpe Eds. Kluwer Academic Publishers and in *Plant Cell Culture Protocols* (*Methods in Molecular Biology* 111, 1999 Hall Eds Humana Press). The genetically modified plant described herein can be cultured in a fermentation medium or grown in a suitable medium such as soil. In some embodiments, a suitable growth medium for higher plants can include any growth medium for plants, including, but not limited to, soil, sand, any other particulate media that support root growth (e.g., vermiculite, perlite, etc.) or hydroponic culture, as well as suitable light, water and nutritional supplements which optimize the growth of the higher plant.

Transformed plant cells which produced by foregoing plant transformation techniques can be cultured to regenerate a whole plant that includes a polynucleotide encoding a cytokinin synthase according to the invention. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture,* pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. *Ann. Rev. of Plant Phys.* 38:467-486 (1987).

A transformed plant cell, callus, tissue or plant may be identified and isolated by selecting or screening the engineered plant material for traits encoded by the marker genes (heterologous sequences) present on the transforming DNA. Such selection and screening methods are well known to those skilled in the art. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, or gfp genes) that may be present on the recombinant nucleic acid constructs. Additionally, molecular confirmation methods can be used to identify transgenic plants. Such method include use of molecular beacons, hydrolysis probe assay, otherwise known as TAQMAN® (Life Technologies, Foster City, Calif.), and KASPar® assays.

In other embodiments, the gene expression cassette may be introduced in the context of inserting a nucleic acid into the genome of a cell, including transformation into the cell, as well as crossing a plant having the sequence with another plant, so that the second plant contains the heterologous sequence, as in conventional plant breeding techniques. Such breeding techniques are well known to one skilled in the art. For a discussion of plant breeding techniques, see Poehlman *Breeding Field Crops*, AVI Publication Co., Westport Conn., 4$^{th}$ Edit. (1995). Backcrossing methods may be used to introduce a gene into the plants. This technique has been used for decades to introduce traits into a plant. An example of a description of this and other plant breeding methodologies that are well known can be found in references such as Poehlman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting.

EXAMPLE 1

Preparation of Plasmid Vectors and Host Cells Containing Polynucleotides Encoding Fungal Cytokinin Synthases According to the Invention The *E. coli* expression vector pET28a(+) was digested with NcoI restriction enzyme and treated with Antarctic Phosphatase ("AP"). Both enzymes were obtained from New England Biolabs (NEB), Ipswich, Mass., USA. NcoI cut and AP-treated vector was purified using a QIAQUICK PCR purification kit according to instructions from the manufacturer (Qiagen, Germantown, Md., USA). Approximately 50 nanograms of the vector was mixed with three synthetic double stranded DNA fragments, which were codon-optimized for *E. coli* and which encode the following fungal cytokinin synthases: SEQ ID NO:3 (EfCKS.1), SEQ ID NO:7 (truncated EfCKS.1 (a.a. 1-255)), SEQ ID NO:15 (N-polyhistidine-BoCKS.1), SEQ ID NO:19 (N-polyhistidine-IrCKS.1), SEQ ID NO:11 (N-polyhistidine-AtCKS.1), SEQ ID NO:23 (N-polyhistidine-AhCKS.1), and SEQ ID NO:27 (N-polyhistidine-FfCKS.1). For comparison, a construct was created that includes the same vector sequence and sequence which was codon-optimized for *E. coli* and encodes *Agrobacterium* IPT SEQ ID NO:29 (N-polyhistidine-AtuIPT). The vector and synthetic gene fragments coding each fungal cytokinin synthase were assembled into a final vector using the Gibson Assembly method and 2× Gibson Assembly Mastermix® from NEB, according to the manufacturer's instructions. Gibson Assembly reaction products were diluted and transformed into OneShot® TOP10 competent E. coli cells from Life Technologies Corp. (Carlsbad, Calif., USA) according to the manufacturer's instructions. Cells were plated onto LB agar containing 50 micrograms/milliliter kanamycin sulfate for selection and clones for each fungal cytokinin synthase were sequenced to identify host cells containing vectors with complete coding sequences for cytokinin synthases according to the invention.

EXAMPLE 2

Methods of Screening and Quantification of Cytokinin Synthase Activity Provided by the Invention Polynucleotide vectors encoding SEQ ID NO:3 (EfCKS.1), SEQ ID NO:7 (truncated EfCKS.1 (a.a. 1-255) were isolated from host cells produced according to Example 1 and vectors were transformed into OneShot® BL21 (DE3) E. coli protein expression strains from Life Technologies Corp. A single colony from each transformation was inoculated into 3 milliliters of LB broth containing 50 micrograms/milliliter kanamycin sulfate in a 15 milliliter culture tube and grown at 37° C. in an orbital shaker at 250 RPM for 4-6 hours. The cells were then diluted into a fresh 3 milliliters of LB broth to a final OD600 of 0.1. The cells were grown for 1 hour at 37° C. in a shaker at 250 RPM and then transferred to ice. 500 microliters of LB containing isopropylthiogalactoside (IPTG) inducer was added to make 100 micromolar final IPTG concentration. These cultures were then grown at 18° C. in a shaker at 250 RPM overnight and samples were taken for analyses of total proteins and cytokinin synthase activity.

Total protein was analyzed by taking 500 microliters of culture, centrifuging at 14,000 RPM for 2 minutes and resuspending the cell pellet in 200 µL of LDS buffer. Samples were heated at 99° C. and loaded onto a SDS-PAGE, 4-12% Bis-Tris gradient gel in MES buffer. The gel was stained with coomassie blue reagent and the presence of overexpressed gene products for EfCKS.1 (about 49 kDa) and truncated EfCKS.1 (about 30 kDa) were confirmed by comparison to molecular weight standard as shown in FIG. 3.

Cytokinin synthase activity was assayed by culture broth assay. Two milliliters samples of the overnight culture were centrifuged at 15,000 RPM for 3 minutes, and the culture broth supernatant was directly analyzed by separating cytokinins and cytokinin precursors on a SunFire C18 5 µM HPLC column from Waters Corp (Milford, Mass., USA) and analyzing the separated compounds using an Agilent 1200 Series high performance liquid chromatography system linked to a G1969A time-of-flight mass spectrometer detector (HPLC-TOF) from Agilent Technologies Inc. (Santa Clara, Calif., USA). The mobile phases used were HPLC grade water with 0.1% v/v formic acid and HPLC grade methanol with 0.1% v/v formic acid. The gradient used was 0% methanol for 1 minute, from 1 to 5 minutes a linear gradient to 60% methanol, from 5 to 7 minutes a linear gradient from 60 to 80% methanol and from 7 to 10 minutes 0% methanol. Using these conditions, trans-zeatin elutes from the column at about 3.1 minutes, isopentenyl adenine elutes from the column at about 4.4 minutes, isopentenyl adenine riboside elutes at 5.6 minutes, and isopentenyladenosine-5'-monophosphate elutes between about 7.2-7.6 minutes.

For these culture broth assays, with the TOF detector in positive ion mode, ions corresponding to the mass to charge ratio (m/z) of isopentenyl adenine (iP, 204.124), isopentenyl adenosine riboside (iPR, 336.166), isopentenyladenosine-5'-monophosphate (iPRMP, 416.133), and trans or cis-zeatin (tZ or cZ, 220.119) were extracted from the chromatogram and used to quantify the amount of each species in the culture broth.

Figure 3:
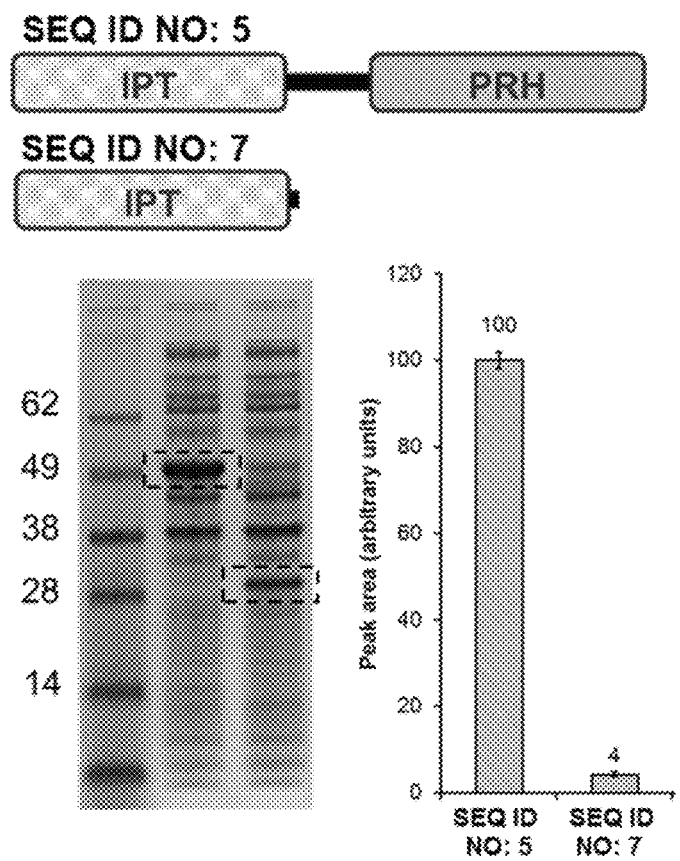
FIG. 3 provides an image of a Coomassie-stained SDS-PAGE gel showing overexpressed recombinant *Epichloe festucae* cytokinin synthase (EfCKS.1) and a truncated version EfCKS.1 (1-255), and FIG. 3 also provides a bar graph showing results of culture broth assays for secreted cytokinin from the host cells expressing EfCKS.1 and EfCKS.1 (1-255). Above these, FIG. 3 further provides a schematic diagram of EfCKS.1 and EfCKS.1 (1-255).

Results of the culture broth assays are shown in the bar graph of FIG. 3 (error bars represent standard deviation three biological replicates). These results demonstrate that the disclosed recombinant polynucleotide can be used to express a two domain cytokinin synthase according to the invention in a host cell and that the recombinant cytokinin synthase is active and produces cytokinin (isopentenyl adenine).

EXAMPLE 3

Purification of Cytokinin Synthases of Invention and Agrobacterium Control, Confirmation and Quantification of the Cytokinin Synthase Activity Provided by the Purified Cytokinin Synthases OneShot® BL21 (DE3) E. coli host cell transformed with vectors containing Epichloe festucae cytokinin synthase (EfCKS) gene with coding sequence for an N-terminal 6× histidine tag (N-polyhistidine EfCKS) (SEQ ID NO:4) and the TAKARA pGro7 chaperone expression plasmid according to instructions from the manufacturer Takara Bio Inc. (Mountain View, Calif., USA). A single colony from each transformation was inoculated into 75 milliliters of LB broth containing 50 micrograms/milliliter kanamycin sulfate and chloramphenicol in a 250 milliliter Erlenmeyer flask and grown at 30° C. in a shaker at 250 RPM overnight. Fifteen milliliters of the overnight culture was inoculated into each of three 2.8-liter fernbach flasks containing 1-liter of LB broth. Each inoculated liter of LB broth contained 50 micrograms per milliliter kanamycin sulfate and chloramphenicol and was grown at 37° C. and 250 RPM for 1.5 hours. Each culture was then placed on ice and supplemented with L-arabinose (0.75 milligrams/milliliters final concentration) and IPTG (100 micromolar final concentration). Cultures were shaken at 18° C. and 250 RPM for 8 hours. The cultures were then centrifuged at 8000 RPM for 15 minutes. The cell pellet was resuspended in approximately 125 milliliters of buffer A containing 25 mM HEPES pH 7.4, 150 mM sodium chloride, 2 mM magnesium chloride, and 2 mM dithiothreitol. Cells were lysed using a microfluidizer. Lysed cells were centrifuged at 20,000 RPM for 20 minutes. Clarified lysate was loaded into a superloop and injected onto a 5 milliliter HisPrep FastFlow® column (GE Healthcare Bioscences, Uppsala, Sweden)) at 5 mL per minute. After loading the column with the clarified lysate, the column was washed with 10 column volumes of buffer A. The column was then washed with buffer A supplemented with 20 millimolar imidazole for 6 column volumes. EfCKS was eluted from the column with buffer A supplemented with 200 millimolar imidazole. Within 5 minutes of elution from the column the eluted protein was assayed for cytokinin synthase activity.

For comparison, Agrobacterium tumefaciens isopentenyl transferase (AtuIPT) fused to N-terminal 6× histidine tag was expressed from a plasmid vector in BL21 (DE3) E. coli host cells as described above, with the following differences:

L-arabinose supplementation was omitted and, following induction with IPTG and centrifugation, the cell pellet was resuspended in approximately 40 milliliters of buffer A. Cells were lysed, sonicated, centrifuged, and the resulting clarified lysate was loaded into a superloop and injected onto a 5 milliliter HisTrap HP® column (GE Healthcare) at 5 mL per minute. After loading the column with the clarified lysate, the column was washed with 8 column volumes of buffer A. The column was then washed with supplemented buffer and AtuIPT was eluted as described above for EfCKS.

Cytokinin synthase activity was assayed by diluting the eluted protein fraction two-fold in buffer A supplemented with 100 micromolar adenosine-5'-monophosphate (AMP) and 0.1 mg/mL dimethylallyl pyrophosphate. The assay was quenched by mixing an equal volume of the reaction mix with a solution of 2% v/v formic acid. The quenched assay was directly analyzed using the HPLC-TOF method described in Example 2. For in vitro enzyme activity assays, the chromatograms were blank corrected with an injection that contained buffer and enzyme, but no reactants, and the absorbance of eluted products at 268 nanometers was used to quantify cytokinins and cytokinin precursors.

Figure 4:
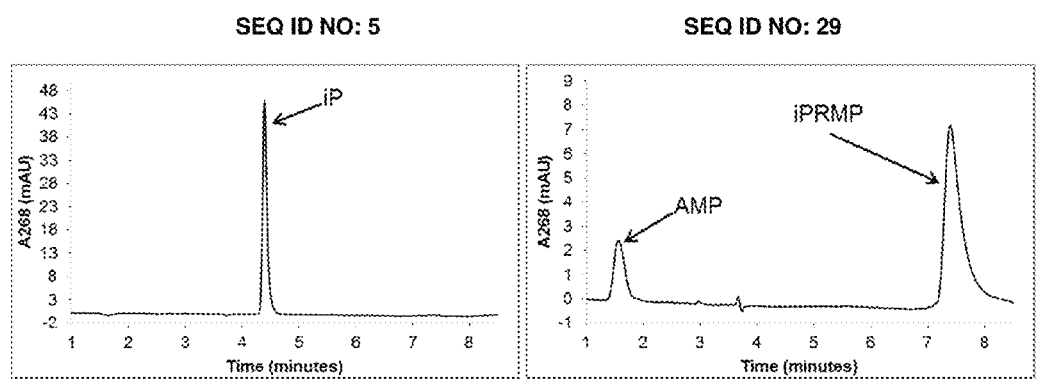
FIG. 4 is a pair of graphs showing the results of in vitro assays for activity of purified EfCKS.1 and purified isopentenyl transferase from *Agrobacterium tumefaciens* (AtuIPT).

The results shown in FIG. 4, first panel, demonstrate that the purified, recombinant cytokinin synthase (EfCKS) according to the invention provides cytokinin biosynthetic activity in vitro. The only detectable major product of EfCKS was cytokinin (isopentenyl adenine or iP). By contrast, as shown in FIG. 4, second panel, the only detectable product of *Agrobacterium tumefaciens* (AtuIPT) was isopentenyladenosine-5'-monophosphate (iPRMP) along with residual, apparently unconverted AMP reactant. These results also show that, as compared with AtuIPT, the cytokinin synthase of the invention has new and different product specificity.

EXAMPLE 4

Identification of Additional Fungal Two-Domain Cytokinin Synthase Enzymes and Amino Acid Sequence Identity Analysis Percentage Cytokinin synthase sequences were identified in the following plant-associated fungi: *Epichloe festucae* (EfCKS), *Balansia obtecta* (BoCKS), *Ilyonectria radicola* cytokinin synthase (IrCKS), *Aciculosporium take* (AtCKS), *Atkinsonella hypoxylon* (AhCKS), and *Fusarium fujikuroi* (FfCKS). Sequences were manually inspected for the presence of sequence errors and mis-predicted exons.

The cytokinin synthase sequences were analyzed for amino acid sequence identity using the BLAST™ (BLASTP or blastp suite) program and BLOSUM62 matrix. The program generated a single sequence alignment for each pair of cytokinin synthases and determined the number of identical amino acids (amino acid percent identity), "Positives" (amino acids that are identical or classified as positive substitutions by the BLOSUM62 matrix), and gaps at each position in the alignment. See Altschul et al. (1997), *Nucl. Acids Res* 25(17):3389-3402. The following tables provide the percentage of amino acid identity, positives, gaps for each pairwise BLASTp alignment of EfCKS, AtCKS, BoCKS, IrCKS, AhCKS, and FfCKS. The number of amino acids that are identical, "Positives," or gaps at each position in each alignment are indicated in parenthesis over the number of positions (length) of the relevant alignment.

TABLE 2

Amino Acid Identity, Positives, and Gaps from EfCKS Alignments

| | CYTOKININ SYNTHASE PAIRS | | | | |
|---|---|---|---|---|---|
| | EfCKS-AtCKS | EfCKS-BoCKS | EfCKS-IrCKS | EfCKS-AhCKS | EfCKS-FfCKs |
| Amino Acid Identity | 67% (343/509) | 67% (332/495) | 66% (323/491) | 70% (346/495) | 57% (284/495) |
| Positives | 80% (412/509) | 80% (400/495) | 80% (394/491) | 83% (412/495) | 70% (350/497) |
| Gaps | 3% (19/509) | 0% (4/495) | 0% (4/491) | %0 (4/495) | 2% (12/495) |

TABLE 3

Amino Acid Identity, Positives, and Gaps from AtCKS Alignments

| | CYTOKININ SYNTHASE PAIRS | | | | |
|---|---|---|---|---|---|
| | AtCKS-BoCKS | AtCKS-IrCKS | AtCKS-AhCKS | AtCKS-FfCKs | AtCKS-EfCKS |
| Amino Acid Identity | 63% (322/510) | 63% (308/486) | 64% (328/510) | 57% (282/497) | 67% (343/509) |
| Positives | 76% (391/510) | 76% (371/486) | 77% (393/510) | 70% (346/492) | 80% (412/509) |
| Gaps | 3% (17/510) | 3% (17/486) | 3% (17/510) | 5% (28/492) | 3% (19/509) |

TABLE 4

Amino Acid Identity, Positives, and Gaps from BoCKS Alignments

| | CYTOKININ SYNTHASE PAIRS | | | | |
|---|---|---|---|---|---|
| | BoCKS-IrCKS | BoCKS-AhCKS | BoCKS-FfCKs | BoCKS-EfCKS | BoCKS-AtCKS |
| Amino Acid Identity | 64% (317/495) | 84% (415/495) | 58% (291/498) | 67% (332/495) | 63% (322/510) |
| Positives | 78% (387/495) | 91% (454/495) | 71% (354/498) | 80% (400/495) | 76% (391/510) |
| Gaps | 1% (8/495) | 0% (0/495) | 2% (14/498) | 0% (4/495) | 3% (17/510) |

TABLE 5

Amino Acid Identity, Positives, and Gaps from IrCKS Alignments

| | CYTOKININ SYNTHASE PAIRS | | | | |
|---|---|---|---|---|---|
| Alignment | IrCKS-AhCKS | IrCKS-FfCKs | IrCKS-EfCKS | IrCKS-AtCKS | IrCKS-BoCKS |
| Amino Acid Identity | 64% (319/495) | 63% (311/491) | 66% (323/491) | 63% (308/486) | 64% (317/495) |
| Positives | 78% (387/495) | 75% (372/491) | 80% (394/491) | 76% (371/486) | 78% (387/495) |
| Gaps | 1% (8/495) | 1% (8/491) | 0% (4/491) | 3% (17/486) | 1% (8/495) |

TABLE 6

Amino Acid Identity, Positives, and Gaps from AhCKS Alignments

| | CYTOKININ SYNTHASE PAIRS | | | | |
|---|---|---|---|---|---|
| | AhCKS-FfCKS | AhCKS-EfCKS | AhCKS-AtCKS | AhCKS-BoCKS | AhCKS-IrCKS |
| Amino Acid Identity | 58% (292/500) | 70% (346/495) | 64% (328/510) | 84% (415/495) | 64% (319/495) |
| Positives | 71% (357/500) | 83% (412/495) | 77% (393/510) | 91% (454/495) | 78% (387/495) |
| Gaps | 3% (18/500) | %0 (4/495) | 3% (17/510) | 0% (0/495) | 1% (8/495) |

TABLE 7

Amino Acid Identity, Positives, and Gaps from FfCKS Alignments

| | CYTOKININ SYNTHASE PAIRS | | | | |
|---|---|---|---|---|---|
| | FfCKs-EfCKS | FfCKs-AtCKS | FfCKs-BoCKS | FfCKs-IrCKS | FfCKs-AhCKS |
| Amino Acid Identity | 57% (284/495) | 57% (282/497) | 58% (291/498) | 63% (311/491) | 58% (292/500) |
| Positives | 70% (350/497) | 70% (346/492) | 71% (354/498) | 75% (372/491) | 71% (357/500) |
| Gaps | 2% (12/495) | 5% (28/492) | 2% (14/498) | 1% (8/491) | 3% (18/500) |

Combined with experiments confirming cytokinin synthase activity described in Example 5, below, the foregoing demonstrates that the invention provides cytokinin synthases with varied amino acid sequences that have, for example, at least 57%-58% amino-acid sequence identity to a disclosed sequence (see, e.g., EfCKS-FfCKS, AtCKS-FfCKs, BoCKS-FfCKs, and AhCKS-FfCKS, which have at least 70%-71% "Positives") that retain functional cytokinin synthase activity. The invention provides cytokinin synthases having at least 63%-64% amino acid sequence identity to a disclosed sequence (see, e.g., AtCKS-BoCKS, AtCKS-IrCKS, IrCKS-FfCKs, AtCKS-AhCKS, BoCKS-IrCKS, IrCKS-AhCKS, AhCKS-FfCKS, which have at least 75%-78% "Positives") that retain functional cytokinin synthase activity. The invention provides cytokinin synthases having at least 65%-68% amino acid sequence identity to a disclosed sequence (see, e.g., EfCKS-AtCKS, EfCKS-BoCKS, and EfCKS-IrCKS, which have at least 80% "Positives") that retain functional cytokinin synthase activity. In further embodiments, the invention provides cytokinin synthases having at least 70% amino acid sequence identity to a disclosed sequence (see, e.g., EfCKS-AhCKS, which have at least 83% "Positives") that retain functional cytokinin synthase activity.

EXAMPLE 5

Methods of Screening and Quantification of Cytokinin Synthase Activity Provided by the Invention Polynucleotide vectors encoding the following cytokinin synthases linked at the N-terminus to a poly-histidine protein fusion tag SEQ ID NO:5 (N-polyhistidine-EfCKS.1), SEQ ID NO:7 (N-polyhistidine-truncated EfCKS.1 (a.a. 1-255); SEQ ID NO:11 (N-polyhistidine-AtCKS.1), SEQ ID NO:15 (N-polyhistidine-BoCKS.1), SEQ ID NO:19 (N-polyhistidine-IrCKS. 1), (v) SEQ ID NO:22 (N-polyhistidine-AhCKS.1), and SEQ ID NO:27 (N-polyhistidine-FfCKS.1) were isolated from host cells produced according to Example 1, transformed into OneShot® BL21 (DE3) E. coli protein expression strains, and directly analyzed for cytokinin synthase activity according to the culture broth assay described in Example 2.

Figure 5:
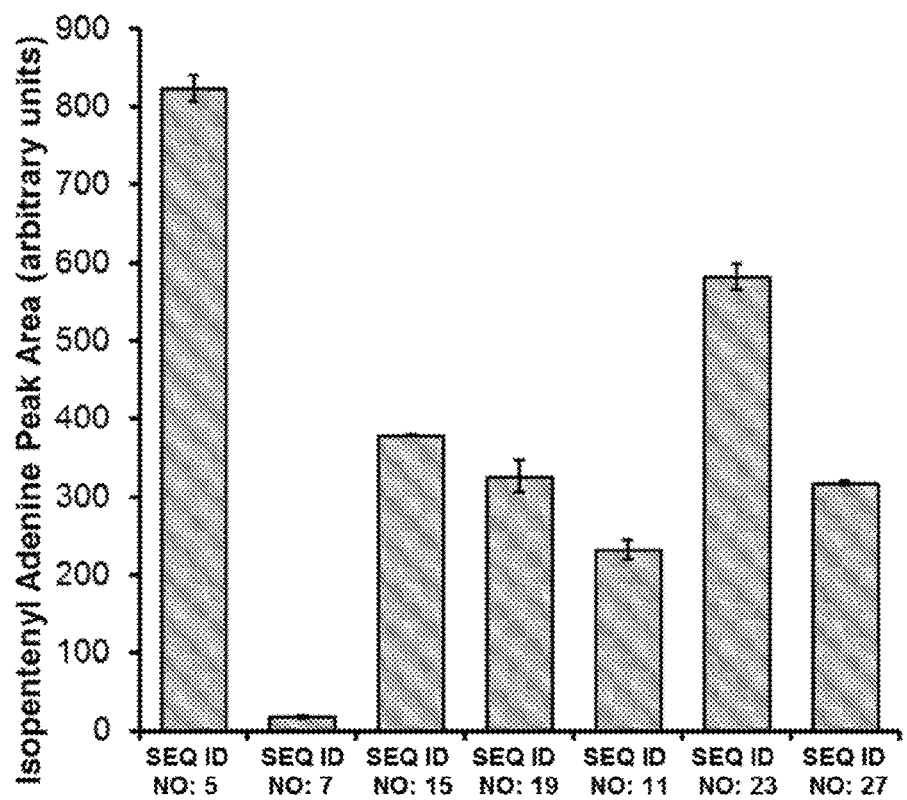
FIG. 5 is a bar graph showing results of broth assays for secreted product of recombinant cytokinin synthases according to the invention.

The results of the culture broth assays shown in FIG. 5 indicate that all of the foregoing two-domain cytokinin synthases produce a greater than 10-fold increase in host cell secretion of cytokinin (isopentenyl adenine), relative to host cell expressing negative control truncated EfCKS.1 (a.a. 1-255) (SEQ ID NO:7). For SEQ ID NOs: 15 and 22 an increase in host cell secretion of trans-zeatin (tZ) was also detected. These results demonstrate that the disclosed recombinant polynucleotides can be used to express two domain cytokinin synthases according to the invention in a host cell and that the recombinant cytokinin synthases actively produce cytokinin.

EXAMPLE 6

Identification of Conserved Residues Among Cytokinin Synthases and Testing to Identify Conserved Residues that Impact Cytokinin Synthase Function EfCKS, AtCKS, BoCKS, IrCKS, AhCKS, and FfCKS sequences were aligned using the T-COFFEE multiple sequence alignment algorithm (default settings) and visualized with Jalview software package as described in *T-Coffee: A novel method for multiple sequence alignments*. Notredame et al., J. Mol. Biol. 302(205-217) 2000, incorporated by reference herein in its entirety. The alignment was then used to identify amino acid residues that are conserved in more than 80% of the cytokinin synthase sequences. The multiple sequence alignment, including conserved residues indicated by boxes, is shown in FIG. 6.

Individual amino acid residues were selected for targeted mutations to determine their effect on cytokinin synthase function based on degree of sequence conservation and proximity to other nearby conserved residues. Selected residues are indicated by wedges below the relevant alignment of FIG. 6. The plasmid containing EfCKS.1.Ec.his (SEQ ID NO:4) was altered by site-directed mutagenesis to create sixty-six different targeted mutants.

Targeted mutations were generated using the following protocol for single primer site-directed mutagenesis. 400 nanograms of pET28a(+) plasmid containing EfCKS.1.Ec.his (see Example 3, above) was mixed with 100 nanomolar of mutagenic primer containing the desired mutation, 200 micromolar dNTPs, 1 microliter of Pfu DNA polymerase, and 1×Pfu reaction buffer in a total volume of 50 microliters. The plasmid was amplified by the polymerase chain reaction with the following conditions: initial denaturation at 95° C. for 3 minutes, followed by 18 cycles of the following; 95° C. for 30 seconds, 53° C. for 1 minute, 68° C. for 15 minutes, and a final extension round at 68° C. for 30 minutes. The mutagenic PCR reaction mix (4 microliters) was added to 0.5 microliters of Dpn1 restriction enzyme, and 1×CutSmart buffer (NEB, Ipswich, Mass., USA) in a total reaction volume of 20 microliters. The restriction digest was incubated at 37° C. for 2.5-3 hours. After the restriction digest was complete, 6 microliters of the restriction digest was used to transform OneShot® Top10 E. coli cells according to the manufacturer's instructions. The cells were plated onto LB+kanamycin sulfate plates and grown overnight. Single colonies were selected and used to isolate sequence-verified clones of the plasmid with the targeted mutation. Each sequence-verified plasmid containing the targeted mutation was then used to transform One-Shot® BL21 DE3 E. coli according to the manufacturer's instructions. Isolated single colonies were used to generate glycerol stocks containing BL21 DE3 *E. coli* containing each targeted mutant of EfCKS.1.Ec.his. in pET28a vectors.

The glycerol stocks were used to inoculate deep well 96-well plates containing 600 microliters of LB broth+ kanamycin sulfate and grown at 33° C. and 250 RPM for about 15 hours. The cultures were used to inoculate three deep well 24-well plates containing 2 mL of LB broth+ kanamycin sulfate. Cultures were then grown at 36° C. for 2.5 hours and induced with 50 micromolar IPTG. The $OD_{600}$ of the cells at induction was 0.65-0.70. Induced cultures were grown at 18° C. and 250 RPM. Samples were collected at 4 hours, 8 hours, and 16 hours by removing 300 microliters of culture broth from the deep well plates. Culture samples were centrifuged at 4,000 RPM for 10 minutes and the supernatant was filtered over 0.2 micron filters and transferred to a 96-well plate for quantification of cytokinins. Quantification involved injecting 20 microliters of filter-sterilized into HPLC-MS time of flight (HPLC-TOF) system as described in Example 2 above, with a modification to the gradient to decrease the run time. The gradient used was 2% methanol to 70% methanol in 3.5 minutes, 1.5 minutes at 70% methanol, then to 2% methanol in 0.9 minutes. To normalize cytokinin production across mutants, the extracted ion chromatogram peak area for isopentenyl adenine (204.124 m/z) was divided by the extracted ion chromatogram peak area at 220.119 m/z, a byproduct of normal *E. coli* metabolism that is excreted into the broth during growth. Residues were determined to be functional if they substantially decreased cytokinin accumulation in the LB broth relative to the wild-type EfCKS.1.Ec.his at each of the time points tested.

Figure 7:
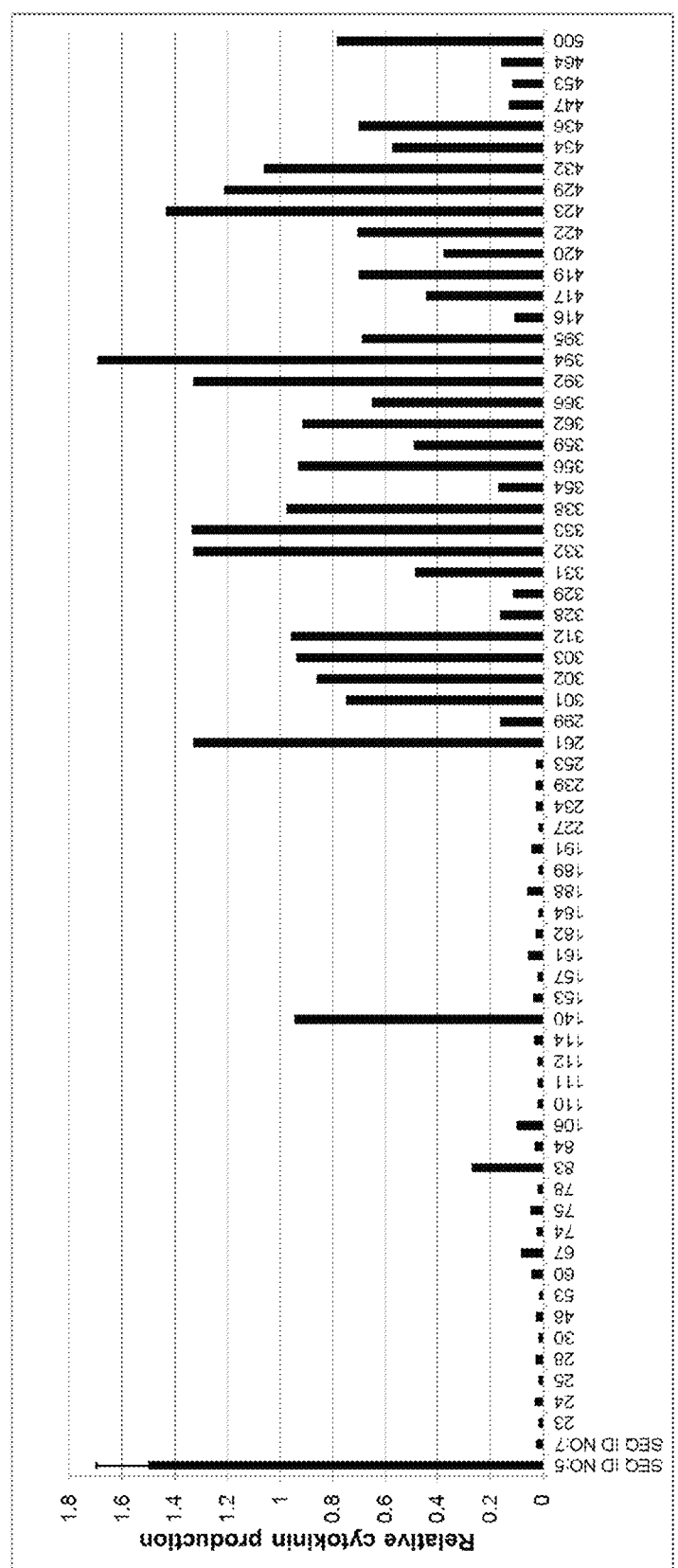
FIG. 7 is a bar graph showing results of broth assays for secreted product of the recombinant cytokinin synthase enzyme and mutants thereof, including sixty-six distinct alanine scanning substitution mutants.

The bar graph in FIG. 7 shows the effect of each mutation on cytokinin synthase activity at 16 hours post-induction relative to the histidine tagged EfCKS ("Wild Type") and to negative control histidine tagged truncated EfCKS.1 SEQ ID NO:7). The activity of each mutant is indicated along the x-axis by reference to the amino acid position of the alanine substitution in histidine-tagged EfCKS (SEQ ID NO:5). Table 8 shows cytokinin synthase activity at 16 hours, 8 hours, and 4 hours post-induction of wild-type EfCKS (SEQ ID NO:5), truncated EfCKS (a.a. 1-255) negative control (SEQ ID NO:7). Table 9 shows cytokinin synthase activity at 16 hours, 8 hours, and 4 hours post-induction of alanine-scanning substitution mutants. The first column of Table 9 (rows G23 to W500) refer to amino acid positions substituted with alanine in histidine-tagged EfCKS (SEQ ID NO:5) and the second column (rows G13 to W490) refers to corresponding amino acid positions in wild type EfCKS (SEQ ID NO:3).

TABLE 8

| His-EFCKs | EfCKS | EFFECT ON CKS ACTIVITY | 16 HOURS | 8 HOURS | 4 HOURS |
|---|---|---|---|---|---|
| WT | | | 100 | 100 | 100 |
| Frameshift (a.a. 1-255) | | SEVERE | 1 | 4 | 10 |

TABLE 9

| His-EFCKs | EfCKS | EFFECT ON CKS ACTIVITY | 16 HOURS | 8 HOURS | 4 HOURS |
|---|---|---|---|---|---|
| G23 | G13 | SEVERE | 1 | 4 | 10 |
| P24 | P14 | SEVERE | 2 | 5 | 19 |
| T25 | T15 | SEVERE | 1 | 2 | 10 |
| G28 | G18 | SEVERE | 2 | 2 | 10 |
| T30 | T20 | SEVERE | 1 | 4 | 10 |
| D48 | D38 | SEVERE | 1 | 2 | 10 |
| Y53 | Y43 | SEVERE | 1 | 2 | 10 |
| T60 | T50 | SEVERE | 3 | 5 | 10 |
| E67 | E57 | SEVERE | 6 | 7 | 19 |
| H74 | H64 | SEVERE | 1 | 2 | 14 |
| L75 | L65 | SEVERE | 4 | 6 | 14 |
| Y78 | Y68 | SEVERE | 1 | 2 | 14 |
| E83 | E73 | SEVERE | 19 | 19 | 29 |
| E84 | E74 | SEVERE | 2 | 4 | 10 |
| P106 | P96 | SEVERE | 7 | 11 | 19 |
| G110 | G100 | SEVERE | 1 | 2 | 10 |
| G111 | G101 | SEVERE | 1 | 4 | 14 |
| S112 | S102 | SEVERE | 1 | 2 | 5 |
| S114 | S104 | SEVERE | 2 | 5 | 10 |
| S140 | S130 | SMALL | 66 | 67 | 71 |
| M153 | M143 | SEVERE | 2 | 4 | 19 |
| G157 | G147 | SEVERE | 1 | 4 | 10 |
| E161 | E151 | SEVERE | 4 | 5 | 10 |
| G182 | G172 | SEVERE | 2 | 4 | 14 |
| W184 | W174 | SEVERE | 1 | 2 | 14 |
| G188 | G178 | SEVERE | 4 | 9 | 14 |
| Y189 | Y179 | SEVERE | 1 | 2 | 10 |
| E191 | E181 | SEVERE | 3 | 6 | 10 |
| Y227 | Y217 | SEVERE | 1 | 2 | 10 |
| W234 | W224 | SEVERE | 1 | 2 | 10 |
| L239 | L229 | SEVERE | 2 | 4 | 10 |
| L253 | L243 | SEVERE | 1 | 2 | 10 |
| W261 | W251 | SMALL | 94 | 77 | 67 |
| F299 | F289 | SEVERE | 11 | 16 | 33 |
| G301 | G291 | SEVERE | 52 | 57 | 52 |
| S302 | S292 | SMALL | 61 | 67 | 62 |
| S303 | S293 | SMALL | 66 | 72 | 71 |
| E312 | E302 | SMALL | 68 | 78 | 76 |
| L328 | L318 | SEVERE | 11 | 12 | 24 |
| V329 | V319 | SEVERE | 8 | 10 | 19 |
| G331 | G321 | SEVERE | 34 | 33 | 38 |
| G332 | G322 | SMALL | 94 | 73 | 71 |
| G333 | G323 | SMALL | 94 | 83 | 10 |
| M338 | M328 | SMALL | 69 | 62 | 57 |
| V354 | V344 | SEVERE | 12 | 14 | 24 |
| G356 | G346 | SMALL | 65 | 77 | 67 |
| P359 | P349 | SEVERE | 35 | 32 | 33 |
| L362 | L352 | SMALL | 64 | 78 | 67 |
| E366 | E356 | SEVERE | 46 | 41 | 33 |
| H392 | H382 | SMALL | 94 | 74 | 62 |
| R394 | R384 | SMALL | 119 | 93 | 81 |
| K395 | K385 | SEVERE | 49 | 48 | 48 |
| G416 | G406 | SEVERE | 8 | 12 | 14 |
| G417 | G407 | SEVERE | 31 | 32 | 33 |
| G419 | G409 | SEVERE | 49 | 54 | 57 |
| T420 | T410 | SEVERE | 27 | 19 | 33 |
| E422 | E412 | SEVERE | 49 | 47 | 52 |
| E423 | E413 | SMALL | 101 | 75 | 67 |
| T429 | T419 | SMALL | 85 | 67 | 62 |
| Q432 | Q422 | SMALL | 75 | 84 | 62 |
| G434 | G424 | SEVERE | 40 | 40 | 33 |
| H436 | H426 | SEVERE | 49 | 58 | 48 |
| G447 | G437 | SEVERE | 9 | 16 | 29 |
| L453 | L443 | SEVERE | 8 | 10 | 24 |
| F464 | F454 | SEVERE | 11 | 12 | 33 |
| W500 | W490 | SEVERE | 55 | 43 | 43 |

For each mutant in Table 9, the corresponding amino acid position in wild-type EfCKS (SEQ ID NO:3) is determined by subtracting 10 amino acids due to the histidine tag added to the N-terminus of SEQ ID NO:5. Furthermore, each corresponding amino acid position can be determined in EfCKS, AtCKS, BoCKS, IrCKS, AhCKS.1, and FfCKS by reference to FIG. 6, which indicates in each cytokinin synthase sequence the conserved amino acids that, when altered, has a (i) severe effect on activity (indicated by wedge ▲), or (ii) small effect on activity (indicated by open diamond ◇).

The foregoing results provide guidance on which amino acid residues should be conserved in cytokinin synthases of the invention to preserve a wild-type level of cytokinin synthase activity. Thus, the invention provides functional cytokinin synthases having, for example, at least 57%-58% amino acid sequence identity to a disclosed sequence (see, e.g., EfCKS-FfCKs, AtCKS-FfCKs, BoCKS-FfCKs, and AhCKS-FfCKS); at least 63%-64% amino acid sequence identity to a disclosed sequence (see, e.g., AtCKS-BoCKS, AtCKS-IrCKS, IrCKS-FfCKs, AtCKS-AhCKS, BoCKS-IrCKS, IrCKS-AhCKS, AhCKS-FfCKS); at least 65%-68% amino acid sequence identity to a disclosed sequence (see, e.g., EfCKS-AtCKS, EfCKS-BoCKS, and EfCKS-IrCKS); or at least 70% amino acid sequence identity to a disclosed sequence (see, e.g., EfCKS-AhCKS) which—when aligned with the disclosed amino acids (as in FIG. 6)—include the residues identified in Table 9 and FIG. 7 as having severe or small effects on activity.

The foregoing results also demonstrate that, in other embodiments, the invention provides cytokinin synthases having cytokinin synthase activity that is reduced by a small amount. In some embodiments, the invention provides functional cytokinin synthases having, for example, at least 57%-58% amino acid sequence identity to a disclosed sequence; at least 63%-64% amino acid sequence identity to a disclosed sequence; at least 65%-68% amino acid sequence identity to a disclosed sequence; or at least 70% amino acid sequence identity to a disclosed sequence, which—when aligned with the disclosed amino acids (as in FIG. 6)—include the residues identified in Table 9 and FIG. 7 as having a small effect on activity.

EXAMPLE 7

Figure 23:
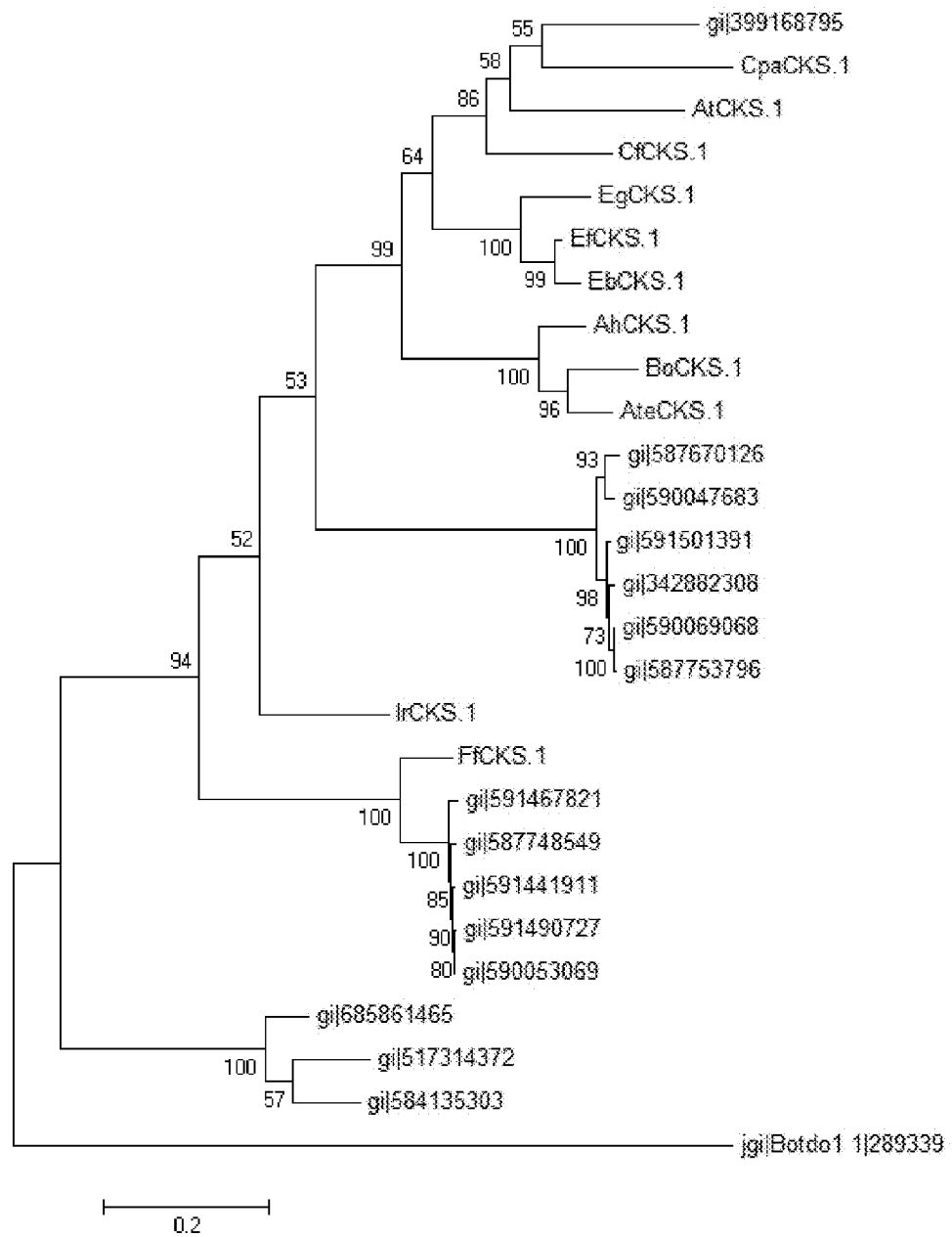
FIG. 23 provides a phylogenetic tree showing evolutionary distances between cytokinin synthases of the invention.

Further Identification of Additional Fungal Two-Domain Cytokinin Synthase Enzymes and Amino Acid Sequence Identity Analysis Percentage Further cytokinin synthase sequences were identified by searching genomic databases for fungal genes encoding an isopentenyl transfer (IPT)-like domain and a phosphoribohydrolase (PRH)-like domain in accordance with the invention. Additional cytokinin synthases are manually inspected for the presence of sequence errors and mis-predicted exons and are assayed to confirm cytokinin synthase activity. The amino acid sequences of the additional cytokinin synthases of the invention are provided as SEQ ID NOs:34 to 54 and are shown in FIGS. 24-29. Table 10 indicates the fungal source for each amino acid sequence (as well as corresponding Gene Id (gi/jgi) or abbreviation for the cytokinin synthase used in the phylogenetic tree in FIG. 23).

TABLE 10

| Fungal Source (CKS gene identifier or abbreviation) | SEQ ID NO |
|---|---|
| *Botryosphaeria dothidea* (jgi\|Botdo1_1\|289339) | SEQ ID NO: 34 |
| *Claviceps purpurea* (gi\|399168795 20.1) | SEQ ID NO: 35 |
| *Fusarium oxysporum vasinfectum* 25433 (gi\|591501391) | SEQ ID NO: 36 |
| *Fusarium oxysporum* f. sp. *raphani* 54005 (gi\|590069068) | SEQ ID NO: 37 |
| *Fusarium oxysporum* Fo5176 (gi\|342882308) | SEQ ID NO: 38 |
| *Fusarium oxysporum* f. sp. *pisi* HDV247 (gi\|587753796) | SEQ ID NO: 39 |
| *Fusarium oxysporum* FOSC 3-a (gi\|587670126) | SEQ ID NO: 40 |
| *Fusarium oxysporum* f. sp. *melonis* 26406 (gi\|590047683) | SEQ ID NO: 41 |
| *Fusarium oxysporum* f. sp. *vasinfectum* 25433 (gi\|591490727) | SEQ ID NO: 42 |
| *Fusarium oxysporum* f. sp. *conglutinans* race 2 54008 (gi\|591441911) | SEQ ID NO: 43 |
| *Fusarium oxysporum* f. sp. *raphani* 54005 (gi\|590053069) | SEQ ID NO: 44 |
| *Fusarium oxysporum* f. sp. *cubense* tropical race 4 54006 (gi\|591467821) | SEQ ID NO: 45 |
| *Fusarium oxysporum* f. sp. *pisi* HDV247 (gi\|587748549) | SEQ ID NO: 46 |
| *Fusarium fujikuroi* IMI 58289 (gi\|517314372) | SEQ ID NO: 47 |
| *Fusarium pseudograminearum* CS3096 (gi\|685861465) | SEQ ID NO: 48 |
| *Fusarium verticillioides* 7600 (gi\|584135303) | SEQ ID NO: 49 |
| *Epichloe gansuensis* EgCKS | SEQ ID NO: 50 |
| *Atkinsonella texensis* AteCKS | SEQ ID NO: 51 |
| *Claviceps fusiformis* CfCKS | SEQ ID NO: 52 |
| *Epichloe baconii* (EbCKS | SEQ ID NO: 53 |
| *Claviceps paspali* (CpaCKS) | SEQ ID NO: 54 |

EXAMPLE 8

Identification of Functional Motifs in Cytokinin Synthases of the Invention and Testing to Identify Conserved Residues that Impact Cytokinin Synthase Function The alignment shown in FIG. 6 and the site-directed mutagenesis results described in Example 6 and Table 8 were analyzed in further view of additional cytokinin synthases identified in Example 7 to identify functionally significant motifs in each fungal cytokinin synthase. Referring to the consensus amino acid sequence positions in the alignment of FIG. 6, the following four motifs were identified: (1) GPTXaa$_1$Xaa$_2$GKT (SEQ ID NO:30), wherein Xaa$_1$ is G or A and Xaa$_2$ is V, S, A, or T, at consensus sequence amino acid positions 13-20, (2) PXaa$_3$Xaa$_4$Xaa$_5$GGSXaa$_6$S (SEQ ID NO:31), wherein Xaa$_3$ is I or V, Xaa$_4$ is L or V, Xaa$_5$ is V or C, and Xaa$_6$ is T or I, at consensus sequence amino acid positions 96-104, (3) Xaa$_7$Xaa$_8$YGGG (SEQ ID NO:32), wherein Xaa$_7$ is L or I, and Xaa$_8$ is V or I, at consensus sequence amino acid positions 333-338, and (4) Xaa$_9$GGYGT Xaa$_{10}$EEL (SEQ ID NO:33), where Xaa$_9$ is S or P and Xaa$_{10}$ is L or M, at consensus sequence amino acid positions 426-438. Table 11 below shows the precise sequence corresponding the foregoing motifs as exemplified in each of the fungal cytokinin synthases disclosed herein.

TABLE 11

| SPECIES (SEQ ID NO) | MOTIF 1 GPTXaa₁Xaa₂G KTK (SEQ ID NO: 30) | MOTIF 2 PXaa₃Xaa₄Xaa₅ GGSXaa₆S (SEQ ID NO: 31) | MOTIF 3 Xaa7Xaa8YGGG (SEQ ID NO: 32) | MOTIF 4 Xaa9GGYGT Xaa10EEL (SEQ ID NO: 33) |
|---|---|---|---|---|
| AhCKS.1 (SEQ ID NO: 21) | GPTGVGKTK (SEQ ID NO: 59) | PILVGGSTS (SEQ ID NO: 63) | LVYGGG (SEQ ID NO: 68) | SGGYGTLEEL (SEQ ID NO: 71) |
| AtCKS.1 (SEQ ID NO: 9) | GPTASGKTK (SEQ ID NO: 60) | PVLVGGSTS (SEQ ID NO: 64) | LVYGGG (SEQ ID NO: 68) | SGGYGTMEEL (SEQ ID NO: 72) |
| AteCKS.1 (SEQ ID NO: 51) | GPTASGKTK (SEQ ID NO: 60) | PILVGGSTS (SEQ ID NO: 63) | LVYGGG (SEQ ID NO: 68) | SGGYGTLEEL (SEQ ID NO: 71) |
| BoCKS.1 (SEQ ID NO: 13) | GPTASGKTK (SEQ ID NO: 60) | PILVGGSTS (SEQ ID NO: 63) | LVYGGG (SEQ ID NO: 68) | SGGYGTLEEL (SEQ ID NO: 71) |
| CfCKS.1 (SEQ ID NO: 52) | GPTASGKTK (SEQ ID NO: 60) | PILVGGSTS (SEQ ID NO: 63) | LVYGGG (SEQ ID NO: 68) | SGGYGTMEEL (SEQ ID NO: 72) |
| CpaCKS.1 *Claviceps paspali* (SEQ ID NO: 54) | GPTASGKTK (SEQ ID NO: 60) | PILVGGSTS (SEQ ID NO: 63) | LVYGGG (SEQ ID NO: 68) | SGGYGTMEEL (SEQ ID NO: 72) |
| EbCKS.1 *Epichlo baconii* (SEQ ID NO: 53) | GPTASGKTK (SEQ ID NO: 60) | PVLVGGSTS (SEQ ID NO: 64) | LVYGGG (SEQ ID NO: 68) | SGGYGTMEEL (SEQ ID NO: 72) |
| EfCKS.1 (SEQ ID NO: 3) | GPTASGKTK (SEQ ID NO: 60) | PVLVGGSTS (SEQ ID NO: 64) | LVYGGG (SEQ ID NO: 68) | SGGYGTMEEL (SEQ ID NO: 72) |
| EgCKS.1 (SEQ ID NO: 50) | GPTASGKTK (SEQ ID NO: 60) | PILVGGSTS (SEQ ID NO: 63) | LVYGGG (SEQ ID NO: 68) | SGGYGTMEEL (SEQ ID NO: 72) |
| FfCKS.1 (SEQ ID NO: 25) | GPTASGKTK (SEQ ID NO: 60) | PILVGGSTS (SEQ ID NO: 63) | LVYGGG (SEQ ID NO: 68) | SGGYGTLEEL (SEQ ID NO: 71) |
| gi\|342882308 (SEQ ID NO: 38) | GPTASGKTK (SEQ ID NO: 60) | PVLVGGSTS (SEQ ID NO: 64) | LIYGGG (SEQ ID NO: 69) | SGGYGTMEEL (SEQ ID NO: 72) |
| gi\|399168795 (SEQ ID NO: 35) | GPTASGKTK (SEQ ID NO: 60) | PILVGGSTS (SEQ ID NO: 63) | LVYGGG (SEQ ID NO: 68) | SGGYGTLEEL (SEQ ID NO: 71) |
| gi\|517314372 (SEQ ID NO: 47) | GPTASGKTK (SEQ ID NO: 60) | PVVVGGSTS (SEQ ID NO: 65) | LVYGGG (SEQ ID NO: 68) | SGGYGTLEEL (SEQ ID NO: 71) |
| gi\|584135303 (SEQ ID NO: 49) | GPTGAGKTK (SEQ ID NO: 61) | PVVVGGSTS (SEQ ID NO: 65) | IVYGGG (SEQ ID NO: 70) | SGGYGTLEEL (SEQ ID NO: 71) |
| gi\|587670126 (SEQ ID NO: 40) | GPTGVGKTK (SEQ ID NO: 59) | PVLVGGSTS (SEQ ID NO: 64) | LIYGGG (SEQ ID NO: 69) | SGGYGTMEEL (SEQ ID NO: 72) |
| gi\|587748549 (SEQ ID NO: 46) | GPTGTGKTK (SEQ ID NO: 62) | PILVGGSIS (SEQ ID NO: 66) | LVYGGG (SEQ ID NO: 68) | SGGYGTLEEL (SEQ ID NO: 71) |
| gi\|587753796 (SEQ ID NO: 39) | GPTASGKTK (SEQ ID NO: 60) | PVLVGGSTS (SEQ ID NO: 64) | LIYGGG (SEQ ID NO: 69) | SGGYGTMEEL (SEQ ID NO: 72) |
| gi\|590047683 (SEQ ID NO: 41) | GPTASGKTK (SEQ ID NO: 60) | PVLVGGSTS (SEQ ID NO: 64) | LIYGGG (SEQ ID NO: 69) | SGGYGTMEEL (SEQ ID NO: 72) |
| gi\|590053069 (SEQ ID NO: 44) | GPTASGKTK (SEQ ID NO: 60) | PILVGGSTS (SEQ ID NO: 63) | LVYGGG (SEQ ID NO: 68) | SGGYGTLEEL (SEQ ID NO: 71) |
| gi\|590069068 (SEQ ID NO: 37) | GPTASGKTK (SEQ ID NO: 60) | PVLVGGSTS (SEQ ID NO: 64) | LIYGGG (SEQ ID NO: 69) | SGGYGTMEEL (SEQ ID NO: 72) |
| gi\|591441911 (SEQ ID NO: 43) | GPTASGKTK (SEQ ID NO: 60) | PILVGGSTS (SEQ ID NO: 63) | LVYGGG (SEQ ID NO: 68) | SGGYGTLEEL (SEQ ID NO: 71) |
| gi\|591467821 (SEQ ID NO: 45) | GPTASGKTK (SEQ ID NO: 60) | PILVGGSTS (SEQ ID NO: 63) | LVYGGG (SEQ ID NO: 68) | SGGYGTLEEL (SEQ ID NO: 71) |
| gi\|591490727 (SEQ ID NO: 42) | GPTASGKTK (SEQ ID NO: 60) | PILVGGSTS (SEQ ID NO: 63) | LVYGGG (SEQ ID NO: 68) | SGGYGTLEEL (SEQ ID NO: 71) |
| gi\|591501391 (SEQ ID NO: 36) | GPTASGKTK (SEQ ID NO: 60) | PVLVGGSTS (SEQ ID NO: 64) | LIYGGG (SEQ ID NO: 69) | SGGYGTMEEL (SEQ ID NO: 72) |
| gi\|685861465 (SEQ ID NO: 48) | GPTASGKTK (SEQ ID NO: 60) | PVVVGGSTS (SEQ ID NO: 65) | LVYGGG (SEQ ID NO: 68) | SGGYGTLEEL (SEQ ID NO: 71) |

TABLE 11-continued

| SPECIES (SEQ ID NO) | MOTIF 1<br>GPTXaa$_1$Xaa$_2$G<br>KTK<br>(SEQ ID NO: 30) | MOTIF 2<br>PXaa$_3$Xaa$_4$Xaa$_5$<br>GGSXaa$_6$S<br>(SEQ ID NO: 31) | MOTIF 3<br>Xaa$_7$Xaa$_8$YGGG<br>(SEQ ID NO: 32) | MOTIF 4<br>Xaa$_9$GGYGT<br>Xaa$_{10}$EEL<br>(SEQ ID NO: 33) |
|---|---|---|---|---|
| IrCKS.1 (SEQ ID NO: 17) | GPTASGKTK<br>(SEQ ID NO: 60) | PILVGGSTS<br>(SEQ ID NO: 63) | LVYGGG<br>(SEQ ID NO: 68) | SGGYGTMEEL<br>(SEQ ID NO: 72) |
| jgi\|Botdo1_1\|289339 1<br>(SEQ ID NO: 34) | GPTASGKTK<br>(SEQ ID NO: 60) | PILCGGSTS<br>(SEQ ID NO: 67) | LVYGGG<br>(SEQ ID NO: 68) | PGGYGTMEEL<br>(SEQ ID NO: 73) |

The foregoing demonstrates embodiments of the invention that relate to a two domain cytokinin synthase that includes (i) an isopentenyl transfer (IPT)-like domain, (ii) a phosphoribohydrolase (PRH)-like domain and (iii) each of the foregoing four motifs.

EXAMPLE 9

Confirmation of the Functional Motifs in Non Fungal Proteins Having an IPT-Like Domain or PRH-Like Domains and their Use for Making Modified Cytokinin Synthases Proteins containing IPT-like domain were interrogated for the presence of the first and second motif identified in foregoing Example 8. Table 12 provides a representative set of such motifs that were identified in bacterial homologues of the *Agrobacterium tumefaciens* isopentenyl transferase (each homologue is identified by Gene ID (gi)).

TABLE 12

| Gene ID | MOTIF 1<br>GlyXaa$_{11}$Xaa$_{12}$Xaa$_{13}$<br>Xaa$_{14}$GlyLysXaa$_{15}$<br>(SEQ ID NO: 55) | MOTIF 2<br>Xaa$_{16}$Xaa$_{17}$Xaa$_{18}$Xaa$_{19}$GlyGly<br>Xaa$_{20}$Xaa$_{21}$Xaa$_{22}$<br>(SEQ ID NO: 56) | MOTIF 3<br>(SEQ ID NO: 57) | MOTIF 4<br>(SEQ ID NO: 58) |
|---|---|---|---|---|
| gi\|787755613 | GPTCSGKT<br>(SEQ ID NO: 74) | VILEGGSIS<br>(SEQ ID NO: 84) | N/A | N/A |
| gi\|763386594 | GATTTGKT<br>(SEQ ID NO: 75) | FILEGGSVS<br>(SEQ ID NO: 85) | N/A | N/A |
| gi\|757628273 | GVTSMGKT<br>(SEQ ID NO: 76) | IIIEGGSVS<br>(SEQ ID NO: 86) | N/A | N/A |
| gi\|748744591 | GPTSTGKT<br>(SEQ ID NO: 77) | VIIEGGSVS<br>(SEQ ID NO: 87) | N/A | N/A |
| gi\|738063466 | GPTTTGKT<br>(SEQ ID NO: 78) | IILEGGSMS<br>(SEQ ID NO: 88) | N/A | N/A |
| gi\|695262623 | GPTCTGKT<br>(SEQ ID NO: 79) | LILEGGSIS<br>(SEQ ID NO: 89) | N/A | N/A |
| gi\|671637394 | GATCTGKT<br>(SEQ ID NO: 80) | VILEGGSIS<br>(SEQ ID NO: 84) | N/A | N/A |
| gi\|658535282 | GPTSTGKT<br>(SEQ ID NO: 77) | VILEGGSVS<br>(SEQ ID NO: 90) | N/A | N/A |
| gi\|653760120 | GPTSTGKT<br>(SEQ ID NO: 77) | LILEGGSIS<br>(SEQ ID NO: 89) | N/A | N/A |
| gi\|652910097 | GPTTAGKT<br>(SEQ ID NO: 81) | LILEGGSVS<br>(SEQ ID NO: 91) | N/A | N/A |
| gi\|652343402 | GPTSTGKT<br>(SEQ ID NO: 77) | IILEGGSVS<br>(SEQ ID NO: 92) | N/A | N/A |
| gi\|504873554 | GATCTGKT<br>(SEQ ID NO: 80) | VILEGGSIS<br>(SEQ ID NO: 84) | N/A | N/A |

TABLE 12-continued

| Gene ID | MOTIF 1<br>GlyXaa$_{11}$Xaa$_{12}$Xaa$_{13}$<br>Xaa$_{14}$GlyLysXaa$_{15}$<br>(SEQ ID NO: 55) | MOTIF 2<br>Xaa$_{16}$Xaa$_{17}$Xaa$_{18}$Xaa$_{19}$GlyGly<br>Xaa$_{20}$Xaa$_{21}$Xaa$_{22}$<br>(SEQ ID NO: 56) | MOTIF 3<br>(SEQ ID NO: 57) | MOTIF 4<br>(SEQ ID NO: 58) |
|---|---|---|---|---|
| gi\|501825808 | GPTSTGKT (SEQ ID NO: 77) | VILEGGSIS (SEQ ID NO: 84) | N/A | N/A |
| gi\|499303622 | GPTSVGKT (SEQ ID NO: 82) | LILEGGSIS (SEQ ID NO: 89) | N/A | N/A |
| gi\|499194825 | GPTCTGKT (SEQ ID NO: 79) | LILEGGSTS (SEQ ID NO: 93) | N/A | N/A |
| gi\|499193920 | GPTCTGKT (SEQ ID NO: 79) | LILEGGSIS (SEQ ID NO: 89) | N/A | N/A |
| gi\|489573415 | GPTCSGKT (SEQ ID NO: 74) | VILEGGSIS (SEQ ID NO: 84) | N/A | N/A |
| gi\|489370511 | GATTTGKT (SEQ ID NO: 75) | LILEGGSVS (SEQ ID NO: 91) | N/A | N/A |
| gi\|4586310 | GPTCTGKT (SEQ ID NO: 79) | LILEGGSIS (SEQ ID NO: 89) | N/A | N/A |
| gi\|441422009 | GATCTGKT (SEQ ID NO: 80) | VILEGGSIS (SEQ ID NO: 84) | N/A | N/A |
| gi\|344175716 | GATTTGKT (SEQ ID NO: 75) | LILEGGSVS (SEQ ID NO: 91) | N/A | N/A |
| gi\|297155133 | GPTGVGKS (SEQ ID NO: 83) | VIVEGGSIS (SEQ ID NO: 94) | N/A | N/A |

Table 13 provides a representative set of such motifs that were identified in bacterial homologues of *Escherichia coli* tRNA isopentenyl transferase (each homologue is identified by Gene ID (gi)).

TABLE 13

| Gene ID | MOTIF 1<br>GlyXaa$_{11}$Xaa$_{12}$Xaa$_{13}$<br>Xaa$_{14}$GlyLysXaa$_{15}$<br>(SEQ ID NO: 55) | MOTIF 2<br>Xaa$_{16}$Xaa$_{17}$Xaa$_{18}$Xaa$_{19}$GlyGly<br>Xaa$_{20}$Xaa$_{21}$Xaa$_{22}$<br>(SEQ ID NO: 56) | MOTIF 3<br>(SEQ ID NO: 57) | MOTIF 4<br>(SEQ ID NO: 58) |
|---|---|---|---|---|
| gi\|164423202 | GSTGTGKS (SEQ ID NO: 95) | PIVVGGTSY (SEQ ID NO: 100) | N/A | N/A |
| gi\|398366035 | GTTGVGKS (SEQ ID NO: 96) | PIVVGGTHY (SEQ ID NO: 101) | N/A | N/A |
| gi\|22326902 | GPTGAGKS (SEQ ID NO: 97) | PIVTGGTGL (SEQ ID NO: 102) | N/A | N/A |
| gi\|25144712 | GCTGTGKS (SEQ ID NO: 98) | PVIVGGTTY (SEQ ID NO: 103) | N/A | N/A |
| gi\|127087 | GPTASGKT (SEQ ID NO: 99) | PLLVGGTML (SEQ ID NO: 104) | N/A | N/A |

Table 14 provides a representative set of such motifs that were identified in bacterial homologues of plant adenylate isopentenyl transferases (each homologue is identified by Gene ID (gi)).

TABLE 14

| Gene ID | MOTIF 1<br>GlyXaa$_{11}$Xaa$_{12}$Xaa$_{13}$Xaa$_{14}$Gly<br>LysXaa$_{15}$<br>(SEQ ID NO: 55) | MOTIF 2<br>Xaa$_{16}$Xaa$_{17}$Xaa$_{18}$Xaa$_{19}$<br>GlyGlyXaa$_{20}$Xaa$_{21}$Xaa$_{22}$<br>(SEQ ID NO: 56) | MOTIF 3<br>(SEQ ID NO: 57) | MOTIF 4<br>(SEQ ID NO: 58) |
|---|---|---|---|---|
| gi\|15221410 | GATGAGKS (SEQ ID NO: 105) | PIIAGGSNS (SEQ ID NO: 111) | N/A | N/A |

TABLE 14-continued

| Gene ID | MOTIF 1<br>GlyXaa$_{11}$Xaa$_{12}$Xaa$_{13}$Xaa$_{14}$Gly<br>LysXaa$_{15}$<br>(SEQ ID NO: 55) | MOTIF 2<br>Xaa$_{16}$Xaa$_{17}$Xaa$_{18}$Xaa$_{19}$<br>GlyGlyXaa$_{20}$Xaa$_{21}$Xaa$_{22}$<br>(SEQ ID NO: 56) | MOTIF 3<br>(SEQ ID NO: 57) | MOTIF 4<br>(SEQ ID NO: 58) |
|---|---|---|---|---|
| gi\|15222583 | GTTGTGKS (SEQ ID NO: 106) | PIVVGGSNS (SEQ ID NO: 112) | N/A | N/A |
| gi\|15230294 | GATGSGKS (SEQ ID NO: 107) | PIIAGGSNS (SEQ ID NO: 111) | N/A | N/A |
| gi\|15233904 | GATGSGKS (SEQ ID NO: 107) | PILAGGSNS (SEQ ID NO: 113) | N/A | N/A |
| gi\|15239638 | GATGTGKS (SEQ ID NO: 108) | PIIAGGSNS (SEQ ID NO: 111) | N/A | N/A |
| gi\|18403831 | GATGSGKS (SEQ ID NO: 107) | PIVAGGSNS (SEQ ID NO: 114) | N/A | N/A |
| gi\|18412615 | GATGTGKS (SEQ ID NO: 108) | PIIVGGSNS (SEQ ID NO: 115) | N/A | N/A |
| gi\|357114975 | GATGTGKS (SEQ ID NO: 108) | PVLAGGSNS (SEQ ID NO: 116) | N/A | N/A |
| gi\|357119123 | GATGTGKT (SEQ ID NO: 109) | PVVAGGSNS (SEQ ID NO: 117) | N/A | N/A |
| gi\|357119795 | GATATGKS (SEQ ID NO: 110) | PVVAGGSNT (SEQ ID NO: 118) | N/A | N/A |
| gi\|357128230 | GATATGKS (SEQ ID NO: 110) | PIVAGGSNR (SEQ ID NO: 119) | N/A | N/A |
| gi\|357128580 | GATGTGKT (SEQ ID NO: 109) | PVVAGGSNS (SEQ ID NO: 117) | N/A | N/A |
| gi\|721643516 | GATGTGKT (SEQ ID NO: 109) | PVVAGGSNS (SEQ ID NO: 117) | N/A | N/A |

Proteins containing PRH-like domain were interrogated for the presence of the third and fourth motif identified in foregoing Example 8. Table 15 provides a representative set of such motifs that were identified in plant cytokinin riboside 5'-monophosphate phosphoribohydrolase (each homologue is identified by Gene ID (gi)).

TABLE 15

| Gene ID | MOTIF 1<br>(SEQ ID NO: 55) | MOTIF 2<br>(SEQ ID NO: 56) | MOTIF 3<br>LVYGGG<br>(SEQ ID NO: 57) | MOTIF 4<br>ProGlyGlyTyrGlyThr<br>Xaa$_{23}$Xaa$_{24}$GluLeu<br>(SEQ ID NO: 58) |
|---|---|---|---|---|
| gi\|79567911 | N/A | N/A | LVYGGG (SEQ ID NO: 57) | PGGYGTFEEL (SEQ ID NO: 120) |
| gi\|79507209 | N/A | N/A | LVYGGG (SEQ ID NO: 57) | PGGYGTLEEL (SEQ ID NO: 121) |
| gi\|721692766 | N/A | N/A | LVYGGG (SEQ ID NO: 57) | PGGYGTLEEL (SEQ ID NO: 121) |
| gi\|721635070 | N/A | N/A | LVYGGG (SEQ ID NO: 57) | PGGYGTLEEL (SEQ ID NO: 121) |
| gi\|357154491 | N/A | N/A | LVYGGG (SEQ ID NO: 57) | PGGYGTLDEL (SEQ ID NO: 122) |
| gi\|357150282 | N/A | N/A | LVYGGG (SEQ ID NO: 57) | PGGYGTLEEL (SEQ ID NO: 121) |
| gi\|357146658 | N/A | N/A | LVYGGG (SEQ ID NO: 57) | PGGYGTLEEL (SEQ ID NO: 121) |
| gi\|357136124 | N/A | N/A | LVYGGG (SEQ ID NO: 57) | PGGYGTMEEL (SEQ ID NO: 123) |

TABLE 15-continued

| Gene ID | MOTIF 1 (SEQ ID NO: 55) | MOTIF 2 (SEQ ID NO: 56) | MOTIF 3 LVYGGG (SEQ ID NO: 57) | MOTIF 4 ProGlyGlyTyrGlyThr Xaa₂₃Xaa₂₄GluLeu (SEQ ID NO: 58) |
|---|---|---|---|---|
| gi\|357135368 | N/A | N/A | LVYGGG (SEQ ID NO: 57) | PGGYGTLDEL (SEQ ID NO: 122) |
| gi\|357118466 | N/A | N/A | LVYGGG (SEQ ID NO: 57) | PGGYGTIEEL (SEQ ID NO: 124) |
| gi\|357114642 | N/A | N/A | LVYGGG (SEQ ID NO: 57) | PGGYGTLEEL (SEQ ID NO: 121) |
| gi\|30687072 | N/A | N/A | LVYGGG (SEQ ID NO: 57) | PGGYGTLEEL (SEQ ID NO: 121) |
| gi\|30683873 | N/A | N/A | LVYGGG (SEQ ID NO: 57) | PGGYGTMEEL (SEQ ID NO: 123) |
| gi\|18418592 | N/A | N/A | LVYGGG (SEQ ID NO: 57) | PGGYGTLEEL (SEQ ID NO: 121) |
| gi\|18401696 | N/A | N/A | LVYGGG (SEQ ID NO: 57) | PGGYGTLEEL (SEQ ID NO: 121) |
| gi\|15231816 | N/A | N/A | LVYGGG (SEQ ID NO: 57) | PGGYGTLEEL (SEQ ID NO: 121) |

The foregoing evidence supports that the four motifs disclosed by the invention are functional in non-fugal proteins that have either an IPT-like domains or a PRH-like domain. The foregoing also provides guidance for modifying the cytokinin synthases disclosed herein to include a motif 1, a motif 2, or both a motif 1 and a motif 2 disclosed in Tables 12, 13 or 14 and/or to include a motif 3, a motif 4, or both a motif 3 and a motif 4 in Table 15. Thus, when aligned with a consensus sequence of SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS) as shown in FIG. 6, any cytokinin synthase disclosed herein can be modified as follows:

(a) motif 1 (SEQ ID NO:30) at consensus sequence amino acid positions 13-20 is substituted with the amino acids of a motif 1 in Tables 12, 13 or 14,
(b) motif 2 (SEQ ID NO:31) at consensus sequence amino acid positions 96-104 is substituted with the amino acids of motif 2 in Tables 12, 13 or 14,
(c) motif 3 (SEQ ID NO:32) at consensus sequence amino acid positions 333-338 is substituted with the amino acids of motif 3 in Table 15,
(d) motif 4 (SEQ ID NO:33) at consensus sequence amino acid positions 333-338 is substituted with the amino acids of motif 4 from Table 15, or
(e) a combination of two or more of the motif substitutions of (a), (b), (c), and (d).

What is claimed is:

1. A recombinant polynucleotide comprising a cytokinin synthase coding sequence, and a heterologous sequence, wherein the cytokinin synthase comprises an isopentenyl transfer (IPT)-like domain and a phosphoribohydrolase (PRH)-like domain and the encoded cytokinin synthase comprises a sequence having at least 90% amino acid sequence identity to SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS).

2. The polynucleotide of claim 1, wherein the cytokinin synthase coding sequence comprises a sequence having at least 70% nucleotide sequence identity to SEQ ID NO:1 (EfCKS), SEQ ID NO:8 (AtCKS), SEQ ID NO:12 (BoCKS), SEQ ID NO:16 (IrCKS), SEQ ID NO:21 (AhCKS), or SEQ ID NO:24 (FfCKS).

3. The polynucleotide of claim 1, wherein the cytokinin synthase coding sequence comprises a sequence having at least 90% nucleotide sequence identity to SEQ ID NO:1 (EfCKS), SEQ ID NO:8 (AtCKS), SEQ ID NO:12 (BoCKS), SEQ ID NO:16 (IrCKS), SEQ ID NO:21 (AhCKS), or SEQ ID NO:24 (FfCKS).

4. The polynucleotide of claim 1, wherein the encoded cytokinin synthase comprises a sequence having at least 95% amino acid sequence identity to SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS).

5. The polynucleotide of claim 1, encoded cytokinin synthase comprises SEQ ID NO:3 (EfCKS), SEQ ID NO:9 (AtCKS), SEQ ID NO:13 (BoCKS), SEQ ID NO:17 (IrCKS), SEQ ID NO:21 (AhCKS), or SEQ ID NO:25 (FfCKS).

6. The polynucleotide of claim 1, wherein the cytokinin synthase coding sequence is optimized for expression in a host cell.

7. The polynucleotide of claim 1, wherein the cytokinin synthase coding sequence is optimized for expression in a host cell selected from the group consisting of a bacteria, yeast, plant, dicot plant, monocot plant, maize, soybean, canola, cotton, wheat, *Arabidopsis thaliana*, rice (*Oryza sativa*), sunflower, grass, creeping bentgrass (*Agrostis stolonifera*), tall fescue (*Festuca arundinacea*), tobacco (*Nicotiana tabacum*), and poplar hybrid.

8. The polynucleotide of claim 1, wherein the heterologous sequence is a heterologous promoter and the promoter is operably linked to the cytokinin synthase coding sequence.

9. The polynucleotide of claim 8, wherein the promoter is a bacteria promoter, heterologous fungal promoter, yeast promoter, or plant promoter.

10. The polynucleotide of claim 8, wherein the promoter is a dicot promoter or a monocot promoter.

11. The polynucleotide of claim 8, wherein the promoter is a maize promoter.

12. The polynucleotide of claim 8, wherein the promoter is a 35S CaMV, 34S FMV, Napin, 7S alpha, 7S alpha', Glob, Lec, ZmGS2, ZmSTP13, or ZmGSTU6 promoter.

13. The polynucleotide of claim 1, wherein the cytokinin synthase coding sequence is flanked by a first upstream heterologous sequence and a second downstream heterologous sequence, and the first and second heterologous sequences are (i) more than 80% identical genomic sequence from a heterologous host and (ii) suitable for catalyzing integration by homologous recombination into the host.

14. A gene expression cassette comprising the polynucleotide of claim 1.

15. A recombinant vector comprising
   a. the gene expression cassette of claim 14; and
   b. a selectable marker.

16. The recombinant vector of claim 15, wherein
   a. the gene expression cassette comprises the polynucleotide of claim 10; and
   b. the vector comprises an origin of replication that is functional in bacteria or yeast.

17. The polynucleotide of claim 1, wherein the heterologous sequence encodes a protein fusion tag.

18. The polynucleotide of claim 17, wherein the encoded protein fusion tag is a poly-histidine, poly-arginine, haloalkane dehalogenase, streptavidin-binding, glutathione s-transferase (GST), maltose-binding protein (MBP), thioredoxin, small ubiquitin-like modifier (SUMO), N-utilization substance A (NusA), protein disulfide isomerase I (DsbA), Mistic, Ketosteroid isomerase (KSI), TrpE, c-myc, hemaglutinin antigen (HA), FLAG, 1D4, calmodulin-binding peptide, chitin-binding domain, cellulose-binding domain, S-tag, or Softag3 protein fusion tag.

19. A host cell comprising the polynucleotide of claim 1.

20. The host cell of claim 19, wherein the host cell is a transformed bacteria cell, a trans-formed fungus cell, a transformed yeast cell, or a transgenic plant cell.

21. The host cell of claim 20, wherein the host cell is a transgenic monocot plant cell or a transgenic dicot plant cell.

22. The host cell of claim 21, wherein the host cell is a soybean host cell or a maize host cell.

23. A transgenic plant comprising the host cell of claim 21.

24. A method for producing recombinant cytokinin synthase, wherein the method comprises,
   a. expressing the recombinant cytokinin synthase in the host cell of claim 19; and
   b. isolating the cytokinin synthase from host cell materials.

25. A transgenic plant comprising the host cell of claim 22.

26. The transgenic plant of claim 25, wherein the transgenic plant is a soybean plant.

27. The transgenic plant of claim 25, wherein the plant is a maize plant.

* * * * *

SEQUENCE LISTING

```
<160> NUMBER OF SEQ ID NOS: 124

<210> SEQ ID NO 1
<211> LENGTH: 1476
<212> TYPE: DNA
<213> ORGANISM: Epichloe festucae

<400> SEQUENCE: 1
atgatgccaa cacgaaagct ctccattgcc atttttggcc ctaccgcttc tggaaagacc      60
aagctaggtg tgaccattgc caaagcatat ctaggcgagg tcatttctat agacagcctg     120
cagtgctata agccgggagg tattgccacg gcgaaacctt gtccggagga gactcagggg     180
gttccccatc atttgataga ctacttggac gccgaagagg agccacaaga ctttgtctcg     240
agagccatcg ccacaataga cgacatcacc actcgtaacg gacttccagt tctcgtcggt     300
gggtcaacat ccctcatcat tcctctgttg cagcaagttt tcagcagaga gtacgaggtt     360
ctcatcatta ccctggtgcc ccatcagtca agctatgggc gactcatcga atccaggggt     420
ggggagatgt tgaagagggg cctgctggac gagctcgccg agctgaagcg cctcgagaaa     480
gtactgctcg acggcaaaag cgatttcaat aaaggtgtct ggaagaccat aggctatcag     540
```

| | |
|---|---|
| gagtttctcc cttatcttcg agccgtcggg aaggtgaatg gcgtgtccaa tacctacgag | 600 |
| gatctatacg aggagggacg agcatcaatg aacgccagca ctcttcgtta cggccagtac | 660 |
| cagctcgaat ggatacgaca caccctgacg cccttcatag accggcacaa ggcggccacc | 720 |
| atcagcctct gtgtcaccga ccaggctgcc tgggcatctg acatagagag acctgcgatg | 780 |
| acaatggctg gcgagttcta ccatggctct caggtgagga gacttccgtc aaggaattct | 840 |
| tcgaatagac gcgttgtttg tctctttggt ggatcgtctt ctggccgcga cgaaagtcac | 900 |
| atcgaggcag ccaaatctct cgccgtcgcc ctgcaccgcc acgaaatcgc actcgtgtac | 960 |
| ggtggaggaa ctactgggat catgggagca gtcgcgagca ccctcgtcgc gctgtctggg | 1020 |
| ccaggggctg tccacggaat cgtccccgcc gctcttgcta gatacgaaga cgagctcggc | 1080 |
| gacggtcgta tcagcgcaga atactcgtca cagtttggca ggagaacgat tgtgagagac | 1140 |
| atgcacacac gaaagcgcct catgacgcag gcggtcctcg aaggagctcc gggaagtgga | 1200 |
| ttcgttgcct tgagtggtgg gtacggcacc atggaggaac tgctcgaggt cacgacatgg | 1260 |
| taccaactgg gaattcatga tcgccgcgtg agcgtcttca atgtgaatgg attctatgac | 1320 |
| ggactgctca gctggattgg ccaagtcgcg cgagacggct tgttagacc aagagacgcc | 1380 |
| aacatacttg tgtcgccaa cacagccgat gaagtgattg cttgtcttgc gaaccagcgg | 1440 |
| ctggatgcgg agaagcccag tttggagtgg ctctga | 1476 |

<210> SEQ ID NO 2
<211> LENGTH: 1476
<212> TYPE: DNA
<213> ORGANISM: Artificial sequence
<220> FEATURE:
<223> OTHER INFORMATION: EfCKS cds codon optimized for E.coli

<400> SEQUENCE: 2

| | |
|---|---|
| atgatgccga cccgtaaact gagcattgca attttggtc cgaccgcaag cggtaaaacc | 60 |
| aaactgggtg ttaccattgc aaaagcatat ctgggtgaag tgattagcat tgatagcctg | 120 |
| cagtgttata aaccgggtgg tattgcaacc gcaaaaccgt gtccggaaga aacccagggt | 180 |
| gttccgcatc atctgattga ttatctggat gcagaagaag aaccgcagga ttttgttagc | 240 |
| cgtgcaattg ccaccattga tgatattacc acccgtaatg gtctgccggt tctggttggt | 300 |
| ggtagcacca gcctgattat tccgctgctg caacaggttt ttagccgtga atatgaagtg | 360 |
| ctgattatta ccctggtgcc gcatcagagc agctatggtc gtctgattga aagccgtggt | 420 |
| ggtgaaatgc tgaaacgtgg tctgctggat gaactggcag aactgaaacg tctggaaaaa | 480 |
| gttctgctgg acggtaaaag cgatttaac aaaggtgtgt ggaaaaccat cggctatcaa | 540 |
| gaatttctgc cgtatctgcg tgcagttggt aaagttaatg gtgtgagcaa tacctatgag | 600 |
| gatctgtatg aagagggtcg tgcaagcatg aatgcaagca ccctgcgtta tggtcagtat | 660 |
| cagctggaat ggattcgtca taccctgacc ccgtttattg atcgtcataa agccgcaacc | 720 |
| attagcctgt gtgttaccga tcaggccgca tgggcaagcg atattgaacg tccggcaatg | 780 |
| accatggcag gcgaatttta tcatggtagc caggttcgtc gtctgccgag ccgtaatagc | 840 |
| agtaatcgtc gtgttgtttg tctgtttggt ggttcaagca gtggtcgtga tgaaagccat | 900 |
| attgaagccg caaaaagcct ggcagttgca ctgcatcgtc atgaaattgc actggtttat | 960 |
| ggtggtggta caaccggtat tatgggtgca gttgccagca ccctggttgc actgagcggt | 1020 |
| ccgggtgccg ttcatggtat tgttccggca gcactggcac gttatgaaga tgagctgggt | 1080 |
| gatggtcgta ttagcgcaga atatagcagt cagtttggtc gtcgtaccat tgttcgtgat | 1140 |

-continued

```
atgcataccc gcaaacgtct gatgacccag gcagttctgg aaggtgcacc gggtagcggt   1200
tttgttgcac tgtcaggtgg ttatggcacc atggaagaac tgctggaagt taccacctgg   1260
tatcaactgg gtattcatga tcgtcgcgtt agcgttttta atgtgaacgg tttttatgat   1320
ggcctgctga gctggattgg tcaggttgca cgtgatggtt tgttcgtcc gcgtgatgca   1380 aatattctgg gtgttgcaaa taccgcagat gaagttattg catgtctggc aaatcagcgt   1440
ctggatgccg aaaaaccgag cctggaatgg ctgtaa                              1476
```

<210> SEQ ID NO 3
<211> LENGTH: 491
<212> TYPE: PRT
<213> ORGANISM: Epichloe festucae

<400> SEQUENCE: 3

```
Met Met Pro Thr Arg Lys Leu Ser Ile Ala Ile Phe Gly Pro Thr Ala
 1               5                  10                  15

Ser Gly Lys Thr Lys Leu Gly Val Thr Ile Ala Lys Ala Tyr Leu Gly
            20                  25                  30

Glu Val Ile Ser Ile Asp Ser Leu Gln Cys Tyr Lys Pro Gly Gly Ile
        35                  40                  45

Ala Thr Ala Lys Pro Cys Pro Glu Glu Thr Gln Gly Val Pro His His
    50                  55                  60

Leu Ile Asp Tyr Leu Asp Ala Glu Glu Pro Gln Asp Phe Val Ser
65                  70                  75                  80

Arg Ala Ile Ala Thr Ile Asp Asp Ile Thr Thr Arg Asn Gly Leu Pro
                85                  90                  95

Val Leu Val Gly Gly Ser Thr Ser Leu Ile Ile Pro Leu Leu Gln Gln
            100                 105                 110

Val Phe Ser Arg Glu Tyr Glu Val Leu Ile Ile Thr Leu Val Pro His
        115                 120                 125

Gln Ser Ser Tyr Gly Arg Leu Ile Glu Ser Arg Gly Gly Glu Met Leu
    130                 135                 140

Lys Arg Gly Leu Leu Asp Glu Leu Ala Glu Leu Lys Arg Leu Glu Lys
145                 150                 155                 160

Val Leu Leu Asp Gly Lys Ser Asp Phe Asn Lys Gly Val Trp Lys Thr
                165                 170                 175

Ile Gly Tyr Gln Glu Phe Leu Pro Tyr Leu Arg Ala Val Gly Lys Val
            180                 185                 190

Asn Gly Val Ser Asn Thr Tyr Glu Asp Leu Tyr Glu Glu Gly Arg Ala
        195                 200                 205

Ser Met Asn Ala Ser Thr Leu Arg Tyr Gly Gln Tyr Gln Leu Glu Trp
    210                 215                 220

Ile Arg His Thr Leu Thr Pro Phe Ile Asp Arg His Lys Ala Ala Thr
225                 230                 235                 240

Ile Ser Leu Cys Val Thr Asp Gln Ala Ala Trp Ala Ser Asp Ile Glu
                245                 250                 255

Arg Pro Ala Met Thr Met Ala Gly Glu Phe Tyr His Gly Ser Gln Val
            260                 265                 270

Arg Arg Leu Pro Ser Arg Asn Ser Asn Arg Arg Val Val Cys Leu
        275                 280                 285

Phe Gly Gly Ser Ser Ser Gly Arg Asp Glu Ser His Ile Glu Ala Ala
    290                 295                 300

Lys Ser Leu Ala Val Ala Leu His Arg His Glu Ile Ala Leu Val Tyr
```

|     |     |     |     |     | 305 |     |     |     |     | 310 |     |     |     |     | 315 |     |     |     |     | 320 |
|---|---|---|---|---|---|---|---|---|---|---|---|---|---|---|---|---|---|---|---|---|

Gly Gly Gly Thr Thr Gly Ile Met Gly Ala Val Ala Ser Thr Leu Val
                325                    330                335

Ala Leu Ser Gly Pro Gly Ala Val His Gly Ile Val Pro Ala Ala Leu
                340                    345                350

Ala Arg Tyr Glu Asp Glu Leu Gly Asp Gly Arg Ile Ser Ala Glu Tyr
                355                    360                365

Ser Ser Gln Phe Gly Arg Arg Thr Ile Val Arg Asp Met His Thr Arg
    370                    375                380

Lys Arg Leu Met Thr Gln Ala Val Leu Glu Gly Ala Pro Gly Ser Gly
385                    390                    395                400

Phe Val Ala Leu Ser Gly Gly Tyr Gly Thr Met Glu Glu Leu Leu Glu
                405                    410                415

Val Thr Thr Trp Tyr Gln Leu Gly Ile His Asp Arg Arg Val Ser Val
                420                    425                430

Phe Asn Val Asn Gly Phe Tyr Asp Gly Leu Leu Ser Trp Ile Gly Gln
                435                    440                445

Val Ala Arg Asp Gly Phe Val Arg Pro Arg Asp Ala Asn Ile Leu Gly
                450                    455                460

Val Ala Asn Thr Ala Asp Glu Val Ile Ala Cys Leu Ala Asn Gln Arg
465                    470                    475                480

Leu Asp Ala Glu Lys Pro Ser Leu Glu Trp Leu
                485                    490

<210> SEQ ID NO 4
<211> LENGTH: 1506
<212> TYPE: DNA
<213> ORGANISM: Epichloe festucae

<400> SEQUENCE: 4

```
atgggtagca gccatcatca tcaccatcat atgatgccga cccgtaaact gagcattgca      60
attttggtc cgaccgcaag cggtaaaacc aaactgggtg ttaccattgc aaaagcatat     120
ctgggtgaag tgattagcat tgatagcctg cagtgttata aaccgggtgg tattgcaacc     180
gcaaaaccgt gtccggaaga aacccagggt gttccgcatc atctgattga ttatctggat     240
gcagaagaag aaccgcagga ttttgttagc cgtgcaattg ccaccattga tgatattacc     300
acccgtaatg gtctgccggt tctggttggt ggtagcacca gcctgattat ccgctgctg     360
caacaggttt ttagccgtga atatgaagtg ctgattatta ccctggtgcc gcatcagagc     420
agctatggtc gtctgattga aagccgtggt ggtgaaatgc tgaaacgtgg tctgctggat     480
gaactggcag aactgaaacg tctggaaaaa gttctgctgg acggtaaaag cgattttaac     540
aaaggtgtgt ggaaaaccat cggctatcaa gaatttctgc cgtatctgcg tgcagttggt     600
aaagttaatg gtgtgagcaa tacctatgag gatctgtatg aagagggtcg tgcaagcatg     660
aatgcaagca ccctgcgtta tggtcagtat cagctggaat ggattcgtca taccctgacc     720
ccgtttattg atcgtcataa agccgcaacc attagcctgt gtgttaccga tcaggccgca     780
tgggcaagcg atattgaacg tccggcaatg accatggcag gcgaatttta tcatggtagc     840
caggttcgtc gtctgccgag ccgtaatagc agtaatcgtc gtgttgtttg tctgtttggt     900
ggttcaagca gtggtcgtga tgaaagccat attgaagccg caaaaagcct ggcagttgca     960
ctgcatcgtc atgaaattgc actggtttat ggtggtggta caccggtat tatgggtgca    1020
gttgccagca ccctggttgc actgagcggt ccgggtgccg ttcatggtat tgttccggca    1080
```

```
gcactggcac gttatgaaga tgagctgggt gatggtcgta ttagcgcaga atatagcagt    1140
cagtttggtc gtcgtaccat tgttcgtgat atgcataccc gcaaacgtct gatgacccag    1200
gcagttctgg aaggtgcacc gggtagcggt tttgttgcac tgtcaggtgg ttatggcacc    1260
atggaagaac tgctggaagt taccacctgg tatcaactgg gtattcatga tcgtcgcgtt    1320 agcgtttta atgtgaacgg ttttatgat ggcctgctga gctggattgg tcaggttgca     1380
cgtgatggtt tgttcgtcc gcgtgatgca aatattctgg gtgttgcaaa taccgcagat    1440
gaagttattg catgtctggc aaatcagcgt ctggatgccg aaaaaccgag cctggaatgg    1500
ctgtaa                                                              1506
```

<210> SEQ ID NO 5
<211> LENGTH: 501
<212> TYPE: PRT
<213> ORGANISM: Epichloe festucae

<400> SEQUENCE: 5

```
Met Gly Ser Ser His His His His His Met Met Pro Thr Arg Lys
1               5                   10                  15

Leu Ser Ile Ala Ile Phe Gly Pro Thr Ala Ser Gly Lys Thr Lys Leu
            20                  25                  30

Gly Val Thr Ile Ala Lys Ala Tyr Leu Gly Glu Val Ile Ser Ile Asp
        35                  40                  45

Ser Leu Gln Cys Tyr Lys Pro Gly Gly Ile Ala Thr Ala Lys Pro Cys
    50                  55                  60

Pro Glu Glu Thr Gln Gly Val Pro His His Leu Ile Asp Tyr Leu Asp
65                  70                  75                  80

Ala Glu Glu Glu Pro Gln Asp Phe Val Ser Arg Ala Ile Ala Thr Ile
                85                  90                  95

Asp Asp Ile Thr Thr Arg Asn Gly Leu Pro Val Leu Val Gly Gly Ser
            100                 105                 110

Thr Ser Leu Ile Ile Pro Leu Leu Gln Gln Val Phe Ser Arg Glu Tyr
        115                 120                 125

Glu Val Leu Ile Ile Thr Leu Val Pro His Gln Ser Ser Tyr Gly Arg
    130                 135                 140

Leu Ile Glu Ser Arg Gly Gly Glu Met Leu Lys Arg Gly Leu Leu Asp
145                 150                 155                 160

Glu Leu Ala Glu Leu Lys Arg Leu Glu Lys Val Leu Leu Asp Gly Lys
                165                 170                 175

Ser Asp Phe Asn Lys Gly Val Trp Lys Thr Ile Gly Tyr Gln Glu Phe
            180                 185                 190

Leu Pro Tyr Leu Arg Ala Val Gly Lys Val Asn Gly Val Ser Asn Thr
        195                 200                 205

Tyr Glu Asp Leu Tyr Glu Gly Arg Ala Ser Met Asn Ala Ser Thr
    210                 215                 220

Leu Arg Tyr Gly Gln Tyr Gln Leu Glu Trp Ile Arg His Thr Leu Thr
225                 230                 235                 240

Pro Phe Ile Asp Arg His Lys Ala Ala Thr Ile Ser Leu Cys Val Thr
                245                 250                 255

Asp Gln Ala Ala Trp Ala Ser Asp Ile Glu Arg Pro Ala Met Thr Met
            260                 265                 270

Ala Gly Glu Phe Tyr His Gly Ser Gln Val Arg Arg Leu Pro Ser Arg
        275                 280                 285

Asn Ser Ser Asn Arg Arg Val Val Cys Leu Phe Gly Gly Ser Ser Ser
```

Gly Arg Asp Glu Ser His Ile Glu Ala Ala Lys Ser Leu Ala Val Ala
305                 310                 315                 320

Leu His Arg His Glu Ile Ala Leu Val Tyr Gly Gly Thr Thr Gly
            325                 330                 335

Ile Met Gly Ala Val Ala Ser Thr Leu Val Ala Leu Ser Gly Pro Gly
                340                 345                 350

Ala Val His Gly Ile Val Pro Ala Ala Leu Ala Arg Tyr Glu Asp Glu
            355                 360                 365

Leu Gly Asp Gly Arg Ile Ser Ala Glu Tyr Ser Ser Gln Phe Gly Arg
    370                 375                 380

Arg Thr Ile Val Arg Asp Met His Thr Arg Lys Arg Leu Met Thr Gln
385                 390                 395                 400

Ala Val Leu Glu Gly Ala Pro Gly Ser Gly Phe Val Ala Leu Ser Gly
                405                 410                 415

Gly Tyr Gly Thr Met Glu Glu Leu Leu Glu Val Thr Thr Trp Tyr Gln
                420                 425                 430

Leu Gly Ile His Asp Arg Arg Val Ser Val Phe Asn Val Asn Gly Phe
            435                 440                 445

Tyr Asp Gly Leu Leu Ser Trp Ile Gly Gln Val Ala Arg Asp Gly Phe
    450                 455                 460

Val Arg Pro Arg Asp Ala Asn Ile Leu Gly Val Ala Asn Thr Ala Asp
465                 470                 475                 480

Glu Val Ile Ala Cys Leu Ala Asn Gln Arg Leu Asp Ala Glu Lys Pro
                485                 490                 495

Ser Leu Glu Trp Leu
            500

<210> SEQ ID NO 6
<211> LENGTH: 798
<212> TYPE: DNA
<213> ORGANISM: Epichloe festucae

<400> SEQUENCE: 6
atgggtagca gccatcatca tcaccatcat atgatgccga cccgtaaact gagcattgca     60 attttggtc cgaccgcaag cggtaaaacc aaactgggtg ttaccattgc aaaagcatat    120
ctgggtgaag tgattagcat tgatagcctg cagtgttata aaccgggtgg tattgcaacc    180
gcaaaaccgt gtccggaaga aacccagggt gttccgcatc atctgattga ttatctggat    240
gcagaagaag aaccgcagga ttttgttagc cgtgcaattg ccaccattga tgatattacc    300
acccgtaatg gtctgccggt tctggttggt ggtagcacca gcctgattat tccgctgctg    360
caacaggttt ttagccgtga aatgaagtg ctgattatta ccctggtgcc gcatcagagc    420
agctatggtc gtctgattga aagccgtggt ggtgaaatgc tgaaacgtgg tctgctggat    480
gaactggcag aactgaaacg tctggaaaaa gttctgctgg acggtaaaag cgattttaac    540
aaaggtgtgt ggaaaaccat cggctatcaa gaatttctgc cgtatctgcg tgcagttggt    600
aaagttaatg gtgtgagcaa taccgatgag gatctgtatg aagagggtcg tgcaagcatg    660
aatgcaagca ccctgcgtta tggtcagtat cagctggaat ggattcgtca taccctgacc    720
ccgtttattg atcgtcataa agccgcaacc attagcctgt gtgttaccga tcaggccgca    780
tgggcaagcg atatttaa                                                  798

<210> SEQ ID NO 7

```
<211> LENGTH: 265
<212> TYPE: PRT
<213> ORGANISM: Epichloe festucae

<400> SEQUENCE: 7

Met Gly Ser Ser His His His His His His Met Met Pro Thr Arg Lys
1               5                   10                  15

Leu Ser Ile Ala Ile Phe Gly Pro Thr Ala Ser Gly Lys Thr Lys Leu
            20                  25                  30

Gly Val Thr Ile Ala Lys Ala Tyr Leu Gly Glu Val Ile Ser Ile Asp
        35                  40                  45

Ser Leu Gln Cys Tyr Lys Pro Gly Gly Ile Ala Thr Ala Lys Pro Cys
    50                  55                  60

Pro Glu Glu Thr Gln Gly Val Pro His His Leu Ile Asp Tyr Leu Asp
65                  70                  75                  80

Ala Glu Glu Glu Pro Gln Asp Phe Val Ser Arg Ala Ile Ala Thr Ile
                85                  90                  95

Asp Asp Ile Thr Thr Arg Asn Gly Leu Pro Val Leu Val Gly Gly Ser
            100                 105                 110

Thr Ser Leu Ile Ile Pro Leu Leu Gln Gln Val Phe Ser Arg Glu Tyr
        115                 120                 125

Glu Val Leu Ile Ile Thr Leu Val Pro His Gln Ser Ser Tyr Gly Arg
    130                 135                 140

Leu Ile Glu Ser Arg Gly Gly Glu Met Leu Lys Arg Gly Leu Leu Asp
145                 150                 155                 160

Glu Leu Ala Glu Leu Lys Arg Leu Glu Lys Val Leu Leu Asp Gly Lys
                165                 170                 175

Ser Asp Phe Asn Lys Gly Val Trp Lys Thr Ile Gly Tyr Gln Glu Phe
            180                 185                 190

Leu Pro Tyr Leu Arg Ala Val Gly Lys Val Asn Gly Val Ser Asn Thr
        195                 200                 205

Tyr Glu Asp Leu Tyr Glu Glu Gly Arg Ala Ser Met Asn Ala Ser Thr
    210                 215                 220

Leu Arg Tyr Gly Gln Tyr Gln Leu Glu Trp Ile Arg His Thr Leu Thr
225                 230                 235                 240

Pro Phe Ile Asp Arg His Lys Ala Ala Thr Ile Ser Leu Cys Val Thr
                245                 250                 255

Asp Gln Ala Ala Trp Ala Ser Asp Ile
            260                 265

<210> SEQ ID NO 8
<211> LENGTH: 1530
<212> TYPE: DNA
<213> ORGANISM: Aciculosporium take

<400> SEQUENCE: 8
atgttgaacc ggaaacccgc cgtcgccatc ctcggcccca cggcctcggg caagacgcag      60
ctcggcgtgg ccatcgccaa ggccttcctc ggcgaggtca tctccgtcga cagcctgcag     120
tgctacaaac ccgggggcat cgtcacggcg cggccgcgcc cggacgagac ggccggcgtg     180
ccgcaccacc tggtgggcta cctcgaggcc gacgaggagc ccacgactac cgtcgcgcag     240
gcggcctcca tcatggacga catgacggcc cgcgacgggc tccccgtcct cgtcggcggc     300
tccacctccc tcaccctccc gctcctgcag gaggtctttg cccgcgacta cgacgtgctg     360
gccgtcacgc tggtgcccca ccgctcgacc taccagcggc tcgtcgaggc acgcgccgac     420
```

```
cagatgctcg agaggggcct cctgggcgag ctggccgagc tgaagcgcct cgagaagacg      480
ctgctgcatg gcaagcgcga ctttggcaag ggcgtctgga aggccatcgg gtaccaggag      540
ctctacccct atcttcaggc cgccgccgcc ggcggcctgg cgcccatgaa cggcgcgggc      600
tccggcgccg ccgccgactg cgagcgtctg cgcgaccagg gatgggccga gatgagcgcc      660
aacacgctgc agtacggcca gtaccagctc gaatggatgc ccacaccct gacgcccttt       720 ctgcaccggc acaaggccgt cgccatcagc tctgcgtca cggacaaggc ctcgtgggag       780
gccgaagtcc tcgggccggc catgaccatg acggggagt ctgccacgg gtctcgcctg        840 acgaggcttc cgccgagggg ggccctggtg aggcgggttg tctgtctctt tggcggatcc     900
tcctcgggcc acacgcccgc ccacgtcgag gccgccaagt ccctcgccgt cgccctccac     960
ctccacgacg tgacgctcgt ctacggcggc ggcacaaccg gcatcatggg cgccgtcgcg    1020 agcacccctcg tcgcgctctc gggccccagc gccgtccatg gcatcgtccc cgccgcgctc   1080
gcccggtacg aggacgagcg ccgcggcggc accggcaccg ggcgcatcaa ccaagactac    1140
gcctggcgct tcggccgccg caccgtcgtc cgcgacatgc acacgcggaa cgcctcatg    1200 acgcagatgg tgctcgacgg cgccccggc agcggcttcg tcgccctcag cggcggctac    1260
ggcaccatgg aggagctcct cgaggccacg acctggcacc agctcggcat ccaccaccgg   1320
cccgtcaccg tcttcaacgt cgacggcttc tacgacgggc tgctcgactg ggtccgccac   1380
gtcgtccgcg cgggcttcgt cggccccaag cacgccgaca tcatcggcgt cgcccactcc   1440
gccgacgagg tcatttcttc cctggcgcgt ccgggcctgc aggacgggcc gctgccggac   1500
aagaagcaac agcggctgga gtggctgtag                                   1530

<210> SEQ ID NO 9
<211> LENGTH: 509
<212> TYPE: PRT
<213> ORGANISM: Aciculosporium take

<400> SEQUENCE: 9

Met Leu Asn Arg Lys Pro Ala Val Ala Ile Leu Gly Pro Thr Ala Ser
1               5                   10                  15

Gly Lys Thr Gln Leu Gly Val Ala Ile Ala Lys Ala Phe Leu Gly Glu
                20                  25                  30

Val Ile Ser Val Asp Ser Leu Gln Cys Tyr Lys Pro Gly Gly Ile Val
            35                  40                  45

Thr Ala Arg Pro Arg Pro Asp Glu Thr Ala Gly Val Pro His His Leu
        50                  55                  60

Val Gly Tyr Leu Glu Ala Asp Glu Glu Pro His Asp Tyr Val Ala Gln
65                  70                  75                  80

Ala Ala Ser Ile Met Asp Asp Met Thr Ala Arg Asp Gly Leu Pro Val
                85                  90                  95

Leu Val Gly Gly Ser Thr Ser Leu Thr Leu Pro Leu Leu Gln Glu Val
            100                 105                 110

Phe Ala Arg Asp Tyr Asp Val Leu Ala Val Thr Leu Val Pro His Arg
        115                 120                 125

Ser Thr Tyr Gln Arg Leu Val Glu Ala Arg Ala Asp Gln Met Leu Glu
    130                 135                 140

Arg Gly Leu Leu Gly Glu Leu Ala Glu Leu Lys Arg Leu Glu Lys Thr
145                 150                 155                 160

Leu Leu His Gly Lys Arg Asp Phe Gly Lys Gly Val Trp Lys Ala Ile
                165                 170                 175
```

```
Gly Tyr Gln Glu Leu Tyr Pro Tyr Leu Gln Ala Ala Ala Gly Gly
            180                 185                 190

Leu Ala Pro Met Asn Gly Ala Gly Ser Gly Ala Ala Asp Cys Glu
            195                 200                 205

Arg Leu Arg Asp Gln Gly Trp Ala Glu Met Ser Ala Asn Thr Leu Gln
            210                 215                 220

Tyr Gly Gln Tyr Gln Leu Glu Trp Met Arg His Thr Leu Thr Pro Phe
225                 230                 235                 240

Leu His Arg His Lys Ala Val Ala Ile Ser Leu Cys Val Thr Asp Lys
            245                 250                 255

Ala Ser Trp Glu Ala Glu Val Leu Gly Pro Ala Met Thr Met Thr Gly
            260                 265                 270

Glu Phe Cys His Gly Ser Arg Leu Thr Arg Leu Pro Pro Arg Gly Ala
            275                 280                 285

Leu Val Arg Arg Val Val Cys Leu Phe Gly Gly Ser Ser Gly His
            290                 295                 300

Thr Pro Ala His Val Glu Ala Ala Lys Ser Leu Ala Val Ala Leu His
305                 310                 315                 320

Leu His Asp Val Thr Leu Val Tyr Gly Gly Thr Thr Gly Ile Met
            325                 330                 335

Gly Ala Val Ala Ser Thr Leu Val Ala Leu Ser Gly Pro Ser Ala Val
            340                 345                 350

His Gly Ile Val Pro Ala Ala Leu Ala Arg Tyr Glu Asp Glu Arg Arg
            355                 360                 365

Gly Gly Thr Gly Thr Gly Arg Ile Asn Gln Asp Tyr Ala Trp Arg Phe
            370                 375                 380

Gly Arg Arg Thr Val Val Arg Asp Met His Thr Arg Lys Arg Leu Met
385                 390                 395                 400

Thr Gln Met Val Leu Asp Gly Ala Pro Gly Ser Gly Phe Val Ala Leu
            405                 410                 415

Ser Gly Gly Tyr Gly Thr Met Glu Glu Leu Leu Glu Ala Thr Thr Trp
            420                 425                 430

His Gln Leu Gly Ile His His Arg Pro Val Thr Val Phe Asn Val Asp
            435                 440                 445

Gly Phe Tyr Asp Gly Leu Leu Asp Trp Val Arg His Val Val Arg Gly
450                 455                 460

Gly Phe Val Gly Pro Lys His Ala Asp Ile Ile Gly Val Ala His Ser
465                 470                 475                 480

Ala Asp Glu Val Ile Ser Ser Leu Ala Arg Pro Gly Leu Gln Asp Gly
            485                 490                 495

Pro Leu Pro Asp Lys Lys Gln Gln Arg Leu Glu Trp Leu
            500                 505
```

<210> SEQ ID NO 10
<211> LENGTH: 1560
<212> TYPE: DNA
<213> ORGANISM: Aciculosporium take

<400> SEQUENCE: 10

```
atgggtagca gccatcatca tcaccatcat atgctgaatc gtaaaccggc agttgcaatt      60
ctgggtccga ccgcaagcgg taaaacacag ctgggtgttg caattgccaa agcatttctg     120
ggtgaagtta ttagcgttga tagcctgcag tgttataaac cgggtggtat tgttaccgca     180
cgtccgcgtc cggatgaaac cgcaggcgtt ccgcatcatc tggttggtta tctggaagca     240
```

-continued

```
gatgaagaac cgcatgatta tgttgcacag gcagcaagca ttatggatga tatgaccgca    300
cgtgatggtc tgccggttct ggtgggtggt agcaccagcc tgaccctgcc gctgctgcaa    360
gaagtttttg cacgcgatta tgatgttctg gcagttaccc tggtgccgca tcgtagcacc    420
tatcagcgtc tggttgaagc acgtgcagat cagatgctgg aacgtggtct gctgggtgaa    480
ctggcagaac tgaaacgtct ggaaaaaacc ctgctgcatg gtaaacgtga ttttggtaaa    540
ggtgtttgga aagccattgg ctatcaagaa ctgtatccgt atctgcaggc agcagcagcc    600
ggtggtctgg caccgatgaa tggtgcaggt agcggtgcag ccgcagattg tgaacgtctg    660
cgtgatcagg gttgggcaga aatgagcgca aataccctgc agtatggtca gtatcagctg    720
gaatggatgc gtcataccct gaccccgttt ctgcatcgtc ataaagcagt tgccattagc    780
ctgtgtgtta ccgataaagc aagctgggaa gcagaagtgc tgggtccggc aatgaccatg    840
accggtgaat tttgtcatgg tagccgtctg acccgtctgc ctccgcgtgg tgcactggtt    900
cgtcgtgttg tttgtctgtt tggtggtagc tcaagcggtc atacaccggc acatgttgaa    960
gcagcaaaaa gcctggccgt tgcactgcat ctgcatgatg tgaccctggt ttatggtggt   1020
ggtacaaccg gtattatggg tgccgttgca agcaccctgg ttgcactgag cggtccgagc   1080
gcagttcatg gcattgttcc ggcagcactg gcacgttatg aagatgaacg tcgtggtggc   1140
accggcaccg gtcgtattaa tcaggattat gcatggcgtt ttggtcgtcg taccgttgtt   1200
cgtgatatgc atacccgtaa acgtctgatg acccagatgg ttctggatgg tgcaccgggt   1260
agcggttttg ttgcactgtc aggtggttat ggcaccatgg aagaactgct ggaagcaacc   1320
acctggcatc agctgggtat tcatcatcgt ccggttaccg tttttaatgt ggatggtttt   1380
tatgatggcc tgctggattg ggttcgtcat gtggttcgtg gtggttttgt gggtccgaaa   1440
catgcagata ttattggtgt tgcacatagt gccgatgaag tgattagcag tctggcacgt   1500
ccgggtctgc aggatggtcc gctgccggat aaaaaacagc agcgcctgga atggctgtaa   1560
```

<210> SEQ ID NO 11
<211> LENGTH: 519
<212> TYPE: PRT
<213> ORGANISM: Aciculosporium take

<400> SEQUENCE: 11

```
Met Gly Ser Ser His His His His His His Met Leu Asn Arg Lys Pro
1               5                   10                  15

Ala Val Ala Ile Leu Gly Pro Thr Ala Ser Gly Lys Thr Gln Leu Gly
            20                  25                  30

Val Ala Ile Ala Lys Ala Phe Leu Gly Glu Val Ile Ser Val Asp Ser
        35                  40                  45

Leu Gln Cys Tyr Lys Pro Gly Gly Ile Val Thr Ala Arg Pro Arg Pro
    50                  55                  60

Asp Glu Thr Ala Gly Val Pro His His Leu Val Gly Tyr Leu Glu Ala
65                  70                  75                  80

Asp Glu Glu Pro His Asp Tyr Val Ala Gln Ala Ala Ser Ile Met Asp
                85                  90                  95

Asp Met Thr Ala Arg Asp Gly Leu Pro Val Leu Val Gly Gly Ser Thr
            100                 105                 110

Ser Leu Thr Leu Pro Leu Leu Gln Glu Val Phe Ala Arg Asp Tyr Asp
        115                 120                 125

Val Leu Ala Val Thr Leu Val Pro His Arg Ser Thr Tyr Gln Arg Leu
    130                 135                 140
```

Val Glu Ala Arg Ala Asp Gln Met Leu Glu Arg Gly Leu Leu Gly Glu
145                 150                 155                 160

Leu Ala Glu Leu Lys Arg Leu Glu Lys Thr Leu Leu His Gly Lys Arg
            165                 170                 175

Asp Phe Gly Lys Gly Val Trp Lys Ala Ile Gly Tyr Gln Glu Leu Tyr
        180                 185                 190

Pro Tyr Leu Gln Ala Ala Ala Gly Gly Leu Ala Pro Met Asn Gly
    195                 200                 205

Ala Gly Ser Gly Ala Ala Ala Asp Cys Glu Arg Leu Arg Asp Gln Gly
    210                 215                 220

Trp Ala Glu Met Ser Ala Asn Thr Leu Gln Tyr Gly Gln Tyr Gln Leu
225                 230                 235                 240

Glu Trp Met Arg His Thr Leu Thr Pro Phe Leu His Arg His Lys Ala
                245                 250                 255

Val Ala Ile Ser Leu Cys Val Thr Asp Lys Ala Ser Trp Glu Ala Glu
                260                 265                 270

Val Leu Gly Pro Ala Met Thr Met Thr Gly Glu Phe Cys His Gly Ser
            275                 280                 285

Arg Leu Thr Arg Leu Pro Pro Arg Gly Ala Leu Val Arg Arg Val Val
        290                 295                 300

Cys Leu Phe Gly Gly Ser Ser Ser Gly His Thr Pro Ala His Val Glu
305                 310                 315                 320

Ala Ala Lys Ser Leu Ala Val Ala Leu His Leu His Asp Val Thr Leu
                325                 330                 335

Val Tyr Gly Gly Gly Thr Thr Gly Ile Met Gly Ala Val Ala Ser Thr
            340                 345                 350

Leu Val Ala Leu Ser Gly Pro Ser Ala Val His Gly Ile Val Pro Ala
        355                 360                 365

Ala Leu Ala Arg Tyr Glu Asp Glu Arg Arg Gly Gly Thr Gly Thr Gly
    370                 375                 380

Arg Ile Asn Gln Asp Tyr Ala Trp Arg Phe Gly Arg Arg Thr Val Val
385                 390                 395                 400

Arg Asp Met His Thr Arg Lys Arg Leu Met Thr Gln Met Val Leu Asp
                405                 410                 415

Gly Ala Pro Gly Ser Gly Phe Val Ala Leu Ser Gly Gly Tyr Gly Thr
            420                 425                 430

Met Glu Glu Leu Leu Glu Ala Thr Thr Trp His Gln Leu Gly Ile His
        435                 440                 445

His Arg Pro Val Thr Val Phe Asn Val Asp Gly Phe Tyr Asp Gly Leu
    450                 455                 460

Leu Asp Trp Val Arg His Val Val Arg Gly Gly Phe Val Gly Pro Lys
465                 470                 475                 480

His Ala Asp Ile Ile Gly Val Ala His Ser Ala Asp Glu Val Ile Ser
                485                 490                 495

Ser Leu Ala Arg Pro Gly Leu Gln Asp Gly Pro Leu Pro Asp Lys Lys
            500                 505                 510

Gln Gln Arg Leu Glu Trp Leu
        515

<210> SEQ ID NO 12
<211> LENGTH: 1488
<212> TYPE: DNA
<213> ORGANISM: Botryosphaeria dothidea

<400> SEQUENCE: 12

-continued

```
atgttggcaa accgaaaact cttcgttgcc attcttggtc ccaccgcttc cggaaagacc     60
aagctgggag tagccattgc caaggcattc cagggcgagg tagtctccgt agacagttta    120
cagtgttaca agccaggaac aatcatcact gcaaaacctc tcccagaaga gattgaggga    180
atccccatc acctaataga ctacctagaa gccgaggagg agccacacga ctataccgac    240
agagctattg cggcaataga caacattacc gcccgcaaca ggctgccaat cctcgtgggc    300
gggtcaacat ctctcactat gcctctcctg cgggaagtgt ttcatgcgca gtacaaagtc    360
ctggccatta gtctggtgcc gcatcatacg gtctaccaac aattaatcga ggacagaggc    420
gaggatatgc tccgcagggg cctattaaac gagctcgtcg agctgcaacg ccttgaaaaa    480
gtcctcctta atggcaaatg cgacttcaag aaaggaatct ggaaagcaat cgggtaccaa    540
gaattctacc cgtatctcca ggcagtgggg aagttaaacg gggcatccaa gaccaatcct    600
ggggatttat acaaaaaggg ccgagccctg ctgtttgcca atacactaca atatggactg    660
ggccagctcg agtggatgcg acacaccctg gcccccttc tgcaccaaca caaggcagtt    720
accatgagcc ttagtgttac ggagaaggcc tcctggatac cagacgtgca agggcctgct    780
atgtctatga tcagcgagtt ctatcatgat tctcaggtga ctaagagtct cttccgaaag    840
aggtctttga agaagcgtgt cgtctgcctt tttggcgggt cgtctgctgg caacgatcca    900
actcacatcg aggcagccaa atctctagct gccgccctgc atcaccacga catctcgctt    960
gtgtacggtg gaggaacgac tggatcatg ggtcaagtcg cgagttccct tgtcgagctg   1020
tccgggccaa acgctgtcaa gggattcatt cctgctgctc tcgccgggca cgaagaggag   1080
ctcggggacg acggtactgt gatgggcggg gagtacttgt ctcggtttgg aaggagaacc   1140
attgtgaaag atatgcacac acgaaagcgc ttcatgatcc agaatgtact tcaaggagcg   1200
cccgggagtg gattcgtcgc gctgagcggc ggctacggca ctttagagga actgctcgag   1260
atcacgacat ggtctcagct gggcatacac gattgcgtgg ttgtcgtttt tagcgttgac   1320
ggcttctacg atggtctgct cgactggatt gagcaggtag ctcgacgtgg cttcatcagc   1380
acgacacatg ccaacatagt ccgcgtcgct aagacggcag acaaggtgat tgcatgtctt   1440
tcggattgtc ggattcaacc gaggagacac gtgttagagt ggctctag                1488
```

<210> SEQ ID NO 13
<211> LENGTH: 495
<212> TYPE: PRT
<213> ORGANISM: Botryosphaeria dothidea

<400> SEQUENCE: 13

```
Met Leu Ala Asn Arg Lys Leu Phe Val Ala Ile Leu Gly Pro Thr Ala
1               5                   10                  15

Ser Gly Lys Thr Lys Leu Gly Val Ala Ile Ala Lys Ala Phe Gln Gly
            20                  25                  30

Glu Val Val Ser Val Asp Ser Leu Gln Cys Tyr Lys Pro Gly Thr Ile
        35                  40                  45

Ile Thr Ala Lys Pro Leu Pro Glu Glu Ile Glu Gly Ile Pro His His
    50                  55                  60

Leu Ile Asp Tyr Leu Glu Ala Glu Glu Glu Pro His Asp Tyr Thr Asp
65                  70                  75                  80

Arg Ala Ile Ala Ala Ile Asp Asn Ile Thr Ala Arg Asn Arg Leu Pro
                85                  90                  95

Ile Leu Val Gly Gly Ser Thr Ser Leu Thr Met Pro Leu Leu Arg Glu
            100                 105                 110
```

Val Phe His Ala Gln Tyr Lys Val Leu Ala Ile Ser Leu Val Pro His
            115                 120                 125

His Thr Val Tyr Gln Gln Leu Ile Glu Asp Arg Gly Glu Asp Met Leu
130                 135                 140

Arg Arg Gly Leu Leu Asn Glu Leu Val Glu Leu Gln Arg Leu Glu Lys
145                 150                 155                 160

Val Leu Leu Asn Gly Lys Cys Asp Phe Lys Lys Gly Ile Trp Lys Ala
                165                 170                 175

Ile Gly Tyr Gln Glu Phe Tyr Pro Tyr Leu Gln Ala Val Gly Lys Leu
            180                 185                 190

Asn Gly Ala Ser Lys Thr Asn Pro Gly Asp Leu Tyr Lys Lys Gly Arg
        195                 200                 205

Ala Leu Leu Phe Ala Asn Thr Leu Gln Tyr Gly Leu Gly Gln Leu Glu
210                 215                 220

Trp Met Arg His Thr Leu Ala Pro Phe Leu His Gln His Lys Ala Val
225                 230                 235                 240

Thr Met Ser Leu Ser Val Thr Glu Lys Ala Ser Trp Ile Pro Asp Val
                245                 250                 255

Gln Gly Pro Ala Met Ser Met Ile Ser Glu Phe Tyr His Asp Ser Gln
            260                 265                 270

Val Thr Lys Ser Leu Phe Arg Lys Arg Ser Leu Lys Lys Arg Val Val
        275                 280                 285

Cys Leu Phe Gly Gly Ser Ser Ala Gly Asn Asp Pro Thr His Ile Glu
290                 295                 300

Ala Ala Lys Ser Leu Ala Ala Leu His His His Asp Ile Ser Leu
305                 310                 315                 320

Val Tyr Gly Gly Gly Thr Thr Gly Ile Met Gly Gln Val Ala Ser Ser
                325                 330                 335

Leu Val Glu Leu Ser Gly Pro Asn Ala Val Lys Gly Phe Ile Pro Ala
            340                 345                 350

Ala Leu Ala Gly His Glu Glu Leu Gly Asp Asp Gly Thr Val Met
        355                 360                 365

Gly Gly Glu Tyr Leu Ser Arg Phe Gly Arg Arg Thr Ile Val Lys Asp
370                 375                 380

Met His Thr Arg Lys Arg Phe Met Ile Gln Asn Val Leu Gln Gly Ala
385                 390                 395                 400

Pro Gly Ser Gly Phe Val Ala Leu Ser Gly Tyr Gly Thr Leu Glu
                405                 410                 415

Glu Leu Leu Glu Ile Thr Thr Trp Ser Gln Leu Gly Ile His Asp Cys
            420                 425                 430

Val Val Val Phe Ser Val Asp Gly Phe Tyr Asp Gly Leu Leu Asp
        435                 440                 445

Trp Ile Glu Gln Val Ala Arg Arg Gly Phe Ile Ser Thr Thr His Ala
450                 455                 460

Asn Ile Val Arg Val Ala Lys Thr Ala Asp Lys Val Ile Ala Cys Leu
465                 470                 475                 480

Ser Asp Cys Arg Ile Gln Pro Arg Arg His Val Leu Glu Trp Leu
                485                 490                 495

<210> SEQ ID NO 14
<211> LENGTH: 1518
<212> TYPE: DNA
<213> ORGANISM: Botryosphaeria dothidea

<400> SEQUENCE: 14

```
atgggtagca gccatcatca tcaccatcat atgctggcaa atcgtaaact gtttgttgca     60
attctgggtc cgaccgcaag cggtaaaacc aaactgggtg ttgccattgc aaaagcattt    120
cagggtgaag ttgttagcgt tgatagcctg cagtgttata aaccgggtac aattattacc    180
gcaaaaccgc tgccggaaga aattgaaggt attccgcatc atctgatcga ttatctggaa    240
gccgaagaag aaccgcacga ttataccgat cgtgcaatcg cagcaattga taacattacc    300
gcacgtaatc gtctgccgat tctggttggt ggtagcacca gcctgaccat gccgctgctg    360
cgtgaagttt ttcatgcaca gtataaagtt ctggccatta gcctggtgcc gcatcatacc    420
gtttatcagc agctgattga agatcgtggt gaagatatgc tgcgtcgtgg tctgctgaat    480
gaactggttg aactgcagcg tctggaaaaa gttctgctga acggtaaatg cgatttcaaa    540
aaaggtatct ggaaagccat cggctaccaa gaattttatc cgtatctgca ggcagttggc    600
aaactgaatg gtgcaagcaa aaccaatccg ggtgatctgt acaaaaaagg ccgtgcactg    660
ctgtttgcaa ataccctgca gtatggtctg ggtcagctgg aatggatgcg tcataccctg    720
gcaccgtttc tgcatcagca taaagcagtt accatgagcc tgagcgttac cgaaaaagca    780
agctggattc cggatgttca gggtccggca atgagcatga ttagcgaatt ttaccatgat    840
agccaggtta ccaaaagcct gtttcgtaaa cgtagcctga aaaaacgtgt tgtttgtctg    900
tttggtggtt caagcgcagg taatgatccg acccatattg aagcagcaaa aagcctggca    960
gcagcactgc atcatcatga tattagtctg gtttatggtg gtggtacaac cggtattatg   1020
ggtcaggttg caagcagcct ggtggaactg agcggtccga atgcagttaa aggttttatt   1080
cctgcagcac tggcaggtca tgaagaggaa ctgggagatg atggtacagt tatgggtggt   1140
gaatatctga gccgttttgg tcgtcgtacc attgttaaag atatgcatac ccgtaaacgc   1200
tttatgattc agaatgttct gcagggtgca ccgggttcag gttttgttgc cctgagcggt   1260
ggttatggca ccctggaaga actgctggaa attaccacct ggtcacagct gggtattcat   1320
gattgcgttg ttgttgtttt tagcgtggat ggtttttatg atggcctgct ggattggatt   1380
gaacaggttg cacgtcgtgg ttttattagt accacccatg caaatattgt tcgtgttgca   1440
aaaaccgcag ataaagttat tgcatgtctg agcgattgtc gtattcagcc tcgtcgtcat   1500
gttctggaat ggctgtaa                                                  1518
```

<210> SEQ ID NO 15
<211> LENGTH: 505
<212> TYPE: PRT
<213> ORGANISM: Botryosphaeria dothidea

<400> SEQUENCE: 15

```
Met Gly Ser Ser His His His His His His Met Leu Ala Asn Arg Lys
1               5                   10                  15

Leu Phe Val Ala Ile Leu Gly Pro Thr Ala Ser Gly Lys Thr Lys Leu
            20                  25                  30

Gly Val Ala Ile Ala Lys Ala Phe Gln Gly Glu Val Val Ser Val Asp
        35                  40                  45

Ser Leu Gln Cys Tyr Lys Pro Gly Thr Ile Ile Thr Ala Lys Pro Leu
    50                  55                  60

Pro Glu Glu Ile Glu Gly Ile Pro His His Leu Ile Asp Tyr Leu Glu
65                  70                  75                  80

Ala Glu Glu Glu Pro His Asp Tyr Thr Asp Arg Ala Ile Ala Ala Ile
                85                  90                  95
```

```
Asp Asn Ile Thr Ala Arg Asn Arg Leu Pro Ile Leu Val Gly Gly Ser
            100                 105                 110

Thr Ser Leu Thr Met Pro Leu Arg Glu Val Phe His Ala Gln Tyr
        115                 120                 125

Lys Val Leu Ala Ile Ser Leu Val Pro His His Thr Val Tyr Gln Gln
    130                 135                 140

Leu Ile Glu Asp Arg Gly Glu Asp Met Leu Arg Arg Gly Leu Leu Asn
145                 150                 155                 160

Glu Leu Val Glu Leu Gln Arg Leu Glu Lys Val Leu Leu Asn Gly Lys
                165                 170                 175

Cys Asp Phe Lys Lys Gly Ile Trp Lys Ala Ile Gly Tyr Gln Glu Phe
            180                 185                 190

Tyr Pro Tyr Leu Gln Ala Val Gly Lys Leu Asn Gly Ala Ser Lys Thr
        195                 200                 205

Asn Pro Gly Asp Leu Tyr Lys Lys Gly Arg Ala Leu Leu Phe Ala Asn
    210                 215                 220

Thr Leu Gln Tyr Gly Leu Gly Gln Leu Glu Trp Met Arg His Thr Leu
225                 230                 235                 240

Ala Pro Phe Leu His Gln His Lys Ala Val Thr Met Ser Leu Ser Val
                245                 250                 255

Thr Glu Lys Ala Ser Trp Ile Pro Asp Val Gln Gly Pro Ala Met Ser
            260                 265                 270

Met Ile Ser Glu Phe Tyr His Asp Ser Gln Val Thr Lys Ser Leu Phe
        275                 280                 285

Arg Lys Arg Ser Leu Lys Lys Arg Val Val Cys Leu Phe Gly Gly Ser
    290                 295                 300

Ser Ala Gly Asn Asp Pro Thr His Ile Glu Ala Ala Lys Ser Leu Ala
305                 310                 315                 320

Ala Ala Leu His His His Asp Ile Ser Leu Val Tyr Gly Gly Thr
                325                 330                 335

Thr Gly Ile Met Gly Gln Val Ala Ser Ser Leu Val Glu Leu Ser Gly
            340                 345                 350

Pro Asn Ala Val Lys Gly Phe Ile Pro Ala Ala Leu Ala Gly His Glu
        355                 360                 365

Glu Glu Leu Gly Asp Asp Gly Thr Val Met Gly Gly Glu Tyr Leu Ser
    370                 375                 380

Arg Phe Gly Arg Arg Thr Ile Val Lys Asp Met His Thr Arg Lys Arg
385                 390                 395                 400

Phe Met Ile Gln Asn Val Leu Gln Gly Ala Pro Gly Ser Gly Phe Val
                405                 410                 415

Ala Leu Ser Gly Gly Tyr Gly Thr Leu Glu Glu Leu Leu Glu Ile Thr
            420                 425                 430

Thr Trp Ser Gln Leu Gly Ile His Asp Cys Val Val Val Phe Ser
        435                 440                 445

Val Asp Gly Phe Tyr Asp Gly Leu Leu Asp Trp Ile Glu Gln Val Ala
    450                 455                 460

Arg Arg Gly Phe Ile Ser Thr Thr His Ala Asn Ile Val Arg Val Ala
465                 470                 475                 480

Lys Thr Ala Asp Lys Val Ile Ala Cys Leu Ser Asp Cys Arg Ile Gln
                485                 490                 495

Pro Arg Arg His Val Leu Glu Trp Leu
            500                 505
```

<210> SEQ ID NO 16
<211> LENGTH: 1464
<212> TYPE: DNA
<213> ORGANISM: Ilyonectria radicola

<400> SEQUENCE: 16

| | | | | | |
|---|---|---|---|---|---|
| atgaaatctg | ttcgcaagct | tgcgattggt | attttcggtc | ctaccgcttc | ggggaagact | 60 |
| aagctgggca | tagccatcgc | cagggcgttt | cttggcgaag | ttgtctcggt | cgacagcctg | 120 |
| caatgttaca | agccagggac | catcactaca | gccaaacctg | agcctgaaga | gacccaagaa | 180 |
| gtgccccacc | atttgattga | tttccttgaa | gctgacgagg | agcctgatga | ttttgtggcg | 240 |
| ttggctctcg | ccaaaatgga | agagatcact | cgtcgcaaaa | ggctccccat | ccttgtcgga | 300 |
| ggatcaacat | cccttactat | tcccctctta | cttgaagcct | tcaacagcaa | gtaccaaatg | 360 |
| cttgcaatta | cattgatgcc | acatcagtca | acttaccagt | cactcattca | atccaggggt | 420 |
| gaagagatgc | tggaaagggg | gctcttggat | gagctcgccg | gacttcaagc | tcttgagcag | 480 |
| gtcttgctca | atggcgaatc | aaacttccgc | aaaggaattt | ggaaggcaat | cggataccag | 540 |
| gagttccatt | cataccttca | agctgaccag | tccgttggag | ggcgtgagca | tttgttccaa | 600 |
| aatggactgg | ccttgacggc | cgccaacact | ttacaatacg | gcttttacca | gcttgaatgg | 660 |
| atacgacaca | ccctcactcc | attcttacac | caagagaaag | ccacttgtat | cagcctttcc | 720 |
| gtcactgaca | aagcatcctg | gccaatggaa | gtggagggc | tggccatttc | catggctagc | 780 |
| gatttcttgt | acggttctca | agtgattgga | tttccaccca | aggaatcatc | cgagtctcgt | 840 |
| gtggtctgtc | tctttggtgg | atcgtcttct | ggcaacaatc | ccgtgcacat | cgaggcagcc | 900 |
| aagtcgctcg | ctgtcgtcct | acaccagcac | gatataaagc | tagtctacgg | cggcggaacc | 960 |
| actggaatca | tgggaaccat | cgcaagcact | cttgtgaaac | tgtctggacc | tagcgctgtt | 1020 |
| cacggcatcg | tacctgctgc | ccttgccagg | tacgaagaaa | agatgacaaa | cgagcacatc | 1080 |
| gaacaatcct | actcctctaa | gttcggtatg | cggactattg | tgagggatat | gcacactcgc | 1140 |
| aagcgactca | tgatccaaag | cgtccttgat | gggactccgg | ggagcggttt | cgtcgctttg | 1200 |
| agtggcggct | atggtacaat | ggaggagctg | cttgagataa | ctacgtggta | ccagttgggc | 1260 |
| atccacaaat | gcagtgtctg | tgttttcagt | gtgaatggat | tctttgatgg | tctggtcact | 1320 |
| tggatcggtc | aagttgcaca | ggacgggttc | ataggcccaa | tggactccga | cataattcaa | 1380 |
| gtcgcaagat | cagcggatga | agttgttgag | tgtcttgctg | atctccaccg | gtactcaagg | 1440 |
| aatggagaac | tagagtggct | ttag | | | | 1464 |

<210> SEQ ID NO 17
<211> LENGTH: 487
<212> TYPE: PRT
<213> ORGANISM: Ilyonectria radicola

<400> SEQUENCE: 17

Met Lys Ser Val Arg Lys Leu Ala Ile Gly Ile Phe Gly Pro Thr Ala
1               5                   10                  15

Ser Gly Lys Thr Lys Leu Gly Ile Ala Ile Ala Arg Ala Phe Leu Gly
            20                  25                  30

Glu Val Val Ser Val Asp Ser Leu Gln Cys Tyr Lys Pro Gly Thr Ile
        35                  40                  45

Thr Thr Ala Lys Pro Glu Pro Glu Glu Thr Gln Glu Val Pro His His
    50                  55                  60

Leu Ile Asp Phe Leu Glu Ala Asp Glu Glu Pro Asp Asp Phe Val Ala

```
                65                  70                  75                  80
Leu Ala Leu Ala Lys Met Glu Glu Ile Thr Arg Arg Lys Arg Leu Pro
                    85                  90                  95

Ile Leu Val Gly Gly Ser Thr Ser Leu Thr Ile Pro Leu Leu Leu Glu
                    100                 105                 110

Ala Phe Asn Ser Lys Tyr Gln Met Leu Ala Ile Thr Leu Met Pro His
                    115                 120                 125

Gln Ser Thr Tyr Gln Ser Leu Ile Gln Ser Arg Gly Glu Glu Met Leu
                    130                 135                 140

Glu Arg Gly Leu Leu Asp Glu Leu Ala Gly Leu Gln Ala Leu Glu Gln
145                 150                 155                 160

Val Leu Leu Asn Gly Glu Ser Asn Phe Arg Lys Gly Ile Trp Lys Ala
                    165                 170                 175

Ile Gly Tyr Gln Glu Phe His Ser Tyr Leu Gln Ala Asp Gln Ser Val
                    180                 185                 190

Gly Gly Arg Glu His Leu Phe Gln Asn Gly Leu Ala Leu Thr Ala Ala
                    195                 200                 205

Asn Thr Leu Gln Tyr Gly Phe Tyr Gln Leu Glu Trp Ile Arg His Thr
                    210                 215                 220

Leu Thr Pro Phe Leu His Gln Glu Lys Ala Thr Cys Ile Ser Leu Ser
225                 230                 235                 240

Val Thr Asp Lys Ala Ser Trp Pro Met Glu Val Glu Gly Leu Ala Ile
                    245                 250                 255

Ser Met Ala Ser Asp Phe Leu Tyr Gly Ser Gln Val Ile Gly Phe Pro
                    260                 265                 270

Pro Lys Glu Ser Ser Glu Ser Arg Val Val Cys Leu Phe Gly Gly Ser
                    275                 280                 285

Ser Ser Gly Asn Asn Pro Val His Ile Glu Ala Ala Lys Ser Leu Ala
                    290                 295                 300

Val Val Leu His Gln His Asp Ile Lys Leu Val Tyr Gly Gly Gly Thr
305                 310                 315                 320

Thr Gly Ile Met Gly Thr Ile Ala Ser Thr Leu Val Glu Leu Ser Gly
                    325                 330                 335

Pro Ser Ala Val His Gly Ile Val Pro Ala Ala Leu Ala Arg Tyr Glu
                    340                 345                 350

Glu Lys Met Thr Asn Glu His Ile Glu Gln Ser Tyr Ser Ser Lys Phe
                    355                 360                 365

Gly Met Arg Thr Ile Val Arg Asp Met His Thr Arg Lys Arg Leu Met
                    370                 375                 380

Ile Gln Ser Val Leu Asp Gly Thr Pro Gly Ser Gly Phe Val Ala Leu
385                 390                 395                 400

Ser Gly Gly Tyr Gly Thr Met Glu Glu Leu Leu Glu Ile Thr Thr Trp
                    405                 410                 415

Tyr Gln Leu Gly Ile His Lys Cys Ser Val Cys Val Phe Ser Val Asn
                    420                 425                 430

Gly Phe Phe Asp Gly Leu Val Thr Trp Ile Gly Gln Val Ala Gln Asp
                    435                 440                 445

Gly Phe Ile Gly Pro Met Asp Ser Asp Ile Ile Gln Val Ala Arg Ser
                    450                 455                 460

Ala Asp Glu Val Val Glu Cys Leu Ala Asp Leu His Arg Tyr Ser Arg
465                 470                 475                 480

Asn Gly Glu Leu Glu Trp Leu
                    485
```

<210> SEQ ID NO 18
<211> LENGTH: 1494
<212> TYPE: DNA
<213> ORGANISM: Ilyonectria radicola

<400> SEQUENCE: 18

```
atgggtagca gccatcatca tcaccatcat atgaaaagcg ttcgtaaact ggccattggt      60
attttggtc cgaccgcaag cggtaaaacc aaactgggta ttgcaattgc ccgtgcattt     120
ctgggtgaag ttgttagcgt tgatagcctg cagtgttata aaccgggtac aattaccacc     180
gcaaaaccgg aaccggaaga aacccaagaa gttccgcatc atctgattga ttttctggaa     240
gcagatgaag aaccggatga ttttgttgca ctggcactgg caaaaatgga agaaattacc     300
cgtcgtaaac gtctgccgat tctggttggt ggtagcacca gcctgaccat tccgctgctg     360
ctggaagcat ttaatagcaa atatcagatg ctggccatta ccctgatgcc tcatcagagc     420
acctatcaga gcctgattca gagccgtggt gaagaaatgc tgaacgtggg tctgctggat     480
gaactggcag gtctgcaggc actggaacag gttctgctga atggtgaaag caattttcgt     540
aaaggtatct ggaaagccat cggctatcaa gaatttcata gctatctgca ggccgatcag     600
agcgttggtg gtcgtgaaca cctgtttcag aatggtctgg cactgaccgc agcaaatacc     660
ctgcagtatg ttttatca gctggaatgg attcgtcata ccctgacccc gtttctgcat     720
caagaaaaag caacctgtat tagcctgagc gttaccgata aagcaagctg gccgatggaa     780
gttgaaggtc tggcaattag catggcaagc gattttctgt atggtagcca ggttattggt     840
tttccgccta agaaagcag cgaaagccgt gttgtttgtc tgtttggtgg ttcaagcagc     900
ggtaataatc cggttcatat tgaagcagca aaaagcctgg cagttgtgct gcatcagcat     960
gatattaaac tggtttatgg tggtggtacg accggtatta tgggcaccat tgcaagcacc    1020
ctggttgaac tgagcggtcc gagcgcagtt catggtattg ttccggcagc cctggcacgt    1080
tatgaagaaa aaatgacgaa cgaacatatc gagcagagct atagcagcaa atttggtatg    1140
cgtaccattg tgcgtgatat gcataccgt aaacgcctga tgattcagtc agttctggat    1200
ggtacaccgg gtagcggttt tgttgccctg agcggtggtt atggcaccat ggaagaactg    1260
ctggaaatta ccacctggta tcagctgggt attcataaat gtagcgttg cgttttagc     1320
gtgaacggtt tttttgatgg tctggttacc tggattggtc aggttgcaca ggatggtttt    1380
atcggtccga tggatagcga tattattcag gttgcccgta gtgccgatga agtggttgaa    1440
tgcctggccg atctgcatcg ttatagccgt aatggtgaac tggaatggct gtaa          1494
```

<210> SEQ ID NO 19
<211> LENGTH: 497
<212> TYPE: PRT
<213> ORGANISM: Ilyonectria radicola

<400> SEQUENCE: 19

```
Met Gly Ser Ser His His His His His His Met Lys Ser Val Arg Lys
1               5                   10                  15

Leu Ala Ile Gly Ile Phe Gly Pro Thr Ala Ser Gly Lys Thr Lys Leu
            20                  25                  30

Gly Ile Ala Ile Ala Arg Ala Phe Leu Gly Glu Val Val Ser Val Asp
        35                  40                  45

Ser Leu Gln Cys Tyr Lys Pro Gly Thr Ile Thr Thr Ala Lys Pro Glu
    50                  55                  60
```

-continued

```
Pro Glu Glu Thr Gln Glu Val Pro His His Leu Ile Asp Phe Leu Glu
 65                  70                  75                  80

Ala Asp Glu Glu Pro Asp Asp Phe Val Ala Leu Ala Leu Ala Lys Met
                 85                  90                  95

Glu Glu Ile Thr Arg Arg Lys Arg Leu Pro Ile Leu Val Gly Gly Ser
            100                 105                 110

Thr Ser Leu Thr Ile Pro Leu Leu Leu Glu Ala Phe Asn Ser Lys Tyr
        115                 120                 125

Gln Met Leu Ala Ile Thr Leu Met Pro His Gln Ser Thr Tyr Gln Ser
    130                 135                 140

Leu Ile Gln Ser Arg Gly Glu Glu Met Leu Glu Arg Gly Leu Leu Asp
145                 150                 155                 160

Glu Leu Ala Gly Leu Gln Ala Leu Glu Gln Val Leu Leu Asn Gly Glu
                165                 170                 175

Ser Asn Phe Arg Lys Gly Ile Trp Lys Ala Ile Gly Tyr Gln Glu Phe
            180                 185                 190

His Ser Tyr Leu Gln Ala Asp Gln Ser Val Gly Gly Arg Glu His Leu
        195                 200                 205

Phe Gln Asn Gly Leu Ala Leu Thr Ala Ala Asn Thr Leu Gln Tyr Gly
210                 215                 220

Phe Tyr Gln Leu Glu Trp Ile Arg His Thr Leu Thr Pro Phe Leu His
225                 230                 235                 240

Gln Glu Lys Ala Thr Cys Ile Ser Leu Ser Val Thr Asp Lys Ala Ser
                245                 250                 255

Trp Pro Met Glu Val Glu Gly Leu Ala Ile Ser Met Ala Ser Asp Phe
            260                 265                 270

Leu Tyr Gly Ser Gln Val Ile Gly Phe Pro Pro Lys Glu Ser Ser Glu
        275                 280                 285

Ser Arg Val Val Cys Leu Phe Gly Ser Ser Ser Gly Asn Asn Pro
    290                 295                 300

Val His Ile Glu Ala Ala Lys Ser Leu Ala Val Val Leu His Gln His
305                 310                 315                 320

Asp Ile Lys Leu Val Tyr Gly Gly Gly Thr Thr Gly Ile Met Gly Thr
                325                 330                 335

Ile Ala Ser Thr Leu Val Glu Leu Ser Gly Pro Ser Ala Val His Gly
            340                 345                 350

Ile Val Pro Ala Ala Leu Ala Arg Tyr Glu Glu Lys Met Thr Asn Glu
        355                 360                 365

His Ile Glu Gln Ser Tyr Ser Ser Lys Phe Gly Met Arg Thr Ile Val
    370                 375                 380

Arg Asp Met His Thr Arg Lys Arg Leu Met Ile Gln Ser Val Leu Asp
385                 390                 395                 400

Gly Thr Pro Gly Ser Gly Phe Val Ala Leu Ser Gly Tyr Gly Thr
                405                 410                 415

Met Glu Glu Leu Leu Glu Ile Thr Thr Trp Tyr Gln Leu Gly Ile His
            420                 425                 430

Lys Cys Ser Val Cys Val Phe Ser Val Asn Gly Phe Phe Asp Gly Leu
        435                 440                 445

Val Thr Trp Ile Gly Gln Val Ala Gln Asp Gly Phe Ile Gly Pro Met
    450                 455                 460

Asp Ser Asp Ile Ile Gln Val Ala Arg Ser Ala Asp Glu Val Val Glu
465                 470                 475                 480

Cys Leu Ala Asp Leu His Arg Tyr Ser Arg Asn Gly Glu Leu Glu Trp
```

Leu

<210> SEQ ID NO 20
<211> LENGTH: 1488
<212> TYPE: DNA
<213> ORGANISM: Atkinsonella hypoxylon

<400> SEQUENCE: 20

```
atgctagcaa gccgaaatct ctgcgttgcc attcttggcc ccaccgcttc tgggaagacc      60
aagcttggtg tggccgttgc caaagccttc ctaggcgagg tcatctctgt agacagctta     120
caatgttaca agccgggaac gatcatcaca gcaaaaccag ttccagaaga gactgaagga     180
atcccccatc acctaataga ctacctagaa gccgaggagg aaccacacga ctatgtcgaa     240
agagccaccg ccacaataga taacattacc actcgcaaca agctcccaat cctcgtggga     300
gggtcaacat ccctcaccat gcctctcttg caggaagttt tcaatgcaca atacgaggtt     360
ctcgttataa ctctagtacc gcatcattcg gtctaccaac aactcaccga ctctagggg t    420
gaggaaatgc tacgcaatgg cctattaaac gagctcatcg agctgcaacg ccttgaaaaa     480
gttctcctta tggccaaag cgacttcacg agaggtatct ggaaagcgat cgggtaccaa     540
gaattctacc cgtatcttca agctgtgggg aagttgaatg aggcatcgaa gaacaaccct     600
ggacatttat ataaaaaggg cagagcattg atgttcgcca acactttaca atatggtcag     660
agccagctcg agtggatgcg gcacaccctg gccccctccc tacaccaaca caaggctgct     720
actattagcc tcaatgtcac cgacaaggcg tcctggatat cagacgtgca aagacctgct     780
ctgactatgg tcagcgagtt ctatcacagt tctcaggtga cgaagagcct ttcactaagg     840
cggtcttcga agaagcgtgt tgtttgcctc tttggcggat cgtcttgcgg caatgaccca     900
actcacattg aggcagccaa atctctagct gtggccctac accaccacga tatctcactt     960
gtgtacggtg gaggaaccac tgggatcatg gccaagtcg cgagctccct cgttgcgctg    1020
tccgggccaa acgctgtcca aggaatcatc cctgctgctc ttgccaggta cgaagaggaa    1080
ctcggagatg acggtcccat catcgatggg gagtacatgt ctcggtttgg aaagagaacg    1140
atagtaagag atatgcgcac gcgaaagcgc ctcatgatcc agaatgttct ccaaggggcg    1200
cccgggagtg gatttgtcgt aatgagtggc ggctatggga cgttagagga attactcgag    1260
atgacgacat ggtcacaact gggactacat gattgcgtca ttaccgtgtt tagtgtcgat    1320
ggcttctacg acggtctgct cgattggatc gaccaagtgg tacgacgcgg cttcatcagt    1380
actaaacacg ccaacatagt ccgggtcgca aagtcggcag acaaagtgat cgcatgtctc    1440
gcggatgggc ggcttcatcc gcggagacat gtgctggagt ggctctag              1488
```

<210> SEQ ID NO 21
<211> LENGTH: 495
<212> TYPE: PRT
<213> ORGANISM: Atkinsonella hypoxylon

<400> SEQUENCE: 21

```
Met Leu Ala Ser Arg Asn Leu Cys Val Ala Ile Leu Gly Pro Thr Ala
1               5                   10                  15

Ser Gly Lys Thr Lys Leu Gly Val Ala Val Ala Lys Ala Phe Leu Gly
            20                  25                  30

Glu Val Ile Ser Val Asp Ser Leu Gln Cys Tyr Lys Pro Gly Thr Ile
        35                  40                  45
```

```
Ile Thr Ala Lys Pro Val Pro Glu Glu Thr Glu Gly Ile Pro His His
    50              55                  60

Leu Ile Asp Tyr Leu Glu Ala Glu Glu Pro His Asp Tyr Val Glu
65              70              75              80

Arg Ala Thr Ala Thr Ile Asp Asn Ile Thr Thr Arg Asn Lys Leu Pro
                85              90              95

Ile Leu Val Gly Gly Ser Thr Ser Leu Thr Met Pro Leu Leu Gln Glu
            100             105             110

Val Phe Asn Ala Gln Tyr Glu Val Leu Val Ile Thr Leu Val Pro His
            115             120             125

His Ser Val Tyr Gln Gln Leu Thr Asp Ser Arg Gly Glu Glu Met Leu
    130             135             140

Arg Asn Gly Leu Leu Asn Glu Leu Ile Glu Leu Gln Arg Leu Glu Lys
145             150             155             160

Val Leu Leu Asn Gly Gln Ser Asp Phe Thr Arg Gly Ile Trp Lys Ala
                165             170             175

Ile Gly Tyr Gln Glu Phe Tyr Pro Tyr Leu Gln Ala Val Gly Lys Leu
            180             185             190

Asn Glu Ala Ser Lys Asn Asn Pro Gly His Leu Tyr Lys Lys Gly Arg
            195             200             205

Ala Leu Met Phe Ala Asn Thr Leu Gln Tyr Gly Gln Ser Gln Leu Glu
    210             215             220

Trp Met Arg His Thr Leu Ala Pro Phe Leu His Gln His Lys Ala Ala
225             230             235             240

Thr Ile Ser Leu Asn Val Thr Asp Lys Ala Ser Trp Ile Ser Asp Val
                245             250             255

Gln Arg Pro Ala Leu Thr Met Val Ser Glu Phe Tyr His Ser Ser Gln
            260             265             270

Val Thr Lys Ser Leu Ser Leu Arg Arg Ser Ser Lys Lys Arg Val Val
        275             280             285

Cys Leu Phe Gly Gly Ser Ser Cys Gly Asn Asp Pro Thr His Ile Glu
    290             295             300

Ala Ala Lys Ser Leu Ala Val Ala Leu His His Asp Ile Ser Leu
305             310             315             320

Val Tyr Gly Gly Gly Thr Thr Gly Ile Met Gly Gln Val Ala Ser Ser
            325             330             335

Leu Val Ala Leu Ser Gly Pro Asn Ala Val Gln Gly Ile Ile Pro Ala
            340             345             350

Ala Leu Ala Arg Tyr Glu Glu Glu Leu Gly Asp Asp Gly Pro Ile Ile
            355             360             365

Asp Gly Glu Tyr Met Ser Arg Phe Gly Lys Arg Thr Ile Val Arg Asp
    370             375             380

Met Arg Thr Arg Lys Arg Leu Met Ile Gln Asn Val Leu Gln Gly Ala
385             390             395             400

Pro Gly Ser Gly Phe Val Val Met Ser Gly Gly Tyr Gly Thr Leu Glu
            405             410             415

Glu Leu Leu Glu Met Thr Thr Trp Ser Gln Leu Gly Leu His Asp Cys
            420             425             430

Val Ile Thr Val Phe Ser Val Asp Gly Phe Tyr Asp Gly Leu Leu Asp
            435             440             445

Trp Ile Asp Gln Val Val Arg Arg Gly Phe Ile Ser Thr Lys His Ala
450             455             460

Asn Ile Val Arg Val Ala Lys Ser Ala Asp Lys Val Ile Ala Cys Leu
```

```
                465                 470                 475                 480
Ala Asp Gly Arg Leu His Pro Arg Arg His Val Leu Glu Trp Leu
                    485                 490                 495
```

<210> SEQ ID NO 22
<211> LENGTH: 1518
<212> TYPE: DNA
<213> ORGANISM: Atkinsonella hypoxylon

<400> SEQUENCE: 22

```
atgggtagca gccatcatca tcaccatcat atgctggcaa gccgtaatct gtgtgttgca    60
attctgggtc cgaccgcaag cggtaaaacc aaactgggtg ttgcagttgc aaaagcattt   120
ctgggtgaag ttattagcgt tgatagcctg cagtgttata aaccgggtac aattattacc   180
gcaaaaccgg ttccggaaga aaccgaaggt attccgcatc atctgattga ttatctggaa   240
gccgaagagg aaccgcatga ttatgttgaa cgtgcaaccg caaccattga taacattacc   300
acccgtaata aactgccgat tctggttggt ggtagcacca gcctgaccat gccgctgctg   360
caagaagttt ttaacgcaca gtatgaagtt ctggttatta ccctggtgcc gcatcatagc   420
gtttatcagc agctgaccga tagccgtggt gaagaaatgc tgcgtaatgg tctgctgaat   480
gaactgattg aactgcagcg tctggaaaaa gttctgctga cggtcagag cgattttacc   540
cgtggtattt ggaaagcaat tggctaccaa gaattctatc cgtatctgca ggcagttggt   600
aaactgaatg aagccagcaa aaacaatccg ggtcatctgt acaaaaaagg tcgtgcactg   660
atgtttgcaa ataccctgca gtatggtcag agccagctgg aatggatgcg tcataccctg   720
gcaccgtttc tgcatcagca taaagcagca accattagcc tgaatgttac cgataaagca   780
agctggatta gtgatgttca gcgtccggca ctgaccatgg ttagcgaatt ttatcatagc   840
agccaggtta ccaaaagcct gagcctgcgt cgtagcagca aaaaacgtgt tgtttgtctg   900
tttggtggtt caagctgtgg taatgatccg acccatattg aagcagcgaa aagcctggca   960
gttgcactgc atcatcatga tattagcctg gtttatggtg tggtacaac cggtattatg  1020
ggtcaggttg caagcagcct ggttgcactg agcggtccga atgcagttca gggtattatt  1080
ccggcagcac tggcacgtta tgaagaggaa ctgggtgatg atggtccgat tattgatggt  1140
gaatatatga ccgttttgg caaacgtacc attgttcgtg atatgcgtac ccgtaaacgt  1200
ctgatgattc agaatgttct gcagggtgca ccgggtagcg ttttgttgt tatgagcggt  1260
ggttatggca ccctggaaga actgctggaa atgaccacct ggtcacagct gggtctgcat  1320
gattgtgtta ttaccgtttt tagcgtggat ggcttttatg atggcctgct ggattggatt  1380
gatcaggttg ttcgtcgtgg ttttattagc accaaacatg ccaatattgt gcgtgttgca  1440
aaaagcgcag ataaagttat tgcatgtctg gcagatggtc gtctgcatcc gcgtcgtcat  1500
gttctggaat ggctgtaa                                                1518
```

<210> SEQ ID NO 23
<211> LENGTH: 505
<212> TYPE: PRT
<213> ORGANISM: Atkinsonella hypoxylon

<400> SEQUENCE: 23

```
Met Gly Ser Ser His His His His His His Met Leu Ala Ser Arg Asn
  1               5                  10                  15

Leu Cys Val Ala Ile Leu Gly Pro Thr Ala Ser Gly Lys Thr Lys Leu
             20                  25                  30
```

```
Gly Val Ala Val Ala Lys Ala Phe Leu Gly Glu Val Ile Ser Val Asp
         35                  40                  45

Ser Leu Gln Cys Tyr Lys Pro Gly Thr Ile Ile Thr Ala Lys Pro Val
 50                  55                  60

Pro Glu Glu Thr Glu Gly Ile Pro His His Leu Ile Asp Tyr Leu Glu
 65                  70                  75                  80

Ala Glu Glu Glu Pro His Asp Tyr Val Glu Arg Ala Thr Ala Thr Ile
                 85                  90                  95

Asp Asn Ile Thr Thr Arg Asn Lys Leu Pro Ile Leu Val Gly Gly Ser
                100                 105                 110

Thr Ser Leu Thr Met Pro Leu Leu Gln Glu Val Phe Asn Ala Gln Tyr
                115                 120                 125

Glu Val Leu Val Ile Thr Leu Val Pro His His Ser Val Tyr Gln Gln
130                 135                 140

Leu Thr Asp Ser Arg Gly Glu Glu Met Leu Arg Asn Gly Leu Leu Asn
145                 150                 155                 160

Glu Leu Ile Glu Leu Gln Arg Leu Glu Lys Val Leu Leu Asn Gly Gln
                165                 170                 175

Ser Asp Phe Thr Arg Gly Ile Trp Lys Ala Ile Gly Tyr Gln Glu Phe
                180                 185                 190

Tyr Pro Tyr Leu Gln Ala Val Gly Lys Leu Asn Glu Ala Ser Lys Asn
            195                 200                 205

Asn Pro Gly His Leu Tyr Lys Lys Gly Arg Ala Leu Met Phe Ala Asn
            210                 215                 220

Thr Leu Gln Tyr Gly Gln Ser Gln Leu Glu Trp Met Arg His Thr Leu
225                 230                 235                 240

Ala Pro Phe Leu His Gln His Lys Ala Ala Thr Ile Ser Leu Asn Val
                245                 250                 255

Thr Asp Lys Ala Ser Trp Ile Ser Asp Val Gln Arg Pro Ala Leu Thr
                260                 265                 270

Met Val Ser Glu Phe Tyr His Ser Ser Gln Val Thr Lys Ser Leu Ser
                275                 280                 285

Leu Arg Arg Ser Ser Lys Lys Arg Val Val Cys Leu Phe Gly Gly Ser
290                 295                 300

Ser Cys Gly Asn Asp Pro Thr His Ile Glu Ala Ala Lys Ser Leu Ala
305                 310                 315                 320

Val Ala Leu His His His Asp Ile Ser Leu Val Tyr Gly Gly Gly Thr
                325                 330                 335

Thr Gly Ile Met Gly Gln Val Ala Ser Ser Leu Val Ala Leu Ser Gly
                340                 345                 350

Pro Asn Ala Val Gln Gly Ile Ile Pro Ala Ala Leu Ala Arg Tyr Glu
            355                 360                 365

Glu Glu Leu Gly Asp Asp Gly Pro Ile Ile Asp Gly Glu Tyr Met Ser
            370                 375                 380

Arg Phe Gly Lys Arg Thr Ile Val Arg Asp Met Arg Thr Arg Lys Arg
385                 390                 395                 400

Leu Met Ile Gln Asn Val Leu Gln Gly Ala Pro Gly Ser Gly Phe Val
                405                 410                 415

Val Met Ser Gly Gly Tyr Gly Thr Leu Glu Glu Leu Leu Glu Met Thr
            420                 425                 430

Thr Trp Ser Gln Leu Gly Leu His Asp Cys Val Ile Thr Val Phe Ser
            435                 440                 445

Val Asp Gly Phe Tyr Asp Gly Leu Leu Asp Trp Ile Asp Gln Val Val
```

```
                    450             455             460
Arg Arg Gly Phe Ile Ser Thr Lys His Ala Asn Ile Val Arg Val Ala
465                 470                 475                 480

Lys Ser Ala Asp Lys Val Ile Ala Cys Leu Ala Asp Gly Arg Leu His
                485                 490                 495

Pro Arg Arg His Val Leu Glu Trp Leu
            500                 505

<210> SEQ ID NO 24
<211> LENGTH: 1470
<212> TYPE: DNA
<213> ORGANISM: Fusarium fujikuroi

<400> SEQUENCE: 24
atgcaatcca atcaaaagct ctgcatcgct atctttggcc ctaccgcctc ggggaagacc      60
aaactggggg tcgccattgc aaaagccttt ccgagcgagg ttatctccgt cgacagtcta     120
cagtgctaca aagcgggaag cattatcaca gctaagccta ctgctcatga gatagctgat     180
gttcctcatc atctgattga ctacctcgag gctgatgagg agcccaatga ctttgtggcc     240
caagctgctg acaagatgga agatatcaca aatcgaggaa aactccccat tcttgtcggc     300
ggttcgactt ctctcgcgat acctttgctg cacgaggcac tgaagcggca gtatcggttc     360
gtggctgcaa ctctgatccc gcgtcagtca acatactggc agtccatcca agtcagagcc     420
agcgagatgc tcgagagggg tcttctggcc gaactagagg agttgagaga cctgcagcag     480
agtctcctcg atgacaacgc atgcttccat aagggagtat ggaaggccat tgggtatcaa     540
gagttctatc cctatctcga ggcagagtcg tcatgcaacg cccgtcagtc gtcattccag     600
agggtctcg cactgatgaa tgcaaacact ctgcagtacg gcttccatca actcgagtgg     660
attcgttcta tcctcaaccc ttttctgcac caagccggcg tcgtatgcat gagcctccct     720
gtcactgaca atgcttcgtg gatgtcagat gtccagatac ctgctatctc aatgctcaac     780
gacctgtgct acagtttgcg aacgatcaaa gtctccacca atggaacact aaactctagc     840
cccaagtttc gagtcgttgg tctatttggc ggatcttctc cggggaatga tccgggtcac     900
atcgatgcgg ctaaaaggct tgcgtttgct ctacaccaac atagctacaa actcgtctac     960
ggcggcggaa caactgggat catgggcgcc attgccagca ctctggtgca actctctgga    1020
ccaagtgccg tccagggcat cattcccgtt gcactcgcca gtacgaagaa agactcact    1080
aagaaaaggg ccgacccttc aaagttcggg aacaggactg tcgtcaaaga catgcataca    1140
cgcaagagac tcatgatcga ggcagtcatt ggtggcgctc agggagcgg ctttgtagct    1200
ctcagtgggg gatacggtac cttggaggaa ctcctcgaga caacgacttg gtaccagctt    1260
ggtattcatc aatgtggaat ctgtgtgttt gacgtatgcg gattttacaa gggtttaatg    1320
gactgggttt gtcaggctgc acaggcaggg tttgttggca cagaggatgc tactattctg    1380
cgggttgcaa cgacggctga ggatgtcatc ggctgcctag cagtaatga tcatcgttat    1440
tcgcggatgg gtgagctgga atgggattag                                    1470

<210> SEQ ID NO 25
<211> LENGTH: 489
<212> TYPE: PRT
<213> ORGANISM: Fusarium fujikuroi

<400> SEQUENCE: 25

Met Gln Ser Asn Gln Lys Leu Cys Ile Ala Ile Phe Gly Pro Thr Ala
1               5                   10                  15
```

```
Ser Gly Lys Thr Lys Leu Gly Val Ala Ile Ala Lys Ala Phe Pro Ser
            20                  25                  30

Glu Val Ile Ser Val Asp Ser Leu Gln Cys Tyr Lys Ala Gly Ser Ile
            35                  40                  45

Ile Thr Ala Lys Pro Thr Ala His Glu Ile Ala Asp Val Pro His His
 50                  55                  60

Leu Ile Asp Tyr Leu Glu Ala Asp Glu Pro Asn Asp Phe Val Ala
 65                  70                  75                  80

Gln Ala Ala Asp Lys Met Glu Asp Ile Thr Asn Arg Gly Lys Leu Pro
                85                  90                  95

Ile Leu Val Gly Gly Ser Thr Ser Leu Ala Ile Pro Leu Leu His Glu
                100                 105                 110

Ala Leu Lys Arg Gln Tyr Arg Phe Val Ala Ala Thr Leu Ile Pro Arg
                115                 120                 125

Gln Ser Thr Tyr Trp Gln Ser Ile Gln Val Arg Ala Ser Glu Met Leu
    130                 135                 140

Glu Arg Gly Leu Leu Ala Glu Leu Glu Glu Leu Arg Asp Leu Gln Gln
145                 150                 155                 160

Ser Leu Leu Asp Asp Asn Ala Cys Phe His Lys Gly Val Trp Lys Ala
                165                 170                 175

Ile Gly Tyr Gln Glu Phe Tyr Pro Tyr Leu Glu Ala Glu Ser Ser Cys
                180                 185                 190

Asn Ala Arg Gln Ser Ser Phe Gln Arg Gly Leu Ala Leu Met Asn Ala
                195                 200                 205

Asn Thr Leu Gln Tyr Gly Phe His Gln Leu Glu Trp Ile Arg Ser Ile
        210                 215                 220

Leu Asn Pro Phe Leu His Gln Ala Gly Val Val Cys Met Ser Leu Pro
225                 230                 235                 240

Val Thr Asp Asn Ala Ser Trp Met Ser Asp Val Gln Ile Pro Ala Ile
                245                 250                 255

Ser Met Leu Asn Asp Leu Cys Tyr Ser Leu Arg Thr Ile Lys Val Ser
                260                 265                 270

Thr Asn Gly Thr Leu Asn Ser Ser Pro Lys Phe Arg Val Val Gly Leu
        275                 280                 285

Phe Gly Gly Ser Ser Pro Gly Asn Asp Pro Gly His Ile Asp Ala Ala
        290                 295                 300

Lys Arg Leu Ala Phe Ala Leu His Gln His Ser Tyr Lys Leu Val Tyr
305                 310                 315                 320

Gly Gly Gly Thr Thr Gly Ile Met Gly Ala Ile Ala Ser Thr Leu Val
                325                 330                 335

Gln Leu Ser Gly Pro Ser Ala Val Gln Gly Ile Pro Val Ala Leu
        340                 345                 350

Ala Lys Tyr Glu Glu Arg Leu Thr Lys Lys Arg Ala Asp Pro Ser Lys
        355                 360                 365

Phe Gly Asn Arg Thr Val Val Lys Asp Met His Thr Arg Lys Arg Leu
        370                 375                 380

Met Ile Glu Ala Val Ile Gly Ala Pro Gly Ser Gly Phe Val Ala
385                 390                 395                 400

Leu Ser Gly Gly Tyr Gly Thr Leu Glu Glu Leu Leu Glu Thr Thr Thr
                405                 410                 415

Trp Tyr Gln Leu Gly Ile His Gln Cys Gly Ile Cys Val Phe Asp Val
        420                 425                 430
```

Cys Gly Phe Tyr Lys Gly Leu Met Asp Trp Val Cys Gln Ala Ala Gln
        435                 440                 445

Ala Gly Phe Val Gly Thr Glu Asp Ala Thr Ile Leu Arg Val Ala Thr
    450                 455                 460

Thr Ala Glu Asp Val Ile Gly Cys Leu Gly Ser Asn Asp His Arg Tyr
465                 470                 475                 480

Ser Arg Met Gly Glu Leu Glu Trp Asp
                485

<210> SEQ ID NO 26
<211> LENGTH: 1500
<212> TYPE: DNA
<213> ORGANISM: Fusarium fujikuroi

<400> SEQUENCE: 26

| | | | | | |
|---|---|---|---|---|---|
| atgggtagca | gccatcatca | tcaccatcat | atgcagagca | atcagaaact | gtgcattgca | 60 |
| attttggtc | cgaccgcaag | cggtaaaacc | aaactgggtg | ttgcaattgc | caaagcattt | 120 |
| ccgagcgaag | ttattagcgt | tgatagcctg | cagtgttata | aagccggtag | cattattacc | 180 |
| gcaaaaccga | ccgcacatga | aattgcagat | gttccgcatc | atctgatcga | ttatctggaa | 240 |
| gcagatgaag | aaccgaatga | ttttgttgca | caggcagcag | ataaaatgga | agatattacc | 300 |
| aatcgtggca | aactgccgat | tctggttggt | ggtagcacca | gcctggcaat | tccgctgctg | 360 |
| catgaagcac | tgaaacgtca | gtatcgtttt | gttgccgcaa | ccctgattcc | gcgtcagagc | 420 |
| acctattggc | agagcattca | ggttcgtgca | agcgaaatgc | tggaacgtgg | tctgctggca | 480 |
| gaactggaag | aactgcgtga | tctgcagcag | agcctgctgg | atgataatgc | atgttttcat | 540 |
| aaaggtgtgt | ggaaagccat | tggctaccaa | gaattttatc | cgtacctgga | agccgaaagc | 600 |
| agctgtaatg | cacgtcagag | tagctttcag | cgtggtctgg | cactgatgaa | tgcaaatacc | 660 |
| ctgcagtatg | gttttcatca | gctggaatgg | attcgtagca | ttctgaatcc | gtttctgcat | 720 |
| caggcaggcg | ttgtttgtat | gagcctgccg | gttaccgata | tgcaagctg | gatgagtgat | 780 |
| gttcagattc | cggcaattag | catgctgaat | gatctgtgtt | atagcctgcg | taccattaaa | 840 |
| gttagcacca | tggcaccct | gaatagcagc | cctaaatttc | gtgttgttgg | tctgtttggt | 900 |
| ggttcaagtc | cgggtaatga | tccgggtcat | attgatgcag | caaaacgtct | ggcatttgca | 960 |
| ctgcatcagc | atagctataa | actggtttat | ggtggtggta | caaccggtat | tatgggtgca | 1020 |
| attgcgagca | ccctggttca | gctgagcggt | ccgagcgcag | ttcagggtat | tattccggtt | 1080 |
| gcactggcaa | atatgaaga | acgtctgacc | aaaaaacgtg | cagatccgag | caaatttggt | 1140 |
| aatcgtaccg | ttgtgaaaga | tatgcatacc | cgtaaacgtc | tgatgattga | agcagttatt | 1200 |
| ggtggcgcac | cgggtagcgg | ttttgtggca | ctgagcggtg | ttatggtac | gctggaagaa | 1260 |
| ctgctggaaa | ccaccacctg | gtatcaactg | ggtatccatc | agtgtggtat | ttgcgttttt | 1320 |
| gatgtgtgcg | gtttctataa | aggcctgatg | gattgggttt | gtcaggcagc | ccaggcaggt | 1380 |
| tttgttggta | cagaagatgc | aaccattctg | cgtgttgcca | ccaccgcaga | agatgttatt | 1440 |
| ggttgtctgg | gtagcaatga | tcatcgttat | agccgtatgg | gtgaactgga | atgggattaa | 1500 |

<210> SEQ ID NO 27
<211> LENGTH: 499
<212> TYPE: PRT
<213> ORGANISM: Fusarium fujikuroi

<400> SEQUENCE: 27

Met Gly Ser Ser His His His His His His Met Gln Ser Asn Gln Lys

```
  1               5                  10                 15
Leu Cys Ile Ala Ile Phe Gly Pro Thr Ala Ser Gly Lys Thr Lys Leu
                20                  25                 30

Gly Val Ala Ile Ala Lys Ala Phe Pro Ser Glu Val Ile Ser Val Asp
                35                  40                 45

Ser Leu Gln Cys Tyr Lys Ala Gly Ser Ile Ile Thr Ala Lys Pro Thr
 50                  55                  60

Ala His Glu Ile Ala Asp Val Pro His His Leu Ile Asp Tyr Leu Glu
 65                  70                  75                 80

Ala Asp Glu Glu Pro Asn Asp Phe Val Ala Gln Ala Ala Asp Lys Met
                85                  90                 95

Glu Asp Ile Thr Asn Arg Gly Lys Leu Pro Ile Leu Val Gly Gly Ser
                100                 105                110

Thr Ser Leu Ala Ile Pro Leu Leu His Glu Ala Leu Lys Arg Gln Tyr
                115                 120                125

Arg Phe Val Ala Ala Thr Leu Ile Pro Arg Gln Ser Thr Tyr Trp Gln
                130                 135                140

Ser Ile Gln Val Arg Ala Ser Glu Met Leu Glu Arg Gly Leu Leu Ala
145                 150                 155                160

Glu Leu Glu Glu Leu Arg Asp Leu Gln Gln Ser Leu Leu Asp Asp Asn
                165                 170                175

Ala Cys Phe His Lys Gly Val Trp Lys Ala Ile Gly Tyr Gln Glu Phe
                180                 185                190

Tyr Pro Tyr Leu Glu Ala Glu Ser Ser Cys Asn Ala Arg Gln Ser Ser
                195                 200                205

Phe Gln Arg Gly Leu Ala Leu Met Asn Ala Asn Thr Leu Gln Tyr Gly
                210                 215                220

Phe His Gln Leu Glu Trp Ile Arg Ser Ile Leu Asn Pro Phe Leu His
225                 230                 235                240

Gln Ala Gly Val Val Cys Met Ser Leu Pro Val Thr Asp Asn Ala Ser
                245                 250                255

Trp Met Ser Asp Val Gln Ile Pro Ala Ile Ser Met Leu Asn Asp Leu
                260                 265                270

Cys Tyr Ser Leu Arg Thr Ile Lys Val Ser Thr Asn Gly Thr Leu Asn
                275                 280                285

Ser Ser Pro Lys Phe Arg Val Val Gly Leu Phe Gly Gly Ser Ser Pro
                290                 295                300

Gly Asn Asp Pro Gly His Ile Asp Ala Ala Lys Arg Leu Ala Phe Ala
305                 310                 315                320

Leu His Gln His Ser Tyr Lys Leu Val Tyr Gly Gly Thr Thr Gly
                325                 330                335

Ile Met Gly Ala Ile Ala Ser Thr Leu Val Gln Leu Ser Gly Pro Ser
                340                 345                350

Ala Val Gln Gly Ile Ile Pro Val Ala Leu Ala Lys Tyr Glu Glu Arg
                355                 360                365

Leu Thr Lys Lys Arg Ala Asp Pro Ser Lys Phe Gly Asn Arg Thr Val
                370                 375                380

Val Lys Asp Met His Thr Arg Lys Arg Leu Met Ile Glu Ala Val Ile
385                 390                 395                400

Gly Gly Ala Pro Gly Ser Gly Phe Val Ala Leu Ser Gly Gly Tyr Gly
                405                 410                415

Thr Leu Glu Glu Leu Leu Glu Thr Thr Thr Trp Tyr Gln Leu Gly Ile
                420                 425                430
```

```
His Gln Cys Gly Ile Cys Val Phe Asp Val Cys Gly Phe Tyr Lys Gly
        435                 440                 445

Leu Met Asp Trp Val Cys Gln Ala Ala Gln Ala Gly Phe Val Gly Thr
    450                 455                 460

Glu Asp Ala Thr Ile Leu Arg Val Ala Thr Thr Ala Glu Asp Val Ile
465                 470                 475                 480

Gly Cys Leu Gly Ser Asn Asp His Arg Tyr Ser Arg Met Gly Glu Leu
                485                 490                 495

Glu Trp Asp

<210> SEQ ID NO 28
<211> LENGTH: 783
<212> TYPE: DNA
<213> ORGANISM: Agobacterium tumefasciens

<400> SEQUENCE: 28
atgggcagca gccatcatca tcatcatcac agcagcggcc tggtgccgcg cggcagccat      60
atggatctgc atctgatttt tggtccgacc tgtaccggta aaaccaccac cgcaattgca     120
ctggcacagc agacaggtct gccggttctg agcctggatc gtgttcagtg ttgtccgcag     180
ctgagcaccg gtagcggtcg tccgaccgtt gaagaactga aaggcaccac ccgtctgtat     240
ctggatgatc gtccgctggt tgaaggtatt attgcagcaa acaggcaca tcatcgtctg      300
attgaagaag tgtataatca cgaagcaaat ggtggtctga ttctggaagg tggtagcacc     360
agcctgctga attgtatggc acgtaatagt tattggagcg cagattttcg ctggcatatt     420
attcgtcata aactgccgga tcaagaaacc tttatgaaag cagcaaaagc ccgtgttaaa     480
caaatgctgc atccggcagc aggtcatagc attattcaag aactggttta tctgtggaat     540
gaaccgcgtc tgcgtccgat tctgaaagaa attgatggtt atcgttatgc catgctgttt     600
gcaagccaga accagattac cgcagatatg ctgctgcagc tggatgcaaa tatggaaggt     660
aaactgatta tggcattgc caagagtat tttatccatg cacgtcagca agaacagaaa      720
tttccgcagg ttaatgcagc agcctttgat ggttttgaag gtcatccgtt tggcatgtat     780
taa                                                                   783

<210> SEQ ID NO 29
<211> LENGTH: 260
<212> TYPE: PRT
<213> ORGANISM: Agobacterium tumefasciens

<400> SEQUENCE: 29

Met Gly Ser Ser His His His His His His Ser Ser Gly Leu Val Pro
1               5                   10                  15

Arg Gly Ser His Met Asp Leu His Leu Ile Phe Gly Pro Thr Cys Thr
                20                  25                  30

Gly Lys Thr Thr Thr Ala Ile Ala Leu Ala Gln Gln Thr Gly Leu Pro
            35                  40                  45

Val Leu Ser Leu Asp Arg Val Gln Cys Cys Pro Gln Leu Ser Thr Gly
        50                  55                  60

Ser Gly Arg Pro Thr Val Glu Glu Leu Lys Gly Thr Thr Arg Leu Tyr
65                  70                  75                  80

Leu Asp Asp Arg Pro Leu Val Glu Gly Ile Ile Ala Ala Lys Gln Ala
                85                  90                  95

His His Arg Leu Ile Glu Glu Val Tyr Asn His Glu Ala Asn Gly Gly
            100                 105                 110
```

```
Leu Ile Leu Glu Gly Gly Ser Thr Ser Leu Leu Asn Cys Met Ala Arg
        115                 120                 125

Asn Ser Tyr Trp Ser Ala Asp Phe Arg Trp His Ile Ile Arg His Lys
    130                 135                 140

Leu Pro Asp Gln Glu Thr Phe Met Lys Ala Ala Lys Ala Arg Val Lys
145                 150                 155                 160

Gln Met Leu His Pro Ala Ala Gly His Ser Ile Ile Gln Glu Leu Val
                165                 170                 175

Tyr Leu Trp Asn Glu Pro Arg Leu Arg Pro Ile Leu Lys Glu Ile Asp
            180                 185                 190

Gly Tyr Arg Tyr Ala Met Leu Phe Ala Ser Gln Asn Gln Ile Thr Ala
        195                 200                 205

Asp Met Leu Leu Gln Leu Asp Ala Asn Met Glu Gly Lys Leu Ile Asn
    210                 215                 220

Gly Ile Ala Gln Glu Tyr Phe Ile His Ala Arg Gln Gln Glu Gln Lys
225                 230                 235                 240

Phe Pro Gln Val Asn Ala Ala Phe Asp Gly Phe Glu Gly His Pro
                245                 250                 255

Phe Gly Met Tyr
            260

<210> SEQ ID NO 30
<211> LENGTH: 8
<212> TYPE: PRT
<213> ORGANISM: Artificial sequences
<220> FEATURE:
<223> OTHER INFORMATION: Consensus motif
<220> FEATURE:
<221> NAME/KEY: misc_feature
<222> LOCATION: (4)..(4)
<223> OTHER INFORMATION: Xaa at position 4 is Gly or Ala
<220> FEATURE:
<221> NAME/KEY: misc_feature
<222> LOCATION: (5)..(5)
<223> OTHER INFORMATION: Xaa at position 5 is Val, Ser, Ala, or Thr

<400> SEQUENCE: 30

Gly Pro Thr Xaa Xaa Gly Lys Thr
1               5

<210> SEQ ID NO 31
<211> LENGTH: 9
<212> TYPE: PRT
<213> ORGANISM: Artificial sequences
<220> FEATURE:
<223> OTHER INFORMATION: Consensus motif
<220> FEATURE:
<221> NAME/KEY: misc_feature
<222> LOCATION: (2)..(2)
<223> OTHER INFORMATION: Xaa at position 2 is Ile or Val
<220> FEATURE:
<221> NAME/KEY: misc_feature
<222> LOCATION: (3)..(3)
<223> OTHER INFORMATION: Xaa at position 3 is Leu or Val
<220> FEATURE:
<221> NAME/KEY: MISC_FEATURE
<222> LOCATION: (4)..(4)
<223> OTHER INFORMATION: Xaa at position 4 is Val or Cys
<220> FEATURE:
<221> NAME/KEY: misc_feature
<222> LOCATION: (8)..(8)
<223> OTHER INFORMATION: Xaa at position 8 is Thr or Ile

<400> SEQUENCE: 31

Pro Xaa Xaa Xaa Gly Gly Ser Xaa Ser
```

<210> SEQ ID NO 32
<211> LENGTH: 6
<212> TYPE: PRT
<213> ORGANISM: Artificial sequences
<220> FEATURE:
<223> OTHER INFORMATION: Consensus motif
<220> FEATURE:
<221> NAME/KEY: misc_feature
<222> LOCATION: (1)..(1)
<223> OTHER INFORMATION: Xaa at position 1 is Leu or Ile
<220> FEATURE:
<221> NAME/KEY: MISC_FEATURE
<222> LOCATION: (2)..(2)
<223> OTHER INFORMATION: Xaa at position 2 is Val or Ile

<400> SEQUENCE: 32

Xaa Xaa Tyr Gly Gly Gly
1               5

<210> SEQ ID NO 33
<211> LENGTH: 10
<212> TYPE: PRT
<213> ORGANISM: Artificial sequences
<220> FEATURE:
<223> OTHER INFORMATION: Consensus motif, wherein X is L or M
<220> FEATURE:
<221> NAME/KEY: misc_feature
<222> LOCATION: (1)..(1)
<223> OTHER INFORMATION: Xaa at position 1 is Ser or Pro
<220> FEATURE:
<221> NAME/KEY: misc_feature
<222> LOCATION: (7)..(7)
<223> OTHER INFORMATION: Xaa at position 7 is Leu or Met

<400> SEQUENCE: 33

Xaa Gly Gly Tyr Gly Thr Xaa Glu Glu Leu
1               5                   10

<210> SEQ ID NO 34
<211> LENGTH: 440
<212> TYPE: PRT
<213> ORGANISM: Botryosphaeria dothidea

<400> SEQUENCE: 34

Met Ile Pro Ile Ile Ala Ile Val Gly Pro Thr Gly Val Gly Lys Thr
1               5                   10                  15

Lys Leu Ser Ile Thr Ile Ala Lys Ala Leu Gly Ala Ala Glu Ile Val
                20                  25                  30

Ser Val Asp Ser Leu Gln Val Tyr Arg Glu Ala Pro Ile Met Thr Ala
            35                  40                  45

Gln Ala Ser Thr Glu Glu Met Glu Gly Val Arg His His Leu Met Cys
        50                  55                  60

Tyr Leu Asn Ala Ala Glu Glu Pro Arg Asp Phe Val Pro Leu Ala Leu
65                  70                  75                  80

Lys Ala Ile Glu Ser Ile Arg Cys Arg Gly Asn Ile Pro Ile Leu Cys
                85                  90                  95

Gly Gly Ser Thr Ser Leu Met Gln Pro Leu Leu Ile His Pro Tyr Leu
            100                 105                 110

Ala Lys Ser Lys Arg Tyr Ile Leu Gly Leu Ala Cys Pro Met Ser Val
        115                 120                 125

Leu Gly Pro Leu Leu Asp Ala Arg Ile Ser Gln Met Val His Asp Gly
    130                 135                 140

Leu Leu Asp Glu Val Cys Lys Leu Leu Arg Leu Glu Ala Glu His His
145 150 155 160

Pro Gln Lys Pro Cys Gly Val Trp Lys Ala Ile Gly Tyr Thr Glu Leu
165 170 175

Lys Pro Trp Ala Ser Ala Arg Ser Val Asp Asp Ala Val Phe Val Leu
180 185 190

Asp Gln Gly Leu Glu Asp Met Arg Gln His Thr Arg His Tyr Ala Glu
195 200 205

Thr Gln Met Leu Trp Met Leu Leu Glu Leu Phe Pro Ser Leu Glu Lys
210 215 220

Leu Pro Ile Lys Thr Glu Met Leu Val Leu Arg Ser Arg Ser Glu Phe
225 230 235 240

Glu Ser Gln Val Val Ala Pro Ala Leu Glu Leu Cys Ser Ser Phe Gly
245 250 255

Leu Ser Asp Glu Phe Ile Glu Ala Thr Arg Ser Leu Ala Leu Glu Ile
260 265 270

His Leu Arg Gly Trp Ser Leu Val Tyr Gly Gly Gly Thr Arg Gly Leu
275 280 285

Met Gly Val Leu Ala Glu Ser Leu Val Lys Leu Ser Gly Pro Ser Ser
290 295 300

Val His Gly Ile Thr Pro Arg Pro Phe Leu Gln Thr Ser Thr Gly Ile
305 310 315 320

Cys Thr Pro Asp Glu Ser Arg Phe Gly Arg Thr Thr Val Val Ser Thr
325 330 335

Met His Glu Arg Lys Ala Leu Met Ala Lys Glu Ala Asp Ala Phe Leu
340 345 350

Ala Leu Pro Gly Gly Tyr Gly Thr Met Glu Glu Leu Phe Glu Met Ile
355 360 365

Thr Trp Asn Gln Leu Gly Ile His Thr Arg Pro Val Val Leu Leu Asn
370 375 380

Thr Asn Gly Phe Phe Asp Gly Leu Ile Cys Trp Ile Glu Lys Ala Met
385 390 395 400

Cys Gln Gly Phe Ile Ser Ala Glu Ala Arg Asn Ile Val Asp Val Ala
405 410 415

Glu Thr Ala Asp Glu Val Ile Glu Lys Ile Glu Ile Tyr Gln Ser Pro
420 425 430

Ile Val Ala Glu Leu Glu Trp Leu
435 440

<210> SEQ ID NO 35
<211> LENGTH: 495
<212> TYPE: PRT
<213> ORGANISM: Claviceps purpurea

<400> SEQUENCE: 35

Met Ser Thr Arg Lys Leu Ala Ile Ala Ile Val Gly Pro Thr Ala Ser
1 5 10 15

Gly Lys Thr Lys Leu Gly Val Ala Ile Ala Lys Ala Tyr Leu Gly Glu
20 25 30

Val Ile Ser Val Asp Ser Leu Gln Cys Tyr Lys Pro Gly Gly Ile Ile
35 40 45

Thr Ala Arg Pro Leu Pro Glu Glu Thr Asp Asp Val Pro His His Leu
50 55 60

Ile Asp Tyr Leu Glu Ala Asp Glu Glu Pro Glu Asp Tyr Val Ser Gln
65 70 75 80

```
Ala Val Arg Ile Met Glu Asp Ile Ser Ala Arg Asp Gly Leu Pro Ile
                 85                  90                  95

Leu Val Gly Gly Ser Thr Ser Leu Thr Met Pro Leu Leu Gln Ala Ala
            100                 105                 110

Phe Ala Arg Glu Tyr Glu Val Leu Ala Leu Thr Leu Val Pro Gln Arg
            115                 120                 125

Ser Ala Tyr Gln Arg Leu Val Glu Thr Arg Gly Glu Glu Met Leu Gln
    130                 135                 140

Arg Gly Leu Leu Glu Glu Leu Glu Glu Leu His His Leu Glu Lys Arg
145                 150                 155                 160

Leu Leu His Gly Val Ser Asp Leu Ser Arg Gly Val Trp Lys Ala Ile
                165                 170                 175

Gly Tyr Arg Glu Tyr Leu Pro Tyr Leu Gln Ala Val Arg Ser Val Asn
            180                 185                 190

Gly Lys Ala Asp Gly Cys Ser Ser Gln Glu Glu Tyr Leu Arg Glu Glu
            195                 200                 205

Gly Arg Leu Ser Met Asn Ala Ser Thr Leu His Tyr Gly Gln Asp Gln
    210                 215                 220

Leu Glu Trp Met Arg His Thr Leu Val Pro Phe Leu His Arg His Arg
225                 230                 235                 240

Ala Ala Thr Val Ser Leu Cys Val Thr Asn Lys Ala Ala Trp Glu Ala
                245                 250                 255

Glu Val Gln Gly Pro Ala Leu Thr Met Ala Gly Glu Phe Cys His Gly
            260                 265                 270

Ala Ser Arg Ala Arg His Ala Leu Gly Phe Phe Pro Lys Lys Lys Arg
            275                 280                 285

Val Val Cys Val Phe Gly Gly Ser Ser Gly Gly His Asp Ser Ser His
    290                 295                 300

Ile Asp Ala Ala Lys Ala Leu Ala Val Thr Leu His Arg His Asp Met
305                 310                 315                 320

Cys Leu Val Tyr Gly Gly Thr Thr Gly Ile Met Gly Ala Val Ala
                325                 330                 335

Ser Thr Leu Val Ala Leu Ser Gly Pro Ser Ala Val His Gly Val Val
            340                 345                 350

Pro Ala Ala Leu Ala Arg Tyr Glu Ser Gly Gly Ala Gly Asp Gly Arg
            355                 360                 365

Val Asn Gly Glu Tyr Ala Ser Arg Phe Gly Arg Arg Thr Val Val Arg
    370                 375                 380

Asp Met His Thr Arg Lys Arg Leu Met Thr Gln Met Val Arg Glu Gly
385                 390                 395                 400

Ala Pro Gly Ser Gly Phe Val Ala Leu Ser Gly Gly Tyr Gly Thr Leu
            405                 410                 415

Glu Glu Leu Leu Glu Ala Ala Thr Trp His Gln Leu Gly Ile His Arg
            420                 425                 430

Cys Gly Val Ser Val Phe Ser Val Asp Gly Phe Tyr Asp Gly Leu Leu
    435                 440                 445

Asp Trp Ile Arg Arg Val Ala Gly His Gly Phe Val Gly Asn Lys Asp
450                 455                 460

Ala Asp Ile Ile Arg Val Ala Arg Thr Ala Glu Glu Val Val Ala Cys
465                 470                 475                 480

Leu Asp Glu Gly Ser Arg Gly Gly Asp His Gly Leu Glu Trp Val
            485                 490                 495
```

<210> SEQ ID NO 36
<211> LENGTH: 484
<212> TYPE: PRT
<213> ORGANISM: Fusarium oxysporum f. sp. vasinfectum

<400> SEQUENCE: 36

```
Met Thr Arg Thr His Lys Pro Ala Val Ala Ile Phe Gly Pro Thr Ala
1               5                   10                  15

Ser Gly Lys Thr Lys Leu Gly Val Ala Val Ser Lys Ala Phe Leu Gly
            20                  25                  30

Glu Val Ile Ser Val Asp Ser Leu Gln Cys Tyr Lys Pro Gly Ser Ile
        35                  40                  45

Ile Thr Ala Lys Pro Glu His Asp Glu Ile Gln Asp Ile Pro His His
    50                  55                  60

Leu Ile Asp Tyr Leu Gln Ala Asp Glu Pro Asp Asp Phe Ile Ser
65                  70                  75                  80

Leu Ala Ile Asn Lys Met Glu Asp Ile Ile Ser Arg Asn Lys Ile Pro
                85                  90                  95

Val Leu Val Gly Gly Ser Thr Ser Leu Thr Thr Pro Leu Leu Gln Gln
            100                 105                 110

Ala Leu Lys His His Tyr Ile Ile Leu Gly Ile Met Leu Val Pro His
        115                 120                 125

Pro Ser Ser Tyr Gln Gln Leu Ile Glu Thr Arg Gly Asp Ala Met Val
    130                 135                 140

Lys Gln Gly Leu Leu Ala Glu Leu Arg Glu Leu Lys Ala Leu Glu Lys
145                 150                 155                 160

Thr Leu Leu Gln Gly Glu Arg Asp Phe Asn Arg Gly Val Trp Lys Ala
                165                 170                 175

Ile Gly Tyr Pro Glu Phe Ser Pro Tyr Leu Asp Tyr Asp Gly Ala Ser
            180                 185                 190

Asp Ile Lys Arg Glu Val Leu Tyr His Gln Gly Val Thr Met Met Arg
        195                 200                 205

Ala Ser Thr Leu Gln Tyr Gly Phe Asn Gln Leu Glu Trp Leu Arg His
    210                 215                 220

Thr Leu Thr Pro Phe Leu His Gln Gln Lys Val Ala Thr Ile Ser Leu
225                 230                 235                 240

Asn Val Thr Asp Lys Gln Ser Trp Ala Ala Glu Val Glu Gly Pro Ala
                245                 250                 255

Leu Ser Met Ala Asn Gln Phe Phe His Gly Thr His Ser Val Thr Pro
            260                 265                 270

Val Pro Gly Lys Val Ser Lys Pro Arg Val Val Cys Leu Phe Gly Gly
        275                 280                 285

Ser Ser Ser Gly Asn Asp Pro Ser His Val Lys Ala Ala Lys Asp Leu
    290                 295                 300

Ser Leu Glu Leu His Arg Asn Asn Ile Thr Leu Ile Tyr Gly Gly Gly
305                 310                 315                 320

Thr Thr Gly Val Met Gly Ala Ala Ser Thr Leu Val Glu Leu Ser
                325                 330                 335

Gly Pro Ser Ser Val His Gly Ile Val Pro Ala Ala Leu Ala Lys Phe
            340                 345                 350

Glu Glu Asn Glu Thr Gly Gln Ser His Met Ser Lys Phe Gly Ser Arg
        355                 360                 365

Thr Val Val Arg Asp Met His Thr Arg Lys Arg Leu Met Ile Glu Ala
    370                 375                 380
```

-continued

Val Leu Asn Gly Gly Pro Gly Ser Gly Phe Val Ala Leu Ser Gly Gly
385                 390                 395                 400

Tyr Gly Thr Met Glu Glu Leu Leu Glu Val Ala Thr Trp Tyr Gln Ile
            405                 410                 415

Gly Ile His Asn Cys Asn Val Cys Val Leu Asn Val Asp Gly Phe Tyr
            420                 425                 430

Asp Gly Leu Leu Asp Trp Val Ser Lys Val Ser Glu Lys Gly Phe Ile
            435                 440                 445

Gly Ala Lys Asp His Thr Ile Ile Gln Val Ala Ser Ser Ala Glu Gly
        450                 455                 460

Leu Val Arg Cys Leu Glu Gly Lys Thr Gln His Ser Glu Gln Arg Arg
465                 470                 475                 480

Ile Glu Trp Ile

<210> SEQ ID NO 37
<211> LENGTH: 484
<212> TYPE: PRT
<213> ORGANISM: Fusarium oxysporum f. sp. raphani

<400> SEQUENCE: 37

Met Thr Arg Thr His Lys Pro Ala Val Ala Ile Phe Gly Pro Thr Ala
1               5                   10                  15

Ser Gly Lys Thr Lys Leu Gly Val Ala Val Ser Lys Ala Phe Leu Gly
            20                  25                  30

Glu Val Ile Ser Val Asp Ser Leu Gln Cys Tyr Lys Pro Gly Ser Ile
            35                  40                  45

Ile Thr Ala Lys Pro Glu His Asp Glu Ile Gln Asp Ile Pro His His
        50                  55                  60

Leu Ile Asp Tyr Leu Gln Ala Glu Glu Pro Asp Asp Phe Ile Ser
65                  70                  75                  80

Leu Ala Ile Asn Lys Met Glu Asp Ile Ile Ser Arg Asn Lys Ile Pro
                85                  90                  95

Val Leu Val Gly Gly Ser Thr Ser Leu Thr Thr Pro Leu Leu Gln Gln
            100                 105                 110

Ala Leu Lys His His Tyr Ile Ile Leu Gly Ile Met Leu Val Pro His
            115                 120                 125

Pro Ser Ser Tyr Gln Gln Leu Ile Glu Thr Arg Gly Asp Ala Met Val
        130                 135                 140

Lys Gln Gly Leu Leu Ala Glu Leu Arg Glu Leu Lys Ala Leu Glu Lys
145                 150                 155                 160

Thr Leu Leu Gln Gly Glu Arg Asp Phe Asn Arg Gly Val Trp Lys Ala
                165                 170                 175

Ile Gly Tyr Pro Glu Phe Ser Pro Tyr Leu Asp Tyr Asp Gly Ala Ser
            180                 185                 190

Asp Ile Lys Arg Glu Val Leu Tyr His Gln Gly Val Thr Met Met Arg
        195                 200                 205

Ala Ser Thr Leu Gln Tyr Gly Phe Asn Gln Leu Glu Trp Leu Arg His
    210                 215                 220

Thr Leu Thr Pro Phe Leu His Gln Arg Lys Val Ala Thr Ile Ser Leu
225                 230                 235                 240

Asn Val Thr Asp Lys Gln Ser Trp Ala Ala Glu Val Glu Gly Pro Ala
                245                 250                 255

Leu Ser Met Ala Asp Gln Phe Phe His Gly Thr His Ser Val Thr Pro
            260                 265                 270

-continued

```
Val Pro Gly Lys Val Ser Ser Pro Arg Val Val Cys Leu Phe Gly Gly
            275                 280                 285

Ser Ser Ser Gly Asn Asp Pro Ser His Val Lys Ala Ala Lys Asp Leu
290                 295                 300

Ser Leu Glu Leu His Arg Asn Asn Ile Thr Leu Ile Tyr Gly Gly Gly
305                 310                 315                 320

Thr Thr Gly Val Met Gly Ala Ala Ser Thr Leu Val Glu Leu Ser
            325                 330                 335

Gly Pro Ser Ser Val His Gly Ile Val Pro Ala Ala Leu Ala Lys Phe
            340                 345                 350

Glu Glu Asn Glu Thr Gly Gln Ser His Arg Ser Lys Phe Gly Ser Arg
            355                 360                 365

Thr Val Val Arg Asp Met His Thr Arg Lys Arg Leu Met Ile Glu Ala
            370                 375                 380

Val Leu Asn Gly Gly Pro Gly Ser Gly Phe Val Ala Leu Ser Gly Gly
385                 390                 395                 400

Tyr Gly Thr Met Glu Glu Leu Leu Glu Val Ala Thr Trp Tyr Gln Ile
            405                 410                 415

Gly Ile His Asn Cys Asn Val Cys Val Leu Asn Val Asp Gly Phe Tyr
            420                 425                 430

Asp Gly Leu Leu Asp Trp Val Ser Lys Val Ser Glu Lys Gly Phe Ile
            435                 440                 445

Arg Ala Lys Asp Arg Thr Ile Ile Gln Val Ala Ser Ser Ala Glu Gly
            450                 455                 460

Leu Val Arg Cys Leu Glu Gly Lys Thr Gln His Ser Glu Gln Arg Arg
465                 470                 475                 480

Ile Glu Trp Ile

<210> SEQ ID NO 38
<211> LENGTH: 484
<212> TYPE: PRT
<213> ORGANISM: Fusarium oxysporum

<400> SEQUENCE: 38

Met Thr Arg Ile His Lys Pro Ala Val Ala Ile Phe Gly Pro Thr Ala
1               5                   10                  15

Ser Gly Lys Thr Lys Leu Gly Val Ala Val Ser Lys Ala Phe Leu Gly
            20                  25                  30

Glu Val Ile Ser Val Asp Ser Leu Gln Cys Tyr Lys Pro Gly Ser Ile
            35                  40                  45

Ile Thr Ala Lys Pro Glu His Asp Glu Ile Gln Asp Ile Pro His His
50                  55                  60

Leu Ile Asp Tyr Leu Gln Ala Asp Glu Pro Asp Asp Phe Ile Ser
65                  70                  75                  80

Leu Ala Ile Asn Lys Met Glu Asp Ile Ile Ser Arg Asn Lys Ile Pro
            85                  90                  95

Val Leu Val Gly Gly Ser Thr Ser Leu Thr Thr Pro Leu Leu Gln Gln
            100                 105                 110

Ala Leu Lys His His Tyr Ile Ile Leu Gly Ile Met Leu Val Pro His
            115                 120                 125

Pro Ser Ser Tyr Gln Gln Leu Ile Glu Thr Arg Gly Asp Ala Met Val
            130                 135                 140

Lys Gln Gly Leu Leu Ala Glu Leu Arg Glu Leu Lys Ala Leu Glu Lys
145                 150                 155                 160
```

```
Thr Leu Leu Gln Gly Glu Arg Asp Phe Asn Arg Gly Val Trp Lys Ala
                165                 170                 175

Ile Gly Tyr Pro Glu Phe Ser Pro Tyr Leu Asp Tyr Asp Gly Ala Ser
            180                 185                 190

Asp Ile Lys Arg Glu Val Leu Tyr His Gln Gly Val Thr Met Met Arg
        195                 200                 205

Ala Ser Thr Leu Gln Tyr Gly Phe Asn Gln Leu Glu Trp Leu Arg His
    210                 215                 220

Thr Leu Thr Pro Phe Leu His Gln Arg Lys Val Ala Thr Ile Ser Leu
225                 230                 235                 240

Asn Val Thr Asp Lys Gln Ser Trp Ala Ala Glu Val Glu Gly Pro Ala
                245                 250                 255

Leu Ser Met Ala Ser Gln Phe Phe His Gly Thr His Ser Val Thr Pro
            260                 265                 270

Val Pro Gly Lys Val Ser Asn Pro Arg Val Val Cys Leu Phe Gly Gly
        275                 280                 285

Ser Ser Ser Gly Asn Asp Pro Ser His Val Lys Ala Ala Lys Asp Leu
    290                 295                 300

Ser Leu Glu Leu His Arg Asn Asn Ile Thr Leu Ile Tyr Gly Gly Gly
305                 310                 315                 320

Thr Met Gly Val Met Gly Ala Ala Ser Thr Leu Val Glu Leu Ser
                325                 330                 335

Gly Pro Ser Ser Val His Gly Ile Val Pro Ala Ala Leu Ala Lys Phe
            340                 345                 350

Glu Glu Asn Glu Thr Gly Gln Ser His Met Ser Lys Phe Gly Ser Arg
        355                 360                 365

Thr Val Val Arg Asp Met His Thr Arg Lys Arg Leu Met Ile Glu Ala
    370                 375                 380

Val Leu Asn Gly Gly Pro Gly Ser Gly Phe Val Ala Leu Ser Gly Gly
385                 390                 395                 400

Tyr Gly Thr Met Glu Glu Leu Leu Glu Val Ala Thr Trp Tyr Gln Ile
                405                 410                 415

Gly Ile His Asn Cys Asn Val Cys Val Leu Asn Val Asp Gly Phe Tyr
            420                 425                 430

Asp Gly Leu Leu Asp Trp Val Ser Lys Val Ser Glu Lys Gly Phe Ile
        435                 440                 445

Gly Ala Thr Asp Arg Thr Ile Ile Gln Val Ala Ser Ser Ala Glu Gly
    450                 455                 460

Leu Val Arg Cys Leu Glu Gly Lys Thr Gln His Ser Glu Gln Arg Arg
465                 470                 475                 480

Ile Glu Trp Ile

<210> SEQ ID NO 39
<211> LENGTH: 484
<212> TYPE: PRT
<213> ORGANISM: Fusarium oxysporum f. sp. pisi

<400> SEQUENCE: 39

Met Thr Arg Thr His Lys Pro Ala Val Ala Ile Phe Gly Pro Thr Ala
1               5                   10                  15

Ser Gly Lys Thr Lys Leu Gly Val Ala Val Ser Lys Ala Phe Leu Gly
            20                  25                  30

Glu Val Ile Ser Val Asp Ser Leu Gln Cys Tyr Lys Pro Gly Ser Ile
        35                  40                  45
```

```
Ile Thr Ala Lys Pro Glu His Asp Glu Ile Gln Asp Ile Pro His His
 50                  55                  60

Leu Ile Glu Tyr Leu Gln Ala Asp Glu Glu Pro Asp Asp Phe Ile Ser
 65                  70                  75                  80

Leu Ala Ile Asn Lys Met Glu Asp Ile Ile Ser Arg Asn Lys Ile Pro
                 85                  90                  95

Val Leu Val Gly Gly Ser Thr Ser Leu Thr Thr Pro Leu Leu Gln Gln
                100                 105                 110

Ala Leu Lys His His Tyr Ile Ile Leu Gly Ile Met Leu Val Pro His
                115                 120                 125

Pro Ser Ser Tyr Gln Gln Leu Ile Glu Thr Arg Gly Asp Ala Met Val
                130                 135                 140

Lys Gln Gly Leu Leu Ala Glu Leu Arg Glu Leu Lys Ala Leu Glu Lys
145                 150                 155                 160

Thr Leu Leu Gln Gly Glu Arg Asp Phe Asn Arg Gly Val Trp Lys Ala
                165                 170                 175

Ile Gly Tyr Pro Glu Phe Ser Pro Tyr Leu Asp Tyr Asp Gly Ala Ser
                180                 185                 190

Asp Ile Lys Arg Glu Val Leu Tyr His Gln Gly Val Thr Met Met Arg
                195                 200                 205

Ala Ser Thr Leu Gln Tyr Gly Phe Asn Gln Leu Glu Trp Leu Arg His
                210                 215                 220

Thr Leu Thr Pro Phe Leu His Gln Arg Lys Val Ala Thr Ile Ser Leu
225                 230                 235                 240

Asn Val Thr Asp Lys Gln Ser Trp Ala Ala Glu Val Glu Gly Pro Ala
                245                 250                 255

Leu Ser Met Ala Asp Gln Phe Phe His Gly Thr His Ser Val Thr Pro
                260                 265                 270

Val Pro Gly Lys Val Ser Ser Pro Arg Val Val Cys Leu Phe Gly Gly
                275                 280                 285

Ser Ser Ser Gly Asn Asp Pro Ser His Val Lys Ala Ala Lys Asp Leu
                290                 295                 300

Ser Leu Glu Leu His Arg Asn Asn Ile Thr Leu Ile Tyr Gly Gly Gly
305                 310                 315                 320

Thr Thr Gly Val Met Gly Ala Ala Ala Ser Thr Leu Val Glu Leu Ser
                325                 330                 335

Gly Pro Ser Ser Val His Gly Ile Val Pro Ala Ala Leu Ala Lys Phe
                340                 345                 350

Glu Glu Asn Glu Thr Gly Gln Ser His Arg Ser Lys Phe Gly Ser Arg
                355                 360                 365

Thr Val Val Arg Asp Met His Thr Arg Lys Arg Leu Met Ile Glu Ala
                370                 375                 380

Val Leu Asn Gly Gly Pro Gly Ser Gly Phe Val Ala Leu Ser Gly Gly
385                 390                 395                 400

Tyr Gly Thr Met Glu Glu Leu Leu Glu Val Ala Thr Trp Tyr Gln Ile
                405                 410                 415

Gly Ile His Asn Cys Asn Val Cys Val Leu Asn Val Asp Gly Phe Tyr
                420                 425                 430

Asp Gly Leu Leu Asp Trp Val Ser Lys Val Ser Glu Lys Gly Phe Ile
                435                 440                 445

Arg Ala Lys Asp Arg Thr Ile Ile Gln Val Ala Ser Ser Ala Glu Gly
450                 455                 460
```

```
Leu Val Arg Cys Leu Glu Gly Lys Thr Gln His Ser Glu Gln Arg Arg
465                 470                 475                 480

Ile Glu Trp Ile

<210> SEQ ID NO 40
<211> LENGTH: 484
<212> TYPE: PRT
<213> ORGANISM: Fusarium oxysporum

<400> SEQUENCE: 40

Met Thr Arg Thr His Lys Pro Ala Val Ala Ile Leu Gly Pro Thr Ala
1               5                   10                  15

Ser Gly Lys Thr Lys Leu Gly Val Ala Val Ser Lys Ala Phe Leu Gly
                20                  25                  30

Glu Val Ile Ser Val Asp Ser Leu Gln Cys Tyr Lys Pro Gly Ser Ile
            35                  40                  45

Ile Thr Ala Lys Pro Glu His Asp Glu Ile Gln Asp Ile Pro His His
        50                  55                  60

Leu Ile Asp Tyr Leu Gln Ala Asp Glu Glu Pro Asp Asp Phe Ile Pro
65                  70                  75                  80

Leu Ala Ile Asn Lys Met Glu Asp Ile Ile Ser Arg Asn Arg Ile Pro
                85                  90                  95

Val Leu Val Gly Gly Ser Thr Ser Leu Thr Ile Pro Leu Leu Gln Gln
            100                 105                 110

Ala Leu Lys His His Tyr Ile Ile Leu Gly Ile Met Leu Val Pro Gln
        115                 120                 125

Pro Ser Asn Tyr Gln Gln Leu Ile Glu Thr Arg Gly Asp Ala Met Val
130                 135                 140

Lys Gln Gly Leu Leu Ala Glu Leu Arg Glu Leu Arg Ala Leu Glu Lys
145                 150                 155                 160

Thr Leu Leu Gln Gly Gly Arg Asp Phe Asn Arg Gly Val Trp Lys Ala
                165                 170                 175

Ile Gly Tyr Pro Glu Phe Ser Pro Tyr Leu Asp Tyr Asp Gly Val Ser
            180                 185                 190

Asp Ile Lys Arg Asp Val Leu Tyr His Gln Gly Val Thr Met Met Arg
        195                 200                 205

Ala Ser Thr Leu Gln Tyr Gly Phe Asn Gln Leu Glu Trp Leu Arg His
210                 215                 220

Thr Leu Thr Pro Phe Leu His Gln Gln Lys Val Ala Thr Ile Ser Leu
225                 230                 235                 240

Asn Val Thr Asp Lys Gln Phe Trp Ala Ala Glu Val Glu Gly Pro Ala
                245                 250                 255

Leu Ser Met Ala Asn Gln Phe Phe His Gly Thr His Ser Val Thr Pro
            260                 265                 270

Val Pro Gly Lys Ile Ser Asn Pro Arg Val Val Cys Leu Phe Gly Gly
        275                 280                 285

Ser Ser Ser Gly Asn Asp Pro Ser His Val Lys Ala Ala Lys Asp Leu
290                 295                 300

Ser Leu Glu Leu His Arg Lys Asn Ile Thr Leu Ile Tyr Gly Gly Gly
305                 310                 315                 320

Met Thr Gly Val Met Gly Ala Ala Ser Thr Leu Val Ala Leu Ser
                325                 330                 335

Gly Pro Ser Val His Gly Ile Val Pro Ala Ala Leu Ala Lys Phe
            340                 345                 350
```

```
Glu Glu Asn Val Thr Gly Gln Ser His Met Ser Lys Phe Gly Ser Arg
        355                 360                 365

Thr Val Val Arg Asp Met His Thr Arg Lys Arg Leu Met Ile Glu Ala
370                 375                 380

Val Leu Asn Gly Gly Pro Gly Ser Gly Phe Val Ala Leu Ser Gly Gly
385                 390                 395                 400

Tyr Gly Thr Met Glu Glu Leu Leu Glu Val Thr Thr Trp Tyr Gln Leu
                405                 410                 415

Gly Ile His Asn Cys Asn Val Cys Val Leu Asn Val Asp Gly Phe Tyr
                420                 425                 430

Asp Gly Leu Leu Asp Trp Val Ser Lys Val Ser Glu Lys Gly Phe Ile
                435                 440                 445

Gly Ala Lys Asp Arg Thr Ile Ile Gln Val Ala Ser Ser Ala Glu Gly
        450                 455                 460

Leu Val Arg Cys Leu Glu Gly Lys Thr Gln Gln Ser Glu Gln Arg Arg
465                 470                 475                 480

Ile Glu Trp Ile

<210> SEQ ID NO 41
<211> LENGTH: 484
<212> TYPE: PRT
<213> ORGANISM: Fusarium oxysporum f. sp. Melonis

<400> SEQUENCE: 41

Met Thr Arg Thr His Lys Pro Ala Val Ala Ile Phe Gly Pro Thr Ala
1               5                   10                  15

Ser Gly Lys Thr Lys Leu Gly Val Ala Val Ser Lys Ala Phe Leu Gly
            20                  25                  30

Glu Val Ile Ser Val Asp Ser Leu Gln Cys Tyr Lys Pro Gly Ser Ile
        35                  40                  45

Ile Thr Ala Lys Pro Glu His Asp Glu Ile Gln Asn Ile Pro His His
    50                  55                  60

Leu Ile Asp Tyr Leu Gln Ala Asp Glu Glu Pro Asp Asp Phe Ile Ser
65                  70                  75                  80

Leu Ala Ile Asn Lys Met Glu Asp Ile Ile Ser Arg Asn Arg Ile Pro
                85                  90                  95

Val Leu Val Gly Gly Ser Thr Ser Leu Thr Ile Pro Leu Leu Gln Gln
            100                 105                 110

Ala Leu Lys His His Tyr Ile Ile Leu Gly Ile Met Leu Val Pro Gln
        115                 120                 125

Pro Ser Asn Tyr Gln Gln Leu Ile Glu Thr Arg Gly Asp Ala Met Val
    130                 135                 140

Lys Gln Gly Leu Leu Ala Glu Leu Ser Glu Leu Lys Ala Leu Glu Lys
145                 150                 155                 160

Thr Leu Leu Gln Gly Glu Arg Asp Phe Asn Arg Gly Val Trp Lys Ala
                165                 170                 175

Ile Gly Tyr Pro Glu Phe Ser Pro Tyr Leu Asp Tyr Asp Gly Val Ser
            180                 185                 190

Asp Ile Lys Arg Glu Val Leu Tyr His Gln Gly Val Thr Met Met Arg
        195                 200                 205

Ala Ser Thr Leu Gln Tyr Gly Phe Asn Gln Leu Glu Trp Leu Arg His
    210                 215                 220

Thr Leu Thr Pro Phe Leu His Gln Gln Lys Val Ala Thr Ile Ser Leu
225                 230                 235                 240
```

```
Asn Val Thr Asp Lys Gln Phe Trp Ala Ala Glu Val Glu Gly Pro Ala
                245                 250                 255

Leu Ser Met Ala Asn Gln Phe Phe His Gly Thr His Ser Val Ile Pro
            260                 265                 270

Val Pro Gly Lys Ala Ser Asn Pro Arg Val Val Cys Leu Phe Gly Gly
        275                 280                 285

Ser Ser Ser Gly Asn Asp Pro Ser His Val Lys Ala Ala Lys Asp Leu
    290                 295                 300

Ser Leu Glu Leu His Arg Asn Asn Ile Thr Leu Ile Tyr Gly Gly Gly
305                 310                 315                 320

Met Thr Gly Val Met Gly Ala Ala Ser Ala Leu Val Ala Leu Ser
                325                 330                 335

Gly Pro Ser Ser Val His Gly Ile Val Pro Ala Ala Leu Ala Lys Phe
            340                 345                 350

Glu Glu Asn Val Thr Gly Gln Ser His Met Ser Lys Phe Gly Ser Arg
        355                 360                 365

Thr Val Val Arg Asp Met His Thr Arg Lys Arg Leu Met Ile Glu Ala
    370                 375                 380

Val Leu Asn Gly Gly Pro Gly Ser Gly Phe Val Ala Leu Ser Gly Gly
385                 390                 395                 400

Tyr Gly Thr Met Glu Glu Leu Leu Glu Val Thr Thr Trp Tyr Gln Leu
                405                 410                 415

Gly Ile His Asn Cys Asn Val Cys Val Leu Asn Val Asp Gly Phe Tyr
            420                 425                 430

Asp Gly Leu Leu Asp Trp Val Ser Lys Val Ser Glu Lys Gly Phe Ile
        435                 440                 445

Gly Ala Lys Asp Arg Thr Ile Ile Gln Val Ala Ser Ser Ala Glu Gly
    450                 455                 460

Leu Val Arg Cys Leu Glu Gly Lys Thr Gln His Ser Glu Gln Arg Arg
465                 470                 475                 480

Ile Glu Trp Ile

<210> SEQ ID NO 42
<211> LENGTH: 489
<212> TYPE: PRT
<213> ORGANISM: Fusarium oxysporum f. sp. vasinfectum

<400> SEQUENCE: 42

Met Gln Ala Asn Gln Lys Leu Cys Ile Ala Ile Phe Gly Pro Thr Ala
1               5                   10                  15

Ser Gly Lys Thr Lys Leu Gly Val Ala Ile Ala Lys Ala Phe Pro Ser
            20                  25                  30

Glu Val Ile Ser Val Asp Ser Leu Gln Cys Tyr Lys Ala Gly Ser Ile
        35                  40                  45

Leu Thr Ala Lys Pro Thr Val Gln Glu Ile Asp Asp Val Pro His His
    50                  55                  60

Met Val Asp Tyr Leu Glu Ala Asp Glu Pro His Asp Phe Val Ala
65                  70                  75                  80

Met Ala Ala Asp Lys Met Glu Glu Val Thr Asn Arg Gly Lys Leu Pro
                85                  90                  95

Ile Leu Val Gly Gly Ser Thr Ser Leu Ala Ile Pro Phe Leu His Glu
            100                 105                 110

Ala Leu Lys Arg Gln Tyr Arg Phe Ile Ala Ala Thr Leu Ile Pro Arg
        115                 120                 125
```

Gln Ser Thr Tyr Trp Gln Phe Ile Gln Val Arg Ala Asn Glu Met Leu
        130                 135                 140

Glu Arg Gly Leu Leu Gly Glu Leu Glu Glu Leu Arg Asp Leu Gln Gln
145                 150                 155                 160

Ser Leu Leu Asp Asp Asn Ala Cys Phe His Lys Gly Val Trp Lys Ala
                165                 170                 175

Ile Gly Tyr Gln Glu Phe Tyr Pro Tyr Leu Glu Ala Asp Met Ser Cys
            180                 185                 190

Ser Ala Arg Gln Ser Ser Phe Gln Arg Gly Leu Ala Leu Met Asn Ala
        195                 200                 205

Asn Thr Leu Gln Tyr Gly Phe His Gln Leu Glu Trp Ile Arg Ser Val
210                 215                 220

Leu Asn Pro Phe Leu Gln Gln Ala Gly Val Val Cys Met Ser Leu Pro
225                 230                 235                 240

Val Thr Asn Lys Ala Ser Trp Thr Leu Asp Val Glu Ile Pro Ala Ile
                245                 250                 255

Ser Met Leu Asn Glu Leu Cys Tyr Ser Phe Arg Thr Ile Arg Leu Ser
            260                 265                 270

Asn Asn Gly Thr Leu Asn Ser Asn Ser Lys Ser Arg Val Val Cys Leu
        275                 280                 285

Phe Gly Gly Ser Ser Gly Asn Asp Pro Lys His Ile Gln Ala Ala
290                 295                 300

Lys Asn Leu Ala Phe Ala Leu His Ser Asn Asn Tyr Lys Leu Val Tyr
305                 310                 315                 320

Gly Gly Gly Thr Thr Gly Ile Met Gly Ala Ile Ala Ser Thr Leu Val
                325                 330                 335

Gln Leu Ser Gly Pro Ser Ala Val Gln Gly Ile Ile Pro Val Ala Leu
            340                 345                 350

Ala Lys Tyr Glu Glu Lys Leu Thr Lys Lys Asn Ala Asp Pro Ser Lys
        355                 360                 365

Phe Gly Ser Arg Thr Val Val Lys Asp Met His Thr Arg Lys Arg Leu
370                 375                 380

Met Ile Asp Ala Val Ile Gly Gly Ala Pro Gly Ser Gly Phe Val Ala
385                 390                 395                 400

Leu Ser Gly Gly Tyr Gly Thr Leu Glu Glu Leu Leu Glu Thr Thr Thr
                405                 410                 415

Trp Tyr Gln Leu Gly Ile His Gln Cys Gly Ile Cys Val Phe Asp Val
            420                 425                 430

Cys Gly Phe Tyr Lys Gly Leu Leu Asp Trp Val Asp Gln Ala Ala Gln
        435                 440                 445

Ala Gly Phe Val Gly Thr Glu Asp Val Asp Ile Leu Arg Ile Ala Thr
450                 455                 460

Thr Ala Glu Glu Val Ile Gly Tyr Leu Gly Ser Gln Asn Gly Arg Tyr
465                 470                 475                 480

Ser Arg Lys Gly Glu Leu Glu Trp Asp
                485

<210> SEQ ID NO 43
<211> LENGTH: 489
<212> TYPE: PRT
<213> ORGANISM: Fusarium oxysporum f. sp. conglutinans race 2

<400> SEQUENCE: 43

Met Gln Ala Asn Glu Lys Leu Cys Ile Ala Ile Phe Gly Pro Thr Ala
1                 5                   10                  15

```
Ser Gly Lys Thr Lys Leu Gly Val Ala Ile Ala Lys Ala Phe Pro Ser
             20                  25                  30

Glu Val Ile Ser Val Asp Ser Leu Gln Cys Tyr Lys Ala Gly Ser Ile
         35                  40                  45

Leu Thr Ala Lys Pro Thr Val Gln Glu Ile Asp Asp Val Pro His His
     50                  55                  60

Met Val Asp Tyr Leu Glu Ala Asp Glu Glu Pro His Asp Phe Val Ala
 65                  70                  75                  80

Met Ala Ala Asp Lys Met Glu Glu Val Thr Asn Arg Gly Lys Leu Pro
                 85                  90                  95

Ile Leu Val Gly Gly Ser Thr Ser Leu Ala Ile Pro Leu Leu His Glu
            100                 105                 110

Ala Leu Lys Arg Gln Tyr Arg Phe Ile Ala Ala Thr Leu Ile Pro Arg
        115                 120                 125

Gln Ser Thr Tyr Trp Gln Phe Ile Gln Val Arg Ala Asn Glu Met Leu
    130                 135                 140

Glu Arg Gly Leu Leu Gly Glu Leu Glu Glu Leu Arg Asp Leu Gln Gln
145                 150                 155                 160

Ser Leu Leu Asp Asp Asn Ala Cys Phe His Lys Gly Val Trp Lys Ala
                165                 170                 175

Ile Gly Tyr Gln Glu Phe Tyr Pro Tyr Leu Glu Ala Asp Met Ser Cys
            180                 185                 190

Ser Ala Arg Gln Ser Ser Phe Gln Arg Gly Leu Ala Leu Met Asn Ala
        195                 200                 205

Asn Thr Leu Gln Tyr Gly Phe His Gln Leu Glu Trp Ile Arg Ser Val
    210                 215                 220

Leu Asn Pro Phe Leu Gln Gln Ala Gly Val Val Cys Met Ser Leu Pro
225                 230                 235                 240

Val Thr Asn Lys Ala Ser Trp Thr Leu Asp Val Glu Ile Pro Ala Ile
                245                 250                 255

Ser Met Leu Asn Glu Leu Cys Tyr Ser Phe Arg Thr Ile Arg Leu Ser
            260                 265                 270

Asn Asn Gly Thr Leu Asn Ser Asn Ser Lys Ser Arg Val Val Cys Leu
        275                 280                 285

Phe Gly Gly Ser Ser Ser Gly Asn Asp Pro Lys His Ile Gln Ala Ala
    290                 295                 300

Lys Asn Leu Ala Phe Ala Leu His Ser Asn Asn Tyr Lys Leu Val Tyr
305                 310                 315                 320

Gly Gly Gly Thr Thr Gly Ile Met Gly Ala Ile Ala Ser Thr Leu Val
                325                 330                 335

Gln Leu Ser Gly Pro Ser Ala Val Gln Gly Ile Ile Pro Val Ala Leu
            340                 345                 350

Ala Lys Tyr Glu Glu Lys Leu Thr Lys Lys Asn Ala Asp Pro Ser Lys
        355                 360                 365

Phe Gly Ser Arg Thr Val Val Lys Asp Met His Thr Arg Lys Arg Leu
    370                 375                 380

Met Ile Asp Ala Val Ile Gly Ala Pro Gly Ser Gly Phe Val Ala
385                 390                 395                 400

Leu Ser Gly Gly Tyr Gly Thr Leu Glu Glu Leu Leu Glu Thr Thr Thr
            405                 410                 415

Trp Tyr Gln Leu Gly Ile His Gln Cys Gly Ile Cys Val Phe Asp Val
        420                 425                 430
```

```
Cys Gly Phe Tyr Lys Gly Leu Leu Asp Trp Val Asp Gln Ala Ala Gln
                435                 440                 445

Ala Gly Phe Val Gly Thr Glu Asp Val Asp Ile Leu Arg Ile Ala Thr
        450                 455                 460

Thr Ala Glu Glu Val Ile Gly Tyr Leu Gly Ser Gln Asn Gly Arg Tyr
465                 470                 475                 480

Ser Arg Met Gly Glu Leu Glu Trp Asp
                485

<210> SEQ ID NO 44
<211> LENGTH: 489
<212> TYPE: PRT
<213> ORGANISM: Fusarium oxysporum f. sp. Raphani

<400> SEQUENCE: 44

Met Gln Ala Asn Gln Lys Leu Cys Ile Ala Ile Phe Gly Pro Thr Ala
1               5                   10                  15

Ser Gly Lys Thr Lys Leu Gly Val Ala Ile Ala Lys Ala Phe Pro Ser
                20                  25                  30

Glu Val Ile Ser Val Asp Ser Leu Gln Cys Tyr Lys Ala Gly Ser Ile
            35                  40                  45

Leu Thr Ala Lys Pro Thr Val Gln Glu Ile Asp Asp Val Pro His His
50                  55                  60

Met Val Asp Tyr Leu Glu Ala Asp Glu Pro His Asp Phe Val Ala
65                  70                  75                  80

Met Ala Ala Asp Lys Met Glu Glu Val Thr Asn Arg Gly Lys Leu Pro
                85                  90                  95

Ile Leu Val Gly Gly Ser Thr Ser Leu Ala Ile Pro Phe Leu His Glu
                100                 105                 110

Ala Leu Lys Arg Gln Tyr Arg Phe Ile Ala Ala Thr Leu Ile Pro Arg
            115                 120                 125

Gln Ser Thr Tyr Trp Gln Phe Ile Gln Val Arg Ala Asn Glu Met Leu
130                 135                 140

Glu Arg Gly Leu Leu Gly Glu Leu Glu Glu Leu Arg Asp Leu Gln Gln
145                 150                 155                 160

Ser Leu Leu Asp Asp Asn Ala Cys Phe His Lys Gly Val Trp Lys Ala
                165                 170                 175

Ile Gly Tyr Gln Glu Phe Tyr Pro Tyr Leu Glu Ala Asp Met Ser Cys
            180                 185                 190

Ser Ala Arg Gln Ser Ser Phe Gln Arg Gly Leu Ala Leu Met Asn Ala
            195                 200                 205

Asn Thr Leu Gln Tyr Gly Phe His Gln Leu Glu Trp Ile Arg Ser Val
210                 215                 220

Leu Asn Pro Phe Leu Gln Ala Gly Val Val Cys Met Ser Leu Pro
225                 230                 235                 240

Val Thr Asn Lys Ala Ser Trp Thr Leu Asp Val Glu Ile Pro Ala Ile
                245                 250                 255

Ser Met Leu Asn Glu Leu Cys Tyr Ser Phe Arg Thr Ile Arg Leu Ser
            260                 265                 270

Asn Asn Gly Thr Leu Asn Ser Asn Ser Lys Ser Arg Val Val Cys Leu
            275                 280                 285

Phe Gly Gly Ser Ser Ser Gly Asn Asp Pro Lys His Ile Gln Ala Ala
        290                 295                 300

Lys Asn Leu Ala Phe Ala Leu His Ser Asn Asn Tyr Lys Leu Val Tyr
305                 310                 315                 320
```

-continued

```
Gly Gly Gly Thr Thr Gly Ile Met Gly Ala Ile Ala Ser Thr Leu Val
                325                 330                 335

Gln Leu Ser Gly Pro Ser Ala Val Gln Gly Ile Ile Pro Val Ala Leu
            340                 345                 350

Ala Lys Tyr Glu Glu Lys Leu Thr Lys Lys Asn Ala Asp Pro Ser Lys
        355                 360                 365

Phe Gly Ser Arg Thr Val Val Lys Asp Met His Thr Arg Lys Arg Leu
    370                 375                 380

Met Ile Asp Ala Val Ile Gly Gly Ala Pro Gly Ser Gly Phe Val Ala
385                 390                 395                 400

Leu Ser Gly Gly Tyr Gly Thr Leu Glu Glu Leu Leu Glu Thr Thr Thr
                405                 410                 415

Trp Tyr Gln Leu Gly Ile His Gln Cys Gly Ile Cys Val Phe Asp Val
            420                 425                 430

Cys Gly Phe Tyr Lys Gly Leu Leu Asp Trp Val Asp Gln Ala Ala Gln
        435                 440                 445

Ala Gly Phe Val Gly Thr Glu Asp Val Asp Ile Leu Arg Ile Ala Thr
    450                 455                 460

Thr Ala Glu Glu Val Ile Gly Tyr Leu Gly Ser Gln Asn Gly Arg Tyr
465                 470                 475                 480

Ser Arg Met Gly Glu Leu Glu Trp Asp
                485

<210> SEQ ID NO 45
<211> LENGTH: 489
<212> TYPE: PRT
<213> ORGANISM: Fusarium oxysporum f. sp. cubense tropical race 4

<400> SEQUENCE: 45

Met Gln Ala Asn Gln Lys Leu Cys Ile Ala Ile Phe Gly Pro Thr Ala
1               5                   10                  15

Ser Gly Lys Thr Lys Leu Gly Val Ala Ile Ala Lys Ala Phe Pro Ser
            20                  25                  30

Glu Val Ile Ser Val Asp Ser Leu Gln Cys Tyr Lys Ala Gly Ser Ile
        35                  40                  45

Leu Thr Ala Lys Pro Thr Val Gln Glu Ile Asp Asp Val Pro His His
    50                  55                  60

Met Val Asp Tyr Leu Glu Ala Asp Glu Glu Pro His Asp Phe Val Asp
65                  70                  75                  80

Met Ala Ala Asp Lys Met Glu Glu Val Thr Asn Arg Gly Lys Leu Pro
                85                  90                  95

Ile Leu Val Gly Gly Ser Thr Ser Leu Ala Ile Pro Leu Leu His Glu
            100                 105                 110

Ala Leu Lys Arg Gln Tyr Arg Phe Ile Ala Ala Thr Leu Ile Pro Arg
        115                 120                 125

Gln Ser Ala Tyr Trp Gln Phe Ile Gln Val Arg Ala Ser Glu Met Leu
    130                 135                 140

Glu Arg Gly Leu Leu Val Glu Leu Glu Glu Leu Arg Asp Leu Gln Gln
145                 150                 155                 160

Ser Leu Leu Asp Asp Asn Ala Cys Phe His Lys Gly Val Trp Lys Ala
                165                 170                 175

Ile Gly Tyr Gln Glu Phe Tyr Pro Tyr Leu Glu Ala Asp Met Ser Cys
            180                 185                 190

Ser Ala Arg Gln Ser Ser Phe Gln Arg Gly Leu Ala Leu Met Asn Ala
```

```
                195                 200                 205
Asn Thr Leu Gln Tyr Gly Phe His Gln Leu Glu Trp Ile Arg Ser Ile
    210                 215                 220

Leu Asn Pro Phe Leu Gln Gln Ala Gly Val Val Cys Met Ser Leu Pro
225                 230                 235                 240

Val Thr Asn Lys Ala Ser Trp Thr Leu Asp Val Glu Ile Pro Ala Ile
                245                 250                 255

Ser Met Leu Asn Glu Leu Cys Tyr Ser Phe Arg Thr Ile Arg Leu Ser
            260                 265                 270

Asn Asn Gly Thr Leu Asn Ser Asn Ser Lys Ser Arg Val Val Ser Leu
        275                 280                 285

Phe Gly Gly Ser Ser Gly Asn Asp Pro Lys His Ile Gln Ala Ala
    290                 295                 300

Lys Asn Leu Ala Phe Ala Leu His Ser Asn Asn Tyr Lys Leu Val Tyr
305                 310                 315                 320

Gly Gly Gly Thr Thr Gly Ile Met Gly Ala Ile Ala Ser Thr Leu Val
                325                 330                 335

Gln Leu Ser Gly Pro Ser Ala Val Gln Gly Ile Ile Pro Val Ala Leu
            340                 345                 350

Ala Lys Tyr Glu Glu Lys Leu Thr Lys Lys Asn Ala Asp Pro Ser Lys
        355                 360                 365

Phe Gly Ser Arg Thr Val Val Lys Asp Met His Thr Arg Lys Arg Leu
    370                 375                 380

Met Ile Asp Ala Val Ile Gly Gly Ala Pro Gly Ser Gly Phe Val Ala
385                 390                 395                 400

Leu Ser Gly Gly Tyr Gly Thr Leu Glu Glu Leu Leu Glu Thr Thr Thr
                405                 410                 415

Trp Cys Gln Leu Gly Ile His Gln Cys Gly Ile Cys Val Phe Asp Val
            420                 425                 430

Cys Gly Phe Tyr Lys Gly Leu Leu Asp Trp Val Asp Gln Ala Ala Gln
        435                 440                 445

Ala Gly Phe Val Gly Thr Glu Asp Val Asp Ile Leu Arg Ile Ala Thr
    450                 455                 460

Thr Ala Glu Glu Val Ile Gly Tyr Leu Gly Ser Gln Asn Gly Arg Tyr
465                 470                 475                 480

Ser Arg Met Gly Glu Leu Glu Trp Asp
                485

<210> SEQ ID NO 46
<211> LENGTH: 489
<212> TYPE: PRT
<213> ORGANISM: Fusarium oxysporum f. sp. Pisi

<400> SEQUENCE: 46

Met Gln Ala Asn Gln Lys Leu Cys Ile Ala Ile Phe Gly Pro Thr Ala
1               5                   10                  15

Ser Gly Lys Thr Lys Leu Gly Val Ala Ile Ala Lys Ala Phe Pro Ser
            20                  25                  30

Glu Val Ile Ser Val Asp Ser Leu Gln Cys Tyr Lys Ala Gly Ser Ile
        35                  40                  45

Leu Thr Ala Lys Pro Thr Val Gln Glu Ile Asp Asp Val Pro His His
    50                  55                  60

Met Val Asp Tyr Leu Glu Ala Asp Glu Glu Pro His Asp Phe Val Ala
65                  70                  75                  80
```

-continued

```
Met Ala Ala Asp Lys Met Glu Glu Val Thr Asn Arg Gly Lys Leu Pro
                 85                  90                  95
Ile Leu Val Gly Gly Ser Ile Ser Leu Ala Ile Pro Leu Leu His Glu
            100                 105                 110
Ala Leu Lys Arg Glu Tyr Arg Phe Ile Ala Ala Thr Leu Ile Pro Arg
        115                 120                 125
Gln Ser Thr Tyr Trp Gln Phe Ile Gln Val Arg Ala Ser Glu Met Leu
    130                 135                 140
Glu Arg Gly Leu Leu Gly Leu Glu Leu Arg Asp Leu Gln Gln
145                 150                 155                 160
Ser Leu Leu Asp Asp Asn Ala Cys Phe His Lys Gly Val Trp Lys Ala
                165                 170                 175
Ile Gly Tyr Gln Glu Phe Tyr Pro Tyr Leu Glu Ala Asp Met Ser Cys
            180                 185                 190
Ser Ala Arg Gln Ser Ser Phe Gln Arg Gly Leu Ala Leu Met Asn Ala
        195                 200                 205
Asn Thr Leu Gln Tyr Gly Phe His Gln Leu Glu Trp Ile Arg Ser Val
    210                 215                 220
Leu Asn Pro Phe Leu Gln Gln Ala Gly Val Val Cys Met Ser Leu Pro
225                 230                 235                 240
Val Thr Asn Lys Ala Ser Trp Thr Leu Asp Val Glu Ile Pro Ala Ile
                245                 250                 255
Ser Met Leu Asn Glu Leu Cys Tyr Ser Phe Arg Thr Ile Arg Leu Ser
            260                 265                 270
Asn Asn Gly Thr Leu Asn Ser Asn Ser Lys Ser Arg Val Val Cys Leu
        275                 280                 285
Phe Gly Gly Ser Ser Ser Gly Asn Asp Pro Lys His Ile Gln Ala Ala
    290                 295                 300
Lys Asn Leu Ala Phe Ala Leu His Ser Asn Asn Tyr Lys Leu Val Tyr
305                 310                 315                 320
Gly Gly Gly Thr Thr Gly Ile Met Gly Ala Ile Ala Ser Thr Leu Val
                325                 330                 335
Gln Leu Ser Gly Pro Ser Ala Val Gln Gly Ile Ile Pro Val Ala Leu
            340                 345                 350
Ala Lys Tyr Glu Glu Lys Leu Thr Lys Lys Asn Ala Asp Pro Ser Lys
        355                 360                 365
Phe Gly Ser Arg Thr Val Leu Lys Asp Met His Thr Arg Lys Arg Leu
    370                 375                 380
Met Ile Asp Ala Val Ile Gly Ala Pro Gly Ser Gly Phe Val Ala
385                 390                 395                 400
Leu Ser Gly Gly Tyr Gly Thr Leu Glu Glu Leu Leu Glu Thr Thr Thr
                405                 410                 415
Trp Tyr Gln Leu Gly Ile His Gln Cys Gly Ile Cys Val Phe Asp Val
            420                 425                 430
Cys Gly Phe Tyr Lys Gly Leu Leu Asp Trp Val Asp Gln Ala Ala Gln
        435                 440                 445
Ala Gly Phe Val Gly Thr Glu Asp Val Asp Ile Leu Arg Ile Ala Thr
    450                 455                 460
Thr Ala Glu Glu Val Ile Gly Tyr Leu Gly Ser Gln Asn Gly Arg Tyr
465                 470                 475                 480
Ser Arg Met Gly Glu Leu Glu Trp Asp
                485
```

```
<210> SEQ ID NO 47
<211> LENGTH: 487
<212> TYPE: PRT
<213> ORGANISM: Fusarium fujikuroi

<400> SEQUENCE: 47

Met Glu Ser Asn Asn Arg Phe Met Ile Gly Val Phe Gly Pro Thr Gly
1               5                   10                  15

Ala Gly Lys Thr Lys Leu Gly Val Ser Ile Ala Lys Ser Val His Gly
            20                  25                  30

Gln Val Ile Ser Val Asp Ser Leu Gln Cys Tyr Ser Pro Gly Ser Ile
        35                  40                  45

Ile Thr Ala Lys Pro Ser Pro Glu Glu Thr Asp Gly Ile Asp His His
    50                  55                  60

Met Ile Gly Tyr Leu Glu Ala Asp Glu Pro Thr Asn Phe Val Ala
65                  70                  75                  80

Glu Ala Ile Glu Thr Leu Glu Lys Leu Cys Asp His Gly Ile Ile Pro
                85                  90                  95

Val Val Val Gly Gly Ser Thr Ser Leu Thr Leu Pro Leu Leu Gln Asp
            100                 105                 110

Ala Leu Asn Arg Gly Trp Arg Met Ala Ala Ile Thr Leu Leu Pro His
        115                 120                 125

Gln Ser Thr Tyr Leu Ser Asn Ile Ala Ser Arg Leu Asp Asp Met Val
    130                 135                 140

Asp Ala Gly Leu Leu Glu Glu Leu Ser Gly Leu Lys Leu Leu Glu Asp
145                 150                 155                 160

Lys Tyr Leu Asn Glu Lys Pro Asn Phe Arg Lys Gly Val Trp Lys Ala
                165                 170                 175

Ile Gly Tyr Gln Glu Leu Tyr Pro Tyr Leu Glu Ala Gln Arg Gly Gly
            180                 185                 190

Gly Gln Tyr Asp Gln Leu Leu Lys Thr Gly Leu Ala Ser Met Lys Glu
        195                 200                 205

Asn Thr Phe Gln Tyr Gly Met Met Gln Leu Glu Trp Ile Arg Gln Glu
    210                 215                 220

Leu Cys Pro Phe Leu His Ala Glu Lys Ile Ala Asn Val Ser Leu Thr
225                 230                 235                 240

Val Val Asp Lys Thr Ser Trp Ile Ser Asp Val Glu Lys Pro Ala Ile
                245                 250                 255

Arg Met Ala Ser Asp Phe Cys His Ala Ser Ala Ser Ile Asn Leu Arg
            260                 265                 270

Ser Ile Asn Gly Ala Arg Pro Arg Val Leu Cys Ile Phe Gly Gly Ser
        275                 280                 285

Ser Ser Gly Asn Glu Pro Ala His Ile Glu Ala Ala Lys Ser Leu Gly
    290                 295                 300

Arg Val Cys His Glu Asn Ser Ile Lys Leu Val Tyr Gly Gly Gly Thr
305                 310                 315                 320

Thr Gly Val Met Gly Ala Ile Ala Ser Thr Leu Val Glu Leu Ser Gly
                325                 330                 335

Pro Asp Ala Val His Gly Ile Ile Pro Glu Ala Leu Leu Lys Tyr Glu
            340                 345                 350

Ala Lys Glu Leu Gly Arg His Pro Lys Asp Pro Thr Cys Ala Arg Tyr
        355                 360                 365

Gly Lys Arg Thr Val Val Gln Asp Met His Thr Arg Lys Arg Leu Met
    370                 375                 380
```

```
Ile Gln Glu Val Ile Asp Gly Gly Glu Gly Ser Gly Phe Val Ala Leu
385                 390                 395                 400

Ser Gly Gly Tyr Gly Thr Leu Glu Glu Leu Phe Glu Val Thr Thr Trp
            405                 410                 415

His Gln Leu Gly Ile His Asp Arg Gly Val Cys Leu Leu Asn Thr Gly
            420                 425                 430

Gly Phe Phe Asp Gly Leu Val Asp Trp Leu Ala Asn Val Val Gln Lys
            435                 440                 445

Gly Phe Ile Gly Leu Glu Asp Ala Ala Ile Leu Asn Ile Ala Ser Thr
            450                 455                 460

Ala Asp Gly Ala Val Lys Cys Leu Asp His Lys Pro Gly Phe Ser Arg
465                 470                 475                 480

Lys Gly Val Leu Asp Trp Val
            485

<210> SEQ ID NO 48
<211> LENGTH: 487
<212> TYPE: PRT
<213> ORGANISM: Fusarium pseudograminearum

<400> SEQUENCE: 48

Met Glu Ser Thr Asn Arg Phe Met Ile Gly Val Phe Gly Pro Thr Gly
1               5                   10                  15

Val Gly Lys Thr Lys Leu Gly Val Ser Ile Ala Lys Ser Val His Gly
            20                  25                  30

Gln Val Ile Ser Val Asp Ser Leu Gln Cys Tyr Ser Pro Gly Gly Ile
            35                  40                  45

Val Thr Ala Lys Pro Thr Pro Glu Glu Met Asp Gly Ile Glu His His
    50                  55                  60

Met Ile Gly Tyr Leu Glu Ala Glu Glu Pro Thr Asn Phe Val Ala
65                  70                  75                  80

Glu Ala Val Glu Arg Leu Glu Lys Leu Cys Asp His Gly Ala Ile Pro
                85                  90                  95

Val Val Val Gly Gly Ser Thr Ser Leu Thr Leu Pro Leu Leu Arg Gly
            100                 105                 110

Ala Leu Asn Arg Gly Trp Arg Met Ala Ala Ile Thr Leu Leu Pro His
            115                 120                 125

Gln Ser Thr Tyr Leu Gly Asn Ile Glu Ser Arg Val Asp Asp Met Leu
    130                 135                 140

Glu Ala Gly Leu Leu Glu Glu Leu Ser Gly Leu Lys Ser Leu Glu Asp
145                 150                 155                 160

Arg Asn Leu Asn Gly Lys Pro Asn Phe His Lys Gly Ile Trp Lys Thr
                165                 170                 175

Ile Gly Tyr Gln Glu Leu Tyr Pro Tyr Leu Glu Ala Gln Arg Ser Asp
            180                 185                 190

Gly His Cys Asp Glu Leu Leu Lys Ser Gly Leu Ala Ser Met Lys Glu
            195                 200                 205

Asn Thr Phe Gln Tyr Gly Asn Thr Gln Leu Glu Trp Ile Arg Gln Ala
    210                 215                 220

Leu Ser Pro Phe Leu His Ala Glu Lys Ile Ala Asn Met Ser Leu Thr
225                 230                 235                 240

Val Val Asp Lys Thr Ser Trp Thr Arg Gly Val Glu Lys Pro Ala Ile
                245                 250                 255

Arg Met Ala Ser Asp Phe Cys Tyr Ala Ser Thr Ser Ile Ser Phe His
            260                 265                 270
```

```
Pro Ile Asn Glu Pro Lys Pro Arg Val Ile Cys Ile Phe Gly Gly Ser
        275                 280                 285

Ser Ser Gly Asn Asp Pro Ala His Met Glu Ala Ala Lys Ser Leu Gly
    290                 295                 300

Arg Val Cys His Glu Asn Ser Ile Lys Leu Val Tyr Gly Gly Gly Thr
305                 310                 315                 320

Thr Gly Val Met Gly Ala Ile Ala Ser Thr Leu Val Glu Leu Ser Gly
                325                 330                 335

Pro Asn Ala Val His Gly Ile Ile Pro Glu Ala Leu Leu Lys Tyr Glu
            340                 345                 350

Ala Lys Glu Ser Gly Arg His Ala Gln Asp Ser Ala Phe Ala Arg Tyr
        355                 360                 365

Gly Arg Arg Thr Val Val Lys Asp Met His Thr Arg Lys Arg Leu Met
    370                 375                 380

Ile Gln Glu Val Ile Asp Gly Asp Gly Ser Gly Phe Val Gly Leu
385                 390                 395                 400

Ser Gly Gly Tyr Gly Thr Leu Glu Glu Leu Phe Glu Val Ile Thr Trp
                405                 410                 415

His Gln Leu Gly Ile His Asp Arg Gly Val Cys Leu Leu Asn Met Asp
            420                 425                 430

Gly Phe Phe Asp Gly Leu Val Asn Trp Leu Gly Asn Val Val Lys Lys
        435                 440                 445

Gly Phe Ile Gly Leu Gln Asp Ala Ala Ile Leu Ser Ile Ala Ser Thr
    450                 455                 460

Ala Glu Gly Val Val Lys Cys Leu Asp Gln Lys Pro Gly Phe Ser Arg
465                 470                 475                 480

Lys Gly Glu Leu Glu Trp Val
                485

<210> SEQ ID NO 49
<211> LENGTH: 487
<212> TYPE: PRT
<213> ORGANISM: Fusarium verticillioides

<400> SEQUENCE: 49

Met Glu Ser Thr Asn Arg Phe Met Ile Gly Val Phe Gly Pro Thr Gly
1               5                   10                  15

Thr Gly Lys Thr Lys Leu Gly Val Ser Ile Ala Lys Ser Ile Tyr Gly
                20                  25                  30

Gln Val Val Ser Val Asp Ser Leu Gln Cys Tyr Ser Pro Gly Ser Ile
            35                  40                  45

Val Thr Ala Lys Pro Thr Thr Glu Glu Thr Asp Gly Val Asp His His
50                  55                  60

Met Ile Gly Tyr Leu Glu Ala Asn Glu Glu Pro Thr Ser Phe Val Ala
65                  70                  75                  80

Glu Ala Ile Glu Arg Leu Glu Glu Leu Arg Asp His Glu Ala Ile Pro
                85                  90                  95

Val Val Val Gly Gly Ser Thr Ser Leu Thr Leu Pro Leu Leu Arg Asp
            100                 105                 110

Ala Leu Asn Arg Gly Trp Arg Met Ala Ala Ile Thr Leu Leu Pro His
        115                 120                 125

Gln Ser Thr Tyr Leu Ser Asn Ile Lys Ser Arg Leu Asp Asp Met Val
    130                 135                 140

Glu Ala Gly Leu Leu Glu Glu Leu Ser Gly Leu Lys Val Leu Glu Asp
```

```
            145                 150                 155                 160
Lys His Leu Asn Gly Lys Pro Asp Phe His Lys Gly Ile Trp Lys Ala
                165                 170                 175

Ile Gly Tyr Gln Glu Leu Tyr Pro Tyr Leu Ala Ala Arg Lys Met Asp
            180                 185                 190

Val His Cys Asp Gln Leu Leu Lys Ser Gly Leu Ala Ser Met Lys Ala
        195                 200                 205

Asn Thr Phe Gln Tyr Gly Ile Thr Gln Leu Glu Trp Ile Arg Gln Val
    210                 215                 220

Leu Cys Pro Phe Leu His Ala Glu Lys Ile Ala Asn Met Ser Leu Thr
225                 230                 235                 240

Val Val Asp Lys Thr Ser Trp Ile Leu Asp Val Gly Lys Pro Ala Ile
                245                 250                 255

Arg Met Ala Ser Asp Phe Cys His Ala Ser Thr Ser Ile Ser Phe His
            260                 265                 270

Ser Ile Asn Gly Ser Asn Pro Arg Val Leu Cys Ile Phe Gly Gly Ser
        275                 280                 285

Ser Ser Gly Asn Asp Pro Ala His Ile Glu Ala Ala Lys Ser Leu Gly
    290                 295                 300

Arg Ile Cys His Glu Asn Asn Ile Lys Ile Val Tyr Gly Gly Gly Thr
305                 310                 315                 320

Thr Gly Val Met Gly Ala Ile Ala Ser Thr Leu Val Asp Leu Ser Gly
                325                 330                 335

Pro Asp Ala Val His Gly Ile Ile Pro Glu Ala Leu Leu Lys Tyr Glu
            340                 345                 350

Ala Lys Glu Ser Gly Arg His Pro Lys Asp Pro Ala Tyr Ala Arg Tyr
        355                 360                 365

Gly Lys Gln Thr Val Val Lys Asp Met His Thr Arg Lys Arg Leu Met
    370                 375                 380

Ile Gln Glu Val Ile Thr Gly Glu Gly Ser Gly Phe Val Gly Leu
385                 390                 395                 400

Ser Gly Gly Tyr Gly Thr Leu Glu Glu Leu Phe Glu Val Val Thr Trp
                405                 410                 415

His Gln Leu Gly Ile His Asp Arg Gly Val Cys Leu Leu Asn Thr Gly
            420                 425                 430

Gly Phe Phe Asp Gly Leu Val Asn Trp Leu Gly Asn Val Val Gln Glu
        435                 440                 445

Gly Phe Ile Gly Leu Glu Asp Ala Ser Val Leu Ser Ile Ala Ser Thr
    450                 455                 460

Ala Glu Gly Val Val Arg Cys Leu Val Gln Thr Pro Glu Phe Ser Arg
465                 470                 475                 480

Lys Gly Glu Leu Glu Trp Val
                485

<210> SEQ ID NO 50
<211> LENGTH: 490
<212> TYPE: PRT
<213> ORGANISM: Epichloe gansuensis

<400> SEQUENCE: 50

Met Pro Thr Arg Lys Leu Ser Val Ala Ile Phe Gly Pro Thr Ala Ser
1               5                   10                  15

Gly Lys Thr Lys Ile Gly Val Thr Ile Ala Lys Ala Tyr Leu Gly Glu
            20                  25                  30
```

Val Ile Ser Ile Asp Ser Leu Gln Cys Tyr Lys Pro Gly Ile Ala
         35                  40                  45

Thr Ala Lys Pro Cys Pro Glu Glu Thr Gln Gly Val Pro His His Leu
 50                  55                  60

Ile Asp Tyr Leu Asp Ala Glu Glu Pro Lys Asp Phe Val Ser Arg
 65                  70                  75                  80

Ala Ile Ala Lys Val Asp Asp Ile Asn Thr Arg Asn Gly Leu Pro Ile
                 85                  90                  95

Leu Val Gly Gly Ser Thr Ser Leu Ile Ile Pro Leu Leu Gln Glu Val
                100                 105                 110

Phe Ser Arg Glu Tyr Glu Val Leu Val Ile Thr Leu Val Pro His Gln
         115                 120                 125

Ser Ser Tyr Leu Arg Leu Ile Glu Ser Arg Gly Arg Glu Met Leu Lys
130                 135                 140

Lys Gly Leu Leu Asn Glu Leu Thr Glu Leu Gln Arg Leu Glu Lys Val
145                 150                 155                 160

Leu Leu Asn Gly Lys Ser Gly Phe Asn Lys Gly Val Trp Lys Val Ile
                165                 170                 175

Gly Tyr Gln Glu Phe Leu Pro Tyr Leu Arg Ala Val Gly Lys Leu Asn
                180                 185                 190

Gly Val Ser Asn Asn Tyr Asp His Leu Tyr Glu Glu Gly Arg Ala Ser
                195                 200                 205

Met Asn Ala Ser Thr Leu His Tyr Gly Gln Tyr Gln Leu Glu Trp Met
210                 215                 220

Arg His Thr Leu Ile Pro Phe Ile His Arg Lys Ala Ile Thr Val
225                 230                 235                 240

Ser Leu Cys Val Thr Asp Gln Ala Ser Trp Val Ser Asp Val Glu Arg
                245                 250                 255

Pro Ala Met Thr Met Thr Gly Glu Phe Tyr His Gly Ser Gln Val Arg
                260                 265                 270

Arg Leu Pro Ser Arg Asn Ser Ser Lys Lys Arg Val Ile Cys Leu Phe
                275                 280                 285

Gly Gly Ser Ser Ser Gly Asn Asn Arg Ile His Ile Glu Ala Ala Lys
                290                 295                 300

Ser Leu Ala Val Ala Leu His Asn His Glu Ile Ala Leu Val Tyr Gly
305                 310                 315                 320

Gly Gly Thr Thr Gly Ile Met Gly Ala Val Ala Ser Thr Leu Val Ala
                325                 330                 335

Leu Ser Gly Pro Glu Thr Val His Gly Ile Val Pro Ala Ala Leu Ala
                340                 345                 350

Lys Tyr Glu Asp Glu Leu Gly Asp Gly Arg Ile Asn Ala Glu Tyr Leu
                355                 360                 365

Ser Gln Phe Gly Arg Arg Thr Ile Val Arg Asp Met His Thr Arg Lys
370                 375                 380

Arg Leu Met Thr Gln Ala Val Phe Glu Gly Ala Pro Gly Ser Gly Phe
385                 390                 395                 400

Val Ala Leu Ser Gly Gly Tyr Gly Thr Met Glu Glu Leu Leu Glu Val
                405                 410                 415

Thr Thr Trp Tyr Gln Leu Gly Ile His Asp Cys Arg Val Ser Val Phe
                420                 425                 430

Asn Val Asp Gly Phe Tyr Asp Gly Leu Leu Asn Trp Met Gly Gln Val
                435                 440                 445

Ala Arg Glu Gly Phe Val Ser Pro Lys Asp Ala Asn Ile Leu Gly Val

```
                450              455              460
Ala Asn Thr Ala Asn Glu Val Ile Ala Cys Leu Ala Asn Gln Gln Gln
465              470              475              480

His Glu Glu Lys Pro Asn Leu Glu Trp Leu
                485              490

<210> SEQ ID NO 51
<211> LENGTH: 494
<212> TYPE: PRT
<213> ORGANISM: Atkinsonella texensis

<400> SEQUENCE: 51

Met Leu Ala Ser Arg Lys Leu Val Ala Ile Leu Gly Pro Thr Ala Ser
1               5               10              15

Gly Lys Thr Lys Leu Gly Val Ala Ile Ala Lys Ala Phe Leu Gly Glu
                20              25              30

Val Val Ser Val Asp Ser Leu Gln Cys Tyr Lys Pro Gly Thr Ile Ile
                35              40              45

Thr Ala Lys Pro Leu Pro Glu Glu Thr Glu Gly Ile Pro His His Leu
        50              55              60

Ile Asp Tyr Leu Glu Ala Glu Lys Glu Pro His Asp Tyr Ile Glu Arg
65              70              75              80

Ala Ile Val Ala Ile Asp Asp Ile Thr Ala Arg Asn Arg Leu Pro Ile
                85              90              95

Leu Val Gly Gly Ser Thr Ser Leu Thr Met Pro Leu Leu Arg Glu Val
                100             105             110

Phe His Ala Gln Tyr Glu Val Leu Ala Ile Asn Leu Val Pro His Pro
            115             120             125

Ser Leu Tyr Gln Gln Leu Ile Glu Ser Arg Gly Glu Glu Met Leu Arg
        130             135             140

Arg Gly Leu Leu Asn Glu Leu Val Glu Leu Gln Arg Leu Glu Lys Val
145             150             155             160

Leu Leu Asn Gly Glu Cys Asp Phe Thr Arg Gly Ile Trp Lys Ala Ile
                165             170             175

Gly Tyr Gln Glu Phe Tyr Pro Tyr Leu Gln Thr Val Gly Lys Leu Asn
            180             185             190

Ala Ala Ser Lys Thr Asn Pro Gly His Leu Tyr Lys Lys Gly Arg Ala
        195             200             205

Leu Leu Phe Ala Asn Thr Leu Arg Tyr Gly Gln Gly Gln Leu Glu Trp
    210             215             220

Met Arg His Thr Leu Ala Pro Phe Leu Tyr Gln His Lys Ala Ala Thr
225             230             235             240

Ile Ser Leu Ser Val Thr Asp Lys Ala Ser Trp Ile Ser Asp Val Gln
                245             250             255

Glu Pro Ala Leu Thr Leu Ile Ser Glu Phe Tyr Asn Asp Thr Gln Val
            260             265             270

Thr Lys Ser Leu Leu Arg Arg Arg Ser Ser Lys Lys Arg Phe Val Cys
        275             280             285

Leu Phe Gly Gly Ser Ser Ala Gly Asn Asp Pro Thr His Ile Glu Ala
    290             295             300

Ala Lys Ser Leu Ala Val Ala Leu His His Asn Asp Ile Ser Leu Val
305             310             315             320

Tyr Gly Gly Gly Thr Thr Gly Ile Met Gly Gln Val Ala Ser Ser Leu
                325             330             335
```

```
Val Ala Leu Ser Gly Pro Asn Ala Val Gln Gly Phe Ile Pro Ala Ala
            340                 345                 350

Leu Ala Arg His Glu Glu Glu Leu Gly Asn Asp Gly Pro Ile Ile Asn
        355                 360                 365

Gly Glu Tyr Leu Ser Arg Phe Gly Arg Arg Thr Ile Val Arg Asp Val
    370                 375                 380

His Thr Arg Lys Arg Leu Met Ile Gln Asn Val Leu Gln Gly Thr Pro
385                 390                 395                 400

Gly Ser Gly Phe Val Ala Leu Ser Gly Gly Tyr Gly Thr Leu Glu Glu
                405                 410                 415

Leu Leu Glu Ile Thr Thr Trp Ser Gln Leu Gly Ile His Asp Cys Val
            420                 425                 430

Val Ala Val Phe Ser Val Asp Gly Phe Tyr Asp Gly Leu Leu Asp Trp
        435                 440                 445

Ile Asp Gln Val Val Arg Ser Gly Phe Ile Ser Thr Lys Asn Ala Asn
    450                 455                 460

Ile Val Arg Val Ala Asn Ser Ala Asp Lys Val Ile Ala Cys Leu Ala
465                 470                 475                 480

Asp Gly Arg Ile Gln Pro Arg Arg His Val Leu Glu Trp Leu
                485                 490

<210> SEQ ID NO 52
<211> LENGTH: 497
<212> TYPE: PRT
<213> ORGANISM: Claviceps fusiformis

<400> SEQUENCE: 52

Met Ser Thr Arg Lys Leu Ala Ile Ala Ile Leu Gly Pro Thr Ala Ser
1               5                   10                  15

Gly Lys Thr Lys Leu Gly Val Ala Phe Gly Lys Ala Tyr Leu Gly Glu
            20                  25                  30

Val Ile Ser Val Asp Ser Leu Gln Cys Tyr Lys Gln Gly Gly Ile Ile
        35                  40                  45

Thr Ala Arg Pro Tyr Pro Glu Glu Met Lys Val Val Pro His His Leu
    50                  55                  60

Ile Asp Tyr Leu Glu Ala Asp Glu Glu Pro His Asp Phe Val Ser Arg
65                  70                  75                  80

Ala Leu Thr Ile Met Asp Asp Ile Ser Ala Arg His Ala Leu Pro Ile
                85                  90                  95

Leu Val Gly Gly Ser Thr Ser Leu Thr Ile Pro Leu Leu Gln Gln Val
            100                 105                 110

Phe Lys Lys Asp Tyr Glu Val Leu Val Ile Thr Leu Val Pro His Arg
        115                 120                 125

Thr Arg Tyr Gln Arg Leu Val Glu Ser Arg Gly Glu Glu Met Leu Arg
    130                 135                 140

Arg Gly Leu Leu Ser Glu Leu Ala Glu Leu His Gly Leu Glu Lys Ile
145                 150                 155                 160

Leu Leu Gln Gly Lys Gly Glu Phe Gly Lys Gly Val Trp Lys Ala Ile
                165                 170                 175

Gly Tyr Gln Glu Phe Phe Pro Tyr Leu Gln Ala Val Gly Ser Val Asn
            180                 185                 190

Gly Ala Ser Asn Thr Lys Thr Asp Arg Asp Leu Leu Asp Lys Gly Arg
        195                 200                 205

Ala Ala Met Asp Ala Asn Thr Val Gln Tyr Gly Gln Tyr Gln Leu Glu
    210                 215                 220
```

```
Trp Ile Arg His Thr Leu Thr Pro Phe Leu His Gln His Lys Thr Thr
225                 230                 235                 240

Ile Ile Ser Leu Ser Val Thr Asp Lys Ala Ser Trp Glu Ser Asp Val
                245                 250                 255

Gln Gly Pro Ala Met Ser Met Ala Ser Glu Phe Cys His Gly Ser Arg
            260                 265                 270

Met Thr Lys His Leu Ser Arg Gly Asp Ser Cys Ser Arg Lys Arg Val
        275                 280                 285

Ile Cys Leu Phe Gly Gly Ser Ser Gly Asn Asp Val Val His Val
290                 295                 300

Glu Ala Ala Lys Ser Leu Ala Ile Ala Leu His Gln His Asp Ile Ser
305                 310                 315                 320

Leu Val Tyr Gly Gly Gly Thr Thr Gly Ile Met Gly Ala Val Ala Ser
                325                 330                 335

Thr Leu Val Ala Leu Ser Gly Pro Ser Ala Val His Gly Ile Val Pro
            340                 345                 350

Ala Ala Leu Ala Thr Tyr Glu Asp Gln Leu Gly Asp Gly Arg Ile Asp
        355                 360                 365

Ser Glu Tyr Ala Leu Arg Phe Gly Lys Arg Ile Val Val Arg Asp Met
370                 375                 380

His Thr Arg Lys Arg Leu Met Thr Gln Met Val Leu Gly Gly Ala Pro
385                 390                 395                 400

Gly Ser Gly Phe Val Ala Leu Ser Gly Gly Tyr Gly Thr Met Glu Glu
                405                 410                 415

Leu Leu Glu Ser Thr Thr Trp Ser Gln Leu Gly Ile His Asn Cys Arg
            420                 425                 430

Val Ser Val Phe Asn Val Asp Gly Phe Tyr Asp Gly Leu Leu Asp Trp
        435                 440                 445

Ile Arg His Val Ala Arg Ser Gly Phe Ile Gly Gly Lys Asp Ala Asp
450                 455                 460

Ile Ile Arg Val Ala Arg Thr Ala Asp Glu Val Val Ala Cys Leu Ala
465                 470                 475                 480

His Gln His Pro Leu Gln Ala Lys Arg Gly Cys Gln Gly Leu Glu Trp
                485                 490                 495

Leu

<210> SEQ ID NO 53
<211> LENGTH: 491
<212> TYPE: PRT
<213> ORGANISM: Epichlo baconii

<400> SEQUENCE: 53

Met Met Pro Thr Arg Lys Leu Ser Ile Ala Ile Phe Gly Pro Thr Ala
1               5                   10                  15

Ser Gly Lys Thr Lys Leu Gly Val Thr Ile Ala Lys Ala Tyr Leu Gly
            20                  25                  30

Glu Val Ile Ser Ile Asp Ser Leu Gln Cys Tyr Lys Pro Gly Gly Ile
        35                  40                  45

Ala Thr Ala Lys Pro Cys Pro Lys Glu Thr Gln Gly Val Pro His His
    50                  55                  60

Leu Ile Asp Tyr Leu Asp Ala Gly Glu Glu Pro Gln Asp Phe Val Ser
65              70                  75                  80

Arg Ala Ile Ala Thr Ile Asp Asp Ile Thr Thr Arg Asn Gly Leu Pro
            85                  90                  95
```

Val Leu Val Gly Gly Ser Thr Ser Leu Ile Ile Pro Leu Leu Gln Gln
            100                 105                 110

Val Phe Ser Arg Glu His Glu Val Leu Ile Ile Thr Leu Val Pro His
            115                 120                 125

Gln Ser Gly Tyr Gly Arg Leu Ile Glu Ser Arg Gly Glu Glu Met Leu
            130                 135                 140

Lys Arg Gly Leu Leu Asp Glu Leu Ala Glu Leu Lys Arg Leu Glu Lys
145                 150                 155                 160

Val Leu Leu Asp Gly Lys Ser Asp Phe Asn Lys Gly Val Trp Lys Thr
                165                 170                 175

Ile Gly Tyr Arg Glu Phe Leu Pro Tyr Leu Gln Ala Val Gly Lys Val
            180                 185                 190

Asn Gly Val Ser Asn Thr Tyr Glu Asp Leu Tyr Glu Glu Gly Arg Val
            195                 200                 205

Ser Met Asn Ala Ser Thr Leu Arg Tyr Gly Gln Tyr Gln Leu Glu Trp
210                 215                 220

Ile Arg His Thr Leu Ala Pro Phe Ile Asp Arg His Lys Ala Ala Thr
225                 230                 235                 240

Leu Ser Leu Cys Val Thr Asp Gln Ala Ser Trp Ala Ser Asp Ile Glu
            245                 250                 255

Arg Pro Ala Met Thr Met Ala Gly Glu Phe Tyr His Gly Ser Gln Leu
            260                 265                 270

Arg Arg Leu Pro Ser Arg Asn Ser Asn Lys Arg Val Val Cys Leu
            275                 280                 285

Phe Gly Gly Ser Ser Gly Arg Asp Glu Ser His Ile Glu Ala Ala
290                 295                 300

Lys Ser Leu Ala Val Ala Leu His Arg His Glu Ile Ala Leu Val Tyr
305                 310                 315                 320

Gly Gly Gly Thr Thr Gly Ile Met Gly Ala Val Ala Ser Thr Leu Val
                325                 330                 335

Ala Leu Ser Gly Pro Gly Ala Val His Gly Ile Val Pro Ala Ala Leu
            340                 345                 350

Ala Arg Tyr Glu Asp Glu Leu Gly Asp Gly Arg Ile Asn Ala Glu Tyr
            355                 360                 365

Ser Ser Gln Phe Gly Arg Arg Thr Ile Val Arg Asp Met His Thr Arg
370                 375                 380

Lys Arg Leu Met Met Gln Thr Val Leu Glu Gly Ala Pro Gly Ser Gly
385                 390                 395                 400

Phe Val Ala Leu Ser Gly Gly Tyr Gly Thr Met Glu Glu Leu Leu Glu
                405                 410                 415

Ile Thr Thr Trp Tyr Gln Leu Gly Ile His Asp Arg Arg Val Ser Val
            420                 425                 430

Phe Asn Val Asn Gly Phe Tyr Asp Gly Leu Leu Ser Trp Ile Gly Gln
            435                 440                 445

Val Ala Arg Asp Gly Phe Ile Arg Pro Arg Asp Ala Asn Ile Leu Gly
            450                 455                 460

Val Ala Asn Thr Ala Asp Gln Val Ile Ala Cys Leu Ala Asn Gln Arg
465                 470                 475                 480

Leu Asp Ala Glu Lys Pro Ser Leu Glu Trp Leu
                485                 490

<210> SEQ ID NO 54
<211> LENGTH: 496

<212> TYPE: PRT
<213> ORGANISM: Claviceps paspali

<400> SEQUENCE: 54

```
Met Ser Thr Ser Lys Ile Ala Ile Ala Ile Leu Gly Pro Thr Ala Ser
1               5                   10                  15

Gly Lys Thr Lys Leu Gly Val Ala Met Ala Arg Ala Tyr Leu Gly Glu
            20                  25                  30

Val Ile Ser Val Asp Ser Leu Gln Cys Tyr Lys Pro Gly Ser Ile Val
        35                  40                  45

Thr Ala Arg Pro Thr Ala Glu Glu Met Cys Asp Val Pro His His Leu
    50                  55                  60

Val Gly Tyr Leu Glu Ala Asp Glu Glu Pro Ser Asp Phe Val Ser Arg
65                  70                  75                  80

Ala Val Ala Ser Met Asp Asp Ile Ser Ser Arg Asp Arg Leu Pro Ile
                85                  90                  95

Leu Val Gly Gly Ser Thr Ser Leu Thr Leu Pro Leu Leu Gln Ala Ala
            100                 105                 110

Leu Asn Arg Gly Tyr Arg Met Leu Ala Val Met Leu Ala Pro His Pro
        115                 120                 125

Ser Thr Tyr Gln Arg Leu Val Glu Ser Arg Ala Asp Glu Met Leu Gln
    130                 135                 140

Met Gly Leu Leu Arg Glu Leu Ala Glu Leu Arg Arg Leu Glu Glu Thr
145                 150                 155                 160

Met Val Gly Ala Gly Ala Gly Cys Gly Arg Gly Val Trp Lys Thr Ile
                165                 170                 175

Gly Tyr Arg Glu Phe Leu Pro Tyr Leu Arg Ala Val Gly Trp Thr Asn
            180                 185                 190

Gly Asn Ser Asn Gly Ser Ala Gly Thr Asp Glu Asp Leu Arg Glu Lys
        195                 200                 205

Gly Arg Arg Ser Met Asn Ala Ser Thr Leu Gln Tyr Gly Gln Tyr Gln
    210                 215                 220

Leu Glu Trp Ala Arg His Thr Leu Met Pro Phe Leu Gln Arg His Thr
225                 230                 235                 240

Val Ala Thr Ile Ser Leu Cys Val Thr Asp Lys Glu Ser Trp Glu Ser
                245                 250                 255

Asp Val Glu Gly Pro Ala Met Thr Met Ala Gly Glu Phe Cys Tyr Gly
            260                 265                 270

Ser Arg Thr Met Arg Leu Pro Ser Arg Gly Pro Gly Pro Lys Lys Arg
        275                 280                 285

Val Val Cys Leu Phe Gly Gly Ser Ser Gly Asn Glu Ala Lys His
    290                 295                 300

Ile Asp Ala Ala Lys Ser Leu Gly Val Ala Leu His Arg His Gly Ile
305                 310                 315                 320

Ser Leu Val Tyr Gly Gly Gly Thr Thr Gly Ile Met Gly Ala Val Ala
                325                 330                 335

Arg Met Leu Val Ala Leu Ser Gly Pro Asp Ala Val His Gly Ile Val
            340                 345                 350

Pro Ala Ala Leu Ala Arg Tyr Glu Asp Met Leu Ser Gly Gly Arg Leu
        355                 360                 365

Asp Asp Asp Glu Arg Val Ala Arg Phe Gly Arg Thr Val Val Arg
    370                 375                 380

Asp Met His Thr Arg Lys Arg Leu Met Thr Arg Ala Val Val Glu Gly
385                 390                 395                 400
```

```
Ala Pro Gly Ser Gly Phe Val Ala Met Ser Gly Gly Tyr Gly Thr Met
                405                 410                 415

Glu Glu Leu Leu Glu Ser Thr Thr Trp Phe Gln Leu Gly Ile His Ser
            420                 425                 430

Cys Arg Ile Ser Val Leu Ser Val Asp Gly Phe Tyr Asp Gly Leu Val
        435                 440                 445

Asp Trp Ile Arg Glu Ala Gly Val Gly Ser Gly Phe Val Gly His Lys
    450                 455                 460

Asp Ala Asp Ile Ile Arg Val Ala Arg Thr Ala Asp Glu Val Ile Ala
465                 470                 475                 480

Asn Leu Ser Glu Gln Pro Ala Phe Pro Arg Leu Gly Leu Glu Trp Leu
            485                 490                 495

<210> SEQ ID NO 55
<211> LENGTH: 8
<212> TYPE: PRT
<213> ORGANISM: Artificial sequences
<220> FEATURE:
<223> OTHER INFORMATION: Non-fungal consensus motif
<220> FEATURE:
<221> NAME/KEY: misc_feature
<222> LOCATION: (2)..(2)
<223> OTHER INFORMATION: Xaa at position 2 is Pro, Ala, Val, Ser, Thr or
      Cys
<220> FEATURE:
<221> NAME/KEY: MISC_FEATURE
<222> LOCATION: (3)..(3)
<223> OTHER INFORMATION: Xaa at position 3 is Thr, Gly, or Ala
<220> FEATURE:
<221> NAME/KEY: MISC_FEATURE
<222> LOCATION: (4)..(4)
<223> OTHER INFORMATION: Xaa at position 4 is Cys, Thr, Ser, Val, Ala,
      or Gly
<220> FEATURE:
<221> NAME/KEY: MISC_FEATURE
<222> LOCATION: (5)..(5)
<223> OTHER INFORMATION: Xaa at position 5 is Ser, Thr, Met, Ala, or Val
<220> FEATURE:
<221> NAME/KEY: misc_feature
<222> LOCATION: (8)..(8)
<223> OTHER INFORMATION: Xaa at position 8 is Ser or Thr

<400> SEQUENCE: 55

Gly Xaa Xaa Xaa Xaa Gly Lys Xaa
1               5

<210> SEQ ID NO 56
<211> LENGTH: 9
<212> TYPE: PRT
<213> ORGANISM: Artificial sequences
<220> FEATURE:
<223> OTHER INFORMATION: Non-fungal consensus motif
<220> FEATURE:
<221> NAME/KEY: misc_feature
<222> LOCATION: (1)..(1)
<223> OTHER INFORMATION: Xaa at position 1 is Val, Ile, Leu, Phe, or Pro
<220> FEATURE:
<221> NAME/KEY: MISC_FEATURE
<222> LOCATION: (2)..(2)
<223> OTHER INFORMATION: Xaa at position 2 is Ile, Val, or Leu
<220> FEATURE:
<221> NAME/KEY: MISC_FEATURE
<222> LOCATION: (3)..(3)
<223> OTHER INFORMATION: Xaa at position 3 is Leu, Ile, or Val
<220> FEATURE:
<221> NAME/KEY: MISC_FEATURE
<222> LOCATION: (4)..(4)
<223> OTHER INFORMATION: Xaa at position 4 is Glu, Val, Thr, or Ala
<220> FEATURE:
<221> NAME/KEY: misc_feature
```

```
<222> LOCATION: (7)..(7)
<223> OTHER INFORMATION: Xaa at position 7 is Ser or Thr
<220> FEATURE:
<221> NAME/KEY: MISC_FEATURE
<222> LOCATION: (8)..(8)
<223> OTHER INFORMATION: Xaa at position 8 is Ile, Val, Met, Thr, Ser,
      His, Gly or Asn
<220> FEATURE:
<221> NAME/KEY: MISC_FEATURE
<222> LOCATION: (9)..(9)
<223> OTHER INFORMATION: Xaa at position 9 is Ser, Tyr, Leu, Thr, or Arg

<400> SEQUENCE: 56

Xaa Xaa Xaa Xaa Gly Gly Xaa Xaa Xaa
1               5

<210> SEQ ID NO 57
<211> LENGTH: 6
<212> TYPE: PRT
<213> ORGANISM: Artificial sequences
<220> FEATURE:
<223> OTHER INFORMATION: Non-fungal consensus motif

<400> SEQUENCE: 57

Leu Val Tyr Gly Gly Gly
1               5

<210> SEQ ID NO 58
<211> LENGTH: 10
<212> TYPE: PRT
<213> ORGANISM: Artificial sequences
<220> FEATURE:
<223> OTHER INFORMATION: Non-fungal consensus motif
<220> FEATURE:
<221> NAME/KEY: misc_feature
<222> LOCATION: (7)..(7)
<223> OTHER INFORMATION: Xaa at position 7 is Phe, Ile, Leu, or Met
<220> FEATURE:
<221> NAME/KEY: MISC_FEATURE
<222> LOCATION: (8)..(8)
<223> OTHER INFORMATION: Xaa at position 8 is Glu or Asp

<400> SEQUENCE: 58

Pro Gly Gly Tyr Gly Thr Xaa Xaa Gly Leu
1               5                   10

<210> SEQ ID NO 59
<211> LENGTH: 9
<212> TYPE: PRT
<213> ORGANISM: Artificial sequence
<220> FEATURE:
<223> OTHER INFORMATION: consensus motif example

<400> SEQUENCE: 59

Gly Pro Thr Gly Val Gly Lys Thr Lys
1               5

<210> SEQ ID NO 60
<211> LENGTH: 9
<212> TYPE: PRT
<213> ORGANISM: Artificial sequence
<220> FEATURE:
<223> OTHER INFORMATION: consensus motif example

<400> SEQUENCE: 60

Gly Pro Thr Ala Ser Gly Lys Thr Lys
1               5

<210> SEQ ID NO 61
```

```
<211> LENGTH: 9
<212> TYPE: PRT
<213> ORGANISM: Artificial sequence
<220> FEATURE:
<223> OTHER INFORMATION: consensus motif example

<400> SEQUENCE: 61

Gly Pro Thr Gly Ala Gly Lys Thr Lys
1               5

<210> SEQ ID NO 62
<211> LENGTH: 9
<212> TYPE: PRT
<213> ORGANISM: Artificial sequence
<220> FEATURE:
<223> OTHER INFORMATION: consensus motif example

<400> SEQUENCE: 62

Gly Pro Thr Gly Thr Gly Lys Thr Lys
1               5

<210> SEQ ID NO 63
<211> LENGTH: 9
<212> TYPE: PRT
<213> ORGANISM: Artificial sequence
<220> FEATURE:
<223> OTHER INFORMATION: consensus motif example

<400> SEQUENCE: 63

Pro Ile Leu Val Gly Gly Ser Thr Ser
1               5

<210> SEQ ID NO 64
<211> LENGTH: 9
<212> TYPE: PRT
<213> ORGANISM: Artificial sequence
<220> FEATURE:
<223> OTHER INFORMATION: consensus motif example

<400> SEQUENCE: 64

Pro Val Leu Val Gly Gly Ser Thr Ser
1               5

<210> SEQ ID NO 65
<211> LENGTH: 9
<212> TYPE: PRT
<213> ORGANISM: Artificial sequence
<220> FEATURE:
<223> OTHER INFORMATION: consensus motif example

<400> SEQUENCE: 65

Pro Val Val Val Gly Gly Ser Thr Ser
1               5

<210> SEQ ID NO 66
<211> LENGTH: 9
<212> TYPE: PRT
<213> ORGANISM: Artificial sequence
<220> FEATURE:
<223> OTHER INFORMATION: consensus motif example

<400> SEQUENCE: 66

Pro Ile Leu Val Gly Gly Ser Ile Ser
1               5

<210> SEQ ID NO 67
<211> LENGTH: 9
```

```
<212> TYPE: PRT
<213> ORGANISM: Artificial sequence
<220> FEATURE:
<223> OTHER INFORMATION: consensus motif example

<400> SEQUENCE: 67

Pro Ile Leu Cys Gly Gly Ser Thr Ser
1               5

<210> SEQ ID NO 68
<211> LENGTH: 6
<212> TYPE: PRT
<213> ORGANISM: Artificial sequence
<220> FEATURE:
<223> OTHER INFORMATION: consensus motif example

<400> SEQUENCE: 68

Leu Val Tyr Gly Gly Gly
1               5

<210> SEQ ID NO 69
<211> LENGTH: 6
<212> TYPE: PRT
<213> ORGANISM: Artificial sequence
<220> FEATURE:
<223> OTHER INFORMATION: consensus motif example

<400> SEQUENCE: 69

Leu Ile Tyr Gly Gly Gly
1               5

<210> SEQ ID NO 70
<211> LENGTH: 6
<212> TYPE: PRT
<213> ORGANISM: Artificial sequence
<220> FEATURE:
<223> OTHER INFORMATION: consensus motif example

<400> SEQUENCE: 70

Ile Val Tyr Gly Gly Gly
1               5

<210> SEQ ID NO 71
<211> LENGTH: 10
<212> TYPE: PRT
<213> ORGANISM: Artificial sequence
<220> FEATURE:
<223> OTHER INFORMATION: consensus motif example

<400> SEQUENCE: 71

Ser Gly Gly Tyr Gly Thr Leu Glu Glu Leu
1               5                   10

<210> SEQ ID NO 72
<211> LENGTH: 10
<212> TYPE: PRT
<213> ORGANISM: Artificial sequence
<220> FEATURE:
<223> OTHER INFORMATION: consensus motif example

<400> SEQUENCE: 72

Ser Gly Gly Tyr Gly Thr Met Glu Glu Leu
1               5                   10

<210> SEQ ID NO 73
<211> LENGTH: 10
<212> TYPE: PRT
```

```
<213> ORGANISM: Artificial sequence
<220> FEATURE:
<223> OTHER INFORMATION: consensus motif example

<400> SEQUENCE: 73

Pro Gly Gly Tyr Gly Thr Met Glu Glu Leu
1               5                   10

<210> SEQ ID NO 74
<211> LENGTH: 8
<212> TYPE: PRT
<213> ORGANISM: Artificial sequence
<220> FEATURE:
<223> OTHER INFORMATION: consensus motif example

<400> SEQUENCE: 74

Gly Pro Thr Cys Ser Gly Lys Thr
1               5

<210> SEQ ID NO 75
<211> LENGTH: 8
<212> TYPE: PRT
<213> ORGANISM: Artificial sequence
<220> FEATURE:
<223> OTHER INFORMATION: consensus motif example

<400> SEQUENCE: 75

Gly Ala Thr Thr Thr Gly Lys Thr
1               5

<210> SEQ ID NO 76
<211> LENGTH: 8
<212> TYPE: PRT
<213> ORGANISM: Artificial sequence
<220> FEATURE:
<223> OTHER INFORMATION: consensus motif example

<400> SEQUENCE: 76

Gly Val Thr Ser Met Gly Lys Thr
1               5

<210> SEQ ID NO 77
<211> LENGTH: 8
<212> TYPE: PRT
<213> ORGANISM: Artificial sequence
<220> FEATURE:
<223> OTHER INFORMATION: consensus motif example

<400> SEQUENCE: 77

Gly Pro Thr Ser Thr Gly Lys Thr
1               5

<210> SEQ ID NO 78
<211> LENGTH: 8
<212> TYPE: PRT
<213> ORGANISM: Artificial sequence
<220> FEATURE:
<223> OTHER INFORMATION: consensus motif example

<400> SEQUENCE: 78

Gly Pro Thr Thr Thr Gly Lys Thr
1               5

<210> SEQ ID NO 79
<211> LENGTH: 8
<212> TYPE: PRT
<213> ORGANISM: Artificial sequence
```

```
<220> FEATURE:
<223> OTHER INFORMATION: consensus motif example

<400> SEQUENCE: 79

Gly Pro Thr Cys Thr Gly Lys Thr
1               5

<210> SEQ ID NO 80
<211> LENGTH: 8
<212> TYPE: PRT
<213> ORGANISM: Artificial sequence
<220> FEATURE:
<223> OTHER INFORMATION: consensus motif example

<400> SEQUENCE: 80

Gly Ala Thr Cys Thr Gly Lys Thr
1               5

<210> SEQ ID NO 81
<211> LENGTH: 8
<212> TYPE: PRT
<213> ORGANISM: Artificial sequence
<220> FEATURE:
<223> OTHER INFORMATION: consensus motif example

<400> SEQUENCE: 81

Gly Pro Thr Thr Ala Gly Lys Thr
1               5

<210> SEQ ID NO 82
<211> LENGTH: 8
<212> TYPE: PRT
<213> ORGANISM: Artificial sequence
<220> FEATURE:
<223> OTHER INFORMATION: consensus motif example

<400> SEQUENCE: 82

Gly Pro Thr Ser Val Gly Lys Thr
1               5

<210> SEQ ID NO 83
<211> LENGTH: 8
<212> TYPE: PRT
<213> ORGANISM: Artificial sequence
<220> FEATURE:
<223> OTHER INFORMATION: consensus motif example

<400> SEQUENCE: 83

Gly Pro Thr Gly Val Gly Lys Ser
1               5

<210> SEQ ID NO 84
<211> LENGTH: 9
<212> TYPE: PRT
<213> ORGANISM: Artificial sequence
<220> FEATURE:
<223> OTHER INFORMATION: consensus motif example

<400> SEQUENCE: 84

Val Ile Leu Glu Gly Gly Ser Ile Ser
1               5

<210> SEQ ID NO 85
<211> LENGTH: 9
<212> TYPE: PRT
<213> ORGANISM: Artificial sequence
<220> FEATURE:
```

```
<223> OTHER INFORMATION: consensus motif example

<400> SEQUENCE: 85

Val Ile Leu Glu Gly Gly Ser Ile Ser
1               5

<210> SEQ ID NO 86
<211> LENGTH: 9
<212> TYPE: PRT
<213> ORGANISM: Artificial sequence
<220> FEATURE:
<223> OTHER INFORMATION: consensus motif example

<400> SEQUENCE: 86

Ile Ile Ile Glu Gly Gly Ser Val Ser
1               5

<210> SEQ ID NO 87
<211> LENGTH: 9
<212> TYPE: PRT
<213> ORGANISM: Artificial sequence
<220> FEATURE:
<223> OTHER INFORMATION: consensus motif example

<400> SEQUENCE: 87

Val Ile Ile Glu Gly Gly Ser Val Ser
1               5

<210> SEQ ID NO 88
<211> LENGTH: 9
<212> TYPE: PRT
<213> ORGANISM: Artificial sequence
<220> FEATURE:
<223> OTHER INFORMATION: consensus motif example

<400> SEQUENCE: 88

Ile Ile Leu Glu Gly Gly Ser Met Ser
1               5

<210> SEQ ID NO 89
<211> LENGTH: 9
<212> TYPE: PRT
<213> ORGANISM: Artificial sequence
<220> FEATURE:
<223> OTHER INFORMATION: consensus motif example

<400> SEQUENCE: 89

Leu Ile Leu Glu Gly Gly Ser Ile Ser
1               5

<210> SEQ ID NO 90
<211> LENGTH: 9
<212> TYPE: PRT
<213> ORGANISM: Artificial sequence
<220> FEATURE:
<223> OTHER INFORMATION: consensus motif example

<400> SEQUENCE: 90

Val Ile Leu Glu Gly Gly Ser Val Ser
1               5

<210> SEQ ID NO 91
<211> LENGTH: 9
<212> TYPE: PRT
<213> ORGANISM: Artificial sequence
<220> FEATURE:
<223> OTHER INFORMATION: consensus motif example
```

<400> SEQUENCE: 91

Leu Ile Leu Glu Gly Gly Ser Val Ser
1               5

<210> SEQ ID NO 92
<211> LENGTH: 9
<212> TYPE: PRT
<213> ORGANISM: Artificial sequence
<220> FEATURE:
<223> OTHER INFORMATION: consensus motif example

<400> SEQUENCE: 92

Ile Ile Leu Glu Gly Gly Ser Val Ser
1               5

<210> SEQ ID NO 93
<211> LENGTH: 9
<212> TYPE: PRT
<213> ORGANISM: Artificial sequence
<220> FEATURE:
<223> OTHER INFORMATION: consensus motif example

<400> SEQUENCE: 93

Leu Ile Leu Glu Gly Gly Ser Thr Ser
1               5

<210> SEQ ID NO 94
<211> LENGTH: 9
<212> TYPE: PRT
<213> ORGANISM: Artificial sequence
<220> FEATURE:
<223> OTHER INFORMATION: consensus motif example

<400> SEQUENCE: 94

Val Ile Val Glu Gly Gly Ser Ile Ser
1               5

<210> SEQ ID NO 95
<211> LENGTH: 8
<212> TYPE: PRT
<213> ORGANISM: Artificial sequence
<220> FEATURE:
<223> OTHER INFORMATION: consensus motif example

<400> SEQUENCE: 95

Gly Ser Thr Gly Thr Gly Lys Ser
1               5

<210> SEQ ID NO 96
<211> LENGTH: 8
<212> TYPE: PRT
<213> ORGANISM: Artificial sequence
<220> FEATURE:
<223> OTHER INFORMATION: consensus motif example

<400> SEQUENCE: 96

Gly Thr Thr Gly Val Gly Lys Ser
1               5

<210> SEQ ID NO 97
<211> LENGTH: 8
<212> TYPE: PRT
<213> ORGANISM: Artificial sequence
<220> FEATURE:
<223> OTHER INFORMATION: consensus motif example

```
<400> SEQUENCE: 97

Gly Pro Thr Gly Ala Gly Lys Ser
1               5

<210> SEQ ID NO 98
<211> LENGTH: 8
<212> TYPE: PRT
<213> ORGANISM: Artificial sequence
<220> FEATURE:
<223> OTHER INFORMATION: consensus motif example

<400> SEQUENCE: 98

Gly Cys Thr Gly Thr Gly Lys Ser
1               5

<210> SEQ ID NO 99
<211> LENGTH: 8
<212> TYPE: PRT
<213> ORGANISM: Artificial sequence
<220> FEATURE:
<223> OTHER INFORMATION: consensus motif example

<400> SEQUENCE: 99

Gly Pro Thr Ala Ser Gly Lys Thr
1               5

<210> SEQ ID NO 100
<211> LENGTH: 9
<212> TYPE: PRT
<213> ORGANISM: Artificial sequence
<220> FEATURE:
<223> OTHER INFORMATION: consensus motif example

<400> SEQUENCE: 100

Pro Ile Val Val Gly Gly Thr Ser Tyr
1               5

<210> SEQ ID NO 101
<211> LENGTH: 9
<212> TYPE: PRT
<213> ORGANISM: Artificial sequence
<220> FEATURE:
<223> OTHER INFORMATION: consensus motif example

<400> SEQUENCE: 101

Pro Ile Val Val Gly Gly Thr His Tyr
1               5

<210> SEQ ID NO 102
<211> LENGTH: 9
<212> TYPE: PRT
<213> ORGANISM: Artificial sequence
<220> FEATURE:
<223> OTHER INFORMATION: consensus motif example

<400> SEQUENCE: 102

Pro Ile Val Thr Gly Gly Thr Gly Leu
1               5

<210> SEQ ID NO 103
<211> LENGTH: 9
<212> TYPE: PRT
<213> ORGANISM: Artificial sequence
<220> FEATURE:
<223> OTHER INFORMATION: consensus motif example

<400> SEQUENCE: 103
```

```
Pro Val Ile Val Gly Gly Thr Thr Tyr
1               5

<210> SEQ ID NO 104
<211> LENGTH: 9
<212> TYPE: PRT
<213> ORGANISM: Artificial sequence
<220> FEATURE:
<223> OTHER INFORMATION: consensus motif example

<400> SEQUENCE: 104

Pro Leu Leu Val Gly Gly Thr Met Leu
1               5

<210> SEQ ID NO 105
<211> LENGTH: 8
<212> TYPE: PRT
<213> ORGANISM: Artificial sequence
<220> FEATURE:
<223> OTHER INFORMATION: consensus motif example

<400> SEQUENCE: 105

Gly Ala Thr Gly Ala Gly Lys Ser
1               5

<210> SEQ ID NO 106
<211> LENGTH: 8
<212> TYPE: PRT
<213> ORGANISM: Artificial sequence
<220> FEATURE:
<223> OTHER INFORMATION: consensus motif example

<400> SEQUENCE: 106

Gly Thr Thr Gly Thr Gly Lys Ser
1               5

<210> SEQ ID NO 107
<211> LENGTH: 8
<212> TYPE: PRT
<213> ORGANISM: Artificial sequence
<220> FEATURE:
<223> OTHER INFORMATION: consensus motif example

<400> SEQUENCE: 107

Gly Ala Thr Gly Ser Gly Lys Ser
1               5

<210> SEQ ID NO 108
<211> LENGTH: 8
<212> TYPE: PRT
<213> ORGANISM: Artificial sequence
<220> FEATURE:
<223> OTHER INFORMATION: consensus motif example

<400> SEQUENCE: 108

Gly Ala Thr Gly Thr Gly Lys Ser
1               5

<210> SEQ ID NO 109
<211> LENGTH: 8
<212> TYPE: PRT
<213> ORGANISM: Artificial sequence
<220> FEATURE:
<223> OTHER INFORMATION: consensus motif example

<400> SEQUENCE: 109
```

Gly Ala Thr Gly Thr Gly Lys Thr
1               5

<210> SEQ ID NO 110
<211> LENGTH: 8
<212> TYPE: PRT
<213> ORGANISM: Artificial sequence
<220> FEATURE:
<223> OTHER INFORMATION: consensus motif example

<400> SEQUENCE: 110

Gly Ala Thr Ala Thr Gly Lys Ser
1               5

<210> SEQ ID NO 111
<211> LENGTH: 9
<212> TYPE: PRT
<213> ORGANISM: Artificial sequence
<220> FEATURE:
<223> OTHER INFORMATION: consensus motif example

<400> SEQUENCE: 111

Pro Ile Ile Ala Gly Gly Ser Asn Ser
1               5

<210> SEQ ID NO 112
<211> LENGTH: 9
<212> TYPE: PRT
<213> ORGANISM: Artificial sequence
<220> FEATURE:
<223> OTHER INFORMATION: consensus motif example

<400> SEQUENCE: 112

Pro Ile Val Val Gly Gly Ser Asn Ser
1               5

<210> SEQ ID NO 113
<211> LENGTH: 9
<212> TYPE: PRT
<213> ORGANISM: Artificial sequence
<220> FEATURE:
<223> OTHER INFORMATION: consensus motif example

<400> SEQUENCE: 113

Pro Ile Leu Ala Gly Gly Ser Asn Ser
1               5

<210> SEQ ID NO 114
<211> LENGTH: 9
<212> TYPE: PRT
<213> ORGANISM: Artificial sequence
<220> FEATURE:
<223> OTHER INFORMATION: consensus motif example

<400> SEQUENCE: 114

Pro Ile Val Ala Gly Gly Ser Asn Ser
1               5

<210> SEQ ID NO 115
<211> LENGTH: 9
<212> TYPE: PRT
<213> ORGANISM: Artificial sequence
<220> FEATURE:
<223> OTHER INFORMATION: consensus motif example

<400> SEQUENCE: 115

Pro Ile Ile Val Gly Gly Ser Asn Ser

```
1               5

<210> SEQ ID NO 116
<211> LENGTH: 9
<212> TYPE: PRT
<213> ORGANISM: Artificial sequence
<220> FEATURE:
<223> OTHER INFORMATION: consensus motif example

<400> SEQUENCE: 116

Pro Val Leu Ala Gly Gly Ser Asn Ser
1               5

<210> SEQ ID NO 117
<211> LENGTH: 9
<212> TYPE: PRT
<213> ORGANISM: Artificial sequence
<220> FEATURE:
<223> OTHER INFORMATION: consensus motif example

<400> SEQUENCE: 117

Pro Val Val Ala Gly Gly Ser Asn Ser
1               5

<210> SEQ ID NO 118
<211> LENGTH: 9
<212> TYPE: PRT
<213> ORGANISM: Artificial sequence
<220> FEATURE:
<223> OTHER INFORMATION: consensus motif example

<400> SEQUENCE: 118

Pro Val Val Ala Gly Gly Ser Asn Thr
1               5

<210> SEQ ID NO 119
<211> LENGTH: 9
<212> TYPE: PRT
<213> ORGANISM: Artificial sequence
<220> FEATURE:
<223> OTHER INFORMATION: consensus motif example

<400> SEQUENCE: 119

Pro Ile Val Ala Gly Gly Ser Asn Arg
1               5

<210> SEQ ID NO 120
<211> LENGTH: 10
<212> TYPE: PRT
<213> ORGANISM: Artificial sequence
<220> FEATURE:
<223> OTHER INFORMATION: consensus motif example

<400> SEQUENCE: 120

Pro Gly Gly Tyr Gly Thr Phe Glu Glu Leu
1               5                   10

<210> SEQ ID NO 121
<211> LENGTH: 10
<212> TYPE: PRT
<213> ORGANISM: Artificial sequence
<220> FEATURE:
<223> OTHER INFORMATION: consensus motif example

<400> SEQUENCE: 121

Pro Gly Gly Tyr Gly Thr Leu Glu Glu Leu
1               5                   10
```

```
<210> SEQ ID NO 122
<211> LENGTH: 10
<212> TYPE: PRT
<213> ORGANISM: Artificial sequence
<220> FEATURE:
<223> OTHER INFORMATION: consensus motif example

<400> SEQUENCE: 122

Pro Gly Gly Tyr Gly Thr Leu Asp Glu Leu
1               5                   10

<210> SEQ ID NO 123
<211> LENGTH: 10
<212> TYPE: PRT
<213> ORGANISM: Artificial sequence
<220> FEATURE:
<223> OTHER INFORMATION: consensus motif example

<400> SEQUENCE: 123

Pro Gly Gly Tyr Gly Thr Met Glu Glu Leu
1               5                   10

<210> SEQ ID NO 124
<211> LENGTH: 10
<212> TYPE: PRT
<213> ORGANISM: Artificial sequence
<220> FEATURE:
<223> OTHER INFORMATION: consensus motif example

<400> SEQUENCE: 124

Pro Gly Gly Tyr Gly Thr Ile Glu Glu Leu
1               5                   10
```